(12) United States Patent
Brady

(10) Patent No.: US 11,472,843 B2
(45) Date of Patent: Oct. 18, 2022

(54) MALACIDINS AND METHODS OF USE

(71) Applicant: The Rockefeller University, New York, NY (US)

(72) Inventor: Sean Brady, New York, NY (US)

(73) Assignee: The Rockefeller University, New York, NY (US)

( * ) Notice: Subject to any disclaimer, the term of this patent is extended or adjusted under 35 U.S.C. 154(b) by 0 days.

(21) Appl. No.: 16/617,052

(22) PCT Filed: May 25, 2018

(86) PCT No.: PCT/US2018/034533
§ 371 (c)(1),
(2) Date: Nov. 26, 2019

(87) PCT Pub. No.: WO2018/222507
PCT Pub. Date: Dec. 6, 2018

(65) Prior Publication Data
US 2020/0148723 A1    May 14, 2020

Related U.S. Application Data

(60) Provisional application No. 62/511,981, filed on May 27, 2017.

(51) Int. Cl.
| C07K 7/56 | (2006.01) |
| A61P 31/04 | (2006.01) |
| A61K 38/07 | (2006.01) |
| A61K 45/06 | (2006.01) |

(52) U.S. Cl.
CPC ............... *C07K 7/56* (2013.01); *A61K 38/07* (2013.01); *A61K 45/06* (2013.01); *A61P 31/04* (2018.01)

(58) Field of Classification Search
None
See application file for complete search history.

(56) References Cited

U.S. PATENT DOCUMENTS

| 2005/0027113 A1 | 2/2005 | Miao |
| 2013/0164317 A1 | 6/2013 | Yousef |
| 2015/0218221 A1 | 8/2015 | Van Der Laan |

OTHER PUBLICATIONS

Charlop-Powers, Zachary et al; "Chemical-giogeographic survey of secondary metabolism in soil." PNAS (2014) 111(10) 3757-3762.*
Altschul et al., 1990, "Basic local alignment search tool", J. Mol. Biol., 215, 403-410.
Brady et al., 2007, "Construction of soil environmental DNA cosmid libraries and screening for clones that produce biologically active small molecules", Nat. Protoc. 2, 1297-1305.
Bunkoczi et al., 2005, "Structure of the lipopeptide antibiotic tsushimycin", Acta Crystallogr. Sect. D. 61, 1160-1164.
Charlop-Powers et al., 2016, "Urban park soil microbiomes are a rich reservoir of natural product biosynthetic diversity", PNAS 113:14811-14816.
Edgar, 2004, "MUSCLE: multiple seguence alignment with high accuracy and high throughpu", Nucleic Acids Res., 32, 1792-1797.
Edgar, 2010, "Search and clustering orders of magnitude faster than BLAST", Bioinformatics, 26, 2460-2461.
Fujii et al., 1997, "A Nonempirical Method Using LC/MS for Determination of the Absolute Configuration of Constituent Amino Acids in a Peptide: Elucidation of Limitations of Marfey's Method and of Its Separation Mechanism", Anal. Chem., 69, 3346-3352.
Gietz & Schiestl, 2007, "Large-scale high-efficiency yeast transformation using the LiAc/SS carrier DNA/PEG method", Nat. Protoc., 2, 38-41.
Heinzelmann et al., 2003, "A glutamate mutase is involved in the biosynthesis of the lipopeptide antibiotic friulimicin in Actinoplanes friuliensis. A", Antimicrob Agents Ch., 47, 447-457.
Hojati, Z. et al., 2002, "Structure, Biosynthetic Origin, and Engineered Biosynthesis of Calcium-Dependent Antibiotics from Streptomyces Coelicolor". Chemistry and Biology, 9, 1175-1187.
Hover, B. et al., 2018, "Culture-Independent Discovery of the Malacidins as Calcium-Dependent Antibiotics with Activity Against Multidrug-Resistant Gram-Positive Pathogens". Nature Microbiology, 3, 415-422.
International Preliminary Report on Patentability for PCT/US2018/034533 dated Dec. 3, 2019, 6 pages.
International Search Report for PCT/US2018/034533 dated Aug. 23, 2018, 3 pages.
Jung, et al., 2004, "Structural transitions as determinants of the action of the calcium-dependent antibiotic daptomycin", Chem. Biol. 11, 949-957.
Kallifidas et al., 2012, "Reassembly of functionally intact environmental DNA-derived biosynthetic gene clusters", Methods Enzymol., 517, 225-239.
Katz et al., 2016, "Culture☐ independendiscovery of natural products from soil metagenomes", J. Ind. Microbiol. Biotechnol. 43, 129-141.
Kim et al., 2010, "Cloning Large Natural Product Gene Clusters from the Environment:Piecing Environmental DNA Gene Clusters Back Together with TAR", Biopolymers 93, 833-844.
Kleinj et al., 2016, "Total Synthesis of Laspartomycin C and Characterization of Its Antibacterial Mechanism of Action", J. Med. Chem. 59, 3569-3574.
Liu et al., 2014, "4-Methylproline Guided Natural Product Discovery: Co-Occurrence of 4-Hydroxy- and 4-Methylprolines in Nostoweipeptins and Nostopeptolides", ACS Chem Biol 9, 2646-2655.
Luesch et al., 2003, "Biosynthesis of 4-Methylproline in Cyanobacteria: Cloning of nosE and nosF Genes and Biochemical Characterization of the Encoded Dehydrogenase and Reductase Activities", J Org Chem 68, 83-91.

(Continued)

*Primary Examiner* — Fred H Reynolds
(74) *Attorney, Agent, or Firm* — Riverside Law LLP

(57) ABSTRACT

The present invention provides methods, compositions and articles of manufacture useful for the prophylactic and therapeutic amelioration and treatment of gram-positive bacteria, and related conditions. The invention provides compositions and methods incorporating and utilizing malacidin antibiotics, and derivatives and variants thereof.

14 Claims, 47 Drawing Sheets
Specification includes a Sequence Listing.

(56) References Cited

OTHER PUBLICATIONS

Medema et al., 2011, "antiSMASH: rapid identification, annotation and analysis of secondary metabolite biosynthesis gene clusters in bacterial and fungal genome sequences", Nucleic Acid Res., 39, W339-W346.
Miao et al., 2005, "Daptomycin biosynthesis in Streptomyces roseosporus: cloning and analysis of the gene cluster and revision of peptide stereochemistry", Microbiol., 151, 1507-1523.
Miao et al., 2006, "The lipopeptide antibiotic A54145 biosynthetic gene cluster from Streptomyces fradiae", J. Ind. Microbiol. Biotechnol., 33, 129-140.
Muller et al., 2007, "Sequencing and Analysis of the Biosynthetic Gene Cluster of the Lipopeptide Antibiotic Friulimicin in Actinoplanes friuliensis", Antimicrob Agents Ch 51, 1028-1037.
Muller, et al., 2016. "Daptomycin inhibits cell envelope synthesis by interfering with fluid membrane microdomains", PNAS 113, E7077-E7086.
Owen et al., 2013, "Mapping gene clusters within arrayed metagenomic libraries to expand the structural diversity of biomedically relevant natural products", PNAS 110, 11797-11802.
Owen et al., 2015, "Multiplexed metagenome mining using short DNA sequence tags facilitates targeted discovery of epoxyketone proteasome inhibitors", PNAS 112:4221-26.
Price et al., 2009, "FastTree: Computing Large Minimum Evolution Trees with Profiles instead of a Distance Matrix", Mol. Biol. Evol., 26, 1641-1650.
Reddy et al., 2014, "eSNaPD: a versatile, web-based bioinformatics platform for surveying and mining natural product biosynthetic diversity from metagenomes", Chem. Biol. 21, 1023-1033.
Reddy, B. V. et al., 2012, "Natural product biosynthetic gene diversity in geographically distinct soil microbiomes", Appl. Environ. Microbiol.78, 3744-3752.

Schneider et al., 2009, "The Lipopeptide Antibiotic Friulimicin B Inhibits Cell Wall Biosynthesis through Complex Formation with Bactoprenol Phosphate", Antimicrob. Agents Ch. .53, 1610-1618.
Schubert et al., 2014, "Stereochemistry and Conformation of Skyllamycin, a Non☐Ribosomally Synthesized Peptide from *Streptomyces* sp. Acta 2897", Chemistry—A European Journal, 20, 4948-4955.
Silverman et al., 2005, "Inhibition of Daptomycin by Pulmonary Surfactant: In Vitro Modeling and Clinical Impact", J. Infect. Dis. 191, 2149-2152.
Straus and Hankcock, 2006, ""Mode of action of the new antibiotic for Gram-positive pathogens daptomycin: comparison with cationic antimicrobial peptides and lipopeptides, Biochim. Biophys. Acta 1758, 1215-1223.
Strieker and Marahiel, 2009, "The structural diversity of acidic lipopeptide antibiotics", ChemBioChem 10, 607-616.
Tringe, S. G. et al., 2005, "Comparative metagenomics of microbial communities", Science 308, 554-557.
Vertesy, L. et al., 2000, "Friulimicins: Novel Lipopeptide Antibiotics with Peptidoglycan Synthesis Inhibiting Activity from *Actinoplanes friuliensis* Sp. Nov. II. Isolation and Structural Characterization". The Journal of Antibiotics, 53, 816-827.
Written Opinion of the International Searching Authority for PCT/US2018/034533 dated Aug. 23, 2018, 5 pages.
Zhang et al., 2012, "BIGrat: a repeat resolver for pyrosequencing-based re-sequencing with Newbler", BMC Res. Notes, 5:567, 5 pages.
Zhang et al., 2016, "Membrane Binding and Oligomerization of the Lipopeptide A54145 Studied by Pyrene Fluorescence", Biophys. J. 111, 1267-1277.
Zhu et al., 2010, "Ab initio gene identification in metagenomic sequences", Nucleic Acids Res., vol. 38, No. 12, e132, 15 pages.
Uncultured bacterium malacidin biosynthetic gene cluster, complete sequence, GenBank KY654519, 2018, 1-33, ncbi.nlm.nih.gov/nuccore/KY654519.
Walsh et al., 2013, "Nonproteinogenic Amino Acid Building Blocks for Nonribosomal Peptide and Hybrid Polyketide Scaffolds", Angew Chem Int, 52:7098-7124.

\* cited by examiner b.

| Malacidin | Friulimicin (A. friuliensis) | Laspartomycin (S. viridochromogenes) | Daptomycin (S. roseosporus) | AS4145 (S. fradiae) |
|---|---|---|---|---|
| MlcA | PstA (54%) | LpmA (54%) | | |
| MlcB | Orf7 (65%) | | | |
| MlcC | | | | LptO (62%) |
| MlcD | ExpA (40%) | Orf20 (47%) | Orf30 (65%) | LptN (51%) |
| MlcE | GmB (39%) | | DptN (56%) | |
| MlcF | GrtA (60%) | | | |
| MlcG | LlpA (52%) | Orf21 (54%) | | LptEF (48%) |
| MlcH | LlpB (52%) | Orf22 (51%) | DptE (48%) | |
| MlcI | LlpB (24%) | Orf22 (31%) | | |
| MlcJ | LlpD (47%) | Orf24 (47%) | | |
| MlcK | PstA (50%) | LpmB (50%) | DptF (41%) | LptA (46%) |
| MlcL | PstC (52%) | LpmC (52%) | DptBA (44%) | LptC (49%) |
| MlcM | PstD (51%) | LpmD (51%) | DptBC (46%) | LptO (46%) |
| MlcN | RegB (55%) | Orf19 (61%) | DptD (47%) | LptU (30%) |
| MlcO | ExpB (57%) | Orf14 (59%) | | LptM (54%) |
| MlcP | | | DptM (%) | |
| MlcQ | | | | |
| MlcR | | | | |
| MlcS | DabCA (39%) | Orf15,17 (40%) | | |
| MlcT | DabB (35%) | Orf16 (31%) | | |
| MlcU | | | | |
| MlcV | Orf21 (71%) | SvH1 (70%) | DptG (68%) | LptG (72%) |
| MlcW | | | | |
| MlcX | | | | |
| MlcY | | | | |

Figure 29B

SEQUENCE LISTING

```
<160> NUMBER OF SEQ ID NOS: 6

<210> SEQ ID NO 1
<211> LENGTH: 37999
<212> TYPE: DNA
<213> ORGANISM: Artificial Sequence
<220> FEATURE:
<223> OTHER INFORMATION: DFD0097-644

<400> SEQUENCE: 1
gcgggctcgt cgtcgcagat gttcactacg ccggtgggcc agtgcagcgc tgacacagcc      60
gcagaagccg cgtcgtcgac atgcacgaag ctggtcacgt ccgcgctcgc ctgaagttga     120
ccgtcgtggg cgagttgcgc catgagcgcg cccgacgtgt accaagtgcc ccggccgtag     180
aacatgccgt agcgcaggac gacccattcg ggcacttctt gcaccgccgt ctcgagtgag     240
aacacggcac gcacggtgtt ctgccggtca gcggtcgaac cgaggtcgag cggcacgtcc     300
tccgtggccg gttcgtcacc tggttcgtag acccagcaga tgctctgggc gatgatccgc     360
tggacgcccg cgccgagtgc cgcgtcgacc aggttgcggg tgccctgctc acgaaccctg     420
gcgttggctg cccgatcgcc gccgctgagg tcggtcagct ggtgcatgac cacgtcgggc     480
tcggccgtcc ggaccgcatc ggccaatgcg gcacggtcgt aggcatcggc gatcgccacc     540
tcggcgccta cctccgcaag gacggggag gggcgccgag tgagtccgac gacctgatga     600
ccatgggcga ccagcatctc cgtcacccgc cgtccgatca cgcccgatgc accggccagg     660
aagatccgca tgtccaccaa agtacggcca ctgccatggg attccgtggt ccagttgagc     720
ctcggtttcg cggaccggtt cgtggcctca ccagcatgga caggaacgag ccgcgaggat     780
ctcgtcgatc acgtgcacgg agttggccgt gatcacggga ttggtctccc ggtagtacgg     840
cagctggatc aacgagatcg acaacgccca gccgcggcca cgggcccacg ccgcgccgtc     900
gacgtccaca gtagaccgga aggtctcccg tgccgagccg gtgaacaggt tccacgccgg     960
gatgaggtcg acagcgggat cgccgacgcc gatcaggccg aagtcgatca cggcggcgag    1020
ccgcccaccc gaggtgagca cgttcccgg ccccaggtcg ccgtgggtcc acaccggctg    1080
cgaagaccat tccggtgcgc gcagtgcctc ttcccacgcg gcagtgaccg catccgtgtc    1140
gatgacgccg tgcagttgct cgatggcctc gcgggtcgcg cggtcacgcc ctgccagcgg    1200
cccgctccgg tcggaaaccg gcccttggcc ggggtcgatc cgccgcaacg cgacgacgaa    1260
ctccgcgaga tcctgggcca ccgacggaat gtcgccgacg accgggttct cgccgtccag    1320
ccagcgaagc accgaccagt cgcacggata gccctcaccg ggcacgcctt ggccgaccgg    1380
aaccggaatg gccaccggaa gcggcgccaa ccgcggcagc caggtctgct cccgccgcac    1440
```

-continued

```
gtccccagcc gcccgttcga ccaacggcag gcgcacgacc atgtcctcgc cgagccggta    1500
cagggcgttg acggtgccgg aagacgtcac tcgggagatc ggcagatccg cccactgggg    1560
gaactgtgcg gtgagcagtc gccgcacaag atcggcggac gtgtcgattt cgtcagcgtg    1620
catcatcatc gagatcgacg ataaccagcc tgccggttcg cccgcacacg attaaccggg    1680
ctgcgggaac cgccagacgg gtgcatcgaa ccggtgtcac acccgcggtg tggatcagtg    1740
tcgcggtcga gctccgggcg caggtggcgc gctcgagggc ggccgctggg gctctcggtg    1800
cgcatcgggg acgggcaccg gcaggtgaca cggacctgcg ggtcggcggg ctgaccccgg    1860
acgactatcc gcccaggcgc cgttgacctg cggattttac ctttcgggcc gctctggacc    1920
ggggtatgac cgtttgaccg gccccgatcg gcgtcacggt accctggcgt gggatcttgc    1980
atcgggtacg ccgacgtcga cgggctgcat tgtggttttc cacagtatgt gcggtgtggt    2040
ttgacgccgt gaagtgggag gcacacttcc ttctgccgcc gtccgcgcat tcctaagctt    2100
gtgggtgtaa aaggttccc ggaagagagc gttgatgtct gtttacctgc tagccgagaa    2160
cgcacacgag cccgtcggcg gtttggccgg ctgggcggtc aacctgatgg acaccctcgg    2220
cggcgtgggt gcggcactcg tggtcgggct ggacaacctt ttcccgccca tccccagtga    2280
actcgtgctg ccactggccg ggttctccgc cagcaagggc gtgttcacgc tggcgggcgc    2340
cctgttctgg acaacgctgg ggtcggttgt cggcgcgatc atcgtgtacc tggtcggcgc    2400
tctgctcggc cgggaccgca cccgggccct ggtcggcaag atcccgctgg tcaaggtgac    2460
cgacttcgac aagaccgaga gtggttcgc caagcacggc acgaaggccg tcttcttcgg    2520
ccggatgatc ccgctgttcc gcagcttcat ctcgctgccg gcaggcgtcg agaagatgaa    2580
cttcctgaag ttcctgctgc tgaccacggc gggcagcctg atctggaaca ccatcttcgt    2640
cgtcgcgggc taccagctcg gcgagaactg gtacctggtc gacgagtacg ccggtgtctt    2700
ccagaagatc gtgatcggcg cggtcgtgct ggccatcgtg ctgttcgtcg tgatgcggct    2760
gcgcaaccgg aacaagggaa aagctgagga cgacccggac gcgacccagg tgcttccgca    2820
gatccggcgc gacaggtgac ctcccggggcg acgcccggtc cccacgaaaa ggatggcggc    2880
ctgaccccca ggggccgcca tccttttcgt cacggcaagg acagccgagc catcgcgggc    2940
cagagcgact cccacgaccg cgtttggccg gtgcacagcc agatcggcgt accgtccgcc    3000
acgctcaagg ctgctgacac cgtcccgacc cgctcgacct gcgtgaagcc ggagcgaagc    3060
acgccaggat cggtgccgac gaacagcacg gtcgttgacg tcggcacgcc gaaataccag    3120
taaccacgat taccgctgta cacgtcatgc acgccgtaga actccagggc ggccgcagtc    3180
cagtaggagt cggtgaccac ggcggcgcct tcgggcgcat gcaccgaaga ggccaccgaa    3240
ggccagccga actccgccgtg gctgaccatg tcgcgcagct tgtcggcgcg ggcgggcgga    3300
tcgatccagg aaaccggccg taccggcaac atcgacaccg cgatcaacgc cgacaccacg    3360
aacgcaggcc acggtagcca ccgcggaatc cgggtgaccg acacgccgc gaccgcgaac    3420 agcaacggga acagcccggc cacgtagtag aaccggccgc cggtgaccag gaagatggcg    3480
atcacgccga ccgaggccca gccaaggaac cggtacgacg gcaatcgcac gagacgccaa    3540
agcccgtaca cggcagccac ggcgccaacc ccgatcccgg cccgcgtcaa ggccagcggc    3600
aggaacatca gcggtcccgc gcctgaagcc gccatttctt ccgcgatcac ggactgcatc    3660
tgcagctgcg gccagccgtg cagggcctgc cagatcaacg tcggcacgga cgccacgacg    3720
gaaatcgccg ccccggccca gagcagcgga cgccgcagca agtcacgagg cccggcaacg    3780
```

```
agtgcgctca caccgatcgc cagccacaac gccaccacaa gccacttcgc ctgcagggtc    3840
acggcggtga ccagaccggc gtacagcagc aggcggtcct gcctgacccg cacccagcgc    3900
acgagcagcc acaggatcac cgcccagagc accgtgtcta cagtggacgt ggccagcatg    3960
tggccgctcg gcaggcggc gatcgcggtc gccgccgccg ccatcacctg cgcgacggga     4020
gaaccgccaa gctcacaggc gatcgccgcg cccaccactg tcaccaggcc gaccaacagg    4080
atcgacggca acctcaacac ggtcaggtcg cccggtgcca gccagtccag gaaggccgcc    4140
atcagcggca ccaggggcgg ctggtcggcg taacccagt ccagatggcg gcccgcggcg     4200
atgaagtaca gctcatcacc gaaatagccg tatctccggc tggtcagcaa cagcaaggac    4260
acggtgatgg ccgcgatggc catcaccggt cgaagcgcca acgcacgcga tgtgacagcc    4320
aaagtggcca ctattccgcc tttcgagctc ccgcgatgtc ggtcacggtc gtgcgcagcg    4380
ctgaggtgaa gtcatgcgcg ggacgccacg agctgagtgc gcgcagccgc cggtcgtcga    4440
gcaggccggg gccggggag acagtcacgg ggtcgccggt gaccaacccg gcgaccatcc     4500
gaaccactga gcggaccgaa aggctttgcc cggagccgac gttgtacacg ccggtcggta    4560
cctcggccgt caggcagtgc acagtggccg cacagaaatc ctcgacatag agccactcgt    4620
gcacgggcga tccgccacgc accaaagcag gttcctcgcc gcgcaacacg gtccgggtca    4680
cggtgggaat gagccgtgac cgctgctggt gaggtccgaa gatgttgccg ctgcgcagaa    4740
cgatgccgcg aagcccatgg cgttgcgcgt agtgcaaagc gatgagctcc gaagtcacct    4800
tcgcgatgcc gtaaggcgcc gcgggccgta cgggatggtc ttcgtggtac agcaggccct    4860
cgctcaaagg cccatacacc tccgcgctcg acgcgagcac cacggcagaa accccggcca    4920
tcccggcggc cgcgaacacc cggtcggtca aggcggcgtt gaccgtcaga taccccaccg    4980
gatcggcgag cgattcgggg atggaggtcc gccggccag gtggatcacg cgtccacct     5040
ggtgccggc gaacaccgag gccagtgcct cggcgtcggt cagctcggtc ggcacgacga     5100
ccgtacccgg gaccggctcg cccggatcac gcagcaggac cacactgccg ggggagcggg    5160
cgagcaggga agtcaggttc cggccgacga accggtgtt gccggtgatc gcgatccgca     5220
cgtgtcagac cgcctcgtcg atcaggtgct cgaacaccag gccgaggtcg gtcaccgcga    5280
ccgcgacggc ggccagcgcg tgccgaacgt tggccgtcgc acacggcggc aagtcggcac    5340
gagcgagctc cttgagccgt gtgtaaacat cgagcagcgc ggtttccgaa gcggtcaacg    5400
gtgttcccag gaggtccgtc atcggcccgg cctttcgtcg atcatccgct tggccttgag    5460
cgtgaagcgc ggcagcgacc cggtctgcgc cagcgtcacg ttgaaccgca ggccctcgtg    5520
cgccgcggac aactccttgg ccagctgttc acgcaaccgg tcccagtccg aggaccgagg    5580
ggtctccact cgcacggtga tctcgtcacg gttgccctcg cggtgcaggc gggtctggaa    5640
ctcgccgatc tccgggaacc gccggacgat cgcctcgacc gctcggatgt acacgttggt    5700
gccacgaatc agcttcatgt cgtcgacccg gccgaggaca ccgccgtcgt acaggtcgaa    5760
cgtgcgcccg caaccacacc gcgaagcagg caccgggtg acgacgtccg cagtccggta     5820
acgcagcaac gggatcatgc tccggccgaa cgaggtgacg acacgctcac cgcgttcccc    5880
gtaaccgacc ggcctgccgg aggcgtcgac cacctcttcg atcatgtggt cctcgatgat    5940
gtgcgcacca cccggctgat gagcgcactc gaacatgaag atcgtcgaga tctcggtcat    6000
ccccgcggtg tcgtaggccc tggcgcccca acgtcttcg atcatcgccc gggtctccga    6060
tgggcacggc tcaccggaca gcacgacctt gcgtaccggc cctgatgtca ggtcgatgcc    6120
gagcgagtcc gcctcttcgg ccagccgcaa cgcgtacgtc ggcgtggagg cgatgacggt    6180
```

-continued

```
ggcgccgaag tcgactatct gccggacacg ggcctccgcg gtctgcgcgc cgcccgggat   6240
caccaacgcg cccagcttct ccagtgcgtg gtgcaggccc cagaaaccga tgaacgagcc   6300
gtacccgaat gccagatagg ccacatcgga cggacgaaca ccttgcgccc acaggccgta   6360
gcaccacatc tcggcggccc atgaccagtc cttacgggag tccgacgcgc gcaggggcat   6420
ccggccggtc gtgccgctgg tggtgtgcaa ccggatcgcg gattccacac cggtcaccgg   6480
aagtgtgccg taaggcgggc gcgcttcctg cccggccatc cattcgtccc tggtcaggaa   6540
cgggatccgc tgcagatcgg cgagagtacg caacttcgag gcatcgagtc cgtgtaaggt   6600
acgccgatag tgcgggctac gcgccgaagc ccactcgaca acggcgcgca gcttcgccag   6660
ctgaagctcg acgagatccg cacgcggcaa cgtctcggtc ttgggattcc agaactccat   6720
cagctcaccc ccgccatcgg atcgccgcgc ggccgcgta gtcaccggcg tgggcgaacg   6780
cggcgagcat gatcagtgat ccgtccttga ccttgcccga ccggatggca cggtccaaag   6840
tgaccgggat gcccgcgccg aacatgttgc cgcactcctc gaacgtgtcc gggtgccggt   6900
ccggtgtcag gccaagcgtg ctgcgccagc tcttgaggaa gagccggttc ggctggttgg   6960
tcaccagtac gtcgatgtcc gttgtggaca cgccgatccg gtcgcacacc tcaccggcga   7020
gttcggggac gagcttcttg ccgcggatca ggacttcccg gatcttcgac tcggtgaacc   7080
cgatgtgcac ctggccgtca cccggctccc agtacttgcg gtcgccgtcg atcgcgagcc   7140
ccatctgccc ggcgtagtcg gggaaggtgc gggaccggac gtccaggacc ggcgagctgt   7200
cgtcggcgac gagcaacgcg gcgccggcac cgtccccggg gatggcggcc tgcggcatgg   7260
tccgggtgcg gctctgccgg tacacctgcc cggcgaagtt ctgcgcgttg cagatcagtg   7320
ccgagcgggc gtccgttgac cgcatcgatg gcgtcgccag ttcgatcatc gtgatgaacg   7380
ccgcgcagct gccgttgtgc acgtcgaaca cccagcccgg ctccaggccg agccgctgtg   7440
ccagctccgc gccgcacccg tagatcggct ggtcggcag ttgcgagtgg gtgatcagga   7500
tgtccacatc ggtcacggcg gaatcgccgt gccgctcacg cagacctgtg gtcgcccgct   7560
ccatcatgtc cactgtggtc tcaccggggcg cgacgtggtg gcggaacgcg gcggcttga   7620 acatcacctg cgcgtcgccg tcctcgccgg ggtcaccgcc gaagtacgac gcgggcacgc   7680
gggtttcggg cagatagctg ctgacatcca gcaggctcac gctcttcatg ggttgacctg   7740
gctccagtcc ggggtgatcg gcaggccgcg ggagtgccgg tactcgcaga tcttcttgag   7800
gttctgcagc tccagccagt gcccggcggc gaacaggtgc cagaactccc cgatccacgg   7860
ccgtccttcc ggcgcggtct ccgggaacgg gttgtcgtcg tagaacgggt ggtggcagtt   7920
ggtccactgc accacgctgc ccggcttgtc gaacacgacc tgggcgtcga tgacccgcat   7980
caggtagatc atccacaggt gttggccctg gtcccaggcg cagtggtagt ccacggtccg   8040
tgcctcggcg ttcgcgacgg tcttggtgta gatcatcgtg tccctggcga tcaggtcgtc   8100
cgacagccac acgtccggct ggtcggtccg ctcgaaccgg cgcagggtga agctccactc   8160
ggccaggctg cgggtgtcgg cgaggtacgc gtagacctcg tccggcggcg cgtcgatgtg   8220
gtcggtgatg gtgcagtacg tgccgtacac gtcgttgtgc gcgtggaact ccggcgtggc   8280
cgccatgatc tgcttgatca ccgagttgac cgggacgatc tcggcgcggg tcaggtcctc   8340
gatgccggcc agcgaccggg gcagcttgtc aacctgcgtg gacgtggaca tgggtgtcct   8400
ccttcgcgag gaacggggcg aacggggaa tctcgtcggg atcgcagtcg atggccacga   8460
aggccgggcc gcgcacggaa ccggcgtgcg ccagtgccgt ccgcaactgg tcggcggacg   8520
```

```
ccgcgtgacc ggcggcgatg ccggggaaca tggccgcgac gcccgcggcg aggtcggagt    8580
accggaagcg gttgaacgtg tagccgccgc cgaagtagat ctgctcacgg gtcacgcaca    8640
tggcgtgcgc gttgttgttg agcaccacga acgtgatcgg caggtcgtac tccaccgcgg    8700
tgtggatctc caggccgtgg gtgagaaagg cgccgtcgcc cgcgatcacg aacgtccggc    8760
gtccgctgaa ggccgcgcct atcccggcac cgaacgtgta gcccatgcca cccatacccca   8820
gtgccacaac gcatcggccg tgacgtgggg cgggcagccg gtggatcgcg gcggcgcccg    8880
cgttcccggc gtcgatgaag acgttggcgt catcgctgat caccttggcg atggcgtcga    8940
ccacctcggt gtagccgagt cgaggaccgt ggtacgtcgg cgcggccagg aattcggcag    9000
gctccgcgac gaccgtgctc aggccgacgg gcccgagtcg ctccgtcagc gcacgcagag    9060
tcggtttgat gtgcccgcgc aacgccaatg cgtcgatgta cggcgtctcc gggtccagcg    9120
acagcacagg aatcccggcc agcaggtcgt ccagtccgcc gcgcgcagtg atcggcaacc    9180
tggtccccac cagtacgcag gcactggcgg tgctcaggtg ccgcgcgagt gcgggatggc    9240
ccatgatgcc cgcgaccccg atgaaccggg gatcggtgtt gtcgaacacg tccttggagt    9300
ccgggcagac cgcgaccctg gcgtccagtg ccccggcgaa cgcccgcagt tcggccctgg    9360
cgtccgctct ggcgacaccg tctccggcga tgacgatcac ccggccggat ttccgtgccg    9420
cgtcggccag gtcggccgcc aggtccacca gttcctcagg cgtggccacc acttcgggcc    9480
ggggcacggc ggcagcgggt gcgtcgaact ccgcttgctg gatgtccttg ggcagcaaca    9540
gaacggccgg gccgtccgcg gtcgcggcca gtgcttcggc gagcaactcc gggaactcgt    9600
ccggatcggt gacagtggcg cagaaccgtg acacgccagc gaaaacctgg gctgcggaca    9660
aggatccagc cagaccgctg gagtcctgga acgcgccttt gccgtgttgc ccggtcggcg    9720
gctgccgac cagcgcgagc accgggacac gggacgcgta cgcctcgccc aggccaggta    9780
ccaggttcag cgcggcaccg ccggaagtcg ccgccaccac accgagcccg ctggtggtcc    9840
gggcgtgccc gtcggccatg gtcgccgcgt tgaactcgtg tttggccagt acgccggtga    9900
cgccgggtct ggcttgtagc gcgtcgtaga ggtcttcgat gttcgcgcca ccgacaccga    9960
acacgcgggt gacgccgagt gcggcagca cgtcgacgag atggtcgacc acccggatac    10020
gagacgacag ggtgacagac aagtgtgacc ctttcccag cacgaaagaa tgagtgcgct    10080
atcgcgcgaa tcagccccag ttggagtcgc ccgaaatcgg cgacgagctg atggaaacag    10140
tgtgcggtgc ggtttgtcaa ttcgcccgaa ccggattcac ccatgatcgg ccgactggaa    10200
actttagggc atcgcctagt ttcattcgcc ccgctcccgg ctagcatcac ctgtggtttc    10260
cgtgcgacgg aggaggcagc tgggtggtcg ccgcactgtt cgacctcgac ctggtggacc    10320
gggatgtcta tcggggagtc agtcgtgggg gcaccgcgct tccggtattc ggcgggcaac    10380
tgctcggaca ggctttggcg gccgcttcgg cgactgttga atccgatcga ctggtgaatt    10440
ccctacattc ctattttctt cgtcccgggg attcggcagg tggattgttt tttgccgtcg    10500
accggctcag ggatggctac gcgttcagca cccgccgggt ggacgtcctg cagaacgacg    10560
tttccgtgtt caccatgacg gcttcgttcc accgggccga tcacggcctg gaccacggcc    10620
ttgaagcgcc ggtggtcccg gatccggagt ccttgccgac gctggacgag cgctacgcgg    10680
gctacgagtc gcagatcccg tggttcggcc tgccgcagcc ggtggagctg cgctacgtcg    10740
acgaccgcc gtggatccag cgcggcaaag gacctcgtgc cccgtcggc cgggtgtggt    10800
tgcggctgaa ggacaagctc ccggacgacc cggtgccgca cacgtgcgca ctggccttcg    10860
cctcggacat gacgttgctc gaaccggcac tggtcgcgca cgcgacctca tgggacggcc    10920
```

```
tgcgttttgc cagtcttgac cactcgttgt ggttccaccg gtcgctccgg gccgacgaat    10980
ggttgttgta cgagaccaca agcccatccg cggcgggcgc aagaggactg ggaacaggcc    11040
ggttctggga ccgcgcgggc cggctggtcg ccagcagcgc gcaggaaggc ctgctgcgca    11100
tccgatcgga ggtccccgcg tgacacacgt gctgttcctg tccgtgccct tacacggaca    11160
catcctgccg agcctgccga tcgtcgccga actggtggcc cgcggccgcc gggtcagcta    11220
tgccgccacg gccgacttcg ccgggttcgt cactgaagcc ggggcacgg ccgtgccctg    11280 caccacgatt tttccggtcg agggctccag caaagcgttg ccacgcaacg acgccgaggg    11340
cgcgctgatg ttcctcgacg aagccatcac ggccatgccg caggtcgccg aagcgctggc    11400
cggggatcca ccggacgtcg tcgtctacga catgggcgcg atgcacggac cgatcctggc    11460
cgagaagtgg ggcgtacccg cggtgcagct gtcgccgtcg cacgtgacgc cgcgtggcgt    11520
cacccagatc ctcggcatca gccaggccga agcaccaccc ggcattgtgg agttccagcg    11580
ccggttcgag gacttcgtgg ccggacaagg cgtgcgcgtc cggcccgagg agatcatggc    11640
cgaaccgcgg cggtgcattg tgacgatccc gcgcgcgttc cagatcgaaa ccgacggcat    11700
caccgatcaa cacacgttcg tcggaccgat gatcgacgac cgggcgccag aaccgtggcc    11760
agacgatcac ggcaagccga tcgtgctggt gtcgctgggt tccgcgttcc gcacgcagac    11820
agacttctac cgaacatgcg ttgaagcctt ccgtggtacg gaatggcacg tggtgctcgc    11880
cctgggcaag ttcatcgacc cggctgacct gggatcgctg ccggacaacg tggaagcaca    11940
cgcatgggtt ccgctggctt cggtgctggc gaaggccaag gcgttcgtga cacaagccgg    12000
gatgggcggc acgatgaccg cgttgtacca cgaggtgccg caagtcgcgg tcccattgat    12060
ggcaggtcag ccattgaccg cacgcaggct ggtcgaactc gggctcggcg cacacctgcc    12120
acctgaggac gtcacaccgg aaagcctgct gacagccgtc cggcaggtcg ccgacaacga    12180
gtcgatcaag accgagctgc gccggatgcg caaggagatc gaggcctgcg gcggcgcagc    12240
gcttgccgct gacgttgtcc tgtccacggt ggatggagaa ctggatgccc aacgaattg    12300 aggtgtcgca gtagcggtgc gcgccagcgc acaagaggtc tgcgtggttc cctcccgtat    12360
ggcctgggtc tgacggagcc cggcagcgcc gagcaccgtg agcaggatgg tcgtcatcgc    12420
ggacctgacg aaccacaacc cgaattcttc agtgctggtc agggcgccca gagatcacga    12480
ttcggccagt ggaggctcgc cgtcttctcc accatgacgc ccgcgtgcgc tcgaaccgtc    12540
aaggggccgc ggttcccgta cggtgagtgt gagcagagcg gcaggcaggg cgatcgcgag    12600
gccgagtgcg accatgagca gtgtgccggt cgtcggcgtg aggtggtcga gcatggtcag    12660
gtgtacgaag aagtgcggga tcgcccaggt caggtacatg atgagcgctg ccagggtgag    12720
ccattgtccc atgtggatgg tcgcggcgcc gagcaccacg cgctggcga gtgtcatggc    12780 gccgtagtcg agcatcaggt gcttgttgta ggccatgccc atgccgacca cctcgagcgc    12840
gaagaaccgt gcggggagga acagtgccca caagccgacg acggcctggg tgacggtgag    12900
aaacccgaga ccggcgcgaa gccaccgccg catcaccggc tccgcccgtg cgcacggtct    12960
ccggcgagga agtcgtcgaa cgtgatcctc cccgtcgccc ggtccggggt gaggtgatgg    13020
cccgcgcgat agtcacggat caccttgccc ggcaagggaa ctgccacac cggtcgacgg    13080 cggccgatcg ccaggaggta gctgcgggcc agttcggcgg cctcccgtac ctccgggccg    13140
ccgatgtccg gtgccggtt cgcggccggt ccgccgcgca acgtgaccag ctggtcggcc    13200
acctcggtga cgtcgaccgg ctggaaacgc accctcgacg gcatcagcgt caccggcagc    13260
```

```
aggcgctgga catcgcagat ggtggcgatc aggtcgtgga actgggtcgc gcgcaggatc   13320
gtccacggca gcccggagcg ctcgaccagc cgttcacagg ccagcttcgc ccggtagtag   13380
ccgagcgcga tgtggtcgat cccgacgatc gacacgtaca ccaggtgcgg gtcgcccgcc   13440
gctgtcgctg cctcgatcag cctgcctgtc gtggccacat caccccgccc gttggtggtc   13500
gccaggtgga tgatcacgtc cgctccggcg gtcgcgccgg ccagcccgct accggtacgc   13560
agatcgccca cgacccagcg gtgcgcggcc ggctcccgct tcctgcgggt cagcacccgc   13620
acgtcgtggc ccatatcgag cagccgcggc accagcgcgc gcccgagccg cccggtgccg   13680
ccggtgacca gaatctgttt cgccatgtct cgctccgtgg tggctggaat ctcgcctcgc   13740
accactagga accgaatgac tccccggaac gtgacaaccg ggccagttgc gcgccgacga   13800
accggagctt gtccggattg cgacaatcc  ggataccggt gatccggccg tccgcgatct   13860
ccggcacgaa cacaccgagc agcgtggacg cggaccagcc gaacaccgcc ggagtcccgt   13920
tcacctcgtg cacggacacc gtgagacctt cggcatactg gctggtgacg gtcgccaggt   13980
accgggcgac cttctccgcg ccgcgcaccg gcaaccgggc gacaccgggc gtgccgccac   14040
catcggcgac cgatgtgacg tcctcggcga gcatccgctc cagaccggcg aggtcaccgc   14100
cacgcgcggc gtcgaggaac cgctcgacca gcatccgatt cccggtgacg tcgcccgcgg   14160
accgcgggag ccgggcggcc gacagccgtt ccgcgcccg  gctgtgcaac tgccggcagt   14220
tcgactccga aagctccacc agtcggcca  cctcgcgatg gctgtagccg aacgcctcac   14280
gcagcacgaa aaccgcccgc tcacccgggg tgagccgttc ggccagcacc aggaaggcca   14340
gtgacaccgt atcccgctgc tcggccgtct ccatcggccc cagcgcgctg tcggggtca   14400
gcaccggctc cggcaaccac gacccgacat aacgctcccg gcgagccgag ccgccccaa    14460
gccggttcag gcacagattc gtggtgactt tgaccagcca cgcggacggg acctcgaccg   14520
agccgggctc ggtaccgtgc caccgcaaga acacgtcctg aacaacatcc tccgcgtcca   14580
cggccgaacc cagcatccga tacgccagcc gaacaaccg  cggccgctgc cgctcgaact   14640
ccgcgaccgg cgcggatccg ggcttctcca ctggacggtt cacaaccgtg attctcgcac   14700
ggcaccgccg atggccgcgg tcactcatcc cgggcacggc gcccgtctcc ggcgtttatg   14760
ttgcgcccag gccgctctga gcttgcgtca ggtcatctgt gggcttgcgc acaggctgtc   14820
cggggcacaa gtttagggtt gcccctagtg cttggggtgc atcgttgaca gtccccgtgg   14880
tcggtcgaca tggttgctgt accgggaaaa ccgcttgtca gttgaacatc cgtctggggg   14940
tccgatgaca gaccggccgc gactgagccc gacccggatt cggccgtgga ttccgccggg   15000
cggtgcacct gccgccgggc tggactcgct gcgcaaggcc gttcccgccg aactggccgc   15060
gcgcctgcgt gaccttggcc agttacgcga cgtcctgctt gccgcgcacc tgaaagtcct   15120
tggtgtgatg ggcggcgagc gaacgcccct caccggctac ctcgtgcctg gtgccgactt   15180
ggcgccgcgc ggggtggcat tggacgatgc cacctggcgt gacctgatcg gcaaggtgca   15240
cgaaccggtc gaagtcgtcg aagacgcgcc cgctttcgac gtggtactgg acttctccgg   15300
cgccgggatg accggcgcgg tgctggacgt ggcctatgtg gacgccgagg acggactgtg   15360
gttggagcta cggttccgtc aggacgtgat cgaccacgcg cacgccgaac ggttcgccgg   15420
atacgaactg cgcgcactgg aactgctcgc caccgatccc gacgcctcgc atgacgcgaa   15480
gagcctggtc gagccggatg agtacgagta ccagatgcgt gcgcattccg gcgccgacat   15540
cccttggcac ggaaagcttt tcgtcgagct gttcgaggaa caggtgcggc tgcgcccgga   15600
tgacctggca gcctcacacg gcgacgtgcg atggacgtac cgcgacctga acgcgaacgc   15660
```

```
caacaaggtc gcgaactctt tgctgcgccg tggtttgctt gccgaagatc cggtcgccgt    15720
ggtgatgaac cgggaactga actgggtcgc ggcgatgctc ggtgtgttca aggcgggcgg    15780
cgtgtacatg ccggttcgcc cggacttccc accggatcgc gtcgccatgc agttcgaacg    15840
cgcggattgc aagttcgtcc tgtcgtccgc ggacgccgtc cacacggcga acgaagcact    15900
ggccggttcc gtccgggact gcccggtgtc gcttgtggaa gacctgctgc gtgacgaaac    15960
cgacgacacc gacccgaagt cgtcgatcca gccggggcag ctggcgtaca tctacttcac    16020
gtccggctcg accggggcgc cgaagggcgc gatgtgcgag cacgccggga tgctcaacca    16080
cctgtacatg aagatcgacg acatggaact ggccgagggc gaggtggtca cccagaccgc    16140
gtcgcagtgc ttcgacatct cgttgtggca ggtcatcgcg ccgtggctgg tcggggcgag    16200
cacgcggatc atcgacaccg aaacacagct ggacgtcgac tggttcctcg acgagatcgc    16260
cgcaggcggc atccaggtga tccagatcgt gccggcgtac ctggacgtga tgacgtcgca    16320
cctggccaaa cacccgcgcg cgctcggtga cctgcggacc atctcggtca ccggggaggc    16380
actgaaactg gagctggtcc gccggtggtt cgcgctctac ccgcagatct cgctggtcaa    16440
cgcgtacggt gcgaccgagg tctccgacga caccatgcac gaggtgctga ccggcctgcc    16500
ggaacgcgac ttcgtcacgg tcggccgtcc actgcggaac gtgcacgtgt acgtgctgga    16560
cgagaagctg cggatcgccc cgctcggtgc tcccggtgag atcgcgttct ccggtgtcgc    16620
cgtcggccgt gggtacatca atgacgagga acggaccgcg cacgcgttcg tcgaagaccc    16680
gcaccggccc ggcacccggc tgtaccggac cggggacttc ggccgttggc tgcccgaagg    16740
caagatcgag ttccttggcc gccgggacga gcaggtcaag gtccgcgggt tccgcatcga    16800
gatcggcgat atcgagaaca agatcctcgg tgtgccgcat gtccgcgagg ccgcggtggt    16860
catcgatggc gactcggaca ccaagaccct ggtggccttc tacagcggcg cggccgagct    16920
gaaagccgag gacatccgcg accacctggc cacgcagctg ccggagtaca tgatcccgac    16980
gtacttccac cggctggact ccctgccgct caccgagaac ggcaaggtca acaagaagct    17040
gctgacctcg ctggccggca cgctcggcca cgcgggcgcc tcctacgtcg cgccggtgac    17100
cgacgcggag cgcaggctcg cgaccgcgtg ggcggaagtg ctcggcgttc cactggaacg    17160
catcggtcga cgggacaact tcttcgagct cggtgggacc tcgctcgcgg ccgtgcggct    17220
cgtggtgaac ctcgaccgcc agatctcgtt gacgcaggtg gtcacgaacc cggtgctgga    17280
ggacctggcc gcgtgcctcg tcgccgcggg cacgcctgac gccggactgg tccaacgtct    17340
gtccatcggt gacttcgacg caacggcgac gctggtctgc ctgccgtacg cgggtggcaa    17400
cgcggtcaac ttccagcaac tggcaaaggc actgcaggac aagggcatcg cggtgtacgc    17460
ggtcgagctg cccggacacg acctggtcgg cgggcaggac gcgccgttgc aggaggtcgc    17520
ggaagtggcc aaggcggtgc acgaagagat caccggcatc accggaccga tcctgttgtg    17580
gggacactgc gccggagccg cgttcgccgt ggagatcgcg cgtctgatgg aggccgatgg    17640
acggccgccg ctgcggatct tcgtcggtgc gctgatgctc gacgccgtac cggacctgga    17700
cgccgagagc gccagggtgt ccgcgatgag caacacggag atcaccgcgt tgctccggca    17760
ggacagcgcg ttcgtcgagc tggacacgct caaaccggaa cggatggacg tggtgggttc    17820
ggcctaccgg cacgatgtct gctccaccaa ccagtacctg gccgacatcc agcaggacgg    17880
ggtcaaactc gccacgcctc tggaggtcgt ggtcgccgcg gacgaccgca cgaccgtggg    17940
acaccagacc cggcattcgc ggtggggcag catcgccgat cacgttgagc tgcgtgagct    18000
```

```
cggtgaaggc gggcactact tcgtccgcac gcgggccgat gaagtcgcgc gactggtcgc  18060
tgacgcatgt cgctgacagt ccagccgctc tatcgcggcg ccaccgggtt gagcaccgcg  18120
ttcggcacct tcggcgaact gctgcagggc aggctggacg aggccgacgg ggacttcctc  18180
gtcacgttgc cgatcgcgcg ctggacagtg gccacgttcc tggccgaccc ggccatgtcg  18240
tcgatcgagg tccggccacg gcacaagaag aagtcgttgc ggctggccga gatgctgatg  18300
cgaaccatgc cggagccggt cggcggcgtg ctcacgctgg acagcggcct ggccgagggc  18360
aagggcatgg ccagttcgtc ggccgatctg gtcgccaccg cacgcgcgat cggcaacgcg  18420
ttggacgtcg agctgacgcc gaagttcatc gagagcctgc tctgccagat cgaaccgaca  18480
gacggtgtgt tgtatcccgg gattgtcgcc taccaccacc gcagcgtccg gctgcgacgg  18540
gtgctcgggt cgctgccgtc gatgactgtg gtcgggctgg acgagggcgg cgccgtggac  18600
actgtggcgt tcaaccgcat tcccaaaccg ttcggctcgg ccgagaaacg cgagtacgcc  18660
aggctgctcg acagactttc cctcgctgtc gctcagcgcg acctggcatc cgttggtgcc  18720
gtggcaactc gcagtgccga gctcaatcag gcgttgcgtc cgaagaggac tttggacgcg  18780
gtgatcagga tctgtgccga catcgacgca ctcggcgtcg tggtcggaca cagcgggacc  18840
gtcctcggcg tgctcatcga ccgttcggac cctgcgtatc cggacaaagt ggccgccgcc  18900
gcgaaggcgt gcgcggcact gaccggcaac gtgaccatgt attcgacctt gagcttcgac  18960
tgaacatcgt gggaggacta gtgaacgcat tgcgcgactg gcggccgcgg gaggtccgcc  19020
cggccgacgt cggagccgag gcgacgaccg acgggctgat caggtatctg aagggcgatg  19080
ccgagttcga caagctgctg acggagtcga aggcggtggt gttccgcgac ttcaacgtca  19140
ccgaggaaac catcgaatcg gtgatggaac tgctgttgcc gaagcggctg cgtacgtgc   19200
acggcaactc gccgcggacc aaggtcggca agaacatcta cacgtcgacg gagtatccgc  19260
ccgagttcac catctcgatg cacaacgagc tgtcgtacgc ccacgcatgg ccggaccggc  19320
tgttgttctt ctgcgccaag gcgcctttga caggcggagc cacgccgatc gtggacggcc  19380
agctgtggct ggagtccctg gatcccgagg ttcgccaggc gttcgcaggc ggagtgcggt  19440
acacgcagaa cctgcacgac ggccttgggc ttggcaagag ctggcaggac acgttcgaga  19500
ccgccgaccg ggctgaggtc gaggcgttcc tggccggtgc ggcagccgag tgggagtgga  19560
agaaggacgg gacgttgcgg atccgccagg tcaggccgtc cacgatccag cacccggaga  19620
cgggtgccga ggtgtggttc aaccagtccg accagtggca cccggccgcc ttgggcgacg  19680
agacggccgc tgagctggcg cagatcctgc ctgaggacga gctgccgcag tcggtgacgt  19740
tcgccgatgg gacgccgatc ccgggggagt gggttgtcca ggtgcgcgac cgtggcctgg  19800
agaacgccgt ggatgtcgac tggcatctgg gtgacctgat gatcatcgac aaccttcagg  19860
tcgcgcacgg ccgccgcccg ttcaccggtc cgcggcgaat cctggtggcc atgtcctgac  19920
cgaactcaaa ggcggcggtg cacaacgaag tgcaccgccg cctttggcta tccgcgacta  19980
cttgtgggtg atcggcttgc gcaggccccg ggccgccgcg aaggcggcga ccgcaccaag  20040
aacggtcgaa ctgagcagag cgaagagcac ggcactgacg tgcgggtcgg ccaggacaag  20100
gctgcgggcg gcatcaatcg cgtatgtcaa cgggttcacg gtggccacga tctgaagcca  20160
cgtcggcagc aaagccaccg gcacgaaggc actcgaagcg aacatcaacg ggaacatcac  20220
cagcaacccg atcgactgca tcacgtcggg gctgcgcagc caggccgcca cgccagaaa   20280
gatccagatc atcgagtgga tcacgaacaa cgccaccagc atcgcggcta tcgacccgac  20340
cacaccaccg gcgggtgagt aggagagcaa ggcgaaagca cacacctgaa gcaccaccaa  20400
```

```
ctgcgcagca ctccgcacca ggtcggtcaa agcccgagcc gtgagcacca aaggcaggtg   20460
cacaggcatg gaccggaacc gcacgagcat cccgttgccg agctcacgga caagagccat   20520
gcccgcggtc tgggccgcgc caatgccgtt gttgagcatc aaggccggga cgaggtactc   20580
gatgtacgtc accccctgccg ggaagtccgc cggattcgcc atgctgccga agacttcgct   20640
cagcacgaac aacaggaaca gggggttgat caggccgaag accgcgaccc ggcgatcggc   20700
gaccagggcg cgcagtgccc ggacggtcag tgcgcgtagt tgggcgaaag gtccggcgcc   20760
gagccagcgt gggccggtca gtgcgtgtgt catggtgatt cccgtcgta agtgcgccgc   20820 acgtaggaca gtgcggtcag cagtccgtct gacgtcaggc ggtttcggcg gtccagctcg   20880
gcgacgtctc cgatgggcag cgagccgatc cgggaccaca ccagccggcc gtcggaggag   20940
atgtggcagc gcgtccggcc ggcgttgtcg gggtgcaggc agtacgggat gtccaggtag   21000
ccgagcgaga aagcgcgtac cagggccttg ccgatgtctg gatccagcga cagcacagcg   21060
tccactagtg cccgagcctc ggcatgcaca ccggtgtccg cgaccggggg aggcgggcct   21120
gcggcacgag ccgcggccgc ggcgctttcc aaggcgagga tgttgtgtgt cacggtcgga   21180
atgcgatacg cctcagcggc cgtcttcacg atcagccgcc ctgcgccgga ccagaccgcg   21240
agcgaagccg catcgtgttg cagggcgagg gcgccgcgtt cggtctccgg ataaaggccc   21300
atgtacgtgt agatcacgat gtgccagtcg acggaggaca gctgctgagc ggcgatccgg   21360
cgcagcgcca gtacggcctc gaggtcctgt tccggattgg tctgctgggc gtagctcagt   21420
gagacgctgc gcaggccgtg ctgtgcgaag aacatcgctt ccaggacact gatcgcgacg   21480
agcatgctcg gcgggcacaa ctgaccgatc atgcagccgc cgaacgtttc cagatgcgcg   21540
ggaatgtccg cggtggtcaa gatcgcacag ctctcttccc agtgccgcaa ggactcacgc   21600
aacggcgtcc gactgtatgg cagacaatag gagacgggcc cgccttcagt ggcgtgcagt   21660
ccagccgcga ccagagtgcg gaagatgtcc tgcggacggg ccgatccgtg ccttacttgc   21720
acaggaaagt cggcggagcc aacggacgag atcatgtccc gggtgaccga cggcccgtgt   21780
gcgacgatgg gaaaaccgtt gagcggcaag ttctctgcca aagcccggcg cgcggcggag   21840
tcgtcacgga cccgggtgta gctgtccaag gtcacggtgc caacggtggt ggcgtcagcc   21900
ttcttggtgg cggtcaagcc gtacagcatg tccctcggct taccgaaacc catgcgcggc   21960
tgcacgacga gttcgccggc gttaccgacg aactcgccga acgacatgcc ggtcaagaag   22020
cggctcgcgt ggcggctgtt ttgtccaagt aggaacggaa tgcgccgatg tcgccggtgt   22080
cgaagacgcc gtcgtagccg gcctcgcgca gttcacgggt gtggctgatg ttgctcaacc   22140
cgtcggtgcc gagcttgccg ccgatcacca ccggcaggtc gtcgaattcg ggtcgggcgc   22200
gcagcgcgcg gatatggtcg agcccgtcgc tgaagccgtg gccgttgacg ctgctgacca   22260
cgacgaggtc gaagttctgc cgggtgcacg tgtccaccag cagtgacggc gtcacgcagc   22320
agccgatgtt ggtcacctcg tgcccgagtt cttcgagcag cagttgcagg tagaccaggt   22380
tccacgtgtg cgagtcggac gcggtgctgg tgaccaggac gcgaagccgc ctgcgatggc   22440
ccggtgggac gaggcaggcg ggcgcggacg agttgtcggc atacattcca gtgatttccc   22500
cagtatttgc cggcatggcc gagatacttg aaaaagctag ccacgcgtca cgcgcggtgt   22560
caagaagtcc gggccgggcc tagggttttc cacagtgtca attccgtttc attgcccgcc   22620
gtgccttccg gcttgtaatt tccattgcgg gagaagcatt tcttgggggg aatcggcgac   22680
actggggagg ctttgacgtg actggcctga cgaacgcggg tacggcgact gccgtgctgc   22740
```

```
tgcgcctcgc cgccgaacgg ccgagcaagc aggccgtgct gctggtggcc gatccggacg   22800
atccggcggc caccaccgcg ttgacctatg ccgaactgga cacgaaggcg cggcggatcg   22860
cgggctggtt gaccgagcga taccagccag gtgagcgtgt tctgctgtta cacccgatgg   22920
gtctcgagtt cgtctcagcc ttcttcggtt gcctctacgc cgggatgatc gccgtccccg   22980
cgccgctgcc tggccggtac cggcacgagc gcaggcgcgt ccaccggatc gccgaggacg   23040
ccggtgtggt cgcggcgttc accgtcgcgg gaagccttgc cactgtgcag gaatgggccg   23100
ccgaggaggg gttggccggc ttgacggttg ccgattcgga aacgctgtgc ggccagtggc   23160
cactggccga gatcaccacg gacaccgtcg cgctgctgca atacacctcg ggtcgaccg    23220 gtgaccccaa gggcgtgatg atctcgcatg ccaatctgct ggcgaatgtg gacagtctgg   23280
ccaggacgtt cggcttcgac gagaacgtcc gcaccggcgg ctggatcccg ctgtaccacg   23340
acatgggcct gatgggacag ctgctgcccg cgctgttcct gggcagcaca tgtgtgctga   23400
tgaacccgat gtcgttcctc aagcggccgg tgaactggct cacaatgatc gaccggtacg   23460
acatcgcctg gtccgcggcg ccgaacttcg cctacgagca ctgctgccgc cggatcgacg   23520
actccgctgt ggacagtctc gacctgagcc ggtggcgcta cgccgcgaac gggtcggagc   23580
cggtccgtgc ggcgacgctg acagcgttcg cgaagaagtt cgccggggcc ggattccgtg   23640
aggacgccat cgccccttgc ttcggaatgg ctgaggcgac cgtgttcgtg tcgggtggcg   23700
gcgttcgccc agcaccggtg cgcaaaatcg acgcggaatc cctcgaacag cacgagatcc   23760
ggcctgctca ggagaaccgg cccgcgcgca gcatcgtcag ctgtggcatt ccccgtgaca   23820
tcgatgtgcg ggcggtcgac ccggagaccg gcgagccgat gccggacggc caggtcggcg   23880
agctctggct gcggggacgc agtgtgtccc gtggttactg ggccagaccg gacgtcaccg   23940
aagcgatctt cggcgcgtac acgaccacgg gtgacgggcc gtacctgcgc acgggagacc   24000
taggcgtgct gttggacggc gagttgtacg tgaccggccg gatcaaggag atggtcacca   24060
gcaacggccg gaacctgtac ccgcaggaca tcgagtacga gctggccacg cagcacgagc   24120
ggctcggtgg tcacgtcggc gcggtgttca ccgtgccggt gtccgaaggg gacaacgaga   24180
ccgaggccct tgtcgtcctg cacgagatga agggccgcgc cagcgaggac gaactgaccc   24240
ggctttcggc gcagatgaag cagacggtgg tgcgcgagtt cggcgtgagc gcggacggga   24300
tcgtcctgct ccgccccgga agcgtgcgcc ggaccaccag cggcaagatc cagcgcacgg   24360
ccatgcgtga gctgttcctc gcggaggaac tgtcgccggt cttcgccgac gctggcagcc   24420
aggctgtcct ggctggggcg accaagggcc ggtcggcctg atgcaggccg tcgacaggct   24480
ggaccgcgca ctcgaccatc cggcgttcgc cccggagcaa ctggccgagt gggaccgtgc   24540
ggaggccttt cccgcagagg cgtgccaggt ccttgacgac ttcggcctgc ccgcgtacta   24600
cgtcccggcg gcacacggcg gcacactgac cgacttcaac gagttggttc agctgttgcg   24660
cacggtcgcc cgccgggatc tcacggtcgc tgtggcgcac ggcaagacgt cctcggtgc    24720 ggcctcggtg tgggtttccg gaacacccga gcaggcgaca agggtgagcg agcgtgtccg   24780
ggccggtgac gtctacagct gggccctgac cgagcgggat cacggcagcg acctgcttgc   24840
cggcgaggtc gcgccacca agaacggtgg ctggcggctg tccggcgaga gtggttgat    24900 caacaatgcc accgggggac acgcggtgtg cgctcttgtt cgcacggatc cggcaggcgg   24960
tgcccgtgga cacagcctgt tcctcctgga caagacggaa ctgacggact accgccacct   25020
gccgaaggtg cccacgcacg gcatccgggg cgcggacatc agcggcatcg ccttcgacaa   25080
cgccctggta ccggatgacg cggtggtggg tgctgtcggc agtggtatcg agacggtgct   25140
```

```
caaggccctg caactcacca ggaccatgtg cgtggcgctc tcactgggcg ccggtgatca   25200
cgcgctgagc ctggcgcggc gattcgtgtc ggaccgtgcg ctctacgacc gcaagctggt   25260
cgatctaccg caggtgcgcc ggattctcga cgaggcggaa gttcaactca agctggctga   25320
ggcggtgagt gtgatcgccg ccggaggggt gcgtgaattc accgcggaga tgagcgtgat   25380
ctcggctgtc gccaaggctt tcgtaccggg cgtcgtgcag cgggtgatca accggctggc   25440
ggagctgatg ggcctgcgcg ggttcctggc cgacgagttc gccaagctcg accgtgacca   25500
ccggatcgtc ggcatcttcg acggcagcac ggcggtcaac cggcactcgt tgatcacaca   25560
gttccctcgg ctggcccgtg cctatcaggc aggcaaggtc tcgcagccca ccggtgagtt   25620
cgacccggcg aacctgcggt tgtcctcccc gaccgggtgc agcgtgctga acgtcgtcaa   25680
ccggggcacc gatttcggag cggccgtcga gcaggtgcac gaagaaatgg ccgcctacac   25740
accgtcggcc cgtggagtcc cggcatcggc gttcgcgttg gccgagcggt acgagctgtg   25800
cttcgccggc gcggcggcct tgcacctgtg gcaggacagc gacccggacg ccgtgcgtgt   25860
gtgcctcagc catgtcttgg agtgcttacg atgacgacac tacggctggg agatccctac   25920
gacacggcca acccggtggg tttccaggct gtgctcgacg ccgacgagcg cggcgagatg   25980
ctggccgcgg gcgagcggat cctggacgac tacaacctga acgcggagtt cgtcccggcc   26040
cagtacggcg gtcggctggt cgcactcgaa aacgtggtca gcgtgatgcg cgaggtctac   26100
cggcgtgacc cgtgccttgg tctcggctac ggcgccagct cgctgatcgc gcggtcaac    26160 gtctggcaag gcgcgaccga accgcaacgc aaggaagtcg cggacttcct gttgtccggc   26220
aagaagctcg cgtgcgcgta ccacgagctg gcgcacggca acgacatcgg ccgcgccgag   26280
ttcgaggcgt tgccgaaggg cgagaacctc gtgctcaacg gccgcaagga agtcatcgcc   26340
aacatccagc gggccgacgc gatggtggcg ttcgcccgga ccggcgaggc cggggggaac   26400
cgcagccaca gccagatcct cgtcacgccg gacgaactgc cccaggaccg gttgcgctac   26460
ctgccgaggt actcgacgac agggatgcgc ggtgttcagc tcggcggcat cgagttcacc   26520
gactgcccag tgcccgcttc ggccgtgctg ggcgagccgg gccgtggcct ggaggtggcg   26580
ctgacctcgt tccaggtcac caggatcggg ctgcccgcga tgatgaccgg catcctggac   26640
accgggttgg cagtgaccgt gcggcatctg ctcagccgca ggctctacgg ctcggcggcg   26700
acggatcttc cctacatcaa gcggtactg gccggtgtgt cgccgacct gatggcgtgc     26760 gaggccctca gcctcgtcac agggcgggga ctgtcactgc tgcccaagca agcgactgtg   26820
cacgcggccg cgacgaagta cgcggtctcg cgcttgctga tcgacgcgat gaacgagctc   26880
tccaccgcac tgggatcgcg gttctacgtc cgcgaaggcg aacacgcgat cttccagaag   26940
ctcctgcggg acatccagcc gatcggtttc ggacatgcgg ctcgcgcggt ctgccagatg   27000
accatgctgc cgcagctgcc gttgctggcg aagcgatcct ggcagaagga ccacgacgtc   27060
ccggccgaac tgttccggtt ggacgccgag gtcgggccga tcgcgttcga ccagttgcgc   27120
atctccgcag gcggccagga ccacctgatg ccggtggaac tgccggatcc cttccgtgcg   27180
gaactgaaaa cgctcacgaa gctgtgcgcg tctttgcccg ccaaggagtt ggtggccacc   27240
gctggcccgg cttcgtacga cctgacaacc cgatacgcca cgaccctgat ggccagttgc   27300
tgcgtgcagg tctggcagca caaccaggac gtggagttcg tcggtgaccc caggtgggcc   27360
gatgccgtgc tgcaccggct ggcgaatccc ggcgggtacc tgccggacga cctggtgtcg   27420
ttcctgttcg ccgaactgct caaccgccac gaggacggcc gtgacttcgg cctgcgcacc   27480
```

-continued

| | | | | |
|---|---|---|---|---|
| cactgaaaga | ggaatcatgc | cggagacgag | cacggaaacg | atcgatgtga cagcactgcg | 27540 |
| gaactggctg | ccggacgga | tcgccgagtt | caccgagcgg | ccgctcgccg agatcgccgg | 27600 |
| agacaaaccg | cttggcgagt | acggcgtgga | ctcggtgtcc | gcgttgaccg tctgcgccga | 27660 |
| gatcgaggac | cacttcgaca | tcaccgtcga | gccgacactg | ctgtgggacc accccacgat | 27720 |
| cgacgccatc | gccgaggtcc | tggtcgaaga | agtcaacgcc | cgataaccac tacacgcgaa | 27780 |
| ggtcggggaa | acgtgtctgg | ggatgtccgt | cgtgctgtca | ccgccgcgca ggcagggatc | 27840 |
| tggttcgccc | agcagttgaa | gccgggcaat | ccgctctaca | actccggcgc ctacttcgag | 27900 |
| atcgacggtc | cgctggacgt | cgcggcgatg | cgtgccgcgg | tgcgccgggc ggtcaccgag | 27960 |
| accgaggcgc | tgcgggtgcg | gttcgaggag | tcgcccgagg | gcctgcacca ggtcctgcag | 28020 |
| gacttcgacg | cgccgttgac | ggacatcgat | ctgtccgatg | cgcctgatcc gcacacggcg | 28080 |
| gcactcgact | ggatccggca | ggatctggcg | actcccgcgg | acctcacgcg cgtccccgcc | 28140 |
| ttcgagcatg | cgttgctccg | cctcggcccg | caacggttct | acttccacct gcggtatcac | 28200 |
| cacatcctga | tggacgggta | cgcccacgcg | ttgtactgca | ggcggatcgc ggagatatac | 28260 |
| acagcgctgg | catcgggccg | gccgcccaag | ccgtgcgagt | tcggcactct gcaacagctt | 28320 |
| ctggacgacg | acaccgagta | ccgggcttcc | cggcggcggg | aacgggacga gaagtactgg | 28380 |
| ctggaaacgt | tcgtcgaggt | tcccgagctc | gccagcctgg | ccgggcgttc ggtgcctgcc | 28440 |
| gcgccgagca | ccctgcgccg | cgaggtcgag | ttaccccggc | ggacttccga gctgctcgcc | 28500 |
| aaggcggccg | ccgagcttgg | tgtgccctgg | tcggtggtcg | cgatcgccac cgtcgcgacg | 28560 |
| tacacgtccc | gcctgaccgg | actgtccgat | gtggtcctgg | gtctcccgtt gaccgcgcgg | 28620 |
| atgagcaagg | tcgccctgcg | cacgccgggc | atggtcgcca | acgacctgcc gctgcgggtg | 28680 |
| acggtccggc | cgtccgtctc | cttccgtgac | ctggtccgtc | agctctccca gcaggtgtcc | 28740 |
| cgcgcggtca | acaccagcg | gtaccgcggt | gaggacctca | acagcgcgct tggtgtctcc | 28800 |
| ggcggtgaac | tcaccggcac | actggtcaac | gtcttctcct | tcgagcagga tgtccggttc | 28860 |
| ggtgacctgc | ccacgacccc | gcaccagctg | tccaccggcg | cggtcaagga cctgatcgtc | 28920 |
| aacttctacg | ccacctcggg | ctcgatccgg | atcgagttcg | acggcaaccc cgagctctac | 28980 |
| ggcgaagaag | acctcgcggc | ccaccaagac | cggctcgtgc | gcttgctcga agaccttctg | 29040 |
| gccggcgtgg | acactgctgt | cgcagcggcg | gacctgatcg | agcccgatgt ccgggatctg | 29100 |
| gtggtacggc | agtggaacaa | caccgcgcgt | gacgtgcccg | tggccacttt cgcgtcgctg | 29160 |
| ttcgccgccc | aggtggtcag | gacacccgag | gcggtcgcga | cgagctaccg cgacgactcg | 29220 |
| gtgacgtacg | ccgaactgga | tgcgcggtcg | aatcgggtgg | cgcgatggct gatgcagctc | 29280 |
| ggtgccggtc | cggagcggtt | cgtcgccatc | gcgttgaacc | ggtcgatcga cctggtggtc | 29340 |
| gcgttggtcg | cggtgctcaa | aaccggtgcg | gcgtacgtgc | cgatcgaccc ggactacccg | 29400 |
| gctgagcgca | tcgggttcat | cctcggcgac | agtgatccgc | tcctggtgct gaccgaacgc | 29460 |
| ggcatcgccg | aatcgctgcc | cgaaacccgc | gcgcccttg | tgttcctcga cgaagccgcc | 29520 |
| gcttcggcag | acccgattcc | gggccgggtg | ctgccgaaag | cacccgcgta cgtgatcttc | 29580 |
| acctcgggct | cgaccggccg | gcccaagggt | gtggtggtcg | aacaccgcgc gatgggtgcc | 29640 |
| tatctggcac | gggctcgtga | ggcctatccg | tggatggctg | gatcgacgtg ggtgcattcg | 29700 |
| ccgatcgcgt | tcgacctgac | cgtgaccggg | ttgttctcgc | cgctggtatc cggcggctgc | 29760 |
| gcgcgtctgg | tgaacctgga | ggacgaactc | cctgagcagc | agccgacttt tgtcaagggc | 29820 |
| acgccctcgc | atctcggttt | gctggacgtg | ttgcccggca | gtgcgtcacc gtccggcgcg | 29880 |

```
ttgatgctgg gtggcgagtt gctggtcggc gaggtcctgc agaactgccg ggatcgcaac   29940
ccgggcgcag tggtctacaa cgtttacggc gccacggaag caaccgtcaa ctcggtggag   30000
aaccggatcg agccgggcgc cgaactgcct gtgggcgcgg tgccggtggg cactccgttc   30060
cgcaacaccc ggatctacgt gctcgactcc ggcctgcagc cggtgccgcc gggcgtggcc   30120
ggtgaggcgt acatcgcgag caccgggctg ccaggggat atctcaaccg gccgggctg    30180 acctcggaga ggttcgtggc ctgcccgttc ggcgcgccgg gggagcggat gtaccgcacc   30240
ggcgacctgc tgcgctggaa caccgacggt gagctggagt cgtcagccg gtcgactcc    30300 caggtcaaga tccgcggctt ccggatcgag ctcggcgaga tcgaggcagt gctgtccgcc   30360
gcggacgccg tcacccaggt ctcggtcctg gtgcgggagg accagccggg ggacaagcgc   30420
ttggtcgcct acgtggtcgg ctcgatcgac ggcctgcggg agcacgcggc cgcgatgctg   30480
cctgagtaca tggtgccgtc ggcgttcgtg caactcgacg agctgccgtt gacgcccaac   30540
ggaaagctgg accgccgagc cctgcctgtc cctgattatg ccgggggtc aggacgcgcc    30600 gcccgtacac cacgcgagga aatcctgtgc ggactgttcg cggaagtgct ttcgctgccc   30660
cacgtgggca ttggcgacaa cttcttcgtc ctcggcggac actccttgtt gacgttgcag   30720
ctcgtcggcc gagtgcggac agtgctgggc gccgagctgt cggtccgcca ggtcttcgag   30780
gcgccgaccg ttgccgagct tgacaaggcg ttgagtgttt cagacgtcgc gcgtccggcc   30840
gtggtgccgg ttcgcccgcg tccggaccgg ctgccgctgt cgttcgcgca gcagcggttg   30900
tggttcctgg acaagctgga ggacggcgcc gcgacgtaca acacaccggt cgcactccgc   30960
ctgtccggcg accttgacgt gactgccctg cgtcaggcga tcgaagacgt ggtgatgcgc   31020
cacgaaagtc tgcgcacgat cttcgcggag gacgaccagg gcgcgtacca ggtcatcctg   31080
gacgccgtcg acatcgagct gcctgtggca gaggtgaccg aggatgcggt cgccgccgaa   31140
ctcgccaggg aagcgtcgac atcgttcgac ctgaccaccg acctgccggt gcgggcacgg   31200
ctcctgcgcg tcgccgacga gcacgtgctg ttgctggtgg tccaccacat cgctggggac   31260
ggcagctcgg tcgtgcccct tcgccaggac ctcgcggcgg cttacgcggc ccgcagcgcg   31320
aaccgggaac cgggctggcc tgagcttgcg gtgcagtaca gcgactacgc gttctggcag   31380
cgtgacctgc tggactccga ggtggtccgc cggcagctgg actactggcg gaaggcgctc   31440
gccggcctgc cggccgagct tgatctcccg gcggatcggg agcgcccggc gcaagccacg   31500
taccgcggcg agaccgtgct gttcgacgtg ccagccgagc tgcacacgcg cctggccgcc   31560
gtggcgagcg agcacaacgc gagcttgttc atggtcatgc aggccgcgct ggcgaccctc   31620
ctgcacaggc tgggtgccgg tgacgacatt ccgctgggaa gcccggtcgc aggccggtcc   31680
gacgacgcgt tgaccgacct tgtcgggttc ttcgtgaaca cgttggtgct gcgcaacgac   31740
ctcagcggcg acccggtgtt cgccgagctg atcgcgcggg tccgggacgc cgacctggcc   31800
gcgtacgagc accaggacct gccgttcgag cgcttggtcg aggtgctcag cccggagcgg   31860
tcgctgtccc ggcatccgct gttccagatc gccctgacgt tcaacaacaa cgaccactgg   31920
gccgaactgc acgagctcgg cgcgggtggg ctgcgggtgc ggcgggagca cttcgacctg   31980
ggcatcgccc agttcgacct gtccttctcc ttcgccgaga cgccggacgg tatcgccggc   32040
cgccttgagt tcgcgctgga catgttcgac cgcggcaccg cggagaagct cgtcgaacgc   32100
ctgatgctcg tgctgcacag tgtcgcggcg accagaacc gcccggtcag cgagatcgac    32160
gtgctgctgc ccggtgagca ggagatccca cgcccggtcc ggcgaagcct ggcggtcgag   32220
```

```
aaggcaccga ctgtgtcgcg ggaaccgcgg acaccgcatg aagagatcct ctgtggcctg    32280
tacgcggaga tgctggacct caagaaggtc ggcatcgacg acagtttctt cgatctgggc    32340
ggacactcgc tggcggcggt ccggctgctc agccgcgtcc gcacggtgct gggcgtggag    32400
ctgccgatcc gcaagctgtt cgacaccccg accgtggcag ggctcgcgga ggcgctgacc    32460
ggcggcgcga cccgggtgaa ggtcacggcc gaccggccga ggcctgagcg catcccactg    32520
tcgttcgccc agcagcggct ctggttcctc gaccacctcg aaggcccccag tgccacgtac    32580 aacgtcgcga tgggactgcg gctgtccggc gtgctggaca tgaccgcgct ggaagccgcg    32640
ctgaacgatg tcgtggaacg gcacgacagc ttgcggaccg tcttcgcgga ggacgacgaa    32700
ggcgcctacc aggttgtgct cgacggtatc gtgctcacgc tggacactgc ggccaccgac    32760
gaggagaggt tgcccggcca gctgatcgac gcggctcagc ggccgttcga cctgactgcc    32820
gacattccgc tgcgagccaa gctgttccgg ctcgacgacc aggaacacgt gctgttgctg    32880
gtcgtacacc acatcgcgtg cgacggttgg tcgaccggcg ccttggccgg tgacctcgcg    32940
tccgcgtacg ccgctcgacg cacgcgacc acgccggact gggccgagct gccggtgcag    33000
tacaccgact atacgctctg gcagcgggag ctcctcggct ccgaagacga cccgcagtcc    33060
gagatcgcgg cacagctcgg ttactggcgc tccacactgg acggcgcgcc ggagcggctc    33120
gagctgccca ccgaccgggc acgtccggca gtgccgacgc atcgcggcgc ccagctggac    33180
ttcgagatcc cggcagcgct gcacgcccag ttgatcgaca tcgcccgaag cggtcacgcc    33240
acgttgttca tggtgttgca ggccggtctg gccgcggccc tcagccggct tggcgcgggt    33300
accgacatcc cgatcggcac tccggtagcc ggccgggccg acgaaggact cgacgacctc    33360
gtcgggttct tcgtcaacac cttggtgctg cgcaacgacc tcaccggcga ccccggattc    33420
gacgagctgc tcgctcgggt ccgggagacc aacctcggcg cgtacgccaa ccaggacgtg    33480
ccgttcgagc gcttggtcga ggtactggcg ccggaacgat cgctggcgca ccacccgctg    33540
ttccaggtga tgctcggctt caaccacacc gacaaccagt cggccctcgg caagctggac    33600
ggtctgccgg ggctggtcac ccgccgggag ccggtcgacg cgggtgtggc caagttcgac    33660
ctgtcgttct tcttcgacga gaaccacgat tccgacggtg aaccggccgg tctgaccggc    33720
ggcctgcagt acagcaccga tctgttcgac ccggccaccg cagcggccat tgtggacctg    33780
ctcgtccgga ttctcggaca gcggccgga aatccggcta cccggttgtc caggttcgag    33840
gtgctcaatg ccgatgagct tgagaccatc gccgcctggt ccgatgtaga cgcttctggc    33900
gccgtgccgg aacggttcgc cgcccaggtc gtcaagacgc cgcaagcgct tgccgtgcgt    33960
gcgccgggcg tcgaactgtc ctatgcggag cttgactcct ggtccgccgc gatcgctcgg    34020
caactcgtcg atgcgggtgt acggaccgag acaccggtgc tgatgctgat gcgccgcacg    34080
gcccagcgcg tggtcgccac cctggctgtg ttgcgcgcgg gcggtgctta cgttcccgtg    34140
cacgattcgg atccgctcga acgaatccgc acgatcgtgg ccgagaccgg cgcgcctgtg    34200
gtgatcaccg accaaccgga ccgtgcggtc ggacttggca tcgaacaggt cgtggtcacg    34260
gacccgatcg ctggtgaggc accgcgaagc gatgtcctgc ccggcaacct cgcgtacatc    34320
atgtacacgt cgggctcgac cgggacgccg aagggagtcg cggtcaccca tcgggacgtg    34380
atcgcactga ccgctcaccg gcacttccac aacggcgcgc acgaacgagt cctgctccac    34440
tcaccgcatg ccttcgacgc ggcgacgtac gagctctggg tccgctgct gaacggcggt    34500 cagctgatcg tcgcgccgcc cgacgagctc gacatcggga cgctgcggca cgtcatcacg    34560
gagaacgacg tcacggcctt gtggctgacg gctggattgt tccggcttgt cgccgaggaa    34620
```

```
gcacccgagt gcttcgcccg ggtccgtgag gtctggaccg gcggtgacgt tgttccacca   34680
gccgccgtgc gcagggtcat ggagcgctgc ccaggcatca cagtggtcga cgggtatggc   34740
ccgaccgaga cgacaacgtt cgccacgtgc cacccggtgc gtgacgagat cgccgacact   34800
gtcccgattg gacgaccgct cgacggcatg cgagcccacg tgctcgacgc ccagttgcgt   34860
ccggtcccac cgcgtgttcc aggtgagctg tacatcgccg gagcgggtct ggcgcgcggg   34920
tacttcggcg atccggcacg gactgcgaaa cggttcgtcg cgggcccggc gggtgagcgg   34980
ctgtaccgga ccggtgacct ggtccgccgg cggccggatg gcgcgctcga gtacgtcggc   35040
cgggtcgacg accaggttaa actgcgcggc ttccggatcg agcccgcgga ggtcgagtcc   35100
gtgctggcgg cccacgtggc cgacgtggcc gtgctcgtcc gcgaggaccc ggacgggcgc   35160
aagcgtttgg tcgcctacgt cgtgccgaat ggtgcgatcg atcacgagca gttgcgcgcg   35220
gaggtcgccg atcggctgcc ggactacatg gtcccgtccg cgttcgtcga gcttgagcgg   35280
cttcccgtga cagcgaacgg aaagctggac cgggcggcgt tgccgagcc ggccttcgct   35340 gcggggacgg gcaggccggc gtcgaacgcg gcagaagagg tgctgtgcgg cctggtcgcc   35400
gagctgcttg gcattgggac gcccggcgtg gacgacgggt tcttcgacct gggcggcgac   35460
agcatcgtgg cgatccagct ggtcagccgc gctcgccggg ccgggctgga gttcgcggtg   35520
cgcgatgtgt tccagcaccg gaccatcgcc gcgctcgccg cgatcgcgac caaggccgcc   35580
ccacgcgagg tcgatccgcg cgcaggtatc ggcacggtgc cgccgactcc gatcgtgcgc   35640
tggctggccg accgcggggg accgatcgac gggttcaacc agtcgaagat cctgcgcgtt   35700
ccggctgacc ttgactggga cacgctcacc gcgggcgtgc agaccttgct cgacacgcac   35760
cactcgttgc ggatgtccct ttcggacgac tggtcgttca ccgtgcccga gccgggcgcg   35820
gtccgcgctg aggaccggat gcgccgggta cccgcgagg cgttcgagtc cgagatcgcc   35880
gcggcccggg agcggctcgc acccggggac gggcggatga tcgacgtcgt cctcggcgag   35940
ccgggcaggc tgctggtgat ggtccaccac ctggccatcg acggggtgtc ctggcgaatc   36000
ctgatcgagg acctcacgca ggcatgccag gggcggcagc cgatccggcc ggtcacatca   36060
ctgcgggaat ggtcgaacgg cctggtcgaa gccgcccgca cccgagcg tgtcgccgaa   36120 ctggaccgct ggaaggccgt cctcgcatcc gcccggccgt ccggaacaga cgtcgaaaag   36180
gacacctacg ccacagcagg gcacctcacc cgcacgcttc cggtggacgt gaccgaagtc   36240
gtgctgaccc ggctgccgc tgccttccaa gccgagatca cgacgtgct gctggccgcg   36300 ttcgcgttgg ccgcgccccg gcctgtgctc ctcgacctgg aaggacatgg ccgggaggag   36360
cacgtggtcg aaggtgccga cctcgccagg acgctcggct ggttcaccag cgtctatccg   36420
gtgagcctcg acgcgggtga tctggacacc gccgacgcca tggccggggg ccggccgcg   36480 ggaaagctga tcaagcgcgt caaggaacag ctgcgcgaga tcccggacaa gggcatcgga   36540
ttcgggctgt tgcggtacct caacgagacc acgggcgcgg aactcgccgg accgggcaag   36600
ccgacgtacg gcttcaacta cctcggccgc ttcacggaac ccgaggacac cgactgggtc   36660
gcggtgggca gcgcgcgga actcggcggc atcgacccgc ggaccccgtt ggcccaccag   36720
gtcgagctga ccgtgcagac ccgtgacacc gcggcgggcc cgcagctcac cgcgacgtgg   36780
gtgtgggcgg ccaggctggt gtccgaacag gacgtccagg acatcgccgg gaagtggttc   36840
caggcattgg aagcgttcgc gcggcatgtg cgcgacccgg aggcgggcgg gctgaccccg   36900
tcggacgtgt tgctcggatc ggtgacacag gacgagatcg acgagttcga agagatgctg   36960
```

| | |
|---|---:|
| accagcgaag cggaggagtt ggcgtgagcc ggaagaccag ggcgatcgag gacatcctgc | 37020 |
| cgctgtcgcc gctccagcag ggcctgctgt tccacagcgt ctacgacgag cagtcaccgg | 37080 |
| acgtctacac cgtgcaggtc gacttcgagc tggacggcga actggacctg gacgtgctgc | 37140 |
| gcaccgcggc ggagacgttg ttgcgcaggc acagcgtgct gcgtgccggg ttccgccagc | 37200 |
| gcaagtccgg cgactgggcg cagctcatca tgcgggaggt gccgctgtcg tggcgtgtgg | 37260 |
| tcgagtcgcc cgagcggatc gaggacgaac tcgcggccga ccgtggcag cggttcgacc | 37320 |
| tggcgaagcc gccactgttg cggttcaccg tgctcaagct ggccgacgac caccaccatt | 37380 |
| tcgtggtgac gagtcatcac ctgttgctgg atggctggtc cttgccggtg ctggtccgcg | 37440 |
| aattgctgcg gctgtacgcc gagaagggcg atgaccggtc gctgccgagc gtccggccgt | 37500 |
| accgggacta cttgagctgg ttgtccgaac aggaccggcc tgctgccgaa gaagcctggc | 37560 |
| gcaccgcttt gtccgggctg gacaagccga ctctcgtcgc tgccgatgcc gtggcggcaa | 37620 |
| ctccggttga tccgcatcgg atcgagcatg agctgtccga tgagacgcac gcggccttgg | 37680 |
| tcgcgctggc caggtccagt ggcgccacat tgaaacggt ggtccagtcc gcgtgggcga | 37740 |
| tcgtgctcgg ccggatcgcc ggcaccgacg acgtggtctt cggcaacgtg gtgtcgggca | 37800 |
| ggccgcccga gctggccggg atcgagtcga tggtcggcat gttcatcaac acgttgccgg | 37860 |
| tgcgcgtgcg gctgcgtccg gccgagacgt tcaccgcgtt gctggctcgg gtgcagcagg | 37920 |
| aacagtcgga tctgcttgcc caccagcaca tcgggctggc cgacatccaa cgtgccgccg | 37980 |
| ggctgccgac cctgttcga | 37999 |

<210> SEQ ID NO 2
<211> LENGTH: 44615
<212> TYPE: DNA
<213> ORGANISM: Artificial Sequence
<220> FEATURE:
<223> OTHER INFORMATION: DFD0097-735

<400> SEQUENCE: 2

| | |
|---|---:|
| gccgagatcg aggaccactt cgacatcacc gtcgagccga cactgctgtg ggaccacccc | 60 |
| acgatcgacg ccatcgccga ggtcctggtc gaagaagtca acgcccgata accactacac | 120 |
| gcgaaggtcg gggaaacgtg tctggggatg tccgtcgtgc tgtcaccgcc gcgcaggcag | 180 |
| ggatctggtt cgcccagcag ttgaagccgg gcaatccgct ctacaactcc ggcgcctact | 240 |
| tcgagatcga cggtccgctg gacgtcgcgg cgatgcgtgc cgcggtgcgc cgggcggtca | 300 |
| ccgagaccga ggcgctgcgg gtgcggttcg aggagtcgcc cgagggcctg caccaggtcc | 360 |
| tgcaggactt cgacgcgccg ttgacggaca tcgatctgtc cgatgcgcct gatccgcaca | 420 |
| cggcggcact cgactggatc cggcaggatc tggcgactcc cgcggacctc acgcgcgtcc | 480 |
| ccgccttcga gcatgcgttg ctccgcctcg gcccgcaacg gttctacttc cacctgcggt | 540 |
| atcaccacat cctgatggac gggtacgccc acgcgttgta ctgcaggcgg atcgcggaga | 600 |
| tatacacagc gctggcatcg ggccggccgc ccaagccgtg cgagttcggc actctgcaac | 660 |
| agcttctgga cgacgacacc gagtaccggg cttcccggcg gcgggaacgg gacgagaagt | 720 |
| actggctgga aacgttcgtc gaggttcccg agctcgccag cctggccggg cgttcggtgc | 780 |
| ctgccgcgcc gagcaccctg cgccgcgagg tcgagttacc ccggcggact tccgagctgc | 840 |
| tcgccaaggc ggccgccgag cttggtgtgc cctggtcggt ggtcgcgatc gccaccgtcg | 900 |
| cgacgtacac gtcccgcctg accggactgt ccgatgtggt cctgggtctc ccgttgaccg | 960 |
| cgcggatgag caaggtcgcc ctgcgcacgc cgggcatggt cgccaacgac ctgccgctgc | 1020 |

```
gggtgacggt ccggccgtcc gtctccttcc gtgacctggt ccgtcagctc tcccagcagg    1080
tgtcccgcgc ggtcaaacac cagcggtacc gcggtgagga cctcaacagc gcgcttggtg    1140
tctccggcgg tgaactcacc ggcacactgg tcaacgtctt ctccttcgag caggatgtcc    1200
ggttcggtga cctgcccacg accccgcacc agctgtccac cggcgcggtc aaggacctga    1260
tcgtcaactt ctacgccacc tcgggctcga tccggatcga gttcgacggc aaccccgagc    1320
tctacggcga agaagacctc gcggcccacc aagaccggct cgtgcgcttg ctcgaagacc    1380
ttctggccgg cgtggacact gctgtcgcag cggcggacct gatcgagccc gatgtccggg    1440
atctggtggt acggcagtgg aacaacaccg cgcgtgacgt gcccgtggcc actttcgcgt    1500
cgctgttcgc cgcccaggtg gtcaggacac ccgaggcggt cgcgacgagc taccgcgacg    1560
actcggtgac gtacgccgaa ctggatgcgc ggtcgaatcg ggtggcgcga tggctgatgc    1620
agctcggtgc cggtccggag cggttcgtcg ccatcgcgtt gaaccggtcg atcgacctgg    1680
tggtcgcgtt ggtcgcggtg ctcaaaaccg gtgcggcgta cgtgccgatc gacccggact    1740
acccggctga gcgcatcggg ttcatcctcg gcgacagtga tccgctcctg gtgctgaccg    1800
aacgcggcat cgccgaatcg ctgcccgaaa cccgcgcgcc ccttgtgttc ctcgacgaag    1860
ccgccgcttc ggcagacccg attccgggcc gggtgctgcc gaaagcaccc gcgtacgtga    1920
tcttcacctc gggctcgacc ggccggccca agggtgtggt ggtcgaacac cgcgcgatgg    1980
gtgcctatct ggcacgggct cgtgaggcct atccgtggat ggctggatcg acgtgggtgc    2040
attcgccgat cgccgttcgac ctgaccgtga ccgggttgtt ctcgccgctg gtatccggcg    2100
gctgcgcgcg tctggtgaac ctggaggacg aactccctga gcagcagccg acttttgtca    2160
agggcacgcc ctcgcatctc ggtttgctgg acgtgttgcc cggcagtgcg tcaccgtccg    2220
gcgcgttgat gctgggtggc gagttgctgg tcggcgaggt cctgcagaac tggcgggatc    2280
gcaacccggg cgcagtggtc tacaacgttt acgcgccac ggaagcaacc gtcaactcgg    2340
tggagaaccg gatcgagccg ggcgccgaac tgcctgtggg cgcggtgccg gtgggcactc    2400
cgttccgcaa cacccggatc tacgtgctcg actccggcct gcagccggtg ccgccgggcg    2460
tggccggtga ggcgtacatc gcgagcaccg ggctggccag gggatatctc aaccgggccg    2520
ggctgacctc ggagaggttc gtggcctgcc cgttcggcgc gccggggag cggatgtacc    2580 gcaccggcga cctgctgcgc tggaacaccg acggtgagct ggagttcgtc agccgggtcg    2640
actcccaggt caagatccgc ggcttccgga tcgagctcgg cgagatcgag gcagtgctgt    2700
ccgccgcgga cgccgtcacc caggtctcgg tcctggtgcg ggaggaccag ccgggggaca    2760
agcgcttggt cgcctacgtg gtcggctcga tcgacggcct gcgggagcac gcggccgcga    2820
tgctgcctga gtacatggtg ccgtcggcgt tcgtgcaact cgacgagctg ccgttgacgc    2880
ccaacggaaa gctggaccgc cgagccctgc ctgtccctga ttatgccggg gggtcaggac    2940
gcgccgcccg tacaccacgc gaggaaatcc tgtgcggact gttcgcggaa gtgctttcgc    3000
tgccccacgt gggcattggc gacaacttct tcgtcctcgg cggacactcc ttgttgacgt    3060
tgcagctcgt cggccgagtg cggacagtgc tgggcgccga gctgtcggtc cgccaggtct    3120
tcgaggcgcc gaccgttgcc gagcttgaca aggcgttgag tgtttcagac gtcgcgcgtc    3180
cggccgtggt gccggttcgc ccgcgtccgg accggctgcc gctgtcgttc gcgcagcagc    3240
ggttgtggtt cctggacaag ctggaggacg cgccgcgac gtacaacaca ccggtcgcac    3300
tccgcctgtc cggcgacctt gacgtgactg ccctgcgtca ggcgatcgaa gacgtggtga    3360
```

-continued

```
tgcgccacga aagtctgcgc acgatcttcg cggaggacga ccagggcgcg taccaggtca    3420
tcctggacgc cgtcgacatc gagctgcctg tggcagaggt gaccgaggat gcggtcgccg    3480
ccgaactcgc cagggaagcg tcgacatcgt tcgacctgac caccgacctg ccggtgcggg    3540
cacggctcct gcgcgtcgcc gacgagcacg tgctgttgct ggtggtccac cacatcgctg    3600
gggacggcag ctcggtcgtg cccttcgcca gggacctcgc ggcggcttac gcggcccgca    3660
gcgcgaaccg ggaaccgggc tggcctgagc ttgcggtgca gtacagcgac tacgcgttct    3720
ggcagcgtga cctgctggac tccgaggtgg tccgccggca gctggactac tggcggaagg    3780
cgctcgccgg cctgccggcc gagcttgatc tcccggcgga tcgggagcgc ccggcgcaag    3840
ccacgtaccg cggcgagacc gtgctgttcg acgtgccagc cgagctgcac acgcgcctgg    3900
ccgccgtggc gagcgagcac aacgcgagct tgttcatggt catgcaggcc gcgctggcga    3960
ccctcctgca caggctgggt gccggtgacg acattccgct gggaagcccg gtcgcaggcc    4020
ggtccgacga cgcgttgacc gaccttgtcg ggttcttcgt gaacacgttg gtgctgcgca    4080
acgacctcag cggcgacccg gtgttcgccg agctgatcgc gcgggtccgg gacgccgacc    4140
tggccgcgta cgagcaccag gacctgccgt tcgagcgctt ggtcgaggtg ctcagcccgg    4200
agcggtcgct gtcccggcat ccgctgttcc agatcgccct gacgttcaac aacaacgacc    4260
actgggccga actgcacgag ctcggcgcgg gtgggctgcg ggtgcggcgg gagcacttcg    4320
acctgggcat cgcccagttc gacctgtcct tctccttcgc cgagacgccg gacggtatcg    4380
ccggccgcct tgagttcgcg ctggacatgt tcgaccgcgg caccgcggag aagctcgtcg    4440
aacgcctgat gctcgtgctg cacagtgtcg cggcggacca gaaccgcccg gtcagcgaga    4500
tcgacgtgct gctgcccggt gagcaggaga tcccacgccc ggtccggcga agcctggcgg    4560
tcgagaaggc accgactgtg tcgcgggaac cgcggacacc gcatgaagag atcctctgtg    4620
gcctgtacgc ggagatgctg gacctcaaga aggtcggcat cgacgacagt ttcttcgatc    4680
tgggcggaca ctcgctggcg gcggtccggc tgctcagccg cgtccgcacg gtgctgggcg    4740
tggagctgcc gatccgcaag ctgttcgaca ccccgaccgt ggcagggctc gcggaggcgc    4800
tgaccggcgg cgcgacccgg gtgaaggtca cggccgaccg gccgaggcct gagcgcatcc    4860
cactgtcgtt cgcccagcag cggctctggt tcctcgacca cctcgaaggc cccagtgcca    4920
cgtacaacgt cgccgatggga ctgcggctgt ccggcgtgct ggacatgacc gcgctggaag    4980
ccgcgctgaa cgatgtcgtg aacggcacg acagcttgcg gaccgtcttc gcggaggacg    5040
acgaaggcgc ctaccaggtt gtgctcgacg gtatcgtgct cacgctggac actgcggcca    5100
ccgacgagga gaggttgccc ggccagctga tcgacgcggc tcagcggccg ttcgacctga    5160
ctgccgacat tccgctgcga gccaagctgt tccggctcga cgaccaggaa cacgtgctgt    5220
tgctggtcgt acaccacatc gcgtgcgacg gttggtcgac cggcgccttg gccggtgacc    5280
tcgcgtccgc gtacgccgct cgacgcacgg cgaccacgcc ggactgggcc gagctgccgg    5340
tgcagtacac cgactatacg ctctggcagc gggagctcct cggctccgaa gacgacccgc    5400
agtccgagat cgcggcacag ctcggttact ggcgctccac actggacggc gcgccggagc    5460
ggctcgagct gcccaccgac cgggcacgtc cggcagtgcc gacgcatcgc ggcgcccagc    5520
tggacttcga gatcccggca gcgctgcacg cccagttgat cgacatcgcc cgaagcggtc    5580
acgccacgtt gttcatggtg ttgcaggccg gtctggccgc ggccctcagc cggcttggcg    5640
cgggtaccga catcccgatc ggcactccgg tagccggccg ggccgacgaa ggactcgacg    5700
acctcgtcgg gttcttcgtc aacaccttgg tgctgcgcaa cgacctcacc ggcgaccccg    5760
```

```
gattcgacga gctgctcgct cgggtccggg agaccaacct cggcgcgtac gccaaccagg    5820
acgtgccgtt cgagcgcttg gtcgaggtac tggcgccgga acgatcgctg gcgcaccacc    5880
cgctgttcca ggtgatgctc ggcttcaacc acaccgacaa ccagtcggcc ctcggcaagc    5940
tggacggtct gccggggctg gtcacccgcc gggagccggt cgacgcgggt gtggccaagt    6000 cgacctgtc gttcttcttc gacgagaacc acgattccga cggtgaaccg gccggtctga     6060
ccggcggcct gcagtacagc accgatctgt tcgacccggc caccgcagcg gccattgtgg    6120
acctgctcgt ccggattctc ggacaagcgg ccggaaatcc ggctacccgg ttgtccaggt    6180
tcgaggtgct caatgccgat gagcttgaga ccatcgccgc ctggtccgat gtagacgctt    6240
ctggcgccgt gccggaacgg ttcgccgccc aggtcgtcaa gacgccgcaa gcgcttgccg    6300
tgcgtgcgcc gggcgtcgaa ctgtcctatg cggagcttga ctcctggtcc gccgcgatcg    6360
ctcggcaact cgtcgatgcg ggtgtacgga ccgagacacc ggtgctgatg ctgatgcgcc    6420
gcacggccca gcgcgtggtc gccaccctgg ctgtgttgcg cgcgggcggt gcttacgttc    6480
ccgtgcacga ttcggatccg ctcgaacgaa tccgcacgat cgtggccgag accggcgcgc    6540
ctgtggtgat caccgaccaa ccggaccgtg cggtcggact tggcatcgaa caggtcgtgg    6600
tcacggaccc gatcgctggt gaggcaccgc gaagcgatgt cctgcccggc aacctcgcgt    6660
acatcatgta cacgtcgggc tcgaccggga cgccgaaggg agtcgcggtc acccatcggg    6720
acgtgatcgc actgaccgct caccggcact tccacaacgg cgcgcacgaa cgagtcctgc    6780
tccactcacc gcatgccttc gacgcggcga cgtacgagct ctgggtcccg ctgctgaacg    6840
gcggtcagct gatcgtcgcg ccgccgacg agctcgacat cgggacgctg cggcacgtca     6900
tcacggagaa cgacgtcacg gccttgtggc tgacggctgg attgttccgg cttgtcgccg    6960
aggaagcacc cgagtgcttc gcccgggtcc gtgaggtctg gaccggcggt gacgttgttc    7020
caccagccgc cgtgcgcagg gtcatggagc gctgcccagg catcacagtg gtcgacgggt    7080
atggcccgac cgagacgaca acgttcgcca cgtgccaccc ggtgcgtgac gagatcgccg    7140
acactgtccc gattggacga ccgctcgacg gcatgcgagc ccacgtgctc gacgcccagt    7200
tgcgtccggt cccaccgcgt gttccaggtg agctgtacat cgccggagcg ggtctggcgc    7260
gcgggtactt cggcgatccg gcacggactg cggaacggtt cgtcgcgggc ccggcgggtg    7320
agcggctgta ccgaccggt gacctggtcc gccggcggcc ggatggcgcg ctcgagtacg     7380
tcggccgggt cgacgaccag gttaaactgc gcggcttccg gatcgagccc gcggaggtcg    7440
agtccgtgct ggcggcccac gtggccgacg tggccgtgct cgtccgcgag gacccggacg    7500
ggcgcaagcg tttggtcgcc tacgtcgtgc cgaatggtgc gatcgatcac gagcagttgc    7560
gcgccgaggt cgccgatcgg ctgccggact acatggtccc gtccgcgttc gtcgagcttg    7620
agcggcttcc cgtgacagcg aacggaaagc tggaccgggc ggcgttgccg gagccggcct    7680
tcgctgcggg gacgggcagg ccggcgtcga acgcggcaga agaggtgctg tgcggcctgg    7740
tcgccgagct gcttggcatt gggacgcccg gcgtggacga cgggttcttc gacctgggcg    7800
gcgacagcat cgtggcgatc cagctggtca gccgcgctcg ccgggccggg ctggagttcg    7860
cggtgcgcga tgtgttccag caccggacca tcgccgcgct cgccgcgatc gcgaccaagg    7920
ccgccccacg cgaggtcgat ccgcgcgcag gtatcggcac ggtgccgccg actccgatcg    7980
tgcgctggct ggccgaccgc gggggaccga tcgacgggtt caaccagtcg aagatcctgc    8040
gcgttccggc tgaccttgac tgggacacgc tcaccgcggg cgtgcagacc ttgctcgaca    8100
```

-continued

```
cgcaccactc gttgcggatg tcccttcgg acgactggtc gttcaccgtg cccgagccgg    8160
gcgcggtccg cgctgaggac cggatgcgcc gggtacccgc ggaggcgttc gagtccgaga    8220
tcgccgcggc ccgggagcgg ctcgcacccc gggacgggcg gatgatcgac gtcgtcctcg    8280
gcgagccggg caggctgctg gtgatggtcc accacctggc catcgacggg gtgtcctggc    8340
gaatcctgat cgaggacctc acgcaggcat gccaggggcg gcagccgatc cggccggtca    8400
catcactgcg ggaatggtcg aacggcctgg tcgaagccgc ccgcacaccc gagcgtgtcg    8460
ccgaactgga ccgctggaag gccgtcctcg catccgcccg gccgtccgga acagacgtcg    8520
aaaaggacac ctacgccaca gcagggcacc tcacccgcac gcttccggtg gacgtgaccg    8580
aagtcgtgct gacccggctg cccgctgcct tccaagccga gatcaacgac gtgctgctgg    8640
ccgcgttcgc gttggccgcg ccccggcctg tgctcctcga cctggaagga catgccgggg    8700
aggagcacgt ggtcgaaggt gccgacctcg ccaggacgct cggctggttc accagcgtct    8760
atccggtgag cctcgacgcg ggtgatctgg acaccgccga cgccatggcc gggggcccgg    8820
ccgcgggaaa gctgatcaag cgcgtcaagg aacagctgcg cgagatcccg gacaagggca    8880
tcggattcgg gctgttgcgg tacctcaacg agaccacggg cgcggaactc gccggaccgg    8940
gcaagccgac gtacggcttc aactacctcg gccgcttcac ggaacccgag gacaccgact    9000
gggtcgcggt gggcagcggc gcggaactcg gcggcatcga cccgcggacc ccgttggccc    9060
accaggtcga gctgaccgtg cagacccgtg cacccgcgc gggcccgcag ctcaccgcga    9120
cgtgggtgtg ggcggccagg ctggtgtccg aacaggacgt ccaggacatc gccgggaagt    9180
ggttccaggc attggaagcg ttcgcgcggc atgtgcgcga cccggaggcg ggcgggctga    9240
ccccgtcgga cgtgttgctc ggatcggtga cacaggacga gatcgacgag ttcgaagaga    9300
tgctgaccag cgaagcggag gagttggcgt gagccggaag accagggcga tcgaggacat    9360
cctgccgctg tcgccgctcc agcagggcct gctgttccac agcgtctacg acgagcagtc    9420
accgacgtc tacaccgtgc aggtcgactt cgagctggac ggcgaactgg acctggacgt    9480
gctgcgcacc gcggcggaga cgttgttgcg caggcacagc gtgctgcgtg ccgggttccg    9540
ccagcgcaag tccggcgact gggcgcagct catcatgcgg gaggtgccgc tgtcgtggcg    9600
tgtggtcgag tcgcccgagc ggatcgagga cgaactcgcg gccgaccggt ggcagcggtt    9660
cgacctggcg aagccgccac tgttgcggtt caccgtgctc aagctggccg acgaccacca    9720
ccatttcgtg gtgacgagtc atcacctgtt gctggatggc tggtccttgc cggtgctggt    9780
ccgcgaattg ctgcggctgt acgccgagaa gggcgatgac cggtcgctgc cgagcgtccg    9840
gccgtaccgg gactacttga gctggttgtc cgaacaggac cggcctgctg ccgaagaagc    9900
ctggcgcacc gctttgtccg ggctggacaa gccgactctc gtcgctgccg atgccgtggc    9960
ggcaactccg gttgatccgc atcggatcga gcatgagctg tccgatgaga cgcacgcggc   10020
cttggtcgcg ctggccaggt ccagtggcgc acattgaac acggtggtcc agtccgcgtg   10080
ggcgatcgtg ctcggccgga tcgccggcac cgacgacgtg gtcttcggca acgtggtgtc   10140
gggcaggccg cccgagctgg ccgggatcga gtcgatggtc ggcatgttca tcaacacgtt   10200
gccggtgcgc gtgcggctgc gtccggccga gacgttcacc gcgttgctgg ctcgggtgca   10260
gcaggaacag tcggatctgc ttgcccacca gcacatcggg ctggccgaca tccaacgtgc   10320
cgccgggctg ccgaccctgt tcgactcgtg gatggtgttc cagaactacc ggtcgagggg   10380
ggtcgccgag gacgaactgg ccttcggtga cgtccgcgtc accaaggcca ccagccagga   10440
cgccacgcac tacccgctcg acctcgttgc caccgcccgc accggacttc gcctgcggct   10500
```

```
ggagacgcgg cctgaggtct tcgacgcggg ccaggccgcg cgcatccttg cccgtctcgt    10560
ccgtgtgctc gaggcgatgg ccgctgaccc gacgcagctg tcggccggg  tcgacgcgct    10620 ggaacccacc gagcgtgctc agctgacctc gggtgatgcc cgccgagagg caccggctgc    10680
cttggtgccc gaactgctgg cccgccaagc cgccgagact cccgacgcgg ttgccgtggt    10740
gtacgagcag acctcgctga cgtacgcgca gctcaacgcg cgtgcgaatc gtcttgcacg    10800
tcacctgatc tcgctgggct gcggaccgga ggacccgggtc gcgctgctgc tgccgcggtc   10860
agcggatctc gtggccgcgg tgttcggcgt actgaagtcg ggcgcagcct acgtgccgat    10920
cgaccacgac tatccggccg accgcatcca gttcctcatc gaggactcca agccgtccgt    10980
actggtggcc accagcgaaa cgatcgtgag caccgacgtt ccgcacgttg tgctgcttga    11040
cgaggcggta ctgcccgccg acgacacgga cccggtggtg cgcgctgtccg agtcgaacga   11100 ggcttacgtg atctacacct cgggctcgac cggccggccc aagggcgtgg tgatcgagca    11160
ccgccagctg cggaacctgg tcttcgagca cagcaccggc ctgatcgaac tcgtcgcatc    11220
gaagcgggag accgtacgtc ccgcgctgac ggcctcgctg tcgttcgaca cctcgtggga    11280
cggcctgttg tggctgctca gcgggcacga gttgcacgtg atcagcgacc aggtccgtcg    11340
tgacccggaa ctactcgtgt cctatgtgga gtcgaagcgg atcgacttca tggacgtcac    11400
gccttcgctg tgccgccagc tggtcaacgg cggcctgctg gccgagggca agcaccgccc    11460
ggccgtgctg atgctcggcg gtgaagcgct ggaccaggct ctgtggaacg acctgcgtgc    11520
ctgttcggcg acggcctcct acaactacta cgggccgact gagaccactg tggacgctct    11580
ggcgtacccg gtgccgatg  gcgcacggcc gttggtgggc aagccgatca ccaacactcg    11640
cgcatacgtg ctcgactccg cgttgcggcc ggttccccat ggtgtcgcgg gggagctgta    11700
cctggctggt gacggactcg cccgtggcta ccacgaccgt tcaggcctca ccgccgaacg    11760
gttcatcgcg gacccgttcg gccggcccgg cacgcgatg  taccggaccg gtgacctggt    11820
tcggcgtggt caggacggga acatcgagtt catcggccgg gtcgacgacc aggtcaagat    11880
ccgcggtttc cggatcgaac tcggtgagat cacctcggcg ctggcccagc acgccgctgt    11940
cgcggaggcc gcggtggtcg tgcgtgcgga ccgtgccgac gaccccaggc tggtcgggta    12000
cttcgtgcct gccaacggtt cgatcgacct ggccgggctg cgcaagcacc tggcggagct    12060 gctgccggc  cacatggtgc cgtcggcctt ggtgcccctt gatgcccctgc cgatgaccac   12120 caacgggaag ctcgaccgca aggcgttgcc cgcaccggaa ggccgtctcg tcagcggtgg    12180
acgggcacct cgctcgccgc acgaagagtt gctgtgcgaa ctgttcgccg acgtgctcga    12240
tgtggcccgg gtcggcatcg acgacagctt cttcgcactg ggcgggcatt cgctgctggc    12300
cacacgcttg gtcagccgga ttcgttcggc ccttggtatc gaggtgtcga ttcgccagct    12360
gttcgagaca ccgaccgtgg ccgggctgtc ggccgcgctc aatgccgcag ccaggggcg    12420 cgaagccgtc actgcggtgg ttccggcgcc tgcgcgcctg ccgctgtcgt acgcacagcg    12480
tggactgtgg ttcctgtacc agatcgaggg tccgagcccg acgtacaaca tgctgggcgc    12540
tctgcggctg accggcggct tggacgagca cgcgatgcgt cgcgcgctgg cggacgtggt    12600
cgcccggcat gagtcgctgc gcacggtctt cgccacggac aacgacggtc cgtaccaggt    12660
cgtcctcgag gacgtacggc cggagatggt ggttgtcgag accaccgagg acgctctgcc    12720
gggcgagttg gagtcagccg ctgcctactg cttcgacctg gtggacgaga tcccgttccg    12780
atcttggctc taccgcctgg gcccggacga gcacgtgctg ctcgtgctcg tgcaccacat    12840
```

```
cgcggctgac ggctggtcca tgccgatcct gggccgtgac ctcgccgcgg cgtacgccca    12900
gcgcttcgag ggcacgccac cggagtgggc cgacctgccg gtgcggtacg ccgactacac    12960
cttgtggcag cagcgcgttc tggggtccga ggacgaccag gacagtgtca tctccgggca    13020
gctggcgtac tgggaacaag cacttgctgg gctgccgggc gagctggacc tgcccaccga    13080
ccgcccgcgt ccggcgaacc cgacctatca cggcgggacc gtgcacttcg acgttcccgc    13140
cgatctgcac cgcggcctgg ccggtctggc tcgggaaagt caggcgagcc tgttcatggt    13200
ggtgcagtcc gcggtctcgg tgttgttgtc acggctgggt gccggggacg acattccgtt    13260
gggcacaccg gtggccggcc ggaccgacga ggccgtggaa gggcttgtcg ggttcttcct    13320
gaacaccctc gtgctgcgga ccgatctgtc gggcgacccg tccttccgtg agctggtcgg    13380
gcgggtccgg gagacggacc tggccgcgta tgccaatcag gacgtgccgt tcgagcgcct    13440
ggtcgaattg ctcaacccgg agcgcgtgct cggccgcaac ccgcttttcc aagtgcggct    13500
ggtgttcaac gacaccgacc gggacgccat gccgacgtg atggccgggc tgcccggcct    13560
gtccgtggcc accgaacagg ccggcttggc ggcagccaag ttcgacctgc tgttccggtt    13620 ctccagcgc ttcgacgagg acggcgggca cgccgggctg tcgtgtggtc tcgagttcgc    13680
cgaggacttg ttcgaccggt cgacggtgga gaccctggcg cagcggctgc tgagcgtgtt    13740
ctctggcgtt gtcaccgatc cggccagtgc tgtgtccagg gtggacgtgt tggtcgacgg    13800
tgagcgcgag cggattctca acgagttcaa cgacaccgcg tgggagaccc ggaaaatctc    13860
gttgccggag ttgttcgccg agcaggttct gcggacccCg tccgcggtcg cggtggagtg    13920
tgatggcgtt gagctgacgt acgccgagct ggatgagtgt gcgaatcggt tggcgcgtta    13980
cctgatctcg cgtggtgtgg gtgcggagaa gttcgtcgcg gtgatgatgc cacggagtat    14040
cgatcttgtg gtgtcgttgt tggcggtgtt gaagtccggt ggtgcttacg tcccggtcga    14100
cccggagtat ccggcggatc gcatcgcttt catggtggcg gacgccgaac cggttctggt    14160
cttgacctcc acgagggggg ccgaggagtt cgacggctcg cctctgtccg atgtggaggt    14220
gtcgctcggt aacccggcgt acatgatcta cacgtcgggt tcgacggggc agccgaaggg    14280
cgtcgtggtc gagcacgggt ctgtcggcgc ctatgcggtg cgtgcgcgtg aggtgtatcc    14340
gtgggcgtcg ggtgtgtcgt tggtgcattc gccggtgtct ttcgacctca cggtcacggc    14400
gctctattca ccgctggttt ccggtggccg ggttgttctg agcagccttg aggatgcttc    14460
gggtccgcgg ccgacgttca tgaaggtgac gccgtcacac cttgggttgt tggatgcctt    14520 gccgacgat gtgtcgccga gtggtgcgct ggtcatcggt ggtgaggcgc ttcgtggtga    14580
cgtgcttgat cgctggcgtt cacgtttccc ggacgtgacc gtgatcaacg cctatggtcc    14640
gaccgaggcg acggtcaact gtgctgaatt ccgtgtgctg ccgggcgatg agacccCgac    14700
gggcgcggtg ccgattggcc gtgcgttctg gaacacgcgg gcctacgtgt tggattcgcg    14760
gctttcccca gtgccccagg gggttgccgg tgaactgtac gtctccggtg tcgtgctggc    14820
ccgagggtac tggcaccggg ccgggttgac gtcggagcgt ttcgtggccg atccgttcgg    14880
tgggcctggt gcacggatgt accgcacggg cgacttggct cgctggaatg ccgatgggca    14940
gctggaattc gtgggtcgtg cggacgatca ggtcaagctg cggggttttcc ggatcgagct    15000 cggtgagatc gaagccgtgc tgaccaggca caacgacgtg tcgcaagcag ctgtggtcgt    15060
gcgtgaggac cagccaggag accagcgcct ggtggcctac gtcgtcgcac cggcggggcga    15120 tgtcgacgga gccgggctcc gggagcacac ggcgtcggcg ttgccggagt acatggttcc    15180
ctcggcgatc gtggtcctcg acgagctgcc gctgaacccg cacggcaagc tcgaccgcaa    15240
```

```
ggcgttgctg cgcgaggagt tcatccccgc cgtcgaggaa accgaagttg tcgcgcgcgg   15300
gccgcgttcg ccgcacgagg agatcctctg tgccctgttc gcggaagtgc tcggcgtggc   15360
cgaggtcagc atcgacgacg ggttcttcga cctgggcggc cactccctgc tcgcgatcag   15420
gctgatcagc aaggctcgca gcgttcttgg cgtcgaactg ccggtacgac agctgttcga   15480
gacgccgacc gtggccggac tggcggcggt cgtcaacgcg gccgggcgcg cacgggaagg   15540
cgtcaaggca gtcgtgccga ggccggaccg tgtgccggtt cccatgcgc aacgcgttt     15600 gtggttcctc aaccagttcg agaacggtgg cgcgacctac aacatcccgg cggctctccg   15660
gctgacgggc gatctggacc gcgtcgcact gcgtgccgcg ctcaacgacg tcatcgccag   15720
gcacgagagc ctgcggacga tcttcgcgga ggacgacaac ggtccgcacc agatcatcct   15780
cccgctggag cacgccgatc tcgatgtcct ggtggtcccg cgaccgaag ccagctgga    15840 cgacctggtc gaccaagccg cccggcacga gttcgacctg gccgccgagt tgccgatgcg   15900
ggtcacgttt tcgagctcg cgccggacga ccacgtcttg ctgctgctga tgcaccacat   15960
cgcgaccgac ggctggtccc tggcgccgct ggcacgagac ctggccaccg cctaccgcgc   16020
tcgtcgcgct ggtcgagcgc cgtcttggtc cgccctgccg gtccagtacg cggactacgc   16080
gctgtggcag cagcgcgtgc tggattcgga ggccgatcag atcggctact ggcaggaggc   16140
gctgccggga ctgccggatg agctgccgtt gccggtcgat cgtccgcgca cggcgaatcc   16200
gtcgttccgg ggcggtgtcg tccggttcga cgttcccgcc gatctgcacc gcggcctggc   16260
cggtctggct cgggaaagtc aggcgagcct gttcatggtg gtgcagtccg cggtctcggt   16320
gttgttgtca cggctgggtg ccggggacga cgttccgttg gcacaccgg tggccggccg    16380 gaccgatgag gcggtggcgg acctcgtcgg gttcttcctg aacacgctgg tgctgcgcac   16440
cgacttgtcc ggtgatccgg tgttccgtga gctggtcggg cgggtccggg agacggacct   16500
ggccgcgtac gccaaccagg acgtgccgtt cgagcgcctg gtcgaggtgc tcaacccgga   16560
tcggtcactg gccaggcacc cgctgttcca ggtgatgatc gtcttcaaca caacgacca    16620 ccaggaatct gtcgacgtgc tggaccggct gcccggcctc acggtcggca aagccatggc   16680
ggacacgcac atcgccaagt tcgacctgtc gttccggttc tccgagctgt tcgacgagga   16740
cggcgggcac gccgggctgt cgtgtggtct cgagttcgcc gaggacctgt tcgaccagtc   16800
gtcggtcgag gttctggtcc agcgcctgct ggcagtgctg gaaggtgttg tcgccgatcc   16860
tggtgtgcgg gtctccgccg tcgacgtgct ggtgaacggt gagcgcgagc ggattctcaa   16920
cgagttcaac gacacttcgc gcgaggttcg gacggtctcg ttgccggagt tgttcgccga   16980
gcaggttctg cggaccccgt ccgcggtcgc ggtggagtgt gatggcgttg agctgacgta   17040
cgccgagttg gatgagcggg cgaatcggtt ggcgcgttac ctgatctcgc gtggtgtggg   17100
tgcggagaag ttcgtcgcgg tgatgatgcc acggagtatc gatcttgtgg tgtcgttgtt   17160
ggcggtgttg aagtccggtg gtgcctacg gccgatcgac cccggctacc ggcggatcg    17220 catcgctttc atggtggcgg acgccgaacc ggttctggtc ttgacctcca cggaaggcgc   17280
cgaggagttc gacggctcgc ctctgtccga tgtggaggtg tcgctcggta acccggcgta   17340
catgatctac acgtcgggtt cgacgggcca gccgaagggc gtggtggtcg aacacggctc   17400
ggtgggtgcg tatgtggagc gggcgcgtga ggtgtatccg tgggcgtcgg gtgtgtcgtt   17460
ggtgcactct ccggtctcgt tcgacctcac ggtcacggcg ctctactcgc cgctggtttc   17520
cggcggacgt gtcgtcctgt ccagccttga ggatgcttcg ggtccgcggc cgacgttcat   17580
```

```
gaaggtcacg ccgtcacacc ttgctctgtt ggacgcgttg cccgatgacg tctcgccgag    17640
cggcgctttg gtcatcggtg gtgaggcgct tcgcggtgac gtgcttgatc gctggcgttc    17700
acgtttcccg gacgtgaccg tgatcaacgc ctacggcccg accgaggcga cggtcaactg    17760
tgccgaattc cgtgtgcttc ccggagagga aacgcctgcc ggtgcggtgc cgatcggccg    17820
tgccttctgg aacacgaggg cttacgtcct cgacgcggca cttcagccgg ttccgcaagg    17880
cgttgcggga gagctctacg tctccggtgt tgtgctggca cgcggctact ggcgcagggc    17940
cggcctcacc tccgagcgtt tcgtggccga cccgttcggt gggcctggtg cccggatgta    18000
ccgcacgggt gacatggctc gctggaatgc cgatgggcag ctggaattcg tgggtcgtgc    18060
ggacgatcag gtcaagctgc ggggtttccg gatcgagctc ggtgagatcg aagccgtgct    18120
ggcgaagcac gtctcccagg ccgccgtcat cgtccgggag gaccagccag gcgaccagcg    18180
cctggtggct tatgtcgtcg ggaacgacgc gggtttgccg gaccgcttgg ccgaagccct    18240
gccggagtac atggttccct cggcgatcgt cgccctcgac gaactgccac tgaacccgca    18300
cggcaagctc gaccggaaag ccttgcgcg tgcggactac gccccggcca tcgaccggga    18360
ggcggtggcc cgcggtccgc gtgggccgca cgaggagatc ctgtgcgacc tgttcgccga    18420
agtcctcggt gttccccagg tcggtgtgga cgacggtttc ttccacctgg gcggccactc    18480
gctgctcgcg acccgttga tcagcaaggt ccgcgccgtg ctgcgcgtcg aactgcctgt    18540
ccggcaactg ttcgacaccc cgacggtcgc cggcctcgcc gccgtgatcg accgggccgc    18600
cggcgcacgg gaagcggtcg aggccgttgt gccgaggccg ggcaccatcc gctgtcgcc    18660 tgcccagcgc aggttctggt tcctcaacca gttcgagcgc aacggtgccg tgtacaacgt    18720
cccggccgcg ctccggctgc tcggtgacct cgaccgggaa gcccttcgag ccgcgctcaa    18780
cgatctggtc gtccggcacg aaagcctgcg cacactgttc tcacaggacg gtccgcacca    18840
gatcatcctg cccgcggcgg aggcccgcct tgacgttgtc gaggcggacg tgcgcgaagc    18900
cgacctcaac gactacctcg acaccgccgc ccggcaggag ttcgacctgg cacgggatct    18960
gccgatccgc gcgcacctgg cgaagatctc ggccgaggac cacgtgctgc tggtcgtcgt    19020
gcaccacatc gccacggacg gctggtccat gccgttgctg gccaaggact tcaccaccgc    19080
gtaccaggcc cgttgtgcgg gccaggcgcc gacctggcct gacctgcttg tccagtacgc    19140
ggactacacc ttgtggcagc agcgcgtgct gggcgccgag gacgacccgg acagcctggc    19200
aagcaagcaa ttggcctatt ggaccgacgc cttggccggg ctgccggggg aactgtccct    19260
gcccaccgac cggccacgcc cgcgaaccgc gtcctaccag ggcgagaccg tgttcttcga    19320
catcccggca ggcctgcagg aacgcctcgc caagctggcg cgagaggcgc aggtcagcct    19380
cttcatggtg gtccaggcgg ccgtggcgac catgctcggc aggctgggcg cggggacga    19440 catcccgctc ggcagcccga tcgccggccg caccgacagc tcgctcgaaa gcgttgtcgg    19500
gctgttcctg aacaccctgg tcctgcgaac cgacctgtcc ggcaggccga ccgtgaacga    19560
actgctgacc cgggttcggg agaccaatct cgcggcgtac gccaaccagg acgtgccgtt    19620
cgagcgcctg gtcgaggtgc tcaacccaca gcggtcgctg gccaggcacc cgttgttcca    19680
ggtgatggtc cagttcaaca acgcaggcca gtacggcgcc tcggaaaccg tgcacgacct    19740
gcccggcatg accgcgaccc tgcggtcgcc ggacaccggt gtggcgcggt tcgacctgtt    19800
gttcggcttc accgagcgca cggtcccgga cggctcggct gccggactgc gtggtgcgct    19860
tgaattcgcc acgacctgt tcgaccggac gaccgcggat gcgctggtgg cacgcctgat    19920
ccgggtgctt gaggcgttcg ctgaccggcc tgaccaggtc atcgacgacg tgaacgtgct    19980
```

```
cagtgcggac gagcgtgagc aggtcttgca tgagtggaac gacaccgcgg tggtcgtgcc    20040
gcaggccggc gtgccggagt tgttcgaacg ccaggtcgcg agcacgcctg acgcggtcgc    20100
cgtgatctgc ggtgagatca cgctcacgta tgccgagttg aacgaacggg cggacaaact    20160
ggctggctac ctggtttccc agggtgccgg gccggaacgc ttcgtcgcag tcgggttgcc    20220
gcgtgacgaa cggctcgtgg tcgcgttgtt ggccgtgctc aaggcaggcg cggcgtacct    20280
gccactggac ctggagtatc cttcggaccg gatcgcgcac atgatcgcgg acgcctcgcc    20340
tgtgctcgcg ctggccactt cggacacctc gagcctgatt cccggtgagc tgcccagagt    20400
tctgcttgac ggcccggttc ctgaggccgt gccggtgacc gtcacgcgga aggcggacca    20460
ggcggcgtac gtgatctaca cgtccggctc gacgggcagg ccgaagggcg tagtcgtgcc    20520
gatggcgccg atggtgaact tcctggacag catgagccgc aggttcccct tgaccactcg    20580
cgacagaatg ctggcggtca ccacggtcgg cttcgacatc gctgtgctgg agttgttcct    20640
gccgctgctg cgcggcgcag gggtggtgct ggcgagccgc gagaccactc gtgacccggt    20700
ggcgttgcgg gcgttgatcg agcagtccgg cgccacgatc atgcaggcga cgccgagcct    20760
ctggcgttcc ttggcggcgg aaggtgttcc gtcgctgcgg atcttggtgg gtggcgaggc    20820
tttgcccgcc gacctggcca gggaactggc cgcggacggc cgggacgtga ccaacctcta    20880
cggaccgacc gaaaccacgg tctggtcggg cgcgacgcgg atcagccagg acgacgcgcc    20940
gatcggcgaa ccgatcggca cacccggct gtacgtgctc gacgccggac ttcaccctgt    21000
accagaaggt gttcctggcg agctgtacat cgccggtgcc ggtctggccc gcggctactg    21060
gcaacggtcc gggctgaccg ccgagaggtt cgtggcgtgt ccgttcggcg ggccgggcga    21120
gcgcatgtac cggaccggtg acttggtcaa actccgtgcc gacgggcgga tcgactatct    21180
cagccgggtc gacaaccagg tcaagctgcg gggtttccgg atcgagctcg gcgagatcga    21240
ggccgtgctg tccggcgtcg actcggtcga ccaggcggtt gtggtggtcc gtgaggaccg    21300
tgaacaggac aagcgtttgg tcgcgtacac ggtcggttcc acgccggacg ccttgcgggc    21360
acacgcggcg gcgcacctgc cggagtacat ggtgccgtcg cgttcgtgg tcctcgacga    21420 gctaccgctg acgcccaacg gaaagatcga tcgacgcgcg ctgcccgctc cggagtacac    21480
cgctgcggcc ggtcgtgcgc cgcggacacc gcaggaggag atcctgtgcg agctgttcgc    21540
ggaggtgctc ggcgtcaccg atgtcggcat cgacgactcg ttcttcgcgc tcggcgggca    21600
ttcgctgctg gccaccaagc tggtcaaccg gatccggtcg ccctcggcg cggagatctc    21660 ggtccgcacc ctgttcgaga cctccaccgt ggccggactg gccccgctga tgtccggcga    21720
cggcaggcgt accgcactgg ttgccggaca gcggccagag cggctgccgt tgtcgttcgc    21780
ccagcggcgg cagtggttcc tgcagcagct cgaaggcgcc aacacggcgt acaacatccc    21840
gagtgcactg cgtctgaccg gtgatctcga cgaggacgcg ctgcgcgccg cgctgttgga    21900
cgtggcggtc cggcacgagt ccctgcgaac ggtcttcgcg gaggacgacc tcggcgcacg    21960
tcaggtcgtg ctgcccgaac aggctgctcg gcctgcgatg acggtcgtgg agaccaccga    22020
gcccgagctg cggacgcgga tggacgaggc cgcggcgtac cggttcgacc tgggcgccga    22080
gccgccgctg cgggcctggg tgttccggct ttcccagacc gagcacgtgc tgttggtgct    22140
gacgcaccac atcgccagcg acggctggtc ggtcccggtg ctgatgcggg atctggccac    22200
cgcgtacgcg gcacgtcgtg gcggccaggc accgggctgg gcgccgttgc ccgtgcaata    22260
cgccgactac acgttgtggc agcacgaaat cctcggcgcc gaggacgatc ccgccagcga    22320
```

```
gttcgcccgt cagatcggct actggaagac cacattggat ggtctgcccg cgcaactgga    22380
cctgccggcc gaccggccgc gcccggcggc accgtcacac cgtggcggca cggtggagtt    22440
cgatgtcccc gccgaactgc acggtgcact ggttgcgttg gcacgtcagc acaacgcgag    22500
tgtgttcatg gtcgtccgtg ctgccgtggc ggccctgctg aaccggcttg gcgcggggga    22560
ggacatcccg ctcggcacgg cgatcgcggg ccggtccgac gacgcactgc acgacctggt    22620
cgggttcttc gtcaacacct tggtgctgcg gaccgacctg gcaggcaacc cgagcttcag    22680
cgagctggtc gaccgggttc gtgaggccga cctggccgcg tacgccaacc aggacgtgcc    22740
gttcgagcgc ctggtggagg tgctcagccc ggctcggtcc atggccagcc acccgctctt    22800
ccagaccatg gtgacctggc acaacaccga ccgtcgcgcc gccgtcgagg cacaacgcga    22860
cctgcctggg ctggccgtca gtccctatga ggtgcgaaac gtgtcggcca agttcgacct    22920
ggcgttctcc ttcaccgaag gcacgggaat cagcgccgag ctcggctaca cgccgacct    22980 gttcgaccgg gccaccgccg aggccttcgc gcagcgtctg cttcgagtgc tggagacggt    23040
cgccgcggac ccggacgttc tggtgagccg gatcagcctg gtcaccgagg acgagcgtga    23100
cctggtgctg agggcgtgga cgacaccgc gcaaccggtg gccgggacca cgttcaccga    23160
actgttcgcc aggcaggccc aggccacgcc ggactccgtc gcggtcgagt gcgacggccg    23220
gaccctgacg tacgccgagt tggacacgcg gtccaaccag ctggcgcatt acctggtcag    23280
caacggggtc gggccggagc ggttcgtcgc gatcgtcatg aacaagtcgg tggacatggt    23340
ggtcgctctg ctcggtgtgc tgaagtcggg cgccgcgtac gtgccgatcg acccggccta    23400
cccgcgcgat cgcatcgagt tcatgttctc cgatgtggcg ccggtcctcg tgctgacttc    23460
acgggatgcg gcctcggcat tgcccgagtc ggaccacgtg ttcctccagg acgtcgattt    23520
ggccgcctac ccggacgccg ccatttcgga ggcgtgcccg gccaacccgg cgtacgtcat    23580
ctacacgtct ggttcgaccg gacgcccgaa gggtgtggtg atcgagcacc gggcgctcgg    23640
cgcctacctg gaccgcgccc gcgaggcgta tccgtggatg tccggcacca cctgggtgca    23700
ctcgccgatc tcgttcgacc tgacggtcac cggcctgttc tcgccgctgg tgagtggtgg    23760
ccgggcgcgg ctggtggacc tcgagggtgg gcgggcgacg ggggagcggc cgtccttcgt    23820
caagggcact ccgtcgcacc tcggtctgtt ggacgtcctg ccggacaacg cttcgccttc    23880
cggcgcgctg atgctcggcg gcgagttgct gatcggtgac gtgctgcagc gctggcggga    23940
ccgcaacccc gatgcggtcg cgttcaacgt ctacggcgcc actgaggcga ccgtgaactc    24000
ggtggagaac cggatcctgc cgggcacgcc gattccttcg ggggcggtgc cggtgggcac    24060
accgttccgc aacacccgga tctacgtgct cgacgagagc ctgcggccgg tgccgccggg    24120
tgttcccggt gacgcctaca tcgcgagcac cggtctggcg cgtggctact ggcgacggtt    24180
cgggctgacc gcggaacggt tcgtggcctg tccgtacggc gagccaggcg agcggatgta    24240
ccgcaccggc gacttgttgc gctggaacaa gcagggggcaa ctggagttcg tcggccgggc    24300
ggactcgcag gtcaaggtcc ggggcttccg gatcgaaccc ggcgaggtcg agtcggcgct    24360
gacgcggtgc gacggcgtga gccgggctgt ggtcgtggtc cgcgagggcc ggctggtcgg    24420
ctacctcctt ggcgatggcg tggacccgga cggtccgg gcgacggcgg cagagctgtt    24480
gccgggctac atggttccgg ccgctttcgt ggttctcgac gagctcccgc tgacgcccaa    24540
cggaaagctc gaccagcggg cgttgccgc accggacttc ggtgccgcga ccacggccac    24600
cgcaccgcgt gacgctgtgg aggaactcct cgccggactg ttcgccgagg tcctcgggct    24660
ggaacaggtc ggcgtcgacg acgggttctt cgacctgggc ggcgacagca tcatgtccat    24720
```

```
tcagctggtc agcagggctc gtcgggcggg tttgacgatc tcgccgcgtg acgtgttcga   24780
ccggcagacg gtcgcgggcc ttgccgctgt ggcaaaggct tccgatgcgg tgacggtcga   24840
ggaaccgggt gcggggatcg gcgagttccc ggcaacgcct gccatcgcgc gattcctgga   24900
gagcggcgcc caggtcgacc agttcaacca gagcgtcgtc gtgcgcgtgc cgtccggact   24960
tggcgaggac cggcttgtgg ccgccgtgca gaagctggtc gaccaccacg atgccctgcg   25020
tactcatctc aactcggtgc tgtcggtgag tgcaccgggc acagtggacg cacgggacct   25080
cgtgtcccgt gtggacgcgg ccgggctcga cgacgaagca ctggttccgg tgatgtcgga   25140
gcacgccgtc acgcccgtc tgaggctggc gcccgccgac gggaaggtca tccagttcgt   25200
ctggttcgac cgcggtgacc tgccgggaca actcgtcgtg gtcgcacacc acctcgtggt   25260
cgacggcgtg tcctggcgtg tgctgttgcc ggatctcgca ctggcatggc agggcgaaga   25320
actggcacct gtgggcactt cggttcgccg ctgggcccag cgcctgaccg agctggcccg   25380
acgttcgtcc gagttggggc tgtggaccga gatcctcggt gacccggaac cggttctcgg   25440
ttcgcgggca ttggatccct ctcgggacaa cgcttccacg gcacgtcacc tcaccacgac   25500
attgccggag gacgtcacag gcgacatcct cacgaccgtt ccgtccgctt ccacgccga   25560 gatcaacgac gtgctcctgg cgaccttcgc cgtggcgttc gacgaatggc gcggcgggag   25620
cgtcctgatc gacctggaag gccacggccg cgaggaacat ctgctcgaca acgtggacct   25680
gtccaggacc gtcggctggt tcaccaacct gtacccagtc cggctggatc ccggtacggg   25740
cgacatcggt gacgcgctga agcggatcaa ggagcagttg cgcgcggtcc cggacaaggg   25800
catgggctac ggcctgctgc gctacctcaa cccgggcacc gccgcccggt tgcgtgaact   25860
gcctggcgcc caggtcaagt tcaactacct cggccgggtc ggcaacgcgg aatcaggcga   25920
ctgggcaccg ggatccggca tcaacggcgt cggcgccggt cgcgacccgc gccatccgtt   25980
gtcgcacgca ctggaggtca acgcccggac gctcgggccg gaactcgtgg tcagctggac   26040
gtggccggac gaggtcctga gtgccgacga agtcacgcgg ctgaacgaga tctggttccg   26100
ggcactgcgg tcgctgaccc agtcgacagc cggtggcctc accccgtcgg acgtctcctt   26160
ggcggaactc agccagagcg agatcgacct gctcgaatcg gaatggacgg actaggcgca   26220
tggcacgatc cgacatcgcg gacatcctgc cgctgacccc gctgcaggaa gggctgctgt   26280
tccacacgct ctacgacgag caggcccgtg acgcctacct cggccagcac gcgttcgagc   26340
tggacgggga gctggacgtc gaagcgttgc gcgccgcggc ggagggcgtg ttgcgcaggc   26400
acggaaatct cagggcttcc ttccggtaca aggggttgag ccggaccgtg caggtgattc   26460
cccggcgggt caccgttccg tggcagtaca tcgacctgtc cgaccggccg gaggaggctg   26520
agcgggtcac cgcggcggac cgcagtgcgc ggttcgacgt caccaaaggc ccgctgctgc   26580
ggttcacggt catcaggctc ggggcgcgtc gtcacctgtt cctgctgacg tatcaccaca   26640
tcctcctgga tggctggtcg accccgttgc tgctgcgtga gctgatgacg ctgtaccaga   26700
gcaagggcga tccgtcgtcg ctgcccgcgg tccggccgta caaggactac ctgggctggc   26760
tgtccaaaca ggacgtttca gtggccgggc aggcctggcg ggaagcgatg tccgggcttg   26820
cggagccgac tcgtgtcgcc agtgacccga acgcggtcac tgtcccggag atgaccgagt   26880
tcgcactgga cgatgccgtg tgtcagcgcc tgcggacgcg gggtgtcacc ttgagcacgg   26940
ctgtccagtg cgcgtgggcg ttggtgctgg ctcagctgac cggccgtgac gacgtggtgt   27000
tcggcatgcc ggtggctggt cgcccgccgg agttgccggg tgtcgagcag atgatcgggc   27060
```

```
tgttcatcaa caccgtgccg gtccggatcc ggttgcgccc ggccgagacg ctcggcgagc    27120
tgttggcccg ggtccagggt gagcaggccg ctttgctgcc gtaccagtac ctggggctct    27180
cggagatcca gcgcgcgtgt ggcatgggtg agctgttcga cgcctcgatg gcgttcgaga    27240
actatcccgt gtccccggac acagtggaca gtccgcgtgg tgacgccctg cgggtgcgca    27300
agaggcgtgg cgtggacacc gggcactacc cgttgacgtt gatcgcggtg tcccgggccg    27360
gcctgaggtt ccggctcaac cggcggcctg acgtcgtgcc tggcatggac gtggccgacc    27420
tgcttgtgcg caccctgaca gccatcgcgg accagcccga tctccggctg gcccaactgc    27480
ctccggccgc tgaggtgcgg cacgtcactc ccgacggcac gcctggggtt gtttcgcgtg    27540
acttcgaaga ggtggctcgg caggcacctg acgccatcgc ggtgacgttc gatgccggga    27600
agctgacgta tcggcagctg gatcagcgcg cgaaccggtt ggcacgttcg ctgatctcgc    27660
gcggtgtgcg gcgaggtgac ttcgtcgcgg tggcgctgcc acggtcggct gacctcgtgg    27720
tcgccttgct cgccgtgctg aaggccggtg ccgcgtacgt tcccctggat ctcaagaatc    27780
cggccgcgcg gaccgatgcg gtgctcgccg atgcccgtcc tgccgttgtg ctgtccgaag    27840
tcggtgatct tgaggacttc tccggcgatg ttctgacgga tgcggagatc ggcggtccgc    27900
tgacgccgaa cgatgccgcg tacatgatct acacctcggg ttccaccggt gtgcccaagg    27960
gcgtgctcgt cgagcggggg tcgatcgacc ggatcgcccg cggcatccct ggcgtcgaac    28020
tgaccgccga cgatgtcgtc gcccagttgg ccgcggtcgc cttcgacgcg acgacattcg    28080
aggtgtgggg cgcattgctg aacggcgcca cgctggccgt cgcgccaccg tccgcgttgt    28140
cggtaggcga actgaggacc ttcctgaccg acgccggtgt gaccgcactc tggctgacgg    28200
ccggactgtt ccacgaggtc gtcgagcagg acatcacggc cttgacgggg ttgcgttacc    28260
tcctcgcagg tggcgacgtc ctgtcgccaa gcgcttgctc ggccgtccgt gccgtgtacc    28320
cggatcttcg gctgatcaac ggttacggcc cgaccgagac cacgacctt gccgccacgc    28380 acgcggtgga tgcgccggac acgaccgtgc cgatcggtgc gccggtgacc gcgactcgtc    28440
ttcacgtcct ggatggctgg ctgcggccgg tgcctccggg cgtcacaggg gagctgtaca    28500
tcgcaggcac aggcttggcg cgtggatacc acgatcggcg tggattgacc gcggaacggt    28560
tcgtcgcttg tccgtccggt gggcggatgt accgcaccgg ggatctcgtc cggtggaact    28620
ccgccggtga cctcgagttc ctcggccgcg tcgactccca ggtgaaggtc cgtggttcc    28680 ggatcgaact cggcgagatc gaggccgcgt tggtcgcgca cccgtcggtg gacgcggcgg    28740
cggtgatcgt gcgggaggac cggccggatg acaagcggat cgtcgcctac gtgcgtccca    28800
ccatcgatcc cgttgtgctg cgggcgcatc tggcctcgat cgtgccggac ttcatgatcc    28860
cggcagcgtt cgtgccggtg acgcagttcc cgctgaccgc caacggaaag ctcgaccgac    28920
gagccttgcc ggtgccggac tacggcgacg gccgggcaca cgcggcggca cggtccccgc    28980
gcgaggagat cctgtgtgag atcttcgccg acgtgctcgg tgtcgaccgg tcggtgtgg    29040 acgccagctt cttcgatctc ggcggccatt cgctgctggc gactcgtctg gtcagccggg    29100
tccgcagcac gctcggcgtg gagatgtcca tccgccggct ctacgactcg cctaccgtgg    29160
ctgggctgtc cgaggccctc gatgccctgg caggcgcccg gacccgggtg accgcggttc    29220
aacggcccga gcgggtgccg cttccttcg cgcagcagcg gctgtggttc atcgaccggc    29280
tcgaaggccc cagccccagc tacaacgtgc cttcggcgtt gcggttgcgt gggccgctcg    29340
atgtgacggc cttgctggcg gcgctcaggg acgtgatcac gcggcacgag tcgttgcgga    29400
cgatctacgc cgaggaccag cacggaccac accaggtggt gctcgccgaa ttctcgacac    29460
```

```
cccttgccgt catggacgtg acgcaggacg agctgtccat ggccctgtcc ggagccgcca   29520
ggtactcgtt cgacaccgcg gccgaaatcc ccatccgggc caccctgttc cggctcggcc   29580
ccgaggaaca cgtgctgctg acggtcgtgc accacatcgc gaccgatggc tggtcgatgc   29640
ccgtgctggc tcgtgacctc gcgcacgcgt acaccgcgcg gcacgccggt cacgcaccgg   29700
gctgggctcc gctgccggtg cagtacatcg actacacggt gtggcagcgg gaagtccttg   29760
gttccgagga cgatccggac agcgtgatct cggcggaact ggcgtactgg cagaggaccc   29820
tggccgggct tcccgaggag atcgcgctcc cagtggaccg gccgcgtccg cgtacggcca   29880
gctatgcggg cgacggaatc cgcttcgcca tcccgcccga gctgcatggg aagctggcct   29940
cgatcgcccg taagcggcac gtcagcctgt tcatggtcgt ccaggccgcc gtggcgacgt   30000
tgctgcaccg cctcggcgcg ggcgaggaca tcgcgctggg cagtccgatc gccggacgga   30060
ccgacgacac gctggattca ctcgtcgggt tcttcgtcaa cacgttggtg ctgcgcaacg   30120
acttgtccgg cgatccgtcg ttcgccgagc tgctgacgcg ggtcagggac accgacttgg   30180
cggcgtacgc gcaccagaac gtgccgttcg agcgcttggt cgaggtggtc aacccggagc   30240
ggtcgctggc ccgtcacccg ctgttccagg tgatgctcgc gtacaacaac accgacttcg   30300
gcactgcgga cgagccggct tccggcctcg tgatcagcca ggaacgcgtc gacaccggta   30360
cctcgaagtt cgacctgctg ttcgccttca ccgaagggca aggcggcggg ttgcgtggcg   30420
aactccgctt cgccacagcg ttgttcgacc gggcgaccgc ccagtcgatt gtggaccgtc   30480
tgctgctggt tctcgattcc gttgccgctc agccggactt gcccgtgtcc gcggtgaacg   30540
tcctggcgga gcacgagcgg gatctcgtgg tcgacggcgg cgcccggcag gtgccttcgt   30600
cacctgtgcc tgctttgttc gaacagcagg ccgtgctcag gccgtccgcg gtcgcgctgg   30660
agacaagttc cggcacgctg acgtacgccg agctcaacga gcgggccaac cacctggcgt   30720
ggcacctgat cgcccagggg atcgggccgg accacctggt cgccgtgctg cttccgcgtg   30780
gcgagtggct tgcggcggcc atgctcggaa tcctcaaggc aggcgccgcg tacgtgccgg   30840
tcgacgtcac ctacccggaa gacgggtcg ccgagatcct ggcggacgct tcaccttcac   30900
tcgtggtgag caccgggtgg cccgccggtc gttcggacaa cccgccgtac accgccgatg   30960
acgcgaaccc gtcgtacgtg atctacacgt ccggatcgac agggaagccc aagggcgtgg   31020
tgatgaccaa cctcgccctg cgcaacctgc tggcatggca ttcgtcggcg gtgcccggcg   31080
aacccggcga ccgggtctcg cagttcacgg cggtgagttt cgacgtgtcg gtgcaggaga   31140
tgctgtccac cttgaccact ggcaagaccc tggtcgtccc ggacgaggac acccggcgcg   31200
atccggcgca gctcgccgcg tggctcgacc ggacgcaggt caacgagttc tacgcgccga   31260
acctggtgat caacgccgtg ttcgaggcgg gactgccgtt gccttcggtc aaacacgtcg   31320
tccagggcgg cgaggcgttc gtgatcagcg aggcgatgcg cgccgcgcac atccccggcc   31380
gccgtctgca caaccactac ggccccagcg aaacccatgc catcaccggt tacgtgctgc   31440
ccgaagaccc cgggtcgtgg gaaccggtga cgccgatcgg caagccgatc ccgaactccc   31500
aggcacacat cctggacact cggttgcgtc cagtcccgcc cggcgtgcca ggggagctgt   31560
acctcgccgg cgacgcgctg gcgcggggat acctcaaccg tccggcactg accgcagaac   31620
gattcatcgc cttccccaac gggcaacgcg cctaccggac aggcgacatc gtccgtcgaa   31680
cgcacaccgg tgacctgatc tacctcggcc gcgcggacaa gcaggtgaaa gtccgcggct   31740
tccgcatcga acccggtgag atcgaagccc gcctcaccgc gcacgtcgac gtcacccaag   31800
```

-continued

```
ccgcggtcgt cgtgcgtgag gaccgccccg gcgatcgtcg cctggtggcc tatgtcgtgg   31860
gtacggcgtc ggccgacgtg cttcgcaaga ccctgagtga cgcactgccc aactacatgg   31920
tcccgtccgc gttcgttcac ctcgacgaac tcccgttgac gcccaacggc aaactcgact   31980
ggcgcgccct gcccgcgccg gacttcaccg cggctcggga aagccgtcag ccccgcacac   32040
cccgtgaaga gatcctgtgt ggcctgttcg ccgaaatcct cggtgtggac agtgtgggga   32100
tcgacgacga cttcttcgaa ctcggcggcc attccatcct ggcggcgaaa ctggccggcc   32160
ggatccgtgc cgaactcggc gaggaactga cggtccgcaa cctcttcgaa acgccttccg   32220
tcgcgggcct taccggtgct tcggcggaca aacgcgctcc gctcggcccg ctgctggccc   32280
tgcggcgcaa cggttgcgcc caaccggtgt tctgcatgca ccccggcggt gggatcggct   32340
ggtcgtatgc gcggctcgtc cggcacctca gcccggacgt accgtctac gcactccagg    32400 cctcggggttt ctcgaccggc tcggcactcc cgtcctcggt tgaggaaatg gccgcgtcct   32460
acgtggcccg gatgctgtcg gtacagcctg aaggcccgta ccggatcatc ggctggtctt   32520
tcggcggcct ggtggctcac gccgtcgcga cccacctgca gtccctgggg cacgaggtgt   32580
cactgctggc cctgctcgac gccttcccac ccaccacgtc cgcgggcgag ctcgacccac   32640
acgcggtgct cgccgcgaac atgcgggcgt ccggttctc gttcgacgag gacgagctgc    32700
gcaacgatga gcagggcgtg ctgaaggcgt tcacggagtt cctcaggcac gagaacatgg   32760
cggtttctct ggcgtacctg gacgaggagg aactggtcaa cgccaagaac gtctacctga   32820
acaacatccg cctgatgcgc cggttcaccc cggcggagtt cgcgggcgac gtggtgttct   32880
tcgcggccac gaaggtcgcc aaggacaagc tcgaccgtgc caggccggaa gcgtggaacc   32940
cgcacatctc ggggacgctg accgcccacc cggtggccac ggcgcacgag aagctgctgg   33000
tggagccgga gcggtggcg gaggtggcca gggtgctcaa ctcacacctg gacaggtcat   33060
gatgtcgtcg tcgaagccca gcgggtcatg gtgcatccgg ccgatgatgc gttccgcttc   33120 cccgccctg ccgcctgtgt gcagtgcggc cacggcgatc ttgcggcact ttgccagccg    33180
ggcgggcgaa ccctcgagcc ggacgtgccg gtaggcctcg ctgatcagtt cgagagcacg   33240
ggcgaacgag ttcccgcggt agtggaaata cgccgctatc gacagcgtct cgcccagtga   33300
ttcaggatga ctggccctgt tgtgggcgat gttctcgtcc atcacccgca gcgccgcggc   33360
gctgtctccg cgtttggcca gcatttgcgc gaggttggtc ttgacctggc tcgtgtaccg   33420
atgagcggcg tcacgctcga ccatgaccca gccgtcgcgc ggaagcagct cgtcggcgtt   33480
gctgatggaa tcgaaggctt ccggggttc gccctgccgg atgaaggcca gggccgcaag    33540
gttcgcgacc agtgcgcaca tcgtcatccg atcagccggg gagatcacat accggctctc   33600
cgcgtcacac gcgcggtgcc gcaggcggtc gaggatctcc agcgcccggc tcggctcatt   33660
ccgtcgcttc agcacgaatg ccgcgagccg cagctcggcg agcatggaat ccacgatggc   33720
aggcgttgcc tcggcagcgc ggacgaagag ctcctccgcg tcgaaaaccg agtcggcgtc   33780
ggatgccatg gccgccgccg cgtagagcag ggcgacatgc gtgccgagcg gcttggcggc   33840
agagagcaca gccgttgtca gctcacgcgc catcgaccag tttccggcga aacacacgtg   33900
cgcgtcgatg agagcgcaga agtcatactc ccggtactgg ccgtcggccc agcgggtggc   33960
ccattcgctc ggcttcatcg gctggatcga gtcgtcggcg tgggatgtga ggtcctggat   34020
gcgtaggtgc ccgtcaagga acgcggccgc ctcggtcatg ccacgaacac ccagatcagt   34080
caggtaattg gtctgcacgg gaaggcgggt gtgcggcagt ccgggcagtg ccgccgacct   34140
ggccctttcg accagaccgt accgtgcggt cagcgtgccg caggcttccg cgtcgagaat   34200
```

-continued

```
cgtcctggcg gttcgggtcg cccagaagac gtcattcgtg ctgtccatcg ccattcctgt    34260
cgggtatggg cggcggcgcc tgtccgggcg ccgccactgg tcatcgagcg tcgttacctg    34320
ggcccgtgct tccagccgcc gagcaggccg ttgatcgtcg cgtcggctga gtccagctcc    34380
gcgacgatct ggtccggcgt gaccgtcgag gagtccgtgc tctgcgcgct tgcgacgcct    34440
gcggccgtca gcaacgacgc cagcgccgcc gcggacaccg ccgcggtctt cacgagaaca    34500
ttcttcatgc acgtgacctt tctctgattt cgtttcacac acccacagcg aaacggtgga    34560
catcaaggaa ctacttccgt cgagcgattg tgagcccgtc accgatgggc agcatcaccg    34620
gctcgacacg gtcgtccgcg agtacgtgct cgttgaattc gcgcagcgca ctgccactcg    34680
cgttcgacgg gtcgtcgtcg acaacgccac caaagccgaa gacgttgtcg acaacgatca    34740
gtccacccgc acgggtccgc gggacaagct cagtccagta ctggacgtat tcgtccttgt    34800
cggcatcgac gaaggcgaga tcgatcgtcc gccggcgcgg gagttcgcgg agcgtgtcga    34860
gggcccgccc cagtttcacg gtgatgaggt gcgccacgcc cgcccgctcc ccgaatgggc    34920
gcgccaccgc gatcgcggcc gaactcgcct cgcaacaaag caagcgccct tgacgtggca    34980
ttcccctggc aatggccatc gccgaatatc cggtgaaggt gccgacctcg accgcgaatc    35040
tgacctccgc cgtccgtgcc agcattgtca gcagtgctgc ctgcagcggc gtgacctgca    35100
tacccgaata ctccggacaa acccgccttg ttgtggcgat gagatcccgc tcgacctcat    35160
ccatcggcgt actgtgatct gccgcgtacg tgaccaggtc agcacgcacg gcgcccgact    35220
ggtgcaccga gtatcaaccc cccgactcat cgatgtcagt gagtttccga caacgaccgt    35280
aaaaaccatg acaggagccg cttgcggttt tcttccgccg atcgccgtga aatgaggaga    35340
agccgcgtga cgatgccggt ggacgagctg atcaagccag gtggtgctgg aaagcagaac    35400
gcgagcgggg gttagggtcg cagcgtggca gagactgagc cgttctcggt gaagaagttc    35460
gtcgcggggc tgagccgcaa gcggatggcg tcagggatgc tgttccggga cgacaccggc    35520
cgtgtccttc tggtggagcc ctcctacaag gagcagtggg agatcccggg cggtgcggtc    35580
gacgagaacg agtccccatg ggcgacggtg tcccgcgagc tgaccgagga actgggcatg    35640
cggcggcccg tcgggcgcct gctggtcgtc gactacgtcc acccggaggg cgactggccg    35700
gaggcggtga tgttcgtgtt cgacggcggc gtcctggcac agtctgatgt ggacgcgatg    35760
gtgttcgccg acggggagat cctctcggca ggcttctacg acctcgcgga agcccggaaa    35820
ctgctgaagc cgcggctcgc cggccgggtc gaggccgcca tctccgcgct gcggcagggc    35880
acgacggtcc tctgcgaaca cggccgccag atcacttagg cgcacctccc cggatcctca    35940
ccacgcgggc cggctgaaaa ccgggtgcgg acggcgggcg cgctggtgtg tgatcaaggg    36000
atggcgatcg tgatgggcaa gccgggagtc gacgggctga gcgcggctgt gggcgtgctg    36060
cgggaatggc agtacgaggg ggcgccgatg caactgcatc cgggggacct gggctggttc    36120
tggcggttcg gtgcggaggc gacggccgcg cggtccgga cctggagccg ggacggacag    36180
attctcgccg tcgggctgct ggacggtccc gagctgttgc ggctgacgat cgcgccggac    36240
gtccagcagg acgaggagtt ggcccagcaa ctggttgagg acgtgactga gccggagcgc    36300
ggtgtcctgc cggcgggaaa ggtgttcatc gaagcgccga tgggcgtgct ggtccaagat    36360
ctgctgttcg agagcggctg gaaggtcgat gagccgtgga cgccactgcg ccgcgacctc    36420
acggaaccgt tgaaggaccc aggcgtgcgg atcgaggtga tcggaccgga gcaggtcac    36480 gtgcggaccg ccatacagcg ggcatcgttc gacagttcga cgttcacaga cgagcgctgg    36540
```

```
cacgcgatgg cggccggatt gccgtacgcc gacgcccggt gtctggtcgc gtacgacgac    36600
cagggcaacg gggtggcggc ggcgacagtg tggtcagccg gtccggggaa gcccgggttg    36660
ctcgagccga tgggcgtaca cccggcacac cgcggccacg gctacggcaa ggcgatcacc    36720
gtcgccgccg cggccgcact ccaggagctg ggctcgtcga gcgcgatcgt ctacaccccg    36780
agccgcaatg tcggcgccgt cgccacctac aagtcggcag gcttccagca gcgccctgag    36840
atccgggacc aatgccggga ctagtcgagt tggcgaaca ccagcacagc ggcttgatca     36900
cccgcgcgaa cgggaatcca cgcctcggtg aggtcgtcca gccggtcgaa gtcgaggctc    36960
agcaggacgc gtgcgtcgga gtcgccgtcg ggcacgaagt aggcgacctt ctcccggacc    37020
aggcgctgca ggtggtccag gtcgtcgacg gtccagttga ccggtggccg cccggcgaac    37080
cggccgaaga agccggtgaa cggcgtcgcc cggccgacca cgacgaggta gccctcaagc    37140
gacttccgca ggcacgcaag accccgcac tggttctcgt acacgacccc ggtcggcgcc     37200
ggcacgatca ggcacagcac ctcggggacc gcgtcatgcg ggttgaaatc cacgcgtacc    37260
tgcatggact caagcgtaac gccggtacta catgaggcgg acgggctctc ccatggccac    37320
gacgatctcc cgaggaccct tgtacggctc gacggcgtgt gccatccgga tgttgtcgac    37380
cagcatgaga tcgccgtcct gccatggctc acggatggtg tgggcgtcgt agacagcgtt    37440
gatggcgtcg acgctctcgc ggtcgagcgg cgtgccatcg cctgcgaagg tgttgaacgg    37500
caggccgccg tcgagcgcca tggtcaggta gtcccgacg tccggatcca tggtccactc     37560
gttcaggaac gcgatctggt tgaaccagcc aggacgcccc gaaaccgggt gccggacgac    37620
cgcagggcgc gtctgagtcg tccgcaggct gccatccggc ccccagttcc aggaaatccc    37680
gtgggactcg caataagcct ccacgacgtc cttgtcggca ctgccgaagg catccgccaa    37740
cggaacgccg accagcgggt tgtagttgcg gaccaactgc cacccgtggc cggagaaccg    37800
ggagaccaag tccgcgggga ggtcgtcgag cacagcctgc gagtcggcca atgccgtcac    37860 gccaccgaa gccggtgccc gcaaacaggt gaaggccagc acagtgggca catcgggcac    37920
gtagctcagt tcgtggtgca tgcacatcgg ctggtccgac ggccatttgg tggacgagta    37980
catgccctgc tcgagcgagt cgcgtggggc gaagccctcg cgctcgacga cgaacgagtc    38040
gatcaaggcg tggctgacgg ccgcggccgt ggacacgtcc gcgattccca gaccacgcac    38100
cagaacagcg ccatcggtgg cgagcagtga gcggagttcc gcacggttcc cggccgccca    38160
ggcagccggg tccgttgtgg acactgagag gatcttcacc ggtcaccctc cagtcgggta    38220
gcggccaggc tgaggtacac gtcgtcgagc gtgggctccc cgatggcgag ctcggccggc    38280
tcgatcaggg cgtcgtccag tgcccgcacc acgatcgcga ggtccgcgga ccggtcgacg    38340
ggcgcggtga tcgtcagccc gtccggtccc gcggtggcgg tcagaccggc gcgccgcagt    38400
gcgtccattg ccggggtggt gtggttgacg tcggacaacg tcacggtcgc ggtccgcttg    38460
cccacggtcg ccttgagctc cgccgttccg ccggtcgcca ccaccttgcc cgcggacaac    38520
accgtgatcg tgtcggcaag gcggtcggct tcctcaaggt actgggtggt cagcaggacg    38580
gtcgtgccgt cggcgaccag cttctccacc gtctcccaca ggccgagacg actgaccgga    38640
tccagtccgg tcgtcggctc gtccaggaag atcacctcgg ggttgccgac caggctcgcg    38700
gccaggtcca gtctgcggcg cattccgccg gagtagtgct gcacctgttt gcgtgccgcg    38760
tccgtgaggt cgaacagctc cagcagatcg tccgcgcgcc ggaccgcctc acgcttgccc    38820
gcgcccagca gcctggcgat gagcacgagg ttgtcccgcc cgttgagctg cccgtccacc    38880
gaggcgaact ggccggtcaa gccgatccgg gaacgtacct gcctgccctc gctggccacg    38940
```

```
tcgtgcccgg cgaccctggc ctgcccggcg tcgaacggca gcatcgtggt gaggacgttg   39000
accattgtgg tcttgccggc gccgttgtgc cccaacagac cgagcacagt tcctcgcggc   39060
gcctcgaggg acacgccgtc gagcacggtc acgtcaccga acttcttgct gacgtcccgt   39120
gcgtcgatca tcaactcggt cacagacaaa gcctatgagg tccgggaccg tagatctcta   39180
gcgaaaaacc cagaatcacc accggtgccg cagttcggcc acctcgtgca ggacgtccgg   39240
gttcccggcg aacacgccac tttcccgtgg ccagtgcaca acgaggtgcg tgatgccggt   39300
ttcggcgtac cgttcggcca tgtcccggca ggcccgcgaa gacttcagcg gatcaccggc   39360
acgcggagtg gcgatgaaga tccggtcgat ctcggtgctg tcccggcccg cttgagcaca   39420
cgccttgtcg agcaactcgt tctggacggc gacctgcgcg gcgacttcgt ccggcgagat   39480
gtcggtcgtc caggccgccg ggccggtcgt gatccacttg gtcccgtagc gggcgacgag   39540
atccatgccg cgtggcccgg tcgccgcgat cgccagcggg acgcggatct ccggcagcat   39600
cagggcctcg gacacggcgt agaactgccc ggagtacgag gtggccggat tgttcagcag   39660
ttctgacgtc agctcgacga actccgcgaa ccggttcgcc cgtgtgcgct gggacaacgg   39720
agcggagtcg agcacggtcg catcggtcgt gcctggtgaa cccgctccga caccgagcac   39780
gaaacggccg cctgagatgt cctgaacggt cgccgcgtcc ttggccagca cggccgggtg   39840
ccggaggttc ggcgtggcga ccatggtgcc gatctcgatc cgccttgtcg ttgccgcgac   39900
ggcggaaagc actggtacag cggagaacca cgggccattg gtgcgccacc acaagtggtc   39960
gtaggtccag gccgagtcga agcccagctc ttcggccgta cgccaccgtt cgacgttgtc   40020
ctgccacgac agctcaggca ggatcacgac tcccaaacgc atgcgggcct tcccctcatc   40080
gacacatcat tcgcacggca gctcagccgt gatcacggtg cgcgccgagc aggatcatca   40140
gcagcacacc cgcgccgagc ccgccggcca tccaccgcag cgcgagagac cggacagcca   40200
ggaatcccgc ttcgacgact gcggtcgcac caccgagggc gactccgaca gtcggacggc   40260
aggcacgaag cgctaactca cgccggagaa aagacaccgc gcagtgtatc gaccaccccg   40320
caagcgaaat tcactaccgg ctcgtcaaca ccgccttcat cacgctgccg ttggcgacat   40380
cccgcaacgc ggcgccgtgc tcggcagcg ggtacgtggt caccaggctg gccaggtcga   40440
atcgtgcggc cagcgcgggc agcagttgta cgtactcgat caggtgcgcg ccggtgaacg   40500
cccacgatcc gatcacgtcg agctgccggt acacgatctg gtgcgggttc acggtcgcgt   40560
caccgctgtc ggtgtactgg ccgacgacga gatacgaccc gccacgccga gcgaggcgca   40620
gaccttcacc gaacgcggac ggcacaccag cgcactcgat caccaggtcg gcgccgccac   40680
caccggtgag ctcgaccacc tcggccagcg cgtcccacgt ctccaccacg ttcacgtggt   40740
ggtcgccgat ccccgcctcg gcggccagct tgagccgatt cgccggacca cccgcgagga   40800
tcaccttgcc agcgccggag atgtgcgcca gtgcggccgc ggccaagccg accggcccgc   40860
tgccttgcac gacaacggtt tcacccagcc ggaccggcct cgttcgaac aacgcgtgca   40920
ccatcgtcgg acccgcacag gcgaacgaca tcgcggcgac cggatcgatc ccgtccggca   40980
ccttgatcac ggtggtgcct tcgcgcagca cgatgaagtc ggcccatgac ccggaaagtg   41040
cgggctcggc ggtggtcggc cggttgacac cgtacgtctg acggttggtg cacaacgtcg   41100
gctcacggta cgaccggcac ggcacacacc gtccacacgc gatggaagac gcccacatga   41160
cccggtcgcc gacgttcagc gcctgcccct tggcgtcagt cgcggtggcc agttcgacga   41220
tggtgccgaa tccctcatga ccgagcacca acgggaccgg aacgtcgaga tgcccctgct   41280
```

```
gcaggtgcag atccgtgccg cacacgccgc cgtactcgct cgccacgacc atcccgccgg    41340
gcggtgcctg cggcaccggg aactcccgca gccggaggtc acggccgaac tcggtgagca    41400
ccaccgcgcg cccgttcacc gggcggcgcc cgcggcaagc agcggttcgt cgacgatctc    41460
cagtgcggtg gtgtcctgct cgaccaggta ccactcgcgc ggcgcgccca gcggcacgtt    41520
cgtgctgtcg ttgtacgtca ccagcagcag ccgcctgctg aacggtgaca tgttggtggc    41580
cgagccgtgc acgatctccg ggtcgaagaa gatcaccgac ccggcggcgc ccttggggct    41640
gtccatgccg caccgccgga caaggccggc catctcggtc gtggtcagct ggatgtcatc    41700
cgggtcgagg tgctgcatgg acttcatcgt gccgctgcgg tccgaccgga tcaacccgtg    41760
ccggtgtgag ccgggcacga acatcagcgg cccgttgaac tcggtgacgt cgtcgaggaa    41820
cagcccgacg ttgaccagcc tcggctcggg caggctgtcg gcgatctgcc acgcggcgaa    41880
gtcctggtgc cacgcccagc cgccgccgac gaacgcgggc ttggcgttga tcttgaactg    41940
gtagacgtac accttgtcgg tcagcaactg ctggaccggt ccgagcagcc tgggggagcg    42000
gaccagccgg gcgaactccg gttgccgtaa gtgcgacgcg tagatcgcgc gcacgtcctt    42060
gccgtcgttc tcggcgatcc gctgctcacc ggggatctcg ccgtcccgca cgaacgcgtc    42120
gcgcagcgac tcgacctcgt cggtgttgaa cagccgctcg acgacgaggt agccgttctc    42180
ccggtagctg ttgatctggt cttcggtgag aatcatcgtt cttccttcag ttcaccgtga    42240
aatggatcga ctgggatgcc gtcgtcagca cgtcgaccaa gtcctcccgg ctcggcgcgg    42300
tggcgatgac gtacccgagg cggccgtacg cgtcgactgg cggagcgacc tcgcggcccg    42360
gcttcgtggt cacgatcacc tgctgcacgc cggccactgc cttcgcgcgc tccacgccgg    42420
agatctcggt gagcacgccg gtgtccggcg tggtcaggaa ctggatcccg gcgaagcagc    42480
cggtgcccga cggcaccgtg acgggcagcc cgcaggcctg cctgacctgc tgttcgagca    42540
ggtcgacgcc gctggcgagg cggatcagct cggggatcat gccgccggcc agccgtgggt    42600
tgatctcgat gatgaccggc ccggactcgg tgatcttgac ctcggtgtgg ctcgcgcccc    42660
tggtcagccc ggccgcccgc aacgcggcgc gcaccacgtc ggcgacctgg ccggccacct    42720
cctctggcac ggacgcgggc acgatgtgcc gcgactccac gaaattcggc gcacccatca    42780
ccgatttccg caccatcgcg accagttcgt ggtcaccgtc ggccgcgaac atctccacgc    42840
tgtactcaag gccatccaca taggactcga tcagcgcgcc gcgagcccgg ggcatgccgc    42900
ggacgttcgt cgtcacggca aggaccgcct cgaccgcgtc gagtgcctgc tcggccgtgt    42960
cgcagcggac cacgccggtc gacccggact cgtcgaccgg tttcaccacg cacggcaatc    43020
ccaccttgtc caccgcggca gccacttcca aagcgttgtc gaccagcacc cacaacggtt    43080
gcggcaaccc cgccttgtcg aggcgatcac gcagcctggc cttgtcacga cagccgtcga    43140
tcgcctccgg ccgttcggcc ggcagcccga actcggccgc cagcctcgcc gcggtggaca    43200
ggtagaactc gctggtggtc gtcaccgcgc tgatccggcg gcgcggcacc tgcgagtgga    43260
gtgccgcggc cagcgcaccg ggatctccgg tgtcgcagcg caacacccgg catccggtct    43320
ccggcagtcc cagataccgt tcgggcttgt tcgtcaggaa aatcggctcg tagccgaggc    43380
gctgggcgat gccgatcgcg gccatcccgg tgccggtcgt gttggactcc acgaacgcga    43440
gcaccggccg ggccgtgtcc gggtcggtca gccgggtgaa cgcccagctg tgcaccaccg    43500
tgccgggcgg aacctgacga ggccgcgtgg ccaacggttg atcgggcagg ccgcgttcga    43560
cccagtacgt cttgttgtgc acggtctcgg catagcgatc gccacgatcg gggaagatcc    43620
cgacaatggt cgtgccaccg ggctcgtgct cggccaggtg cgtcatcacc cggtacaccg    43680
```

```
agccggacgt gttgcccgcg aacagtttct gctctcgtgc caacgcgacc gacgcctcga    43740
aggcctcccg gtcgttgagc cagtgcacct cgtcgatctg gccgtgatcc aggttcttcg    43800
ggtgcatgct gttgccgagc ccgctctgca gccgttgcgg ccagtccggc tgtccgaaca    43860
ggacactgcc gacgcagtcg atgccgacca cccgcaggtc gggcagggtc tcgcgcagcg    43920
ctcgtgccgt gccgcacaac gatccgccgc tgccgaccga gccgaccagg atgtcgatcc    43980
ggccaaggtc gttgaccagt cgccggcca gtgtccggta tgccgccggg ttgtccgggt     44040
tctcgtactg ccgtggccag aacgagccgg ggttggcggc catgatctcg gccagccgct    44100
tgagccgggc gccctgccag ccgtgctcgt ccatctccgg cacgacatgg acctcgcagc    44160
ccagcgactc cagtttggcc agcgtgatcc ggtcgatccg cgggtcggtg acgatgtgca    44220
ccgggtgccc catgagcgtg ccgacgagtg ccacgcccag cgccatcgtg ccggacgagc    44280
tctccacgat cggggcgccg tcggccagtg caccgctttg cttggcgcgc agcaggatgt    44340
tgcgggccac ccggtccttc atcgcgaaca ggttctggat ctccagcttg gcgtagcagg    44400
caggcgcgtc cgcgccgttg ttcagcgcca gccggacgag cggggtgttg ccgatggcgt    44460
cgagcaggtt ctcactgatc acgcgctggc ctccgggaga tgggtcgatg cttcggtgag    44520
cgccttgagc agccggtctg tctcggcgta ggcctcggtg atccgggcac ggcgggtggc    44580
ccaccgccgt tccgccaggt cgaacgccgc cgcct                              44615

<210> SEQ ID NO 3
<211> LENGTH: 37049
<212> TYPE: DNA
<213> ORGANISM: Artificial Sequence
<220> FEATURE:
<223> OTHER INFORMATION: DFD0097-388

<400> SEQUENCE: 3
cgcgctgcgc gccgcgctgt tggacgtggc ggtccggcac gagtccctgc gaacggtctt      60
cgcggaggac gacctcggcg cacgtcaggt cgtgctgccc gaacaggctg ctcggcctgc     120
gatgacggtc gtggagacca ccgagcccga gctgcggacg cggatggacg aggccgcggc     180
gtaccggttc gacctgggcg ccgagccgcc gctgcgggcc tgggtgttcc ggcttttccca    240 gaccgagcac gtgctgttgg tgctgacgca ccacatcgcc agcgacggct ggtcggtccc     300
ggtgctgatg cgggatctgg ccaccgcgta cgcggcacgt cgtggcggcc aggcaccggg     360
ctgggcgccg ttgcccgtgc aatacgccga ctacacgttg tggcagcacg aaatcctcgg     420
cgccgaggac gatcccgcca gcgagttcgc ccgtcagatc ggctactgga agaccacatt     480
ggatggtctg cccgcgcaac tggacctgcc ggccgaccgg ccgcgcccgg cggcaccgtc     540
acaccgtggc ggcacggtgg agttcgatgt ccccgccgaa ctgcacggtg cactggttgc     600
gttggcacgt cagcacaacg cgagtgtgtt catggtcgtc cgtgctgccg tggcggccct     660
gctgaaccgg cttggcgcgg gggaggacat cccgctcggc acggcgatcg cgggccggtc     720
cgacgacgca ctgcacgacc tggtcgggtt cttcgtcaac accttggtgc tgcggaccga     780
cctggcagga aacccgagct tcagcgagct ggtcgaccgg gttcgtgagg ccgacctggc     840
cgcgtacgcc aaccaggacg tgccgttcga gcgcctggtg gaggtgctca gcccggctcg     900
gtccatggcc agccaccgc tcttccagac catggtgacc tggcacaaca ccgaccgtcg     960
cgccgccgtc gaggcacaac gcgacctgcc tgggctggcc gtcagtccct atgaggtgcg    1020
gaacgtgtcg gccaagttcg acctggcgtt ctccttcacc gaaggcacgg gaatcagcgc    1080
```

```
cgagctcggc tacagcgccg acctgttcga ccgggccacc gccgaggcct tcgcgcagcg   1140
tctgcttcga gtgctggaga cggtcgccgc ggacccggac gttctggtga gccggatcag   1200
cctggtcacc gaggacgagc gtgacctggt gctgagggcg tggaacgaca ccgcgcaacc   1260
ggtggccggg accacgttca ccgaactgtt cgccaggcag gcccaggcca cgccggactc   1320
cgtcgcggtc gagtgcgacg gccggaccct gacgtacgcc gagttggaca cgcggtccaa   1380
ccagctggcg cattacctgg tcagcaacgg ggtcgggccg gagcggttcg tcgcgatcgt   1440
catgaacaag tcggtggaca tggtggtcgc tctgctcggt gtgctgaagt cgggcgccgc   1500
gtacgtgccg atcgacccgg cctacccgcg cgatcgcatc gagttcatgt tctccgatgt   1560
ggcgccggtc ctcgtgctga cttcacggga tgcggcctcg gcattgcccg agtcggacca   1620
cgtgttcctc caggacgtcg atttggccgc ctacccggac gccgccattt cggaggcgtg   1680
cccggccaac ccggcgtacg tcatctacac gtctggttcg accggacgcc cgaagggtgt   1740
ggtgatcgag caccgggcgc tcggcgccta cctggaccgc gcccgcgagg cgtatccgtg   1800
gatgtccggc accacctggg tgcactcgcc gatctcgttc gacctgacgg tcaccggcct   1860
gttctcgccg ctggtgagtg gtggccgggc gcggctggtg gacctcgagg gtggcgcggc   1920
gacggggag cggccgtcct tcgtcaaggg cactccgtcg cacctcggtc tgttggacgt   1980
cctgccggac aacgcttcgc cttccggcgc gctgatgctc ggcggcgagt tgctgatcgg   2040
tgacgtgctg cagcgctggc gggaccgcaa ccccgatgcg gtcgcgttca acgtctacgg   2100
cgccactgag gcgaccgtga actcggtgga gaaccggatc ctgccgggca cgccgattcc   2160
ttcggggcg gtgccggtgg gcacaccgtt ccgcaacacc cggatctacg tgctcgacga   2220
gagcctgcgg ccggtgccgc cgggtgttcc cggtgacgcc tacatcgcga gcaccggtct   2280
ggcgcgtggc tactgcgac ggttcgggct gaccgcggaa cggttcgtgg cctgtccgta   2340
cggcgagcca ggcgagcgga tgtaccgcac cggcgacttg ttgcgctgga caagcaggg   2400
gcaactggag ttcgtcggcc gggcggactc gcaggtcaag gtccggggct tccggatcga   2460
acccggcgag gtcgagtcgg cgctgacgcg gtgcgacggc gtgagccggg ctgtggtcgt   2520
ggtccgcgag ggccggctgg tcggctacct ccttggcgat ggcgtggacc cggagacggt   2580
ccgggcgacg gcggcagagc tgttgccggg ctacatggtt ccggccgctt tcgtggttct   2640
cgacgagctc ccgctgacgc caacggaaa gctcgaccag cgggcgttgc ccgcaccgga   2700
cttcggtgcc gcgaccacgg ccaccgcacc gcgtgacgct gtggaggaac tcctcgccgg   2760
actgttcgcc gaggtcctcg ggctggaaca ggtcggcgtc gacgacgggt tcttcgacct   2820
gggcggcgac agcatcatgt ccattcagct ggtcagcagg gctcgtcggg cgggtttgac   2880
gatctcgccg cgtgacgtgt tcgaccggca gacggtcgcg ggccttgccg ctgtggcaaa   2940
ggcttccgat gcggtgacgg tcgaggaacc gggtgcgggg atcggcgagt tcccggcaac   3000
gcctgccatc gcgcgattcc tggagagcgg cgcccaggtc gaccagttca accagagcgt   3060
cgtcgtgcgc gtgccgtccg gacttggcga ggaccggctt gtggccgccg tgcagaagct   3120
ggtcgaccac cacgatgccc tgcgtactca tctcaactcg gtgctgtcgg tgagtgcacc   3180
gggcacagtg gacgcacggg acctcgtgtc ccgtgtggac gcggccgggc tcgacgacga   3240
agcactggtt ccggtgatgt cggagcacgc cgtcacggcc cgtctgaggc tggcgcccgc   3300
cgacgggaag gtcatccagt tcgtctggtt cgaccgcggt gacctgccgg acaactcgt   3360
cgtggtcgca caccacctcg tggtcgacgg cgtgtcctgg cgtgtgctgt tgccggatct   3420
cgcactggca tggcagggcg aagaactggc acctgtgggc acttcggttc gccgctgggc   3480
```

```
ccagcgcctg accgagctgg cccgacgttc gtccgagttg gggctgtgga ccgagatcct   3540
cggtgacccg gaaccggttc tcggttcgcg ggcattggat ccctctcggg acaacgcttc   3600
cacggcacgt cacctcacca cgacattgcc ggaggacgtc acaggcgaca tcctcacgac   3660
cgttccgtcc gctttccacg ccgagatcaa cgacgtgctc ctggcgacct cgccgtggc   3720
gttcgacgaa tggcgcggcg ggagcgtcct gatcgacctg aaggccacg gccgcgagga   3780
acatctgctc gacaacgtgg acctgtccag gaccgtcggc tggttcacca acctgtaccc   3840
agtccggctg gatcccggta cgggcgacat cggtgacgcg ctgaagcgga tcaaggagca   3900
gttgcgcgcg gtcccggaca agggcatggg ctacggcctg ctgcgctacc tcaacccggg   3960
caccgccgcc cggttgcgtg aactgcctgg cgcccaggtc aagttcaact acctcggccg   4020
ggtcggcaac gcggaatcag gcgactgggc accgggatcc ggcatcaacg cgtcggcgc   4080
cggtcgcgac ccgcgccatc cgttgtcgca cgcactggag gtcaacgccc ggacgctcgg   4140
gccggaactc gtggtcagct ggacgtgcc ggacgaggtc ctgagtgccg acgaagtcac   4200
gcggctgaac gagatctggt tccgggcact gcggtcgctg acccagtcga cagccggtgg   4260
cctcaccccg tcggacgtct ccttggcgga actcagccag agcgagatcg acctgctcga   4320
atcggaatgg acggactagg cgcatggcac gatccgacat cgcggacatc ctgccgctga   4380
ccccgctgca ggaagggctg ctgttccaca cgctctacga cgagcaggcc cgtgacgcct   4440
acctcggcca gcacgcgttc gagctggacg gggagctgga cgtcgaagcg ttgcgcgccg   4500
cggcggaggg cgtgttgcgc aggcacggaa atctcagggc ttccttccgg tacaaggggt   4560
tgagccggac cgtgcaggtg attccccggc gggtcaccgt tccgtggcag tacatcgacc   4620
tgtccgaccg gccggaggag gctgagcggg tcaccgcggc ggaccgcagt gcgcggttcg   4680
acgtcaccaa aggcccgctg ctgcggttca cggtcatcag gctcggggcg cgtcgtcacc   4740
tgttcctgct gacgtatcac cacatcctcc tggatggctg gtcgaccccg ttgctgctgc   4800
gtgagctgat gacgctgtac cagagcaagg gcgatccgtc gtcgctgccc gcggtccggc   4860
cgtacaagga ctacctgggc tggctgtcca acaggacgt ttcagtgcc gggcaggcct   4920
ggcgggaagc gatgtccggg cttgcggagc cgactcgtgt cgccagtgac ccgaacgcgg   4980
tcactgtccc ggagatgacc gagttcgcac tggacgatgc cgtgtgtcag cgcctgcgga   5040
cgcggggtgt caccttgagc acggctgtcc agtgcgcgtg ggcgttggtg ctggctcagc   5100
tgaccggccg tgacgacgtg gtgttcggca tgccggtggc tggtcgcccg ccggagttgc   5160
cgggtgtcga gcagatgatc gggctgttca tcaacaccgt gccggtccgg atccggttgc   5220
gcccggccga acgctcggc gagctgttgg cccgggtcca gggtgagcag gccgctttgc   5280
tgccgtacca gtacctgggg ctctcggaga tccagcgcgc gtgtggcatg ggtgagctgt   5340
tcgacgcctc gatggcgttc gagaactatc ccgtgtcccc ggacacagtg gacagtccgc   5400
gtggtgacgc cctgcgggtg cgcaagaggc gtggcgtgga caccgggcac tacccgttga   5460
cgttgatcgc ggtgtcccgg gccggcctga ggttccggct caaccggcgg cctgacgtcg   5520
tgcctggcat ggacgtggcc gacctgcttg tgcgcaccct gacagccatc gcggaccagc   5580
ccgatctccg gctgcccaa ctgcctccgg ccgctgaggt gcggcacgtc actcccgacg   5640
gcacgcctgg ggttgtttcg cgtgacttcg aagaggtggc tcggcaggca cctgacgcca   5700
tcgcggtgac gttcgatgcc gggaagctga cgtatcggca gctggatcag cgcgcgaacc   5760
ggttggcacg ttcgctgatc tcgcgcggtg tgcggcgagg tgacttcgtc gcggtggcgc   5820
```

```
tgccacggtc ggctgacctc gtggtcgcct tgctcgccgt gctgaaggcc ggtgccgcgt   5880
acgttcccct ggatctcaag aatccggccg cgcggaccga tgcggtgctc gccgatgccc   5940
gtcctgccgt tgtgctgtcc gaagtcggtg atcttgagga cttctccggc gatgttctga   6000
cggatgcgga gatcggcggt ccgctgacgc cgaacgatgc cgcgtacatg atctacacct   6060
cgggttccac cggtgtgccc aagggcgtgc tcgtcgagcg ggggtcgatc gaccggatcg   6120
cccgcggcat ccctggcgtc gaactgaccg ccgacgatgc cgtcgcccag ttggccgcgg   6180
tcgccttcga cgcgacgaca ttcgaggtgt ggggcgcatt gctgaacggc gccacgctgg   6240
ccgtcgcgcc accgtccgcg ttgtcggtag gcgaactgag gaccttcctg accgacgccg   6300
gtgtgaccgc actctggctg acggccggac tgttccacga ggtcgtcgag caggacatca   6360
cggccttgac ggggttgcgt tacctcctcg caggtggcga cgtcctgtcg ccaagcgctt   6420
gctcggccgt ccgtgccgtg tacccggatc ttcggctgat caacggttac ggcccgaccg   6480
agaccacgac ctttgccgcc acgcacgcgg tggatgcgcc ggacacgacc gtgccgatcg   6540
gtgcgccggt gaccgcgact cgtcttcacg tcctggatgg ctggctgcgg ccggtgcctc   6600
cgggcgtcac aggggagctg tacatcgcag gcacaggctt ggcgcgtgga taccacgatc   6660
ggcgtggatt gaccgcggaa cggttcgtcg cttgtccgtc cggtgggcgg atgtaccgca   6720
ccggggatct cgtccggtgg aactccgccg gtgacctcga gttcctcggc cgcgtcgact   6780
cccaggtgaa ggtccgtggt ttccggatcg aactcggcga gatcgaggcc gcgttggtcg   6840
cgcacccgtc ggtggacgcg gcggcggtga tcgtgcggga ggaccggccg gatgacaagc   6900
ggatcgtcgc ctacgtgcgt cccaccatcg atcccgttgt gctgcgggcg catctggcct   6960
cgatcgtgcc ggacttcatg atcccggcag cgttcgtgcc ggtgacgcag ttcccgctga   7020
ccgccaacgg aaagctcgac cgacgagcct tgccggtgcc ggactacggc gacggccggg   7080
cacacgcggc ggcacggtcc ccgcgcgagg agatcctgtg tgagatcttc gccgacgtgc   7140
tcggtgtcga ccgggtcggt gtggacgcca gcttcttcga tctcggcggc cattcgctgc   7200
tggcgactcg tctggtcagc cgggtccgca gcacgctcgg cgtggagatg tccatccgcc   7260
ggctctacga ctcgcctacc gtggctgggc tgtccgaggc cctcgatgcc ctggcaggcg   7320
cccggacccg ggtgaccgcg gttcaacggc ccgagcgggt gccgcttttcc ttcgcgcagc   7380
agcggctgtg gttcatcgac cggctcgaag gccccagccc cagctacaac gtgccttcgg   7440
cgttgcggtt gcgtgggccg ctcgatgtga cggccttgct ggcggcgctc agggacgtga   7500
tcacgcggca cgagtcgttg cggacgatct acgccgagga ccagcacgga ccacaccagg   7560
tggtgctcgc cgaattctcg acaccccttg ccgtcatgga cgtgacgcag gacgagctgt   7620
ccatggccct gtccggagcc gccaggtact cgttcgacac cgcggccgaa atccccatcc   7680
gggccaccct gttccggctc ggccccgagg aacacgtgct gctgacggtc gtgcaccaca   7740
tcgcgaccga tggctggtcg atgccgtgc tggctcgtga cctcgcgcac gcgtacaccg   7800
cgcggcacgc cggtcacgca ccgggctggg ctccgctgcc ggtgcagtac atcgactaca   7860
cggtgtggca gcgggaagtc cttggttccg aggacgatcc ggacagcgtg atctcggcgg   7920
aactggcgta ctggcagagg accctggccg ggcttcccga ggagatcgcg ctcccagtgg   7980
accggccgcg tccgcgtacg gccagctatg cgggcgacgg aatccgcttc gccatcccgc   8040
ccgagctgca tgggaagctg gcctcgatcg cccgtaagcg gcacgtcagc ctgttcatgg   8100
tcgtccaggc cgccgtggcg acgttgctgc accgcctcgg cgcggcgag acatcgcgc   8160
tgggcagtcc gatcgccgga cggaccgacg acacgctgga ttcactcgtc gggttcttcg   8220
```

```
tcaacacgtt ggtgctgcgc aacgacttgt ccggcgatcc gtcgttcgcc gagctgctga      8280
cgcgggtcag ggacaccgac ttggcggcgt acgcgcacca gaacgtgccg ttcgagcgct      8340
tggtcgaggt ggtcaacccg gagcggtcgc tggcccgtca cccgctgttc caggtgatgc      8400
tcgcgtacaa caacaccgac ttcggcactg cggacgagcc ggcttccggc ctcgtgatca      8460
gccaggaacg cgtcgacacc ggtacctcga agttcgacct gctgttcgcc ttcaccgaag      8520
ggcaaggcgg cgggttgcgt ggcgaactcc gcttcgccac agcgttgttc gaccgggcga      8580
ccgcccagtc gattgtggac cgtctgctgc tggttctcga ttccgttgcc gctcagccgg      8640
acttgcccgt gtccgcggtg aacgtcctgg cggagcacga gcgggatctc gtggtcgacg      8700
gcggcgcccg gcaggtgcct tcgtcacctg tgcctgcttt gttcgaacag caggccgtgc      8760
tcaggccgtc cgcggtcgcg ctggagacaa gttccggcac gctgacgtac gccgagctca      8820
acgagcgggc caaccacctg gcgtggcacc tgatcgccca ggggatcggg ccggaccacc      8880
tggtcgccgt gctgcttccg cgtggcgagt ggcttgcggc ggccatgctc ggaatcctca      8940
aggcaggcgc cgcgtacgtg ccggtcgacg tcacctaccc ggaagaccgg gtcgccgaga      9000
tcctggcgga cgcttcacct tcactcgtgg tgagcaccgg gtggcccgcc ggtcgttcgg      9060
acaacccgcc gtacaccgcc gatgacgcga accgtcgta cgtgatctac acgtccggat      9120
cgacagggaa gcccaagggc gtggtgatga ccaacctcgc cctgcgcaac ctgctggcat      9180
ggcattcgtc ggcggtgccc ggcgaacccg gcgaccgggt ctcgcagttc acggcggtga      9240
gtttcgacgt gtcggtgcag gagatgctgt ccaccttgac cactggcaag accctggtcg      9300
tcccggacga ggacacccgg cgcgatccgg cgcagctcgc cgcgtggctc gaccggacgc      9360
aggtcaacga gttctacgcg ccgaacctgg tgatcaacgc cgtgttcgag gcgggactgc      9420
cgttgccttc ggtcaaacac gtcgtccagg gcggcgaggc gttcgtgatc agcgaggcga      9480
tgcgcgccgc gcacatcccc ggccgccgtc tgcacaacca ctacggcccc agcgaaaccc      9540
atgccatcac cggttacgtg ctgcccgaag accccgggtc gtgggaaccg gtgacgccga      9600
tcggcaagcc gatcccgaac tcccaggcac acatcctgga cactcggttg cgtccagtcc      9660
cgcccggcgt gccaggggag ctgtacctcg ccggcgacgc gctggcgcgg ggataccctca     9720 accgtccggc actgaccgca gaacgattca tcgccttccc caacgggcaa cgcgcctacc      9780
ggacaggcga catcgtccgt cgaacgcaca ccggtgacct gatctacctc ggccgcgcgg      9840
acaagcaggt gaaagtccgc ggcttccgca tcgaacccgg tgagatcgaa gcccgcctca      9900
ccgcgcacgt cgacgtcacc caagccgcgc tcgtcgtgcg tgaggaccgc cccggcgatc      9960
gtcgcctggt ggcctatgtc gtgggtacgg cgtcggccga cgtgcttcgc aagaccctga     10020
gtgacgcact gcccaactac atggtcccgt ccgcgttcgt tcacctcgac gaactcccgt     10080
tgacgcccaa cggcaaactc gactggcgcg ccctgcccgc gccggacttc accgcggctc     10140
gggaaagccg tcagccccgc acaccccgtg aagagatcct gtgtggcctg ttcgccgaaa     10200
tcctcggtgt ggacagtgtg gggatcgacg acgacttctt cgaactcggc ggccattcca     10260
tcctggcggc gaaactggcc ggccggatcc gtgccgaact cggcgaggaa ctgacggtcc     10320
gcaacctctt cgaaacgcct tccgtcgcgg gccttaccgg tgcttcggcg acaaacgcg      10380 ctccgctcgg cccgctgctg gccctgcggc gcaacggttg cgcccaaccg gtgttctgca     10440
tgcaccccgg cggtgggatc ggctggtcgt atgcgcggct cgtccggcac ctcagcccgg     10500
acgtacccgt ctacgcactc caggcctcgg gtttctcgac cggctcggca ctcccgtcct     10560
```

-continued

```
cggttgagga aatggccgcg tcctacgtgg cccggatgct gtcggtacag cctgaaggcc   10620
cgtaccggat catcggctgg tctttcggcg gcctggtggc tcacgccgtc gcgacccacc   10680
tgcagtccct ggggcacgag gtgtcactgc tggccctgct cgacgccttc ccacccacca   10740
cgtccgcggg cgagctcgac ccacacgcgg tgctcgccgc gaacatgcgg gcgtccgggt   10800
tctcgttcga cgaggacgag ctgcgcaacg atgagcaggg cgtgctgaag gcgttcacgg   10860
agttcctcag gcacgagaac atggcggttt ctctggcgta cctggacgag gaggaactgg   10920
tcaacgccaa gaacgtctac ctgaacaaca tccgcctgat gcgccggttc accccggcgg   10980
agttcgcggg cgacgtggtg ttcttcgcgg ccacgaaggt cgccaaggac aagctcgacc   11040
gtgccaggcc ggaagcgtgg aacccgcaca tctcggggac gctgaccgcc cacccggtgg   11100
ccacggcgca cgagaagctg ctggtggagc cggaagcggt ggcggaggtg gccagggtgc   11160
tcaactcaca cctggacagg tcatgatgtc gtcgtcgaag cccagcgggt catggtgcat   11220
ccggccgatg atgcgttccg cttccccggc cctgccgcct gtgtgcagtg cggccacggc   11280
gatcttgcgg cactttgcca gccgggcggg cgaaccctcg agccgacgt gccggtaggc   11340
ctcgctgatc agttcgagag cacgggcgaa cgagttcccg cggtagtgga aatacgccgc   11400
tatcgacagc gtctcgccca gtgattcagg atgactggcc ctgttgtggg cgatgttctc   11460
gtccatcacc cgcagcgccg cggcgctgtc tccgcgtttg ccagcatttt gcgcgaggtt   11520
ggtcttgacc tggctcgtgt accgatgagc ggcgtcacgc tcgaccatga cccagccgtc   11580
gcgcggaagc agctcgtcgg cgttgctgat ggaatcgaag gcttcccggg gttcgccctg   11640
ccggatgaag gccagggccg caaggttcgc gaccagtgcg cacatcgtca tccgatcagc   11700
cggggagatc acataccggc tctccgcgtc acacgcgcgg tgccgcaggc ggtcgaggat   11760
ctccagcgcc cggctcggct cattccgtcg cttcagcacg aatgccgcga ccgcagctc   11820
ggcgagcatg gaatccacga tggcaggcgt tgcctcggca gcgcggacga agagctcctc   11880
cgcgtcgaaa accgagtcgg cgtcggatgc catggccgcc gccgcgtaga gcagggcgac   11940
atgcgtgccg agcggcttgg cggcagagag cacagccgtt gtcagctcac gcgccatcga   12000
ccagtttccg gcgaaacaca cgtgcgcgtc gatgagagcg cagaagtcat actcccggta   12060
ctggccgtcg gcccagcggg tggcccattc gctcggcttc atcggctgga tcgagtcgtc   12120
ggcgtgggat gtgaggtcct ggatgcgtag gtgcccgtca aggaacgcgg ccgcctcggt   12180
catgccacga acacccagat cagtcaggta attggtctgc acgggaaggc gggtgtgcgg   12240
cagtccgggc agtgccgccg acctggccct ttcgaccaga ccgtaccgtg cggtcagcgt   12300
gccgcaggct tccgcgtcga gaatcgtcct ggcggttcgg gtcgcccaga agacgtcatt   12360
cgtgctgtcc atcgccattc ctgtcgggta tgggcggcgg cgcctgtccg ggcgccgcca   12420
ctggtcatcg agcgtcgtta cctgggcccg tgcttccagc cgccgagcag gccgttgatc   12480
gtcgcgtcgg ctgagtccag ctccgcgacg atctggtccg gcgtgaccgt cgaggagtcc   12540
gtgctctgcg cgcttgcgac gcctgcgcc gtcagcaacg acgccagcgc cgccgcggac   12600
accgccgcgg tcttcacgag aacattcttc atgcacgtga cctttctctg atttcgtttc   12660
acacacccac agcgaaacgg tggacatcaa ggaactactt ccgtcgagcg attgtgagcg   12720
cgtcaccgat gggcagcatc accggctcga cacggtcgtc cgcgagtacg tgctcgttga   12780
attcgcgcag cgcactgcca ctcgcgttcg acgggtcgtc gtcgacaacg ccaccaaagc   12840
cgaagacgtt gtcgacaacg atcagtccac ccgcacgggt ccgcgggaca agctcagtcc   12900
agtactggac gtattcgtcc ttgtcggcat cgacgaaggc gagatcgatc gtccgccggc   12960
```

```
gcgggagttc gcggagcgtg tcgagggccc gccccagttt cacggtgatg aggtgcgcca   13020
cgcccgcccg ctccccgaat gggcgcgcca ccgcgatcgc ggccgaactc gcctcgcaac   13080
aaagcaagcg cccttgacgt ggcattcccc tggcaatggc catcgccgaa tatccggtga   13140
aggtgccgac ctcgaccgcg aatctgacct ccgccgtccg tgccagcatt gtcagcagtg   13200
ctgcctgcag cggcgtgacc tgcatacccg aatactccgg acaaacccgc cttgttgtgg   13260
cgatgagatc ccgctcgacc tcatccatcg gcgtactgtg atctgccgcg tacgtgacca   13320
ggtcagcacg cacggcgccc gactggtgca ccgagtatca accccccgac tcatcgatgt   13380
cagtgagttt ccgacaacga ccgtaaaaac catgacagga gccgcttgcg gttttcttcc   13440
gccgatcgcc gtgaaatgag gagaagccgc gtgacgatgc cggtggacga gctgatcaag   13500
ccaggtggtg ctgaaaagca gaacgcgagc gggggttagg gtcgcagcgt ggcagagact   13560
gagccgttct cggtgaagaa gttcgtcgcg gggctgagcc gcaagcggat ggcgtcaggg   13620
atgctgttcc gggacgacac cggccgtgtc cttctggtgg agccctccta caaggagcag   13680
tgggagatcc cgggcggtgc ggtcgacgag aacgagtccc catgggcgac ggtgtcccgc   13740
gagctgacca aggaactggg catgcggcgg cccgtcgggc gcctgctggt cgtcgactac   13800
gtccacccgg agggcgactg gccggaggcg gtgatgttcg tgttcgacgg cggcgtcctg   13860
gcacagtctg atgtggacgc gatggtgttc gccgacgggg agatcctctc ggcaggcttc   13920
tacgacctcg cggaagcccg gaaactgctg aagccgcggc tcgccggccg ggtcgaggcc   13980
gccatctccg cgctgcggca gggcacgacg gtcctctgcg aacacggccg ccagatcact   14040
taggcgcacc tccccggatc ctcaccacgc gggccggctg aaaaccgggt gcggacggcg   14100
ggcgcgctgg tgtgtgatca agggatggcg atcgtgatgg gcaagccggg agtcgacggg   14160
ctgagcgcgg ctgtgggcgt gctgcgggaa tggcagtacg aggggcgcc gatgcaactg   14220
catccggggg acctgggctg gttctggcgg ttcggtgcgg aggcgacggc cgcggcggtc   14280
cggacctgga gccgggacgg acagattctc gccgtcgggc tgctggacgg tcccgagctg   14340
ttgcggctga cgatcgcgcc ggacgtccag caggacgagg agttggccca gcaactggtt   14400
gaggacgtga ctgagccgga gcgcggtgtc ctgccggcgg gaaaggtgtt catcgaagcg   14460
ccgatgggcg tgctggtcca agatctgctg ttcgagagcg gctggaaggt cgatgagccg   14520
tggacgccac tgcgccgcga cctcacggaa ccggtgaagg acccaggcgt gcggatcgag   14580
gtgatcggac cggagcaggt gcacgtgcgg accgccatac agcgggcatc gttcgacagt   14640
tcgacgttca cagacgagcg ctggcacgcg atggcggccg gattgccgta cgccgacgcc   14700
cggtgtctgg tcgcgtacga cgaccagggc aacggggtgg cggcggcgac agtgtggtca   14760
gccggtccgg ggaagcccgg gttgctcgag ccgatgggcg tacacccggc acaccgcggc   14820
cacggctacg gcaaggcgat caccgtcgcc gccgcggccg cactccagga gctgggctcg   14880
tcgagcgcga tcgtctacac cccgagccgc aatgtcggcg ccgtcgccac ctacaagtcg   14940
gcaggcttcc agcagcgccc tgagatccgg gaccaatgcc gggactagtc ggagttggcg   15000
aacaccagca cagcggcttg atcacccgcg cgaacgggaa tccacgcctc ggtgaggtcg   15060
tccagccggt cgaagtcgag gctcagcagg acgcgtgcgt cggagtcgcc gtcgggcacg   15120
aagtaggcga ccttctcccg gaccaggcgc tgcaggtggt ccaggtcgtc gacggtccag   15180
ttgaccggtg gccgcccggc gaaccggccg aagaagccgg tgaacggcgt cgcccggccg   15240
accacgacga ggtagccctc aagcgacttc cgcaggcacg caagacccc gcactggttc    15300
```

```
tcgtacacga ccccggtcgg cgccggcacg atcaggcaca gcacctcggg gaccgcgtca   15360
tgcgggttga aatccacgcg tacctgcatg gactcaagcg taacgccggt actacatgag   15420
gcggacgggc tctcccatgg ccacgacgat ctcccgagga cccttgtacg gctcgacggc   15480
gtgtgccatc cggatgttgt cgaccagcat gagatcgccg tcctgccatg gctcacggat   15540
ggtgtgggcg tcgtagacag cgttgatggc gtcgacgctc tcgcggtcga gcggcgtgcc   15600
atcgcctgcg aaggtgttga acggcaggcc gccgtcgagc gccatggtca ggtagtcccg   15660
gacgtccgga tccatggtcc actcgttcag gaacgcgatc tggttgaacc agccaggacg   15720
ccccgaaacc gggtgccgga cgaccgcagg gcgcgtctga gtcgtccgca ggctgccatc   15780
cggcccccag ttccaggaaa tcccgtggga ctcgcaataa gcctccacga cgtccttgtc   15840
ggcactgccg aaggcatccg ccaacggaac gccgaccagc gggttgtagt tgcggaccaa   15900
ctgccacccg tggccggaga accgggagac caagtccgcg gggaggtcgt cgagcacagc   15960
ctgcgagtcg gccaatgccg tcacgccacc cgaagccggt gcccgcaaac aggtgaaggc   16020
cagcacagtg ggcacatcgg gcacgtagct cagttcgtgg tgcatgcaca tcggctggtc   16080
cgacggccat ttggtggacg agtacatgcc ctgctcgagc gagtcgcgtg gggcgaagcc   16140
ctcgcgctcg acgacgaacg agtcgatcaa ggcgtggctg acggccgcgg ccgtggacac   16200
gtccgcgatt cccagaccac gcaccagaac agcgccatcg gtggcgagca gtgagcggag   16260
ttccgcacgg ttcccggccg cccaggcagc cgggtccgtt gtggacactg agaggatctt   16320
caccggtcac cctccagtcg ggtagcggcc aggctgaggt acacgtcgtc gagcgtgggc   16380
tccccgatgg cgagctcggc cggctcgatc agggcgtcgt ccagtgcccg caccacgatc   16440
gcgaggtccg cggaccggtc gacgggcgcg gtgatcgtca gcccgtccgg tcccgcggtg   16500
gcggtcagac cggcgcgccg cagtgcgtcc attgccgggg tggtgtggtt gacgtcggac   16560
aacgtcacgg tcgcggtccg cttgcccacg gtcgccttga gctccgccgt tccgccggtc   16620
gccaccacct tgcccgcgga caacaccgtg atcgtgtcgg caaggcggtc ggcttcctca   16680
aggtactggg tggtcagcag gacggtcgtg ccgtcggcga ccagcttctc caccgtctcc   16740
cacaggccga gacgactgac cggatccagt ccggtcgtcg gctcgtccag gaagatcacc   16800
tcggggttgc cgaccaggct cgcggccagg tccagtctgc ggcgcattcc gccggagtag   16860
tgctgcacct gtttgcgtgc cgcgtccgtg aggtcgaaca gctccagcag atcgtccgcg   16920
cgccggaccg cctcacgctt gcccgcgccc agcagcctgg cgatgagcac gaggttgtcc   16980
cgcccgttga gctgcccgtc caccgaggcg aactggccgg tcaagccgat ccgggaacgt   17040
acctgcctgc cctcgctggc cacgtcgtgc ccggcgaccc tggcctgccc ggcgtcgaac   17100
ggcagcatcg tggtgaggac gttgaccatt gtggtcttgc cggcgccgtt gtgcccaac    17160 agaccgagca cagttcctcg cggcgcctcg agggacacgc cgtcgagcac ggtcacgtca   17220
ccgaacttct tgctgacgtc ccgtgcgtcg atcatcaact cggtcacaga caaagcctat   17280
gaggtccggg accgtagatc tctagcgaaa aacccagaat caccaccggt gccgcagttc   17340
ggccacctcg tgcaggacgt ccgggttccc ggcgaacacg ccactttccc gtggccagtg   17400
cacaacgagg tgcgtgatgc cggtttcggc gtaccgttcg gccatgtccc ggcaggcccg   17460
cgaagacttc agcggatcac cggcacgcgg agtggcgatg aagatccggt cgatctcggt   17520
gctgtcccgg cccgcttgag cacacgcctt gtcgagcaac tcgttctgga cggcgacctg   17580
cgcggcgact tcgtccggcg agatgtcggt cgtccaggcc gccgggccgg tcgtgatcca   17640
cttggtcccg tagcgggcga cgagatccat gccgcgtggc ccggtcgccg cgatcgccag   17700
```

```
cgggacgcgg atctccggca gcatcagggc ctcggacacg gcgtagaact gcccggagta  17760
cgaggtggcc ggattgttca gcagttctga cgtcagctcg acgaactccg cgaaccggtt  17820
cgcccgtgtg cgctgggaca acggagcgga gtcgagcacg gtcgcatcgg tcgtgcctgg  17880
tgaacccgct ccgacaccga gcacgaaacg gccgcctgag atgtcctgaa cggtcgccgc  17940
gtccttggcc agcacggccg ggtgccggag gttcggcgtg gcgaccatgg tgccgatctc  18000
gatccgcctt gtcgttgccg cgacggcgga aagcactggt acagcggaga accacgggcc  18060
attggtgcgc caccacaagt ggtcgtaggt ccaggccgag tcgaagccca gctcttcggc  18120
cgtacgccac cgttcgacgt tgtcctgcca cgacagctca ggcaggatca cgactcccaa  18180
acgcatgcgg gccttcccct catcgacaca tcattcgcac ggcagctcag ccgtgatcac  18240
ggtgcgcgcc gagcaggatc atcagcagca caccccgcgcc gagcccgccg gccatccacc  18300
gcagcgcgag agaccggaca gccaggaatc ccgcttcgac gactgcggtc gcaccaccga  18360
gggcgactcc gacagtcgga cggcaggcac gaagcgctaa ctcacgccgg agaaaagaca  18420
ccgcgcagtg tatcgaccac cccgcaagcg aaattcacta ccggctcgtc aacaccgcct  18480
tcatcacgct gccgttggcg acatcccgca acgcggcgcc gtgctcggcg agcgggtacg  18540
tggtcaccag gctggccagg tcgaatcgtg cggccagcgc gggcagcagt tgtacgtact  18600
cgatcaggtg cgcgccggtg aacgccacg atccgatcac gtcgagctgc cggtacacga  18660
tctggtgcgg gttcacggtc gcgtcaccgc tgtcggtgta ctggccgacg acgagatacg  18720
acccgccacg ccgagcgagg cgcagacctt caccgaacgc ggacggcaca ccagcgcact  18780
cgatcaccag gtcggcgccg ccaccaccgg tgagctcgac cacctcggcc agcgcgtccc  18840
acgtctccac cacgttcacg tggtggtcgc cgatccccgc ctcggcggcc agcttgagcc  18900
gattcgccgg accaccgcg aggatcacct tgccagcgcc ggagatgtgc gccagtgcgg  18960
ccgcggccaa gccgaccggc ccgctgcctt gcacgacaac ggtttcaccc agccggaccg  19020
gcctgcgttc gaacaacgcg tgcaccatcg tcggacccgc acaggcgaac gacatcgcgg  19080
cgaccggatc gatcccgtcc ggcaccttga tcacggtggt gccttcgcgc agcacgatga  19140
agtcggccca tgacccggaa agtgcgggct cggcggtggt cggccggttg acaccgtacg  19200
tctgacggtt ggtgcacaac gtcggctcac ggtacgaccg gcacggcaca caccgtccac  19260
acgcgatgga agacgcccac atgacccggt cgccgacgtt cagcgcctgc cccttggcgt  19320
cagtcgcggt ggccagttcg acgatggtgc cgaatccctc atgaccgagc accaacggga  19380
ccggaacgtc gagatgcccc tgctgcaggt gcagatccgt gccgcacacg ccgccgtact  19440
cgctcgccac gaccatcccg ccgggcggtg cctgcggcac cgggaactcc cgcagccgga  19500
ggtcacggcc gaactcggtg agcaccaccg cgcgcccgtt caccgggcgg cgcccgcggc  19560
aagcagcggt tcgtcgacga tctccagtgc ggtggtgtcc tgctcgacca ggtaccactc  19620
gcgcggcgcg cccagcggca cgttcgtgct gtcgttgtac gtcaccagca gcagccgcct  19680
gctgaacggt gacatgttgg tggccgagcc gtgcacgatc tccgggtcga agaagatcac  19740
cgacccggcg gcgcccttgg ggctgtccat gccgcaccgc cggacaaggc cggccatctc  19800
ggtcgtggtc agctggatgt catccgggtc gaggtgctga tggacttca tcgtgccgct  19860 gcggtccgac cggatcaacc cgtgccggtg tgagccgggc acgaacatca gcggcccgtt  19920
gaactcggtg acgtcgtcga ggaacagccc gacgttgacc agcctcggct cgggcaggct  19980
gtcggcgatc tgccacgcgg cgaagtcctg gtgccacgcc cagccgccgc cgacgaacgc  20040
```

```
gggcttggcg ttgatcttga actggtagac gtacaccttg tcggtcagca actgctggac    20100
cggtccgagc agcctggggg agcggaccag ccgggcgaac tccggttgcc gtaagtgcga    20160
cgcgtagatc gcgcgcacgt ccttgccgtc gttctcggcg atccgctgct caccggggat    20220
ctcgccgtcc cgcacgaacg cgtcgcgcag cgactcgacc tcgtcggtgt tgaacagccg    20280
ctcgacgacg aggtagccgt tctcccggta gctgttgatc tggtcttcgg tgagaatcat    20340
cgttcttcct tcagttcacc gtgaaatgga tcgactggga tgccgtcgtc agcacgtcga    20400
ccaagtcctc ccggctcggc gcggtggcga tgacgtaccc gaggcggccg tacgcgtcga    20460
ctggcggagc gacctcgcgg cccggcttcg tggtcacgat cacctgctgc acgccggcca    20520
ctgccttcgc gcgctccacg ccggagatct cggtgagcac gccggtgtcc ggcgtggtca    20580
ggaactggat cccggcgaag cagccggtgc ccgacggcac cgtgacgggc agcccgcagg    20640
cctgcctgac ctgctgttcg agcaggtcga cgccgctggc gaggcggatc agctcgggga    20700
tcatgccgcc ggccagccgt gggttgatct cgatgatgac cggcccggac tcggtgatct    20760
tgacctcggt gtggctcgcg ccctggtca gcccggccgc ccgcaacgcg gcgcgcacca    20820
cgtcggcgac ctggccggcc acctcctctg gcacggacgc gggcacgatg tgccgcgact    20880
ccacgaaatt cggcgcaccc atcaccgatt tccgcaccat cgcgaccagt tcgtggtcac    20940
cgtcggccgc gaacatctcc acgctgtact caaggccatc cacataggac tcgatcagcg    21000
cgccgcgagc ccggggcatg ccgcggacgt tcgtcgtcac ggcaaggacc gcctcgaccg    21060
cgtcgagtgc ctgctcggcc gtgtcgcagc ggaccacgcc ggtcgacccg gactcgtcga    21120
ccggtttcac cacgcacggc aatcccacct tgtccaccgc ggcagccact tccaaagcgt    21180
tgtcgaccag cacccacaac ggttgcggca accccgcctt gtcgaggcga tcacgcagcc    21240
tggccttgtc acgacagccg tcgatcgcct ccggccgttc ggccggcagc ccgaactcgg    21300
ccgccagcct cgccgcggtg gacaggtaga actcgctggt ggtcgtcacc gcgctgatcc    21360
ggcggcgcgg cacctgcgag tggagtgccg cggccagcgc accgggatct ccggtgtcgc    21420
agcgcaacac ccggcatccg gtctccggca gtcccagata ccgttcgggc ttgttcgtca    21480
ggaaaatcgg ctcgtagccg aggcgctggg cgatgccgat cgcggccatc ccggtgccgg    21540
tcgtgttgga ctccacgaac gcgagcaccg gccgggccgt gtccgggtcg gtcagccggg    21600
tgaacgccca gctgtgcacc accgtgccgg gcggaacctg acgaggccgc gtggccaacg    21660
gttgatcggg caggccgcgt tcgacccagt acgtcttgtt gtgcacggtc tcggcatagc    21720
gatcgccacg atcggggaag atcccgacaa tggtcgtgcc accgggctcg tgctcggcca    21780
ggtgcgtcat caccceggtac accgagccgg acgtgttgcc cgcgaacagt ttctgctctc    21840
gtgccaacgc gaccgacgcc tcgaaggcct cccggtcgtt gagccagtgc acctcgtcga    21900
tctggccgtg atccaggttc ttcgggtgca tgctgttgcc gagcccgctc tgcagccgtt    21960
gcggccagtc cggctgtccg aacaggacac tgccgacgca gtcgatgccg accacccgca    22020
ggtcgggcag ggtctcgcgc agcgctcgtg ccgtgccgca caacgatccg ccgctgccga    22080
ccgagccgac caggatgtcg atccggccaa ggtcgttgac cagttcgccg gccagtgtcc    22140
ggtatgccgc cggguttgtcc gggttctcgt actgccgtgg ccagaacgag ccggggttgg    22200
cggccatgat ctcggccagc cgcttgagcc gggcgccctg ccagccgtgc tcgtccatct    22260
ccggcacgac atggacctcg cagcccagcg actccagttt ggccagcgtg atccggtcga    22320
tccgcgggtc ggtgacgatg tgcaccgggt gccccatgag cgtgccgacg agtgccacgc    22380
ccagcgccat cgtgccggac gagctctcca cgatcggggc gccgtcggcc agtgcaccgc    22440
```

```
tttgcttggc gcgcagcagg atgttgcggg ccacccggtc cttcatcgcg aacaggttct   22500
ggatctccag cttggcgtag caggcaggcg cgtccgcgcc gttgttcagc gccagccgga   22560
cgagcggggt gttgccgatg gcgtcgagca ggttctcact gatcacgcgc tggcctccgg   22620
gagatgggtc gatgcttcgg tgagcgcctt gagcagccgg tctgtctcgg cgtaggcctc   22680
ggtgatccgg gcacggcggg tggcccaccg ccgttccgcc aggtcgaacg ccgccgcctg   22740
ttgatcgagc atggtccgta cgctgtcctg gcccgcggag cccgtcgtgc gtttcgccga   22800
caacgccttg tccacatcga acgcccgcgt cagcaattgc tcggcgccgg acaccgcgaa   22860
cccgcgttcc tcagccacct gcctcagcag tccggcgtcc ggctcggccg gggaaagtcc   22920
tttgtcgaca gcggcgacga tgtagcggcc cgcgatcacc tgtgccgtgc gccagggcac   22980
acccgcgttc agacagagtc cgttggccag gctgaaaccg ccgaggtatt cggtggtgca   23040
gacgtcacgc agccgttcgg tccgtagccg caaggcatca aggaccgctg tgaacagtcg   23100
cagcaccgag ctcgcctggt cgaacgcgag cgggacgtgt ctgcccgctt ccttggacac   23160
ttcgatggtg ttgctgaagg gcgtcgcccg ttggccgagc acaacgccca tgaacccgc    23220 tgccagctgc gcggtccggc cgcgcaggcg ttcgagcacg gggaagttct tcttctgcgg   23280
catggccgag gagatgccgc tgaactcgtc gggcaggtcg atgaacccgt aacccgcgcc   23340
gctccacgtc agcaggtcgg tgacgaaccg gctgagcggc acgccgagca ggcacagctc   23400
cgcggtggcc tccagcgccc agtcccgtgc ggccacaccg atcagggcgt gcccgtcgcc   23460
ggaactgaag ccgagcagcc gcgccatccg tgtccggtcc cagtccagct cgcccccggt   23520
catcgcaccc gcacccatcg gcgaggcgtc gacgctggcg tacaccatgt cgaaccggtg   23580
caaactgtgc agcacctggg cggacagggc ggagaagtag aaaccggcgc tggccacctg   23640
ggcgggctgg gagtgcgtgt accccggcat cagggtgtcg atctcgcggc cggccagccg   23700
gtgcgcggcc ctgccgaggc cgatcagctc gtcgaccgtg ctgagcaccc ggtcacgtcc   23760
gtagatcgtc tgtgccgtgg cttgcaggtc gttgcggctg cgatccacgt gccatgcgtg   23820
cgcggcaccg ccgatccggt cggtgacgta ccgctcgatg gtgaacgcga tgtcgctcat   23880
cgcggcgtcg gccagctccc ggacgaccga gctgtccagc tcggacagga cggaagcgat   23940
cgcggcgacg tcagcggtgc cgagcaggcc cattcggtgg tactcgagca acagcacctg   24000
ttccagccgc aggtagccgg gcagcaggtg ctcggcctcg aagtccagct gcggccgcag   24060
cacctcccgc cgcagcagtt cgtcggggcc cgcggtgatc cgcccggtca gttcggccgc   24120
ggtgtcgtgc cggtccttt ccgcgcacac cgatgaaacc tccctcgagg ggtggaaatt   24180
cgccagatcg gcgccgaatg cgatcgatcg tgccagtggc gcttctccga aaggttcgcc   24240
ggatttcccg gcggcccgcc ttcccgctgg ccgcaccggc cgaaagcgcc ggaacaaccc   24300
ggcacaggcc ccttcgtccg gcactcccag cggaaacccg gatcagccga atgaacccag   24360
cgaccttccg agacgcacca ctagtccggc gggctgcttt gaattcctct caccttcccc   24420
agtaggctcg ccggcccca gtcagccgtg gtcgagtccg cacaagagtg cccagaccgg   24480
tgcgcggcag tcaaccgtga ccgggctatg actaggggtt tccccggcgt tgccgaatgc   24540
cgccggtgag agcggggcga gagcaccgtg agagcatgct gttccactct ggacacctca   24600
cgatggcgca cagtgatggg aggtttggtt ggacgtccta gcgattcagt cttttggcgg   24660
ccgtccgtta cggtccgctt catcccagcg tcacctgcgg ataccacaca ccatcgggca   24720
ggcgctcgcg ctggttgtgg cctagatcgc ggtcagcact acggtcctgg tcaccggggt   24780
```

```
tgtgacgcgc tgtcacaccc tgggagccct tgcgtggccg ccggggtgga tggcattctc  24840
aggccggtag tacgggtagt tggtgaacta ctgacggggg ttgctgccag atatcacgtc  24900
gaagttcgtt gccattatgg gggaactact ttcgggggag tagcccgatg tcctgcgaat  24960
cagtgataga cacgcacaaa accttaagtg tattgagcgc gaaggttctc gaaggcgtcg  25020
ctgccggttc ctcgacgatc caactcgcgt ccgaactgta cctcagccga caaggagtgg  25080
aatatcacgt taacgtaatg ctgcggaagt tcaaggtgcc caaccgtgtg gcactcgtgt  25140
ccagggtgta ctcgatgggg atgttcgacc acaccgcatg gccgcctgcc gtgctccccg  25200
aatacatccg ctgacggggt tctctaggga attccccacc cgctgagctc gtagactccg  25260
atgggagcag attcccggac aggaggagcg ccgaccgtga gcaccaaccc gtttgaagat  25320
cctgacggta cctaccacgt actcgtgaac gacgagggac agcactcact gtggccctcg  25380
ttcgtcgagg tgccgtccgg ctggaccgtg gtggtgcgcg agacggaccg tcagtccgcg  25440
ctcgactacg tcgagcagaa ctggacggac atgcgaccga agagcctgat ccgtgcgatg  25500
gaaggctcag cctgacaggg gggccgggac gaacccgggc cggtgcggtc gtgtgagacg  25560
actgggaaca actggggtgg atgcgacccg tccggcacct gccgggcggg ttcacctgtt  25620
tgccgtttgt ggcgcgaggg cctcctttcg gtagatgtgg tacgtggtcc agatcgtggg  25680
tcggaactac gacccggatc cggcgggcac ccgcgcacgc ttccgtgcca tcctcgaccg  25740
gctgttgccg aagctctccg gcgacgaagc ctcggacggc gaagcctcgg acgacggtgg  25800
cgagctgatc cgaaaccccg tgcgccacta tgaaagcggc aacctcgaac tcgtcggcgg  25860
cggtatcggc gagttcactg tagacggcgg cgttgacgtg atccggtgca tgaacgtgtt  25920
catgtacttc gaccacccgt tccgcgagaa ggcgttgtca tgggcgacga cgatgctgcg  25980
tcccggcggg ctgttgctct gcggcaactg gatcgactcg gccgaggaac gcgcccggtg  26040
cagttccatc ctcgcctcgc aactggacga tgagggcttc gtcggtgagg ccgtcgacgt  26100
cctgcgccga tcaggacgac atgcgtggcg caatcacgtt ggccacgttg ccatgcggcc  26160
cgtgacaccg ccaccgctgg cgccgtcgtc ggtgctctga cggacgcgtt cggaccggac  26220
atgtccgtta cgatgaccga gtggcccttc aacgcgcctg caaccggcgc gagcgaccgg  26280
cgacgccggt actgacgcgc gacgggaccg tcgcgaccgc cgtgtctgtc atggggggcgg  26340 acgggcttga gcgggtgccg atgcgccgcc tcgccgggga actggacacc ggccccgctt  26400
cgcttgacgt gtacgtcaag gacaccgacg agtcgcacgg cgagatcctg gacgcgccac  26460
ttgacgaagt ggatctgaaa accgcgccgg attccgcgc tggtgactgg cgcgaacgcc  26520
tgtggacagt cctcggccgg taccgcgaag tgctcgtcgc gaacccgaat ctggccaagg  26580
tcgcgctggt gacgcggctg aacgggccga accacctcgc cgtgacggag accgggccgg  26640
cgctgccggc cgaaggcggc gtgcctccgg gtcaagccga gtgggccgcg gacgtcctat  26700
tgttggtgtt cacggcgacc gcggtcgaag ccgggacgag gaaggggatg cctggtgcga  26760
cagaggaaca cgatgccttg gtcaacaccg tgctcgcggc atcggcgcga acccacccccc  26820 acatcgcggc cctaggcgcc gatctggtct cgggacccgg caccgcgcgc gcccggtggg  26880
cgatcgacct ggtgctcgac agaatcctca gcgcccttg ccagtagtcg tccacgtgac  26940
gcgaccagac gaaggtgaca catccatggc cgatcacgcc gaactcatgc ccattgccac  27000
cagggccgtt tcgttggcca gacggatcat ccaggagcgg acaccgtcca ctgtgtccgc  27060
caagggtgac cgagacatgg tgaccgacgt cgacctcgcc gtcgaggatg cggtacgcga  27120
cttcctcgcg aaggagaccc ccgagatcgg gatgctcggc gaggagcacg ggcagtccgg  27180
```

```
agcgggcggc gggctgttga actgggtcct cgacccgatc gacggaaccg ccaacttcgc   27240
ccgtggcatc ccgttgtgcg cggtgtccct cgcactggtc gacggtacgg aagccaggct   27300
cgcggcgatc gacctgccgt tcctggacac ctggtacacc gcgcgggccg agaacggcgc   27360
gtacgccaac ggtgagccgc tgcggtgctc cgcggtcacg caggagtccg acgccatgat   27420
ctcgatcggg gacttctcgg tcggcgagga ctcgaccgag aagaaccgga tccggctcgc   27480
gctgctgacc gacctgggcg cccgtgtcca gcggatcagg atgatcggca ccgccgcgat   27540
cgatctggcc tgggtcgcgc agggcaagct ggacgccacg atcaacctct ccaacatgcc   27600
ttgggacacc atggcgggcg cgctgatggt gcgtgaggcg ggcggcatgg tcgtcgacta   27660
cgacggcacg ccgcacacgt ccgagtcgac caatacgatc gctgtggcgc cgggactcta   27720
cgatgtgctg atgaagaggc tggccgaagc ccggctatga cacgtcgagt ggtcgttctc   27780
ggccttggcg ggaccatcgc gatgaccgcc gacgccagtg gtggtgtggt tccggcactg   27840
tccgccgagc aactggtcgc ggcggtgccg ggattggccg agacgggcat caccgtcgac   27900
gtggtggact ccgccgcgt cccgggcgcc tcattgtcct ttgcggacat ccgcgcgctt   27960
gccgaggccg tcgggcgaca cctggccgag ggagtggacg tgtcgtggt cacccaaggc   28020 accgacacca tcgaggaaac cgcgtacctg ctcgacctga cccatgccag ggacgaaccg   28080
cttgtggtga cgggcgcgat gcgcaatccc acatcggcgg cgcggatgg acccgccaac   28140 atattggccg ccgtgcacac tgcggcctcc ccggcggctc gtggactcgg tgcggttgtc   28200
gttttcgccg acgagatcca cgccgcctcg cgcgtgcgca agacgcacac cacgagtggg   28260
catacgttcc agtccgtgaa cggcggcccg ttgggctacg tggtcgaagg tacgccccgg   28320
atcgtcaaca gaccgaattc ccgcgtcacg gttcccgctg tgcaaggcga accggttgag   28380
gtcgcagttg tccccatggt gttgggcgac aacgggactg ttctcgaggc cgtcgctgac   28440
cgggtggatg tcttgtcgt ggcggcgttc ggtgtgggc acgtgcccgc cggggtcgtg   28500
gacgtcttga gtggactcgc cgaacggatc ccggtcgtgc tggcctcccg cacgggttcc   28560
ggctccgtgc tcgagcggac gtactccttc ccagggtccg aattggacat gatcgggcgg   28620
gggctggtcc cagcgggttt ccttgacccg ttgaaggcgc ggatcctgtt gtggcacttg   28680
ctcagcagtg gccacgaccg cgcgagcatc cggcgcgtgt tcgccgcggc gtcagtctga   28740
gtcgagcacg tccgtaccg ctgtgcacgg tccgcgccgg gttcttctga gtgaatccgg   28800
cccgccgccc ggtgcatcat ctcctggaac acggcttgtt catccggacc gaggcccgca   28860
agtacgacat cttcgaccgc ggcgacccgt cgttccgcct cggtgagcac cttttccgtg   28920
atccgttttg tccgcgccgc gacccagctc aacaacgtcc aggtgtccag caggcccacg   28980
ttgtacgggt ggtcctggaa ggtcgccgcg tccagtccgg cggcctcggt cagctccgcc   29040
agccccacca cccgctcggg gtccttcgcc gacggcgtga tgaaggtgcc cagcaccagg   29100
gcatgaccgt agtcagtcat cccaaacccc acttgtccgt tgccggacct tctgtacgaa   29160
atatgatatt tcgagcaaca tggtcggtgg ctggtcgggc atcggcccag acggatctgt   29220
cacggcagaa cccgggatga gcagactgtc caccccggac ggcgagccgc gaagggtgac   29280
gtgcggtccg acgcctgacg tggtcatcac gcgtgccgac taggctggga acgttctcgg   29340
caggaaggcg gtatcgagct atcgctgggg gaacggtgac ggcagtggag ttcggtctgc   29400
ttggcgcgat cgaggcgcgt atcgacgcc atcaggtgga gctggggcat gcccggcagc   29460
gacacgttct cgcggcgttg ctcgtcgacg ccgaccggct ggtgcccatc gcggatctcg   29520
```

| | | | | | |
|---|---|---|---|---|---|
| ccgcccgcat | ctggggtgag | cgcacgccgc | acagtggcct | gaccccgctt | tacggttacc | 29580 |
| tttcccgtct | gaggcaagcg | ttggcgcctg | ccgaacagag | cgtgcggatc | gtgcgtcagc | 29640 |
| ccggtgggta | catggctgcg | gtcaacccgg | cgacggtgga | tctgcacagt | ttccggcagt | 29700 |
| tgatggctcg | cgccaggaca | accgacgaac | cgaccagcgc | gatcggcttg | ttcaacgagg | 29760 |
| ctctggcgtt | gtggcggggc | gaaccgttcg | ccggggtcga | caacccgtgg | ttcaacggac | 29820 |
| aacgcgcggc | actgctgcgg | gaacgggagt | ccgccgagat | cgatctgcgt | gatctgcggc | 29880 |
| tgcgctgcgg | catgcacgcc | gaggtgttga | ccgaggtgac | cggcgcgttc | gaggccgacc | 29940 |
| cgatgaacga | acgcgttgcc | gggcaactga | tgctcgcgtt | gtaccggcag | gggcgcccgg | 30000 |
| cagaggcgtt | gacgtgctac | gaccggatgc | gcgcccggtt | ggccgaggaa | ctggggtgc | 30060 |
| cgccgagctc | gcagttgcag | cggctttacc | tgcgcatcct | ggaagccgac | ccggaactgc | 30120 |
| tggcgaccgg | tcagcctgcg | gcgccggagc | agcaggccag | cacgcaagca | agggcctggt | 30180 |
| cggcaccggc | gttgctgccg | ccgaaggtcg | ccgacttcac | cggcaggctg | gccgagaccg | 30240 |
| ccgcgctgat | caagcacttg | accgacggct | ggggtcgtc | gccggtcacc | accatcgtcg | 30300 |
| gcatgggcgg | catcggcaaa | accgcgttga | gcgtctacgt | cgcgcacaac | gcagccgcct | 30360 |
| cgtacacaga | cggccagtta | tgggccaacc | tgcacgcgc | gagcgcgaac | ccggcgaaac | 30420 |
| ccgccgacgt | gttggcccgg | ttcctgcgcg | cactcggcgt | cccggaacgg | gcgatccccg | 30480 |
| ccgacccgga | cgagcgcgtc | gagacatacc | ggacgctcgt | caacggcagg | aagatcctga | 30540 |
| tcctgctgga | cgacgccgcg | tccgaagaac | aggtaaggcc | attgctgccg | ggaactccca | 30600 |
| cgtgtgcggt | ggtgatcacg | agccgggcca | ggctgatcgg | gctcgaaggc | gcacaccgca | 30660 |
| tcgacctcga | cgtcttcgcc | gcgaacgagg | ccatcgacct | gctcacccag | atcgtcggtg | 30720 |
| agaaccgggt | caccgccgag | ctgtccgcgg | cgacggagat | cgtcgaactc | tgcgcggcc | 30780 |
| tgccgctcgc | cgtccggatc | gcgggtgccc | gcctcgcggc | cagatccgcg | tggcggctgg | 30840 |
| cacatctggc | gtcgatgctc | agtgacgaac | ggcgtcggct | ggatcagttg | tccgcggtg | 30900 |
| atctggccgt | ccgagcctcg | gtcgcgttga | gctaccgcgg | gttggacgac | cagccgcgca | 30960 |
| ggttgttccg | actgctcggc | ttgttcagtg | cgccggactt | cccgccgtgg | ctggccgctg | 31020 |
| tgctgctgga | gtgcccgctc | gacgaggcca | ccgagtacgc | cgaggcgttg | gtggacgcgc | 31080 |
| agctgctgac | cacgtccggc | acggacgccg | ccggccagta | ccgtaccgg | ttccacgatc | 31140 |
| tggtgcggct | gttcgcggcg | gaacgagccg | cggaagagga | gaccggggaa | agccgcgccc | 31200 |
| gtgcgctgga | gcaaggcttg | ggcggctggc | tcagcctcgc | ggaacggatg | tcggcctcgg | 31260 |
| tcccgggacc | gtgcttcgcg | ccgatcagca | gccccgcgcc | acggccgcgg | atggactatg | 31320 |
| tgctgcggga | cttccggccc | gaatgggccg | ccaactggtt | cgacgccgaa | cgcggcgcgt | 31380 |
| tgctgtccgc | ggtgcgccag | gcgtgccgcc | tcggcatggc | ggacctggcg | ttcgacctgg | 31440 |
| ctgcccgcat | ggagaagtac | ttcgacgtac | gcgggatgta | cacggactgg | atcgcgctca | 31500 |
| acaccgaggt | gctggcggtg | tgccgggaat | ccggcaacgc | cttgggcgag | gcgatcatgc | 31560 |
| tgcgcggcct | catcgacgtc | acgacgtggg | ccacggaggg | cacggacggc | gacgccatgg | 31620 |
| cacgccagta | cgccgaagcc | acgcggttga | aagagatgtt | caccgaactc | ggtctgccac | 31680 |
| aaggcagtgc | ggacgcggca | ctgatgtgct | catggtccct | gaccgcgaac | ggcgcgtaca | 31740 |
| cggacgcgat | caccatggcc | aacgaggcac | tcgaactcgc | cacgcggtcc | ggtcacgtcg | 31800 |
| gcggccaggc | cagggccgaa | ctctcactgg | cgttggcgca | cttcgagaac | cgcgatgtga | 31860 |
| tggtcgcgat | cggccacgcc | ggcaacgcgc | tcgaacgtgc | ccgtgagctc | ggcaacgccc | 31920 |

```
ggtgttacgc caccgcgctg cagttcgccg gcatcggcca ccgcgcactg ggccatttcg   31980
acaccagcag gcagatgctc gacgagtcgc tggccatctc gcggtcctat cgcgacacct   32040
acaccgaggt actgacgctc ttggcgttgg cacggctgta cttcaggatc ggtgacgagg   32100
ccgcgcgacc caccgccgag gccgcggtct cgctgagccg tgactacaac atgagccatc   32160
acctcgctga ggcactggag atcctcggct cgatcgaagt cgccgacggc aatccggcca   32220
aggccatccc gcacctcgag gagtccgtcg cgttgtggcg gacgcgcggc tggcacacgt   32280
tccacgcgat cgcgttgacc agtctgggca aggcgtacgc ggacagtgac ccggcggcgg   32340
cgcgggaggc tttccgttcc gcacacgatc tcttcgtcca ggtgggaaac tgggaccagg   32400
ccgccgaggt cgcccggctc gcggagggt gaacgcgtga acgcaggacg tgtggtgctg   32460
atcctgacgt gcctggtcgt cgcaggtctt ggcgtctggt tcgtgctggc ccagtgggac   32520
gtggccaacc gtgcggcaac agtgtcctcg gcgttgggcg cggtcgccgc tgtcggcgtg   32580
gcgatccggg cggccctgcg cgacccggac gggcaacgcg accgcgtccg acggcggttc   32640
ggcgaacacc ggcatgtggc tgacgagccg cggccgccgc ccgcaggat cgaagcgggc   32700 cggacgggcc acgcgcgggc cgagtccggg ggatacgcca acagcggcgt gcactcggat   32760
cgatctactc ctagcgcagg aggggccga accccgcgga ctcgatccgc aggccgagtt   32820
gtgcctcggt caacccgagc gcggcggcgg cgttccccag gtgccagtcg tgcccggcca   32880
gctgggtcag caggtgcccg cggcggatct ggttctccga cagccggaac gtcttcaggt   32940
acgccgtgcg cccgtgccgg tcggtgatca gctcgccgat gtggttctcc tgcttgagct   33000
ggaaaccagg caggaaacgc gacagcgtgt agtcgcccat gcggtacacg cggcgcacgt   33060
cgtacgaggc gtccagcagt cctgacgcca tggtcgaatc gtggaaatcc ggccacgcca   33120
gctgttgcct tgtcgccgcc gccctgagat ccgacagggt gttgatgtgg gtctcgttca   33180
gccgcacacg gaactgcggt acgggcgagg cgaacatcgc gtactggtag accaggtcgc   33240
cgtacagatc ctggagcagc gtgtggtgca gtgcgcggta gtcgtccggg tgcggcacga   33300
cgaacgcggc ggcgagggca tcggccacgt agaccaacac gccgcactgg ccagggtgga   33360
tttcgaagat ccgcaacgcg tccgccagac cgtccacctc ggcaccggtg taggcctgct   33420
cggcgcgcgg cgaaagcccg tgccggatcg cgcgctgcga ccactccgcc cacacgacct   33480
gcggcccacc gaagtgcagc gccaggtatc cctccatcgc caggtgcatg ggcagaaaac   33540
gcaggcgggt cttgtcggtg cgccgtgcca tccgccggtg gaagtgcagc ggcatgcagg   33600
acgcgggatc ttcggcgatt tcagtgccgt acgccgcggc gggtgtgccg tcacgcgtcc   33660
acgtcgccac aaaccgtgc gggatgtacg acatgtacga ggtacggcga tcgacgtcca   33720
ccacacccaa ggagcggtag atctcggcgt gcagccgcaa ggcgcggatc ggttcgtcgc   33780
ggaccagcgg cacgagccgg acaccgcccc acacctggga aggccggacc gacagtccgg   33840
tcaggtcgaa gccgcccatc atccctccag aaaccgggcg atccggtcgt cgaagtgcgc   33900
gcgcagctcg gcaaggccgg tccggccctc ggtgaaccgg gcgaactcca ccagggcagg   33960
cacgtcctcc gcgtcccgca cgcccactgt gggcacgtgc ccgaggcgct tcacgtcaaa   34020
ggtgtccgcg tcgtactccg ggttcaggtg gacgacactg acctcgtgcc gcggatccac   34080
cttggcccgc cacacccgca gcacctccga ggccagcccg tccggcgcgt tgtcccagcc   34140 gtcgacacg atcaccagcc ggtcgggctt gtgctccaac gcgtcgagga tccgctcacc   34200
cagcggcgtc acgccgtgcg gatgcgtcat caacgcgtcg gtccgccctg acgtccacag   34260
```

```
tggaacatag ctgtccgcca gcgcctcgaa caggtaatgg caggcaagcg cgacggccag    34320
cggacgcctg cgtttctgcc gagacccgga cgctgagaag ctgtcgtcga gcacggccac    34380
gacccgtccc caacgtcctg gcgtacgcga ggccgcagca cgcagagcgc ccgtcagctc    34440
gtcccgcctt gcggcacgcg ccgacaacgg caaggacagg acataagacg cgagccgggt    34500
caacggcatg gccgagaggt ccgcggcgac gtcgacgtcg tcgcggattg ccgattcctg    34560
cagtcgcagc cgttccaccc tggtcatccg gggcgcgatg cgttcgagga atgtggcacg    34620
gtcgaccttg tgcttggccg cgaacccttc cgcgaccgtg tacggcaggt cgtagatcgc    34680
cgcgcgctcg tagtgcgccc gccgccacgc ctccaggatc ggcgtgtcat aacgggtttt    34740
cccggtgaac aggaacggcc cgagctcatc acccgcgggg gtgaggtgtg cgtgccgcac    34800
ggccagcttg agcgtggtgc ggtacttcac ggcgtcgaac gccggatcag gccggtgcgt    34860
caaccagtcc cggatgatcg ccctggtccg gcggttgttc acacgagact gtcgcagcct    34920
gcggaaaagc ccgtacaccc gttgcggcgc cacaagacgc aaccgcttgc cgatcagctg    34980
cccttccagg cgtcgttgtt gttcgtccgc gtccctggat gtcgccagta gccggtacgc    35040
gatcaacgtg gcgttgtggt cgttgatgtc cagtgccagt gccgcggcgt acagctcccg    35100
gtagttgccg atcatgtact cgtgcaggaa gtccagtgac agctgctgct cctgcgccgc    35160
actgtggaac tcacgctgtc cgctcgaggt gatcgcggcg ttgacgaaca tgagcatgtc    35220
gtcagcggtg acgcggtcca tgatttcccc cccgtgagca ggcgccggcc ggggaaaggg    35280
ggcacgaact gcgaagcatc gcttcagagg cgggttccgg gagtcgcacc gaagtcccac    35340
ggccggccag cgaacggtac cagcccatga tcccacgtgc atcgaattag gccgtgtatc    35400
gcggccctgc ccgccatagc ggggccgccc cactgaattc cggctccggc ctccggccgg    35460
ggcaggctct cgtcgaacgg agacttcgat acacgaccta agcgggtagt tgcgagtgct    35520
cgtcgctgtc cgagcagagc gaggcgatgt agtccagcga gatgtcgagc acgtccgcga    35580
tcgcggcgac tgtgaagaac gaggggctcg ggatccggcc tgcctcgatc ttgcgcaacg    35640
tctcgtgtga caagcctgtc tccgtggcca gctgcaccag gctcatcgag ccgcgtgccg    35700
cacgcagtac cgccggccagt tgcttaccgc gttcccgttc ctggggtgtc agcggagccc    35760
gcaccatgga tcaacggtaa cccagatcct ggtgcgagtc acctcaagat ggtgatgtgc    35820
tcaaggacat cctcgagtac gtcgatgtct ccggtcacga tcgtgacgtc gccgaccgac    35880
accaagggct gcgccgaagc cggtgcaccg atcaggatga caggaacgac aagggcggtg    35940
agcagtcgtc cgcgcatgtg aactcctgga gtgacgaggg gtttcttccc agcgaacacc    36000
cgggtcgcgt gcttgttcaa tcggccggcg cgggaattct cgttccattc tggacacgct    36060
gggccagcgg tccggccacg tgatgggccg ttcggttggc cgatcgggtg atgtgggcag    36120
cgtccagatt gtcccgtcga gtttatttt caacagccct gagctcgcac gacacgctct    36180
ggtgtgcggg cgttgtgcgt cggctgtgcg ggagtgatgt ggtgggtttg gcacggtcat    36240
gccacgtcgc cgggagcgac ggtgtggatc tctacaggag gagcatgacc atgcgagtgg    36300
gcaagatgat gggggttgct gtcgccctgt cggccgcgac catgctgggt ggcggtatgg    36360
ccgcggcagc ggccccgtg ccgcggagg ccgaggtcgc ggacttcgag gacatcacgg    36420
cgttggagga gaccgaggac acgaccctcg cggccaagcc gaagttctcc gcgcccttca    36480
agtgcaagca gaagtggaag ggcaccacgt acaacggtca ctggccgaac acgcacagcc    36540
gggacttctg gcggtccggt gccaagacca aggggtcacc ggtgctggcc gcggccgcgg    36600
gcaaggtcat ccacgccaag ttcggcagcc gtcagggctg gggcgtgtcc atggacaacg    36660
```

```
gcagtggtta caagacgtac tacttccacc tgaccgcgaa gccgaaggtc aagaatggcc    36720
agaaggtcaa gaagggccag ctgctcggct acgccgggga caccggccag gccaagggca    36780
acccgcacct gcactacacg gtcacgttga agaacaaggg catcaagccg gtcttcgacg    36840
gcaaggcgca caaggccggc acgacgatca ccagcaagaa cggttgctga ccacgggtgg    36900
gcccccgcca tgcggccggg cccacccctg ctgaaaggct ctgacatgag agtgctttcc    36960
ggactggtgg cgttgctgtg cggcctggtg ctggccgccg cgcccgcgag cgcggggatc    37020
cgtcgtgact gggaaaaccc tggcggccg                                      37049
```

<210> SEQ ID NO 4
<211> LENGTH: 86580
<212> TYPE: DNA
<213> ORGANISM: Artificial Sequence
<220> FEATURE:
<223> OTHER INFORMATION: DFD0097-644:735:388

<400> SEQUENCE: 4

```
gcgggctcgt cgtcgcagat gttcactacg ccggtgggcc agtgcagcgc tgacacagcc      60
gcagaagccg cgtcgtcgac atgcacgaag ctggtcacgt ccgcgctcgc ctgaagttga     120
ccgtcgtggg cgagttgcgc catgagcgcg cccgacgtgt accaagtgcc ccggccgtag     180
aacatgccgt agcgcaggac gacccattcg ggcacttctt gcaccgccgt ctcgagtgag     240
aacacggcac gcacggtgtt ctgccggtca gcggtcgaac cgaggtcgag cggcacgtcc     300
tccgtggccg gttcgtcacc tggttcgtag acccagcaga tgctctgggc gatgatccgc     360
tggacgcccg cgccgagtgc cgcgtcgacc aggttgcggg tgccctgctc acgaaccctg     420
gcgttggctg cccgatcgcc gccgctgagg tcggtcagct ggtgcatgac cacgtcgggc     480
tcggccgtcc ggaccgcatc ggccaatgcg gcacggtcgt aggcatcggc gatcgccacc     540
tcggcgccta cctccgcaag gacggggag gggcgccgag tgagtccgac gacctgatga     600
ccatgggcga ccagcatctc cgtcacccgc cgtccgatca cgcccgatgc accggccagg     660
aagatccgca tgtccaccaa agtacggcca ctgccatggg attccgtggt ccagttgagc     720
ctcggtttcg cggaccggtt cgtggcctca ccagcatgga caggaacgag ccgcgaggat     780
ctcgtcgatc acgtgcacgg agttggccgt gatcacggga ttggtctccc ggtagtacgg     840
cagctggatc aacgagatcg acaacgccca gccgcggcca cgggcccacg ccgcgccgtc     900
gacgtccaca gtagaccgga aggtctcccg tgccgagccg gtgaacaggt tccacgccgg     960
gatgaggtcg acagcgggat cgccgacgcc gatcaggccg aagtcgatca cggcggcgag    1020
ccgcccaccc gaggtgagca cgttccccgg cccaggtcg ccgtgggtcc acaccggctg     1080
cgaagaccat tccggtgcgc gcagtgcctc ttcccacgcg gcagtgaccg catccgtgtc    1140
gatgacgccg tgcagttgct cgatggcctc gcgggtcgcg cggtcacgcc ctgccagcgg    1200
cccgctccgg tcggaaaccg gcccttggcc ggggtcgatc cgccgcaacg cgacgacgaa    1260
ctccgcgaga tcctgggcca ccgacggaat gtcgccgacg accgggttct cgccgtccag    1320
ccagcgaagc accgaccagt cgcacggata gccctcaccg ggcacgcctt ggccgaccgg    1380
aaccggaatg ccaccggaa gcggcgccaa ccgcggcagc caggtctgct cccgccgcac     1440
gtccccagcc gcccgttcga ccaacgcag gcgcacgacc atgtcctcgc cgagccggta    1500
cagggcgttg acggtgccgg aagacgtcac tcgggagatc ggcagatccg cccactgggg    1560
gaactgtgcg gtgagcagtc gccgcacaag atcggcggac gtgtcgattt cgtcagcgtg    1620
```

```
catcatcatc gagatcgacg ataaccagcc tgccggttcg cccgcacacg attaaccggg    1680
ctgcgggaac cgccagacgg gtgcatcgaa ccggtgtcac acccgcgtg tggatcagtg     1740
tcgcggtcga gctccgggcg caggtggcgc gctcgagggc ggccgctggg gctctcggtg    1800
cgcatcgggg acgggcaccg gcaggtgaca cggacctgcg ggtcggcggg ctgaccccgg    1860
acgactatcc gcccaggcgc cgttgacctg cggatttttac ctttcgggcc gctctggacc  1920
ggggtatgac cgtttgaccg gccccgatcg gcgtcacggt accctggcgt gggatcttgc   1980
atcgggtacg ccgacgtcga cgggctgcat tgtggttttc cacagtatgt gcggtgtggt   2040
ttgacgccgt gaagtgggag gcacacttcc ttctgccgcc gtccgcgcat tcctaagctt   2100
gtgggtgtaa gaaggttccc ggaagagagc gttgatgtct gtttacctgc tagccgagaa   2160
cgcacacgag cccgtcggcg gtttggccgg ctgggcggtc aacctgatgg acaccctcgg   2220
cggcgtgggt gcggcactcg tggtcgggct ggacaacctt ttcccgccca tccccagtga   2280
actcgtgctg ccactggccg ggttctccgc cagcaagggc gtgttcacgc tggcgggcgc   2340
cctgttctgg acaacgctgg ggtcggttgt cggcgcgatc atcgtgtacc tggtcggcgc   2400
tctgctcggc cgggaccgca cccgggcccct ggtcggcaag atcccgctgg tcaaggtgac 2460
cgacttcgac aagaccgaga agtggttcgc caagcacgga acgaaggccg tcttcttcgg   2520
ccggatgatc ccgctgttcc gcagcttcat ctcgctgccg gcaggcgtcg agaagatgaa   2580
cttcctgaag ttcctgctgc tgaccacggc gggcagcctg atctggaaca ccatcttcgt   2640
cgtcgcgggc taccagctcg gcgagaactg gtacctggtc gacgagtacg ccggtgtctt   2700
ccagaagatc gtgatcggcg cggtcgtgct ggccatcgtg ctgttcgtcg tgatgcggct   2760
gcgcaaccgg aacaagggaa aagctgagga cgacccggac gcgacccagg tgcttccgca   2820
gatccggcgc gacaggtgac ctcccgggcg acgcccggtc cccacgaaaa ggatggcggc   2880
ctgaccccca ggggccgcca tccttttcgt cacggcaagg acagccgagc catcgcgggc   2940
cagagcgact cccacgaccg cgtttggccg gtgcacagcc agatcggcgt accgtccgcc   3000
acgctcaagg ctgctgacac cgtcccgacc cgctcgacct gcgtgaagcc ggagcgaagc   3060
acgccaggat cggtgccgac gaacagcacg gtcgttgacg tcggcacgcc gaaataccag   3120
taaccacgat taccgctgta cacgtcatgc acgccgtaga actccagggc ggccgcagtc   3180
cagtaggagt cggtgaccac ggcggcgcct tcgggcgcat gcaccgaaga ggccaccgaa   3240
ggccagccga actcgccgtg gctgaccatg tcgcgcagct tgtcggcgcg gcgggcgga   3300
tcgatccagg aaaccggccg taccggcaac atcgacaccg cgatcaacgc cgacaccacg   3360
aacgcaggcc acggtagcca ccgcggaatc cgggtgaccg acacggccgc gaccgcgaac   3420
agcaacggga acagcccggc cacgtagtag aaccggccgc cggtgaccag gaagatggcg   3480
atcacgccga ccgaggccca gccaaggaac cggtacgacg gcaatcgcac gagacgccaa   3540
agcccgtaca cggcagccac ggcgccaacc ccgatcccgg cccgcgtcaa ggccagcggc   3600
aggaacatca gcgtcccgc gcctgaagcc gccatttctt ccgcgatcac ggactgcatc   3660
tgcagctgcg gccagccgtg cagggcctgc cagatcaacg tcggcacgga cgccacgacg   3720
gaaatcgccg ccccggccca gagcagcgga cgccgcagca agtcacgagg cccggcaacg   3780
agtgcgctca caccgatcgc cagccacaac gccaccacaa gccacttcgc ctgcagggtc   3840
acggcggtga ccagaccggc gtacagcagc aggcggtcct gcctgacccg cacccagcgc   3900
acgagcagcc acaggatcac cgcccagagc accgtgtcta cagtggacgt ggccagcatg   3960
tggccgctcg gcagggcggc gatcgcggtc gccgccgccg ccatcacctg cgcgacggga   4020
```

```
gaaccgccaa gctcacaggc gatcgccgcg cccaccactg tcaccaggcc gaccaacagg    4080
atcgacggca acctcaacac ggtcaggtcg cccggtgcca gccagtccag gaaggccgcc    4140
atcagcggca ccaggggcgg ctggtcggcg taaccccagt ccagatggcg gcccgcggcg    4200
atgaagtaca gctcatcacc gaaatagccg tatctccggc tggtcagcaa cagcaaggac    4260
acggtgatgg ccgcgatggc catcaccggt cgaagcgcca acgcacgcga tgtgacagcc    4320
aaagtggcca ctattccgcc tttcgagctc ccgcgatgtc ggtcacggtc gtgcgcagcg    4380
ctgaggtgaa gtcatgcgcg ggacgccacg agctgagtgc gcgcagccgc cggtcgtcga    4440
gcaggccggg gccgggggag acagtcacgg ggtcgccggt gaccaacccg gcgaccatcc    4500
gaaccactga gcggaccgaa aggctttgcc cggagccgac gttgtacacg ccggtcggta    4560
cctcggccgt caggcagtgc acagtggccg cacagaaatc ctcgacatag agccactcgt    4620
gcacgggcga tccgccacgc accaaagcag gttcctcgcc gcgcaacacg gtccgggtca    4680
cggtgggaat gagccgtgac cgctgctggt gaggtccgaa gatgttgccg ctgcgcagaa    4740
cgatgccgcg aagcccatgg cgttgcgcgt agtgcaaagc gatgagctcc gaagtcacct    4800
tcgcgatgcc gtaaggcgcc gcgggccgta cgggatggtc ttcgtggtac agcaggccct    4860
cgctcaaagg cccatacacc tccgcgctcg acgcgagcac cacggcagaa accccggcca    4920
tcccggcggc cgcgaacacc cggtcggtca aggcggcgtt gaccgtcaga tacccccaccg   4980 gatcggcgag cgattcgggg atggaggtcc gcccggccag gtggatcacg gcgtccacct    5040
ggtgcccggc gaacaccgag gccagtgcct cggcgtcggt cagctcggtc ggcacgacga    5100
ccgtacccgg gaccggctcg cccggatcac gcagcaggac cacactgccg ggggagcggg    5160
cgagcaggga agtcaggttc cggccgacga accggtgtt gccggtgatc gcgatccgca     5220
cgtgtcagac cgcctcgtcg atcaggtgct cgaacaccag gccgaggtcg gtcaccgcga    5280
ccgcgacggc ggccagcgcg tgccgaacgt tggccgtcgc acacggcggc aagtcggcac    5340
gagcgagctc cttgagccgt gtgtaaacat cgagcagcgc ggtttccgaa gcggtcaacg    5400
gtgttcccag gaggtccgtc atcggcccgg ccttcgtcg atcatccgct tggccttgag    5460
cgtgaagcgc ggcagcgacc cggtctgcgc cagcgtcacg ttgaaccgca ggccctcgtg    5520
cgccgcggac aactccttgg ccagctgttc acgcaaccgg tcccagtccg aggaccgagg    5580
ggtctccact cgcacggtga tctcgtcacg gttgccctcg cggtgcaggc gggtctggaa    5640
ctcgccgatc tccgggaacc gccggacgat cgcctcgacc gctcggatgt acacgttggt    5700
gccacgaatc agcttcatgt cgtcgacccg gccgaggaca ccgccgtcgt acaggtcgaa    5760
cgtgcgcccg caaccacacc gcgaagcagg cacccgggtg acgacgtccg cagtccggta    5820
acgcagcaac gggatcatgc tccggccgaa cgaggtgacg acacgctcac cgcgttcccc    5880
gtaaccgacc ggcctgccgg aggcgtcgac cacctcttcg atcatgtggt cctcgatgat    5940
gtgcgcacca cccggctgat gagcgcactc gaacatgaag atcgtcgaga tctcggtcat    6000
ccccgcggtg tcgtaggccc tggcgcccca acggtcttcg atcatcgccc gggtctccga    6060
tgggcacggc tcaccggaca gcacgacctt gcgtaccggc cctgatgtca ggtcgatgcc    6120
gagcgagtcc gcctcttcgg ccagccgcaa cgcgtacgtc ggcgtggagg cgatgacggt    6180
ggcgccgaag tcgactatct gccggacacg ggcctccgcg gtctgcgcgc cgcccgggat    6240
caccaacgcg cccagcttct ccagtgcgtg gtgcaggccc cagaaaccga tgaacgagcc    6300
gtacccgaat gccagatagg ccacatcgga cggacgaaca ccttgcgccc acaggccgta    6360
```

```
gcaccacatc tcggcggccc atgaccagtc cttacgggag tccgacgcgc gcagggcat     6420
ccggccggtc gtgccgctgg tggtgtgcaa ccggatcgcg gattccacac cggtcaccgg    6480
aagtgtgccg taaggcgggc gcgcttcctg cccggccatc cattcgtccc tggtcaggaa    6540
cgggatccgc tgcagatcgg cgagagtacg caacttcgag gcatcgagtc cgtgtaaggt    6600
acgccgatag tgcgggctac gcgccgaagc ccactcgaca acggcgcgca gcttcgccag    6660
ctgaagctcg acgagatccg cacgcggcaa cgtctcggtc ttgggattcc agaactccat    6720
cagctcaccc ccgccatcgg atcgccgcgg cggccgcgta gtcaccggcg tgggcgaacg    6780
cggcgagcat gatcagtgat ccgtccttga ccttgcccga ccggatggca cggtccaaag    6840
tgaccgggat gcccgcgccg aacatgttgc cgcactcctc gaacgtgtcc gggtgccggt    6900
ccggtgtcag gccaagcgtg ctgcgccagc tcttgaggaa gagccggttc ggctggttgg    6960
tcaccagtac gtcgatgtcc gttgtggaca cgccgatccg gtcgcacacc tcaccggcga    7020
gttcggggac gagcttcttg ccgcggatca ggacttcccg gatcttcgac tcggtgaacc    7080
cgatgtgcac ctggccgtca cccggctccc agtacttgcg gtcgccgtcg atcgcgagcc    7140
ccatctgccc ggcgtagtcg gggaaggtgc gggaccggac gtccaggacc ggcgagctgt    7200
cgtcggcgac gagcaacgcg gcgccggcac cgtccccggg gatggcggcc tgcggcatgg    7260
tccgggtgcg gctctgccgg tacacctgcc cggcgaagtt ctgcgcgttg cagatcagtg    7320
ccgagcgggc gtccgttgac cgcatcagat gcgtcgccag ttcgatcatc gtgatgaacg    7380
ccgcgcagct gccgttgtgc acgtcgaaca cccagcccgg ctccaggccg agccgctgtg    7440
ccagctccgc gccgcacccg tagatcggct ggtcgggcag ttgcgagtgg gtgatcagga    7500
tgtccacatc ggtcacggcg gaatcgccgt gccgctcacg cagacctgtg gtcgcccgct    7560
ccatcatgtc cactgtggtc tcaccggcg cgacgtggtg gcggaacgcg gcggcttga    7620
acatcacctg cgcgtcgccg tcctcgccgg ggtcaccgcc gaagtacgac gcgggcacgc    7680
gggtttcggg cagatagctg ctgacatcca gcaggctcac gctcttcatg ggttgacctg    7740
gctccagtcc ggggtgatcg gcaggccgcg ggagtgccgg tactcgcaga tcttcttgag    7800
gttctgcagc tccagccagt gcccggcggc gaacaggtgc cagaactccc cgatccacgg    7860
ccgtccttcc ggcgcggtct ccgggaacgg gttgtcgtcg tagaacgggt ggtggcagtt    7920
ggtccactgc accacgctgc ccggcttgtc gaacacgacc tgggcgtcga tgacccgcat    7980
caggtagatc atccacaggt gttggccctg gtcccaggcg cagtggtagt ccacggtccg    8040
tgcctcggcg ttcgcgacgg tcttggtgta gatcatcgtg tccctggcga tcaggtcgtc    8100
cgacagccac acgtccggct ggtcggtccg ctcgaaccgg cgcagggtga agctccactc    8160
ggccaggctg cgggtgtcgg cgaggtacgc gtagacctcg tccggcggcg cgtcgatgtg    8220
gtcggtgatg gtgcagtacg tgccgtacac gtcgttgtgc gcgtggaact ccggcgtggc    8280
cgccatgatc tgcttgatca ccagttgac cgggacgatc tcggcgcggg tcaggtcctc    8340
gatgccggcc agcgaccggg gcagcttgtc aacctgcgtg gacgtggaca tgggtgtcct    8400
ccttcgcgag gaacggggcg aacgggggaa tctcgtcggg atcgcagtcg atggccacga    8460
aggccgggcc gcgcacggaa ccggcgtgcg ccagtgccgt ccgcaactgg tcggcggacg    8520
ccgcgtgacc ggcggcgatg ccggggaaca tggccgcgac gcccgcggcg aggtcggagt    8580
accggaagcg gttgaacgtg tagccgccgc cgaagtagat ctgctcacgg gtcacgcaca    8640
tggcgtgcgc gttgttgttg agcaccacga acgtgatcgg caggtcgtac tccaccgcgg    8700
tgtggatctc caggccgtgg gtgagaaagg cgccgtcgcc cgcgatcacg aacgtccggc    8760
```

```
gtccgctgaa ggccgcgcct atcccggcac cgaacgtgta gcccatgcca cccataccca   8820
gtgccacaac gcatcggccg tgacgtgggg cgggcagccg tggatcgcg gcggcgcccg   8880 cgttcccggc gtcgatgaag acgttggcgt catcgctgat caccttggcg atggcgtcga   8940
ccacctcggt gtagccgagt cgaggaccgt ggtacgtcgg cgcggccagg aattcggcag   9000
gctccgcgac gaccgtgctc aggccgacgg gcccgagtcg ctccgtcagc gcacgcagag   9060
tcggtttgat gtgcccgcgc aacgccaatg cgtcgatgta cggcgtctcc gggtccagcg   9120
acagcacagg aatcccggcc agcaggtcgt ccagtccgcc gcgcgcagtg atcggcaacc   9180
tggtccccac cagtacgcag gcactggcgg tgctcaggtg ccgcgcgagt gcgggatggc   9240
ccatgatgcc cgcgaccccg atgaaccggg gatcggtgtt gtcgaacacg tccttggagt   9300
ccgggcagac cgcgaccctg gcgtccagtg ccccggcgaa cgcccgcagt tcggccctgg   9360
cgtccgctct ggcgacaccg tctccggcga tgacgatcac ccggccggat ttccgtgccg   9420
cgtcggccag gtcggccgcc aggtccacca gttcctcagg cgtggccacc acttcgggcc   9480
ggggcacggc ggcagcgggt gcgtcgaact ccgcttgctg gatgtccttg ggcagcaaca   9540
gaacggccgg gccgtccgcg gtcgcggcca gtgcttcggc gagcaactcc gggaactcgt   9600
ccggatcggt gacagtggcg cagaaccgtg acacgccagc gaaaacctgg gctgcggaca   9660
aggatccagc cagaccgctg gagtcctgga acgcgccttt gccgtgttgc ccggtcggcg   9720
gctggccgac cagcgcgagc accgggacac gggacgcgta cgcctcgccc aggccaggta   9780
ccaggttcag cgcggcaccg ccggaagtcg ccgccaccac accgagcccg ctggtggtcc   9840
gggcgtgccc gtcggccatg gtcgccgcgt tgaactcgtg tttggccagt acgccggtga   9900
cgccgggtct ggcttgtagc gcgtcgtaga ggtcttcgat gttcgcgcca ccgacaccga   9960
acacgcgggt gacgccgagt gcggcgagca cgtcgacgag atggtcgacc accggatac  10020 gagacgacag ggtgacagac aagtgtgacc ctttccccag cacgaaagaa tgagtgcgct  10080
atcgcgcgaa tcagccccag ttggagtcgc ccgaaatcgg cgacgagctg atggaaacag  10140
tgtgcggtgc ggtttgtcaa ttcgcccgaa ccggattcac ccatgatcgg ccgactggaa  10200
actttagggc atcgcctagt ttcattcgcc ccgctcccgg ctagcatcac ctgtggtttc  10260
cgtgcgacgg aggaggcagc tgggtggtcg ccgcactgtt cgacctcgac ctggtggacc  10320
gggatgtcta tcggggagtc agtcgtgggg gcaccgcgct tccggtattc ggcgggcaac  10380
tgctcggaca ggctttggcg gccgcttcgg cgactgttga atccgatcga ctggtgaatt  10440
ccctacattc ctatttctt cgtcccgggg attcggcagg tggattgttt tttgccgtcg  10500
accggctcag ggatggctac gcgttcagca cccgccgggt ggacgtcctg cagaacgacg  10560
tttccgtgtt caccatgacg gcttcgttcc accgggccga tcacggcctg gaccacggcc  10620
ttgaagcgcc ggtggtcccg gatccggagt ccttgccgac gctggacgag cgctacgcgg  10680
gctacgagtc gcagatcccg tggttcggcc tgccgcagcc ggtggagctg cgctacgtcg  10740
acgacccgcc gtggatccag cgcggcaaag gacctcgtgc ccccgtcggc cgggtgtggt  10800
tgcggctgaa ggacaagctc ccggacgacc cggtgccgca cacgtgcgca ctggccttcg  10860
cctcggacat gacgttgctc gaaccggcac tggtcgcgca cgcgacctca tgggacggcc  10920
tgcgttttgc cagtcttgac cactcgttgt ggttccaccg gtcgctccgg gccgacgaat  10980
ggttgttgta cgagaccaca agcccatccg cggcgggcgc aagaggactg ggaacaggcc  11040
ggttctggga ccgcgcgggc cggctggtcg ccagcagcgc gcaggaaggc ctgctgcgca  11100
```

```
tccgatcgga ggtccccgcg tgacacacgt gctgttcctg tccgtgccct tacacggaca   11160
catcctgccg agcctgccga tcgtcgccga actggtggcc cgcggccgcc gggtcagcta   11220
tgccgccacg gccgacttcg ccgggttcgt cactgaagcc ggggccacgg ccgtgccctg   11280
caccacgatt tttccggtcg agggctccag caaagcgttg ccacgcaacg acgccgaggg   11340
cgcgctgatg ttcctcgacg aagccatcac ggccatgccg caggtcgccg aagcgctggc   11400
cggggatcca ccggacgtcg tcgtctacga catgggcgcg atgcacggac cgatcctggc   11460
cgagaagtgg ggcgtacccg cggtgcagct gtcgccgtcg cacgtgacgc cgcgtggcgt   11520
cacccagatc ctcggcatca gccaggccga agcaccaccc ggcattgtgg agttccagcg   11580
ccggttcgag gacttcgtgg ccggacaagg cgtgcgcgtc cggcccgagg agatcatggc   11640
cgaaccgcgg cggtgcattg tgacgatccc gcgcgcgttc cagatcgaaa ccgacggcat   11700
caccgatcaa cacacgttcg tcggaccgat gatcgacgac cgggcgccag aaccgtggcc   11760
agacgatcac ggcaagccga tcgtgctggt gtcgctgggt tccgcgttcc gcacgcagac   11820
agacttctac cgaacatgcg ttgaagcctt ccgtggtacg gaatggcacg tggtgctcgc   11880
cctgggcaag ttcatcgacc cggctgacct gggatcgctg ccggacaacg tggaagcaca   11940
cgcatgggtt ccgctggctt cggtgctggc gaaggcaag gcgttcgtga cacaagccgg   12000
gatgggcggc acgatgaccg cgttgtacca cgaggtgccg caagtcgcgg tcccattgat   12060
ggcaggtcag ccattgaccg cacgcaggct ggtcgaactc gggctcggcg cacacctgcc   12120
acctgaggac gtcacaccgg aaagcctgct gacagccgtc cggcaggtcg ccgacaacga   12180
gtcgatcaag accgagctgc gccggatgcg caaggagatc gaggcctgcg gcggcgcagc   12240
gcttgccgct gacgttgtcc tgtccacggt ggatggagaa ctggatgccc aacgaattg   12300 aggtgtcgca gtagcggtgc gcgccagcgc acaagaggtc tgcgtggttc cctcccgtat   12360
ggcctgggtc tgacggagcc cggcagcgcc gagcaccgtg agcaggatgg tcgtcatcgc   12420
ggacctgacg aaccacaacc cgaattcttc agtgctggtc agggcgccca gagatcacga   12480
ttcggccagt ggaggctcgc cgtcttctcc accatgacgc ccgcgtgcgc tcgaaccgtc   12540
aaggggccgc ggttcccgta cggtgagtgt gagcagagcg gcaggcaggg cgatcgcgag   12600
gccgagtgcg accatgagca gtgtgccggt cgtcggcgtg aggtggtcga gcatggtcag   12660
gtgtacgaag aagtgcggga tcgcccaggt caggtacatg atgagcgctg ccagggtgag   12720
ccattgtccc atgtggatgg tcgcggcgcc gagcaccacg gcgctggcga gtgtcatggc   12780
gccgtagtcg agcatcaggt gcttgttgta ggccatgccc atgccgacca cctcgagcgc   12840
gaagaaccgt gcggggagga acagtgccca caagccgacg acggcctggg tgacggtgag   12900
aaacccgaga ccggcgcgaa gccaccgccg catcaccggc tccgcccgtg cgcacggtct   12960
ccggcgagga agtcgtcgaa cgtgatcctc cccgtcgccc ggtccggggt gaggtgatgg   13020
cccgcgcgat agtcacggat caccttgccc ggcaagggaa ctgccacac cggtcgacgg   13080 cggccgatcg ccaggaggta gctgcgggcc agttcggcgg cctcccgtac ctccgggccg   13140
ccgatgtccg gtgcccggtt cgcggccggt cccgccgcga acgtgaccag ctggtcggcc   13200
acctcggtga cgtcgaccgg ctggaaacgc ccctcgacg gcatcagcgt caccggcagc   13260
aggcgctgga catcgcagat ggtggcgatc aggtcgtgga actgggtcgc gcgcaggatc   13320
gtccacggca gccggagcg ctcgaccagc cgttcacagg ccagcttcgc ccggtagtag   13380
ccgagcgcga tgtggtcgat cccgacgatc gacacgtaca ccaggtgcgg gtcgcccgcc   13440
gctgtcgctg cctcgatcag cctgcctgtc gtggccacat caccccgccc gttggtggtc   13500
```

```
gccaggtgga tgatcacgtc cgctccggcg gtcgcgccgg ccagcccgct accggtacgc   13560
agatcgccca cgacccagcg gtgcgcggcc ggctcccgct tcctgcgggt cagcacccgc   13620
acgtcgtggc ccatatcgag cagccgcggc accagcgcgc gcccgagccg cccggtgccg   13680
ccggtgacca gaatctgttt cgccatgtct cgctccgtgg tggctggaat ctcgcctcgc   13740
accactagga accgaatgac tccccggaac gtgacaaccg ggccagttgc gcgccgacga   13800
accggagctt gtccggattg gcgacaatcc ggataccggt gatccggccg tccgcgatct   13860
ccggcacgaa cacaccgagc agcgtggacg cggaccagcc gaacaccgcc ggagtcccgt   13920
tcacctcgtg cacggacacc gtgagacctt cggcatactg gctggtgacg gtcgccaggt   13980
accgggcgac cttctccgcg ccgcgcaccg gcaaccgggc gacaccgggc gtgccgccac   14040
catcggcgac cgatgtgacg tcctcggcga gcatccgctc cagaccggcg aggtcaccgc   14100
cacgcgcggc gtcgaggaac cgctcgacca gcatccgatt cccggtgacg tcgcccgcgg   14160
accgcgggag ccggcggcc gacagccgtt tccgcgcccg gctgtgcaac tgccggcagt   14220
tcgactccga aagctccacc agctcggcca cctcgcgatg gctgtagccg aacgcctcac   14280
gcagcacgaa aaccgcccgc tcacccgggg tgagccgttc ggccagcacc aggaaggcca   14340
gtgacaccgt atcccgctgc tcggccgtct ccatcggccc cagcgcgctg tcggggtca    14400 gcaccggctc cggcaaccac gacccgacat aacgctcccg gcgagccgag gccgccccaa   14460
gccggttcag gcacagattc gtggtgactt tgaccagcca cgcggacggg acctcgaccg   14520
agccgggctc ggtaccgtgc caccgcaaga acacgtcctg aacaacatcc tccgcgtcca   14580
cggccgaacc cagcatccga tacgccagcc cgaacaaccg cggccgctgc cgctcgaact   14640
ccgcgaccgg cgcggatccg ggcttctcca ctggacggtt cacaaccgtg attctcgcac   14700
ggcaccgccg atggccgcgg tcactcatcc cgggcacggc gccgtctcc ggcgtttatg    14760 ttgcgcccag gccgctctga gcttgcgtca ggtcatctgt gggcttgcgc acaggctgtc   14820
cggggcacaa gtttagggtt gcccctagtg cttgggggtgc atcgttgaca gtccccgtgg  14880
tcggtcgaca tggttgctgt accgggaaaa ccgcttgtca gttgaacatc cgtctggggg   14940
tccgatgaca gaccggccgc gactgagccc gacccggatt cggccgtgga ttccgccggg   15000
cggtgcacct gccgccgggc tggactcgct gcgcaaggcc gttccccgccg aactggccgc   15060 gcgcctgcgt gaccttggcc agttacgcga cgtcctgctt gccgcgcacc tgaaagtcct   15120
tggtgtgatg ggcggcgagc gaacgcccct caccggctac ctcgtgcctg gtgccgactt   15180
ggcgccgcgc ggggtggcat tggacgatgc cacctggcgt gacctgatcg gcaaggtgca   15240
cgaaccggtc gaagtcgtcg aagacgcgcc cgctttcgac gtggtactgg acttctccgg   15300
cgccgggatg accggcgcgg tgctggacgt ggcctatgtg gacgccgagg acggactgtg   15360
gttggagcta cggttccgtc aggacgtgat cgaccacgcg cacgccgaac ggttcgccgg   15420
atacgaactg cgcgcactgg aactgctcgc caccgatccc gacgcctcgc atgacgcgaa   15480
gagcctggtc gagccggatg agtacgagta ccagatgcgt gcgcattccg gcgccgacat   15540
cccttggcac ggaaagcttt tcgtcgagct gttcgaggaa caggtgcggc tgcgcccgga   15600
tgacctggca gcctcacacg gcgacgtgcg atggacgtac cgcgacctga acgcgaacgc   15660
caacaaggtc gcgaactctt tgctgcgccg tggtttgctt gccgaagatc cggtcgccgt   15720
ggtgatgaac cggaactga actgggtcgc ggcgatgctc ggtgtgttca aggcgggcgg   15780
cgtgtacatg ccggttcgcc cggacttccc accggatcgc gtcgccatgc agttcgaacg   15840
```

```
cgcggattgc aagttcgtcc tgtcgtccgc ggacgccgtc cacacggcga acgaagcact    15900
ggccggttcc gtccgggact gcccggtgtc gcttgtggaa gacctgctgc gtgacgaaac    15960
cgacgacacc gacccgaagt cgtcgatcca gccggggcag ctggcgtaca tctacttcac    16020
gtccggctcg accggggcgc cgaagggcgc gatgtgcgag cacgccggga tgctcaacca    16080
cctgtacatg aagatcgacg acatggaact ggccgagggc gaggtggtca cccagaccgc    16140
gtcgcagtgc ttcgacatct cgttgtggca ggtcatcgcg ccgtggctgg tcggggcgag    16200
cacgcggatc atcgacaccg aaacacagct ggacgtcgac tggttcctcg acgagatcgc    16260
cgcaggcggc atccaggtga tccagatcgt gccggcgtac ctggacgtga tgacgtcgca    16320
cctggccaaa cacccgcgcg cgctcggtga cctgcgacc atctcggtca ccggggaggc    16380
actgaaactg gagctggtcc gccggtggtt cgcgctctac ccgcagatct cgctggtcaa    16440
cgcgtacggt gcgaccgagg tctccgacga caccatgcac gaggtgctga ccggcctgcc    16500
ggaacgcgac ttcgtcacgg tcggccgtcc actgcggaac gtgcacgtgt acgtgctgga    16560
cgagaagctg cggatcgccc cgctcggtgc tcccggtgag atcgcgttct ccggtgtcgc    16620
cgtcggccgt gggtacatca atgacgagga acggaccgcg cacgcgttcg tcgaagaccc    16680
gcaccggccc ggcacccggc tgtaccggac cgggggacttc ggccgttggc tgcccgaagg    16740
caagatcgag ttccttggcc gccgggacga gcaggtcaag gtccgcgggt tccgcatcga    16800
gatcggcgat atcgagaaca agatcctcgg tgtgccgcat gtccgcgagg ccgcggtggt    16860
catcgatggc gactcggaca ccaagaccct ggtggccttc tacagcggcg cggccgagct    16920
gaaagccgag gacatccgcg accacctggc cacgcagctg ccggagtaca tgatcccgac    16980
gtacttccac cggctggact ccctgccgct caccgagaac ggcaaggtca acaagaagct    17040
gctgacctcg ctggccggca cgctcggcca cgcgggcgcc tcctacgtcg cgccggtgac    17100
cgacgcggag cgcaggctcg cgaccgcgtg ggcggaagtg ctcggcgttc cactggaacg    17160
catcggtcga cgggacaact tcttcgagct cggtgggacc tcgctcgcgg ccgtgcggct    17220
cgtggtgaac ctcgaccgcc agatctcgtt gacgcaggtg gtcacgaacc cggtgctgga    17280
ggacctggcc gcgtgcctcg tcgccgcggg cacgcctgac gccggactgg tccaacgtct    17340
gtccatcggt gacttcgacg caacggcgac gctggtctgc ctgccgtacg cgggtggcaa    17400
cgcggtcaac ttccagcaac tggcaaaggc actgcaggac aagggcatcg cggtgtacgc    17460
ggtcgagctg cccggacacg acctggtcgg cgggcaggac gcgccgttgc aggaggtcgc    17520
ggaagtggcc aaggcggtgc acgaagagat caccggcatc accggaccga tcctgttgtg    17580
gggacactgc gccggagccg cgttcgccgt ggagatcgcg cgtctgatgg aggccgatgg    17640
acggccgccg ctgcggatct tcgtcggtgc gctgatgctc gacgccgtac cggacctgga    17700
cgccgagagc gccagggtgt ccgcgatgag caacacggag atcaccgcgt tgctccggca    17760
ggacagcgcg ttcgtcgagc tggacacgct caaaccggaa cggatggacg tggtgggttc    17820
ggcctaccgg cacgatgtct gctccaccaa ccagtacctg gccgacatcc agcaggacgg    17880
ggtcaaactc gccacgcctc tggaggtcgt ggtcgccgcg gacgaccgca cgaccgtggg    17940
acaccagacc cggcattcgc ggtggggcag catcgccgat cacgttgagc tgcgtgagct    18000
cggtgaaggc gggcactact tcgtccgcac gcgggccgat gaagtcgcgc gactggtcgc    18060
tgacgcatgt cgctgacagt ccagccgctc tatcgcggcg ccaccgggtt gagcaccgcg    18120
ttcggcacct tcgcgaaact gctgcagggc aggctgacg aggccgacgg ggacttcctc    18180
gtcacgttgc cgatcgcgcg ctggacagtg gccacgttcc tggccgaccc ggccatgtcg    18240
```

```
tcgatcgagg tccggccacg gcacaagaag aagtcgttgc ggctggccga gatgctgatg   18300
cgaaccatgc cggagccggt cggcggcgtg ctcacgctgg acagcggcct ggccgagggc   18360
aagggcatgg ccagttcgtc ggccgatctg gtcgccaccg cacgcgcgat cggcaacgcg   18420
ttggacgtcg agctgacgcc gaagttcatc gagagcctgc tctgccagat cgaaccgaca   18480
gacggtgtgt tgtatcccgg gattgtcgcc taccaccacc gcagcgtccg gctgcgacgg   18540
gtgctcgggt cgctgccgtc gatgactgtg gtcgggctgg acgagggcgg cgccgtggac   18600
actgtggcgt tcaaccgcat tcccaaaccg ttcggctcgg ccgagaaacg cgagtacgcc   18660
aggctgctcg acagactttc cctcgctgtc gctcagcgcg acctggcatc cgttggtgcc   18720
gtggcaactc gcagtgccga gctcaatcag gcgttgcgtc gaagaggac tttggacgcg    18780 gtgatcagga tctgtgccga catcgacgca ctcggcgtcg tggtcggaca cagcgggacc   18840
gtcctcggcg tgctcatcga ccgttcggac cctgcgtatc cggacaaagt ggccgccgcc   18900
gcgaaggcgt gcgcggcact gaccggcaac gtgaccatgt attcgacctt gagcttcgac   18960
tgaacatcgt gggaggacta gtgaacgcat tgcgcgactg gcggccgcgg gaggtccgcc   19020
cggccgacgt cggagccgag gcgacgaccg acgggctgat caggtatctg aagggcgatg   19080
ccgagttcga caagctgctg acggagtcga aggcggtggt gttccgcgac ttcaacgtca   19140
ccgaggaaac catcgaatcg gtgatggaac tgctgttgcc gaagcggctg gcgtacgtgc   19200
acggcaactc gccgcggacc aaggtcggca agaacatcta cacgtcgacg gagtatccgc   19260
ccgagttcac catctcgatg cacaacgagc tgtcgtacgc ccacgcatgg ccggaccggc   19320
tgttgttctt ctgcgccaag gcgcctttga caggcggagc cacgccgatc gtggacggcc   19380
agctgtggct ggagtccctg gatcccgagg ttcgccaggc gttcgcaggc ggagtgcggt   19440
acacgcagaa cctgcacgac ggccttgggc ttggcaagag ctggcaggac acgttcgaga   19500
ccgccgaccg ggctgaggtc gaggcgttcc tggccggtgc ggcagccgag tgggagtgga   19560
agaaggacgg gacgttgcgg atccgccagg tcaggccgtc cacgatccag cacccggaga   19620
cgggtgccga ggtgtggttc aaccagtccg accagtggca cccggccgcc ttgggcgacg   19680
agacggccgc tgagctggcg cagatcctgc ctgaggacga gctgccgcag tcggtgacgt   19740
tcgccgatgg gacgccgatc ccgggggagt gggttgtcca ggtgcgcgac cgtggcctgg   19800
agaacgccgt ggatgtcgac tggcatctgg gtgacctgat gatcatcgac aaccttcagg   19860
tcgcgcacgg ccgccgcccg ttcaccggtc cgcggcgaat cctggtggcc atgtcctgac   19920
cgaactcaaa ggcggcggtg cacaacgaag tgcaccgccg cctttggcta tccgcgacta   19980
cttgtgggtg atcggcttgc gcaggccccg ggccgccgcg aaggcggcga ccgcaccaag   20040
aacggtcgaa ctgagcagag cgaagagcac ggcactgacg tgcgggtcgg ccaggacaag   20100
gctgcgggcg gcatcaatcg cgtatgtcaa cgggttcacg gtggccacga tctgaagcca   20160
cgtcggcagc aaagccaccg gcacgaaggc actcgaagcg aacatcaacg gaacatcac    20220 cagcaacccg atcgactgca tcacgtcggg gctgcgcagc caggccgcca gcgccagaaa   20280
gatccagatc atcgagtgga tcacgaacaa cgccaccagc atcgcggcta tcgacccgac   20340
cacaccaccg gcgggtgagt aggagagcaa ggcgaaagca cacacctgaa gcaccaccaa   20400
ctgcgcagca ctccgcacca ggtcggtcaa agcccgagcc gtgagcacca aaggcaggtg   20460
cacaggcatg gaccggaacc gcacgagcat cccgttgccg agctcacgga caagagccat   20520
gcccgcggtc tgggccgcgc caatgccgtt gttgagcatc aaggccggga cgaggtactc   20580
```

```
gatgtacgtc accccctgccg ggaagtccgc cggattcgcc atgctgccga agacttcgct    20640
cagcacgaac aacaggaaca gggggttgat caggccgaag accgcgaccc ggcgatcggc    20700
gaccagggcg cgcagtgccc ggacggtcag tgcgcgtagt tgggcgaaag gtccggcgcc    20760
gagccagcgt gggccggtca gtgcgtgtgt catggtgatt ccccgtcgta agtgcgccgc    20820
acgtaggaca gtgcggtcag cagtccgtct gacgtcaggc ggtttcggcg gtccagctcg    20880
gcgacgtctc cgatgggcag cgagccgatc cgggaccaca ccagccgcc gtcggaggag    20940 atgtggcagc gcgtccggcc ggcgttgtcg gggtgcaggc agtacgggat gtccaggtag    21000
ccgagcgaga aagcgcgtac cagggccttg ccgatgtctg gatccagcga cagcacagcg    21060
tccactagtg cccgagcctc ggcatgcaca ccggtgtccg cgaccggggg aggcgggcct    21120
gcggcacgag ccgcggccgc ggcgctttcc aaggcgagga tgttgtgtgt cacggtcgga    21180
atgcgatacg cctcagcggc cgtcttcacg atcagccgcc ctgcgccgga ccagaccgcg    21240
agcgaagccg catcgtgttg cagggcgagg gcgccgcgtt cggtctccgg ataaaggccc    21300
atgtacgtgt agatcacgat gtgccagtcg acggaggaca gctgctgagc ggcgatccgg    21360
cgcagcgcca gtacggcctc gaggtcctgt tccggattgg tctgctgggc gtagctcagt    21420
gagacgctgc gcaggccgtg ctgtgcgaag aacatcgctt ccaggacact gatcgcgacg    21480
agcatgctcg gcgggcacaa ctgaccgatc atgcagccgc cgaacgtttc cagatgcgcg    21540
ggaatgtccg cggtggtcaa gatcgcacag ctctcttccc agtgccgcaa ggactcacgc    21600
aacggcgtcc gactgtatgg cagacaatag gagacgggcc cgccttcagt ggcgtgcagt    21660
ccagccgcga ccagagtgcg gaagatgtcc tgcggacggg ccgatccgtg ccttacttgc    21720
acaggaaagt cggcggagcc aacggacgag atcatgtccc gggtgaccga cggcccgtgt    21780
gcgacgatgg gaaaaccgtt gagcggcaag ttctctgcca aagcccggcg cgcggcggag    21840
tcgtcacgga cccgggtgta gctgtccaag gtcacggtgc caacggtggt ggcgtcagcc    21900
ttcttggtgg cggtcaagcc gtacagcatg tccctcggct taccgaaacc catgcgcggc    21960
tgcacgacga gttcgccggc gttaccgacg aactcgccga acgacatgcc ggtcaagaag    22020
cggctcgcgt ggcggctgtt ttgtccaagt aggaacggaa tgcgccgatg tcgccggtgt    22080
cgaagacgcc gtcgtagccg gcctcgcgca gttcacgggt gtggctgatg ttgctcaacc    22140
cgtcggtgcc gagcttgccg ccgatcacca ccggcaggtc gtcgaattcg gtcgggcgc    22200 gcagcgcgcg gatatggtcg agcccgtcgc tgaagccgtg gccgttgacg ctgctgacca    22260
cgacgaggtc gaagttctgc cgggtgcacg tgtccaccag cagtgacggc gtcacgcagc    22320
agccgatgtt ggtcacctcg tgcccgagtt cttcgagcag cagttgcagg tagaccaggt    22380
tccacgtgtg cgagtcggac gcggtgctgg tgaccaggac gcgaagccgc ctgcgatggc    22440
ccggtgggac gaggcaggcg ggcgcggacg agttgtcggc atacattcca gtgatttccc    22500
cagtatttgc cggcatggcc gagatacttg aaaaagctag ccacgcgtca cgcgcggtgt    22560
caagaagtcc gggccgggcc tagggttttc cacagtgtca attccgtttc attgcccgcc    22620
gtgccttccg gcttgtaatt ccattgcgg gagaagcatt tcttgggg aatcggcgac    22680 actggggagg ctttgacgtg actggcctga cgaacgcggg tacggcgact gccgtgctgc    22740
tgcgcctcgc cgccgaacgg ccgagcaagc aggccgtgct gctggtggcc gatccggacg    22800
atccggcggc caccaccgcg ttgacctatg ccgaactgga cacgaaggcg cggcggatcg    22860
cgggctggtt gaccgagcga taccagccag gtgagcgtgt tctgctgtta cacccgatgg    22920
gtctcgagtt cgtctcagcc ttcttcggtt gcctctacgc cgggatgatc gccgtccccg    22980
```

| | |
|---|---|
| cgccgctgcc tggccggtac cggcacgagc gcaggcgcgt ccaccggatc gccgaggacg | 23040 |
| ccggtgtggt cgcggcgttc accgtcgcgg gaagccttgc cactgtgcag gaatgggccg | 23100 |
| ccgaggaggg gttggccggc ttgacggttg ccgattcgga aacgctgtgc ggccagtggc | 23160 |
| cactggccga gatcaccacg gacaccgtcg cgctgctgca atacacctcg ggtcgaccg | 23220 |
| gtgaccccaa gggcgtgatg atctcgcatg ccaatctgct ggcgaatgtg gacagtctgg | 23280 |
| ccaggacgtt cggcttcgac gagaacgtcc gcaccggcgg ctggatcccg ctgtaccacg | 23340 |
| acatgggcct gatgggacag ctgctgcccg cgctgttcct gggcagcaca tgtgtgctga | 23400 |
| tgaacccgat gtcgttcctc aagcggccgg tgaactggct cacaatgatc gaccggtacg | 23460 |
| acatcgcctg gtccgcggcg ccgaacttcg cctacgagca ctgctgccgc cggatcgacg | 23520 |
| actccgctgt ggacagtctc gacctgagcc ggtggcgcta cgccgcgaac gggtcggagc | 23580 |
| cggtccgtgc ggcgacgctg acagcgttcg cgaagaagtt cgccggggcc ggattccgtg | 23640 |
| aggacgccat cgcccttgc ttcggaatgg ctgaggcgac cgtgttcgtg tcgggtggcg | 23700 |
| gcgttcgccc agcaccggtg cgcaaaatcg acgcggaatc cctcgaacag cacgagatcc | 23760 |
| ggcctgctca ggagaaccgg cccgcgcgca gcatcgtcag ctgtggcatt ccccgtgaca | 23820 |
| tcgatgtgcg ggcggtcgac ccggagaccg gcgagccgat gccggacggc caggtcggcg | 23880 |
| agctctggct gcggggacgc agtgtgtccc gtggttactg ggccagaccg gacgtcaccg | 23940 |
| aagcgatctt cggcgcgtac acgaccacgg gtgacgggcc gtacctgcgc acgggagacc | 24000 |
| taggcgtgct gttggacggc gagttgtacg tgaccggccg gatcaaggag atggtcacca | 24060 |
| gcaacggccg gaacctgtac ccgcaggaca tcgagtacga gctggccacg cagcacgagc | 24120 |
| ggctcggtgg tcacgtcggc gcggtgttca ccgtgccggt gtccgaaggg gacaacgaga | 24180 |
| ccgaggccct tgtcgtcctg cacgagatga agggccgcgc cagcgaggac gaactgaccc | 24240 |
| ggctttcggc gcagatgaag cagacggtgg tgcgcgagtt cggcgtgagc gcggacggga | 24300 |
| tcgtcctgct ccgccccgga agcgtgcgcc ggaccaccag cggcaagatc cagcgcacgg | 24360 |
| ccatgcgtga gctgttcctc gcggaggaac tgtcgccggt cttcgccgac gctggcagcc | 24420 |
| aggctgtcct ggctggggcg accaagggcc ggtcggcctg atgcaggccg tcgacaggct | 24480 |
| ggaccgcgca ctcgaccatc cggcgttcgc cccggagcaa ctggccgagt gggaccgtgc | 24540 |
| ggaggccttt cccgcagagg cgtgccaggt ccttgacgac ttcggcctgc ccgcgtacta | 24600 |
| cgtcccggcg gcacacggcg gcacactgac cgacttcaac gagttggttc agctgttgcg | 24660 |
| cacggtcgcc cgccgggatc tcacggtcgc tgtggcgcac ggcaagacgt tcctcggtgc | 24720 |
| ggcctcggtg tgggtttccg gaacacccga gcaggcgaca agggtgagcg agcgtgtccg | 24780 |
| ggccggtgac gtctacagct gggccctgac cgagcgggat cacggcagcg acctgcttgc | 24840 |
| cggcgaggtc gcggccacca agaacggtgg ctggcggctg tccggcgaga gtggttgat | 24900 |
| caacaatgcc acccggggac acgcggtgtg cgctcttgtt cgcacggatc cggcaggcgg | 24960 |
| tgcccgtgga cacagcctgt tcctcctgga caagacggaa ctgacggact accgccacct | 25020 |
| gccgaaggtg cccacgcacg gcatccgggg cgcggacatc agcggcatcg ccttcgacaa | 25080 |
| cgccctggta ccgatgacg cggtggtggg tgctgtcggc agtggtatcg agacggtgct | 25140 |
| caaggccctg caactcacca ggaccatgtg cgtggcgctc tcactgggcg ccggtgatca | 25200 |
| cgcgctgagc ctggcgcggc gattcgtgtc ggaccgtgcg ctctacgacc gcaagctggt | 25260 |
| cgatctaccg caggtgcgcc ggattctcga cgaggcggaa gttcaactca agctggctga | 25320 |

```
ggcggtgagt gtgatcgccg ccggaggggt gcgtgaattc accgcggaga tgagcgtgat    25380
ctcggctgtc gccaaggctt tcgtaccggg cgtcgtgcag cgggtgatca accggctggc    25440
ggagctgatg ggcctgcgcg ggttcctggc cgacgagttc gccaagctcg accgtgacca    25500
ccggatcgtc ggcatcttcg acggcagcac ggcggtcaac cggcactcgt tgatcacaca    25560
gttccctcgg ctggcccgtg cctatcaggc aggcaaggtc tcgcagccca ccggtgagtt    25620
cgacccggcg aacctgcggt tgtcctcccc gaccgggtgc agcgtgctga acgtcgtcaa    25680
ccggggcacc gatttcggag cggccgtcga gcaggtgcac gaagaaatgg ccgcctacac    25740
accgtcggcc cgtggagtcc cggcatcggc gttcgcgttg ccgagcggt acgagctgtg     25800
cttcgccggc gcggcggcct tgcacctgtg gcaggacagc gacccggacg ccgtgcgtgt    25860
gtgcctcagc catgtcttgg agtgcttacg atgacgacac tacggctggg agatccctac    25920
gacacggcca accggtgggt tttccaggct gtgctcgacg ccgacgagcg cggcgagatg    25980
ctggccgcgg gcgagcggat cctggacgac tacaacctga cgcggagtt cgtcccggcc     26040
cagtacggcg gtcggctggt cgcactcgaa aacgtggtca gcgtgatgcg cgaggtctac    26100
cggcgtgacc cgtgccttgg tctcggctac ggcgccagct cgctgatcgc gcgcggtcaac    26160
gtctggcaag gcgcgaccga accgcaacgc aaggaagtcg cggacttcct gttgtccggc    26220
aagaagctcg cgtgcgcgta ccacgagctg gcgcacggca acgacatcgg ccgcgccgag    26280
ttcgaggcgt tgccgaaggg cgagaacctc gtgctcaacg gccgcaagga agtcatcgcc    26340
aacatccagc gggccgacgc gatggtggcg ttcgcccgga ccggcgaggc cgggggaac    26400
cgcagccaca gccagatcct cgtcacgccg gacgaactgc cccaggaccg gttgcgctac    26460
ctgccgaggt actcgacgac agggatgcgc ggtgttcagc tcggcggcat cgagttcacc    26520
gactgcccag tgcccgcttc ggccgtgctg ggcgagccgg gccgtggcct ggaggtggcg    26580
ctgacctcgt tccaggtcac caggatcggg ctgcccgcga tgatgaccgg catcctggac    26640
accgggttgg cagtgaccgt gcggcatctg ctcagccgca ggctctacgg ctcggcggcg    26700
acggatcttc cctacatcaa ggcggtactg gccggtgtgt tcgccgacct gatggcgtgc    26760
gaggcccctca gcctcgtcac agggcgggga ctgtcactgc tgcccaagca agcgactgtg    26820
cacgcggccg cgacgaagta cgcggtctcg cgcttgctga tcgacgcgat gaacgagctc    26880
tccaccgcac tgggatcgcg gttctacgtc cgcgaaggcg aacacgcgat cttccagaag    26940
ctcctgcggg acatccagcc gatcggtttc ggacatgcgg ctcgcgcggt ctgccagatg    27000
accatgctgc cgcagctgcc gttgctggcg aagcgatcct ggcagaagga ccacgacgtc    27060
ccggccgaac tgttccggtt ggacgccgag gtcgggccga tcgcgttcga ccagttgcgc    27120
atctccgcag gcggccagga ccacctgatg ccggtggaac tgccggatcc cttccgtgcg    27180
gaactggaaa cgctcacgaa gctgtgcgcg tctttgcccg ccaaggagtt ggtggccacc    27240
gctggcccgg cttcgtacga cctgacaacc cgatacgcca cgaccctgat ggccagttgc    27300
tgcgtgcagg tctggcagca caaccaggac gtggagttcg tcggtgaccc caggtgggcc    27360
gatgccgtgc tgcaccggct ggcgaatccc ggcgggtacc tgccggacga cctggtgtcg    27420
ttcctgttcg ccgaactgct caaccgccac gaggacggcc gtgacttcgg cctgcgcacc    27480
cactgaaaga ggaatcatgc cggagacgag cacggaaacg atcgatgtga cagcactgcg    27540
gaactggctg gccggacgga tcgccgagtt caccgagcgg ccgctcgccg agatcgccgg    27600
agacaaaccg cttggcgagt acggcgtgga ctcggtgtcc gcgttgaccg tctgcgccga    27660
gatcgaggac cacttcgaca tcaccgtcga gccgacactg ctgtgggacc accccacgat    27720
```

```
cgacgccatc gccgaggtcc tggtcgaaga agtcaacgcc cgataaccac tacacgcgaa   27780
ggtcggggaa acgtgtctgg ggatgtccgt cgtgctgtca ccgccgcgca ggcagggatc   27840
tggttcgccc agcagttgaa gccgggcaat ccgctctaca actccggcgc ctacttcgag   27900
atcgacggtc cgctggacgt cgcggcgatg cgtgccgcgg tgcgccgggc ggtcaccgag   27960
accgaggcgc tgcgggtgcg gttcgaggag tcgcccgagg gcctgcacca ggtcctgcag   28020
gacttcgacg cgccgttgac ggacatcgat ctgtccgatg cgcctgatcc gcacacggcg   28080
gcactcgact ggatccggca ggatctggcg actcccgcgg acctcacgcg cgtccccgcc   28140
ttcgagcatg cgttgctccg cctcggcccg caacggttct acttccacct gcggtatcac   28200
cacatcctga tggacgggta cgcccacgcg ttgtactgca ggcggatcgc ggagatatac   28260
acagcgctgg catcgggccg gccgcccaag ccgtgcgagt tcggcactct gcaacagctt   28320
ctggacgacg acaccgagta ccgggcttcc cggcggcggg aacgggacga gaagtactgg   28380
ctggaaacgt tcgtcgaggt tcccgagctc gccagcctgg ccgggcgttc ggtgcctgcc   28440
gcgccgagca ccctgcgccg cgaggtcgag ttaccccggc ggacttccga gctgctcgcc   28500
aaggcggccg ccgagcttgg tgtgccctgg tcggtggtcg cgatcgccac cgtcgcgacg   28560
tacacgtccc gcctgaccgg actgtccgat gtggtcctgg gtctcccgtt gaccgcgcgg   28620
atgagcaagg tcgccctgcg cacgccgggc atggtcgcca acgacctgcc gctgcgggtg   28680
acggtccggc cgtccgtctc cttccgtgac ctggtccgtc agctctccca gcaggtgtcc   28740
cgcgcggtca acaccagcg gtaccgcggt gaggacctca acagcgcgct tggtgtctcc   28800
ggcggtgaac tcaccggcac actggtcaac gtcttctcct tcgagcagga tgtccggttc   28860
ggtgacctgc ccacgacccc gcaccagctg tccaccggcg cggtcaagga cctgatcgtc   28920
aacttctacg ccacctcggg ctcgatccgg atcgagttcg acggcaaccc cgagctctac   28980
ggcgaagaag acctcgcggc ccaccaagac cggctcgtgc gcttgctcga agaccttctg   29040
gccggcgtgg acactgctgt cgcagcggcg gacctgatcg agcccgatgt ccgggatctg   29100
gtggtacggc agtggaacaa caccgcgcgt gacgtgcccg tggccacttt cgcgtcgctg   29160
ttcgccgccc aggtggtcag gacacccgag gcggtcgcga cgagctaccg cgacgactcg   29220
gtgacgtacg ccgaactgga tgcgcggtcg aatcgggtgg cgcgatggct gatgcagctc   29280
ggtgccggtc cggagcggtt cgtcgccatc gcgttgaacc ggtcgatcga cctggtggtc   29340
gcgttggtcg cggtgctcaa aaccggtgcg gcgtacgtgc cgatcgaccc ggactacccg   29400
gctgagcgca tcgggttcat cctcggcgac agtgatccgc tcctggtgct gaccgaacgc   29460
ggcatcgccg aatcgctgcc cgaaacccgc gcgccccttg tgttcctcga cgaagccgcc   29520
gcttcggcag cccgattcc gggccgggtg ctgccgaaag cacccgcgta cgtgatcttc   29580
acctcgggct cgaccggccg gcccaagggt gtggtggtcg aacaccgcgc gatgggtgcc   29640
tatctggcac gggctcgtga ggcctatccg tggatggctg atcgacgtg ggtgcattcg   29700 ccgatcgcgt tcgacctgac cgtgaccggg ttgttctcgc cgctggtatc cggcggctgc   29760
gcgcgtctgg tgaacctgga ggacgaactc cctgagcagc agccgacttt tgtcaagggc   29820
acgccctcgc atctcggttt gctggacgtg ttgcccggca gtgcgtcacc gtccggcgcg   29880
ttgatgctgg gtggcgagtt gctggtcggc gaggtcctgc agaactggcg ggatcgcaac   29940
ccgggcgcag tggtctacaa cgtttacggc gccacggaag caaccgtcaa ctcggtggag   30000
aaccggatcg agccgggcgc cgaactgcct gtgggcgcgg tgccggtggg cactccgttc   30060
```

-continued

| | |
|---|---|
| cgcaacaccc ggatctacgt gctcgactcc ggcctgcagc cggtgccgcc gggcgtggcc | 30120 |
| ggtgaggcgt acatcgcgag caccgggctg gccaggggat atctcaaccg ggccgggctg | 30180 |
| acctcggaga ggttcgtggc ctgcccgttc ggcgcgccgg gggagcggat gtaccgcacc | 30240 |
| ggcgacctgc tgcgctggaa caccgacggt gagctggagt cgtcagccg ggtcgactcc | 30300 |
| caggtcaaga tccgcggctt ccggatcgag ctcggcgaga tcgaggcagt gctgtccgcc | 30360 |
| gcggacgccg tcacccaggt ctcggtcctg gtgcgggagg accagccggg ggacaagcgc | 30420 |
| ttggtcgcct acgtggtcgg ctcgatcgac ggcctgcggg agcacgcggc cgcgatgctg | 30480 |
| cctgagtaca tggtgccgtc ggcgttcgtg caactcgacg agctgccgtt gacgcccaac | 30540 |
| ggaaagctgg accgccgagc cctgcctgtc cctgattatg ccggggggtc aggacgcgcc | 30600 |
| gcccgtacac cacgcgagga aatcctgtgc ggactgttcg cggaagtgct ttcgctgccc | 30660 |
| cacgtgggca ttggcgacaa cttcttcgtc ctcggcggac actccttgtt gacgttgcag | 30720 |
| ctcgtcggcc gagtgcggac agtgctgggc gccgagctgt cggtccgcca ggtcttcgag | 30780 |
| gcgccgaccg ttgccgagct tgacaaggcg ttgagtgttt cagacgtcgc gcgtccggcc | 30840 |
| gtggtgccgg ttcgcccgcg tccggaccgg ctgccgctgt cgttcgcgca gcagcggttg | 30900 |
| tggttcctgg acaagctgga ggacggcgcc gcgacgtaca acacaccggt cgcactccgc | 30960 |
| ctgtccggcg accttgacgt gactgccctg cgtcaggcga tcgaagacgt ggtgatgcgc | 31020 |
| cacgaaagtc tgcgcacgat cttcgcggag gacgaccagg gcgcgtacca ggtcatcctg | 31080 |
| gacgccgtcg acatcgagct gcctgtggca gaggtgaccg aggatgcggt cgccgccgaa | 31140 |
| ctcgccaggg aagcgtcgac atcgttcgac ctgaccaccg acctgccggt gcgggcacgg | 31200 |
| ctcctgcgcg tcgccgacga gcacgtgctg ttgctggtgg tccaccacat cgctggggac | 31260 |
| ggcagctcgg tcgtgcccctt cgccaggggac ctcgcggcgg cttacgcggc ccgcagcgcg | 31320 |
| aaccgggaac cgggctggcc tgagcttgcg gtgcagtaca gcgactacgc gttctggcag | 31380 |
| cgtgacctgc tggactccga ggtggtccgc cggcagctgg actactggcg gaaggcgctc | 31440 |
| gccggcctgc cggccgagct tgatctcccg gcggatcggg agcgcccggc gcaagccacg | 31500 |
| taccgcggca gaccgtgctg gttcgacgtg ccagccgagc tgcacacgcg cctggccgcc | 31560 |
| gtggcgagcg agcacaacgc gagcttgttc atggtcatgc aggccgcgct ggcgaccctc | 31620 |
| ctgcacaggc tgggtgccgg tgacgacatt ccgctgggaa gcccggtcgc aggccggtcc | 31680 |
| gacgacgcgt tgaccgacct tgtcgggttc ttcgtgaaca cgttggtgct gcgcaacgac | 31740 |
| ctcagcggcg acccggtgtt cgccgagctg atcgcgcggg tccgggacgc cgacctggcc | 31800 |
| gcgtacgagc accaggacct gccgttcgag cgcttggtcg aggtgctcag cccggagcgg | 31860 |
| tcgctgtccc ggcatccgct gttccagatc gccctgacgt tcaacaacaa cgaccactgg | 31920 |
| gccgaactgc acgagctcgg cgcgggtggg ctgcgggtgc ggcgggagca cttcgacctg | 31980 |
| ggcatcgccc agttcgacct gtccttctcc ttcgccgaga cgccggacgg tatcgccggc | 32040 |
| cgccttgagt tcgcgctgga catgttcgac cgcggcaccg cggagaagct cgtcgaacgc | 32100 |
| ctgatgctcg tgctgcacag tgtcgcggcg gaccagaacc gcccggtcag cgagatcgac | 32160 |
| gtgctgctgc ccggtgagca ggagatccca cgcccggtcc ggcgaagcct ggcggtcgag | 32220 |
| aaggcaccga ctgtgtcgcg ggaaccgcgg acaccgcatg aagagatcct ctgtggcctg | 32280 |
| tacgcggaga tgctggacct caagaaggtc ggcatcgacg acagtttctt cgatctgggc | 32340 |
| ggacactcgg tggcggcggt ccggctgctc agccgcgtcc gcacggtgct gggcgtggag | 32400 |
| ctgccgatcc gcaagctgtt cgacaccccg accgtggcag ggctcgcgga ggcgctgacc | 32460 |

```
ggcggcgcga cccgggtgaa ggtcacggcc gaccggccga ggcctgagcg catcccactg   32520
tcgttcgccc agcagcggct ctggttcctc gaccacctcg aaggcgccag tgccacgtac   32580
aacgtcgcga tgggactgcg gctgtccggc gtgctggaca tgaccgcgct ggaagccgcg   32640
ctgaacgatg tcgtggaacg gcacgacagc ttgcggaccg tcttcgcgga ggacgacgaa   32700
ggcgcctacc aggttgtgct cgacggtatc gtgctcacgc tggacactgc ggccaccgac   32760
gaggagaggt tgcccggcca gctgatcgac gcggctcagc ggccgttcga cctgactgcc   32820
gacattccgc tgcgagccaa gctgttccgg ctcgacgacc aggaacacgt gctgttgctg   32880
gtcgtacacc acatcgcgtg cgacggttgg tcgaccggcg ccttggccgg tgacctcgcg   32940
tccgcgtacg ccgctcgacg cacggcgacc acgccggact gggccgagct gccggtgcag   33000
tacaccgact atacgctctg gcagcgggag ctcctcggct ccgaagacga cccgcagtcc   33060
gagatcgcgg cacagctcgg ttactggcgc tccacactgg acggcgcgcc ggagcggctc   33120
gagctgccca ccgaccgggc acgtccggca gtgccgacgc atcgcggcgc ccagctggac   33180
ttcgagatcc cggcagcgct gcacgcccag ttgatcgaca tcgcccgaag cggtcacgcc   33240
acgttgttca tggtgttcca ggccggtctg gccgcgccc tcagccggct tggcgcgggt   33300
accgacatcc cgatcggcac tccggtagcc ggccgggccg acgaaggact cgacgacctc   33360
gtcgggttct tcgtcaacac cttggtgctg cgcaacgacc tcaccggcga ccccggattc   33420
gacgagctgc tcgctcgggt ccgggagacc aacctcggcg cgtacgccaa ccaggacgtg   33480
ccgttcgagc gcttggtcga ggtactggcg ccggaacgat cgctggcgca ccacccgctg   33540
ttccaggtga tgctcggctt caaccacacc gacaaccagt cggccctcgg caagctggac   33600
ggtctgccgg ggctggtcac ccgccgggag ccggtcgacg cgggtgtggc caagttcgac   33660
ctgtcgttct tcttcgacga gaaccacgat tccgacggtg aaccggccgg tctgaccggc   33720
ggcctgcagt acagcaccga tctgttcgac ccggccaccg cagcggccat tgtggacctg   33780
ctcgtccgga ttctcggaca gcggccggaa aatccggcta cccggttgtc caggttcgag   33840
gtgctcaatg ccgatgagct tgagaccatc gccgcctggt ccgatgtaga cgcttctggc   33900
gccgtgccgg aacggttcgc cgcccaggtc gtcaagacgc cgcaagcgct tgccgtgcgt   33960
gcgccgggcg tcgaactgtc ctatgcggag cttgactcct ggtccgccgc gatcgctcgg   34020
caactcgtcg atgcgggtgt acggaccgag acaccggtgc tgatgctgat gcgccgcacg   34080
gcccagcgcg tggtcgccac cctggctgtg ttgcgcgcgg gcggtgctta cgttcccgtg   34140
cacgattcgc atccgctcga acgaatccgc acgatcgtgg ccgagaccgg cgcgcctgtg   34200
gtgatcaccg accaaccgga ccgtgcggtc ggacttggca tcgaacaggt cgtggtcacg   34260
gacccgatcg ctggtgaggc accgcgaagc gatgtcctgc ccgcaaccct cgcgtacatc   34320
atgtacacgt cgggctcgac cgggacgccg aagggagtcg cggtcaccca tcgggacgtg   34380
atcgcactga ccgctcaccg gcacttccac aacggcgcgc acgaacgagt cctgctccac   34440
tcaccgcatg ccttcgacgc ggcgacgtac gagctctggg tcccgctgct gaacggcggt   34500
cagctgatcg tcgcgccgcc cgacgagctc gacatcggga cgctgcggca cgtcatcacg   34560
gagaacgacg tcacggcctt gtggctgacg gctggattgt tccggcttgt cgccgaggaa   34620
gcacccgagt gcttcgcccg ggtccgtgag gtctggaccg gcggtgacgt tgttccacca   34680
gccgccgtgc gcagggtcat ggagcgctgc ccaggcatca cagtggtcga cgggtatggc   34740
ccgaccgaga cgacaacgtt cgccacgtgc cacccggtgc gtgacgagat cgccgacact   34800
```

```
gtcccgattg gacgaccgct cgacggcatg cgagcccacg tgctcgacgc ccagttgcgt    34860
ccggtcccac cgcgtgttcc aggtgagctg tacatcgccg gagcgggtct ggcgcgcggg    34920
tacttcggcg atccggcacg gactgcggaa cggttcgtcg cgggcccggc gggtgagcgg    34980
ctgtaccgga ccggtgacct ggtccgccgg cggccggatg cgcgcgctcga gtacgtcggc    35040 cgggtcgacg accaggttaa actgcgcggc ttccggatcg agcccgcgga ggtcgagtcc    35100
gtgctggcgg cccacgtggc cgacgtggcc gtgctcgtcc gcgaggaccc ggacgggcgc    35160
aagcgtttgg tcgcctacgt cgtgccgaat ggtgcgatcg atcacgagca gttgcgcgcc    35220
gaggtcgccg atcggctgcc ggactacatg gtcccgtccg cgttcgtcga gcttgagcgg    35280
cttcccgtga cagcgaacgg aaagctggac cgggcggcgt tgccggagcc ggccttcgct    35340
gcggggacgg gcaggccggc gtcgaacgcg gcagaagagg tgctgtgcgg cctggtcgcc    35400
gagctgcttg gcattgggac gcccggcgtg gacgacgggt tcttcgacct gggcggcgac    35460
agcatcgtgg cgatccagct ggtcagccgc gctcgccggg ccgggctgga gttcgcggtg    35520
cgcgatgtgt tccagcaccg gaccatcgcc gcgctcgccg cgatcgcgac caaggccgcc    35580
ccacgcgagg tcgatccgcg cgcaggtatc ggcacggtgc cgccgactcc gatcgtgcgc    35640
tggctggcca ccgcggggg accgatcgac gggttcaacc agtcgaagat cctgcgcgtt    35700
ccggctgacc ttgactggga cacgctcacc gcgggcgtgc agaccttgct cgacacgcac    35760
cactcgttgc ggatgtccct ttcggacgac tggtcgttca ccgtgcccga gccgggcgcg    35820
gtccgcgctg aggaccggat gcgccgggta ccgcggagg cgttcgagtc cgagatcgcc    35880
gcggcccggg agcggctcgc accccgggac gggcggatga tcgacgtcgt cctcggcgag    35940
ccgggcaggc tgctggtgat ggtccaccac ctggccatcg acggggtgtc ctggcgaatc    36000
ctgatcgagg acctcacgca ggcatgccag gggcggcagc cgatccggcc ggtcacatca    36060
ctgcgggaat ggtcgaacgg cctggtcgaa gccgcccgca cacccgagcg tgtcgccgaa    36120
ctggaccgct ggaaggccgt cctcgcatcc gcccggccgt ccggaacaga cgtcgaaaag    36180
gacacctacg ccacagcagg gcacctcacc cgcacgcttc cggtggacgt gaccgaagtc    36240
gtgctgaccc ggctgcccgc tgccttccaa gccgagatca cgacgtgct gctggccgcg    36300 ttcgcgttgg ccgcgccccg gcctgtgctc ctcgacctgg aaggacatgg ccgggaggag    36360
cacgtggtcg aaggtgccga cctcgccagg acgctcggct ggttcaccag cgtctatccg    36420
gtgagcctcg acgcgggtga tctggacacc gccgacgcca tggccggggg cccggccgcg    36480
ggaaagctga tcaagcgcgt caaggaacag ctgcgcgaga tcccgacaa gggcatcgga    36540 ttcgggctgt tgcggtacct caacgagacc acgggcgcgg aactcgccgg accgggcaag    36600
ccgacgtacg gcttcaacta cctcggccgc ttcacggaac ccgaggacac cgactgggtc    36660
gcggtgggca gcggcgcgga actcggcggc atcgacccgc ggaccccgtt ggcccaccag    36720
gtcgagctga ccgtgcagac ccgtgacacc gcggcgggcc cgcagctcac cgcgacgtgg    36780
gtgtgggcgg ccaggctggt gtccgaacag gacgtccagg acatcgccgg gaagtggttc    36840
caggcattgg aagcgttcgc gcggcatgtg cgcgacccgg aggcgggcgg gctgaccccg    36900
tcggacgtgt tgctcggatc ggtgacacag gacgagatcg acgagttcga agagatgctg    36960
accagcgaag cggaggagtt ggcgtgagcc ggaagaccag ggcgatcgag gacatcctgc    37020
cgctgtcgcc gctccagcag ggcctgctgt tccacagcgt ctacgacgag cagtcaccgg    37080
acgtctacac cgtgcaggtc gacttcgagc tggacgcgca actggacctg gacgtgctgc    37140
gcaccgcggc ggagacgttg ttgcgcaggc acagcgtgct gcgtgccggg ttccgccagc    37200
```

```
gcaagtccgg cgactgggcg cagctcatca tgcgggaggt gccgctgtcg tggcgtgtgg   37260
tcgagtcgcc cgagcggatc gaggacgaac tcgcggccga ccggtggcag cggttcgacc   37320
tggcgaagcc gccactgttg cggttcaccg tgctcaagct ggccgacgac caccaccatt   37380
tcgtggtgac gagtcatcac ctgttgctgg atggctggtc cttgccggtg ctggtccgcg   37440
aattgctgcg gctgtacgcc gagaagggcg atgaccggtc gctgccgagc gtccggccgt   37500
accgggacta cttgagctgg ttgtccgaac aggaccggcc tgctgccgaa gaagcctggc   37560
gcaccgcttt gtccgggctg acaagccga ctctcgtcgc tgccgatgcc gtggcggcaa   37620
ctccggttga tccgcatcgg atcgagcatg agctgtccga tgagacgcac gcggccttgg   37680
tcgcgctggc caggtccagt ggcgccacat tgaacacggt ggtccagtcc gcgtgggcga   37740
tcgtgctcgg ccggatcgcc ggcaccgacg acgtggtctt cggcaacgtg gtgtcgggca   37800
ggccgcccga gctggccggg atcgagtcga tggtcggcat gttcatcaac acgttgccgg   37860
tgcgcgtgcg gctgcgtccg gccgagacgt tcaccgcgtt gctggctcgg gtgcagcagg   37920
aacagtcgga tctgcttgcc caccagcaca tcgggctggc cgacatccaa cgtgccgccg   37980
ggctgccgac cctgttcgac tcgtcgatgg tgttccagaa ctacccggtc gaggggtcg   38040 ccgaggacga actggccttc ggtgacgtcc gcgtcaccaa ggccaccagc caggacgcca   38100
cgcactaccc gctcgacctc gttgccaccg cccgcaccgg acttcgcctg cggctggaga   38160
cgcggcctga ggtcttcgac gcgggccagg ccgcgcgcat ccttgcccgt ctcgtccgtg   38220
tgctcgaggc gatggccgct gacccgacgc agctggtcgg ccgggtcgac gcgctggaac   38280
ccaccgagcg tgctcagctg acctcgggtg atgcccgccg agaggcaccg gctgccttgg   38340
tgcccgaact gctggcccgc caagccgccg agactcccga cgcggttgcc gtggtgtacg   38400
agcagacctc gctgacgtac gcgcagctca acgcgcgtgc gaatcgtctt gcacgtcacc   38460
tgatctcgct gggctgcgga ccggaggacc gggtcgcgct gctgctgccg cggtcagcgg   38520
atctcgtggc cgcggtgttc ggcgtactga agtcgggcgc agcctacgtg ccgatcgacc   38580
acgactatcc ggccgaccgc atccagttcc tcatcgagga ctccaagccg tccgtactgg   38640
tggccaccag cgaaacgatc gtgagcaccg acgttccgca cgttgtgctg cttgacgagg   38700
cggtactgcc cgccgacgac acggacccgg tggtggcgct gtccgagtcg aacgaggctt   38760
acgtgatcta cacctcgggc tcgaccgcc ggcccaaggg cgtggtgatc gagcaccgcc   38820
agctgcggaa cctggtcttc gagcacagca ccggcctgat cgaactcgtc gcatcgaagc   38880
gggagaccgt acgtcccgcg ctgacggcct cgctgtcgtt cgacacctcg tgggacggcc   38940
tgttgtggct gctcagcggg cacgagttgc acgtgatcag cgaccaggtc cgtcgtgacc   39000
cggaactact cgtgtcctat gtggagtcga agcggatcga cttcatggac gtcacgcctt   39060
cgctgtgccg ccagctggtc aacggcggcc tgctggccga gggcaagcac cgcccggccg   39120
tgctgatgct cggcggtgaa gcgctggacc aggctctgtg gaacgacctg cgtgcctgtt   39180
cggcgacggc ctcctacaac tactacgggc cgactgagac cactgtggac gctctggcgt   39240
acccggtggc cgatggcgca cggccgttgg tgggcaagcc gatcaccaac actcgcgcat   39300
acgtgctcga ctccgcgttg cggccggttc cccatggtgt cgcggggag ctgtacctgg   39360 ctggtgacgg actcgcccgt ggctaccacg accgttcagg cctcaccgcc gaacggttca   39420
tcgcggaccc gttcggccgg cccggcacgc ggatgtaccg gaccggtgac ctggttcggc   39480
gtggtcagga cgggaacatc gagttcatcg gccgggtcga cgaccaggtc aagatccgcg   39540
```

```
gtttccggat cgaactcggt gagatcacct cggcgctggc ccagcacgcc gctgtcgcgg    39600
aggccgcggt ggtcgtgcgt gcggaccgtg ccgacgaccc caggctggtc gggtacttcg    39660
tgcctgccaa cggttcgatc gacctggccg ggctgcgcaa gcacctggcg gagctgctgc    39720
ccggccacat ggtgccgtcg gccttggtgc cccttgatgc cctgccgatg accaccaacg    39780
ggaagctcga ccgcaaggcg ttgcccgcac cggaaggccg tctcgtcagc ggtggacggg    39840
cacctcgctc gccgcacgaa gagttgctgt gcgaactgtt cgccgacgtg ctcgatgtgg    39900
cccgggtcgg catcgacgac agcttcttcg cactgggcgg gcattcgctg ctggccacac    39960
gcttggtcag ccggattcgt tcggcccttg gtatcgaggt gtcgattcgc cagctgttcg    40020
agacaccgac cgtggccggg ctgtcggccg cgctcaatgc cgcaggccag gggcgcgaag    40080
ccgtcactgc ggtggttccg gcgcctgcgc gcctgccgct gtcgtacgca cagcgtggac    40140
tgtggttcct gtaccagatc gagggtccga gcccgacgta caacatgctg ggcgctctgc    40200
ggctgaccgg cggcttggac gagcacgcga tgcgtcgcgc gctggcggac gtggtcgccc    40260
ggcatgagtc gctgcgcacg gtcttcgcca cggacaacga cggtccgtac caggtcgtcc    40320
tcgaggacgt acggccggag atggtggttg tcgagaccac cgaggacgct ctgccgggcg    40380
agttggagtc agccgctgcc tactgcttcg acctggtgga cgagatcccg ttccgatctt    40440
ggctctaccg cctgggcccg gacgagcacg tgctgctcgt gctcgtgcac cacatcgcgg    40500
ctgacggctg gtccatgccg atcctgggcc gtgacctcgc cgcggcgtac gcccagcgct    40560
tcgagggcac gccaccggag tgggccgacc tgccggtgcg gtacgccgac tacaccttgt    40620
ggcagcagcg cgttctgggg tccgaggacg accaggacag tgtcatctcc gggcagctgg    40680
cgtactggga acaagcactt gctgggctgc cgggcgagct ggacctgccc accgaccgcc    40740
cgcgtccggc gaacccgacc tatcacgcg ggaccgtgca cttcgacgtt cccgccgatc    40800
tgcaccgcgg cctggccggt ctggctcggg aaagtcaggc gagcctgttc atggtggtgc    40860
agtccgcggt ctcggtgttg ttgtcacggc tgggtgccgg ggacgacatt ccgttgggca    40920
caccggtggc cggccggacc gacgaggccg tggaagggct tgtcgggttc ttcctgaaca    40980
ccctcgtgct gcggaccgat ctgtcggcg accgtcctt ccgtgagctg gtcgggcggg    41040
tccgggagac ggacctggcc gcgtatgcca atcaggacgt gccgttcgag cgcctggtcg    41100
aattgctcaa cccggagcgc gtgctcggcc gcaaccgct ttccaagtg cggctggtgt    41160 tcaacgacac cgaccgggac gccatgccgg acgtgatggc cgggctgccc ggcctgtccg    41220
tggccaccga acaggccggc ttggcggcag ccaagttcga cctgctgttc cggttctccg    41280
agcgcttcga cgaggacggc gggcacgccg ggctgtcgtg tggtctcgag ttcgccgagg    41340
acttgttcga ccggtcgacg gtggagaccc tggcgcagcg gctgctgagc gtgttctctg    41400
gcgttgtcac cgatccggcc agtgctgtgt ccagggtgga cgtgttggtc gacggtgagc    41460
gcgagcggat tctcaacgag ttcaacgaca ccgcgtggga gacccggaaa atctcgttgc    41520
cggagttgtt cgccgagcag gttctgcgga ccccgtccgc ggtcgcggtg gagtgtgatg    41580
gcgttgagct gacgtacgcc gagctggatg agtgtgcgaa tcggttggcg cgttacctga    41640
tctcgcgtgg tgtgggtgcg gagaagttcg tcgcggtgat gatgccacgg agtatcgatc    41700
ttgtggtgtc gttgttggcg gtgttgaagt ccggtggtgc ttacgtcccg gtcgacccgg    41760
agtatccggc ggatcgcatc gctttcatgg tggcggacgc cgaaccggtt ctggtcttga    41820
cctccacgga gggcgccgag gagttcgacg gctcgcctct gtccgatgtg gaggtgtcgc    41880 tcggtaacccc ggcgtacatg atctacacgt cgggttcgac ggggcagccg aagggcgtcg    41940
```

```
tggtcgagca cgggtctgtc ggcgcctatg cggtgcgtgc cgtgaggtg tatccgtggg    42000 cgtcgggtgt gtcgttggtg cattcgccgg tgtctttcga cctcacggtc acggcgctct    42060
attcaccgct ggtttccggt ggccgggttg ttctgagcag ccttgaggat gcttcgggtc    42120
cgcggccgac gttcatgaag gtgacgccgt cacaccttgg gttgttggat gccttgccgg    42180
acgatgtgtc gccgagtggt gcgctggtca tcggtggtga ggcgcttcgt ggtgacgtgc    42240
ttgatcgctg gcgttcacgt ttcccggacg tgaccgtgat caacgcctat ggtccgaccg    42300
aggcgacggt caactgtgct gaattccgtg tgctgccggg cgatgagacc ccgacgggcg    42360
cggtgccgat tggccgtgcg ttctggaaca cgcgggccta cgtgttggat cgcggctttt    42420
ccccagtgcc ccaggggggtt gccggtgaac tgtacgtctc cggtgtcgtg ctggcccgag    42480
ggtactggca ccgggccggg ttgacgtcgg agcgtttcgt ggccgatccg ttcggtgggc    42540
ctggtgcacg gatgtaccgc acgggcgact ggctcgctg gaatgccgat gggcagctgg    42600
aattcgtggg tcgtgcggac gatcaggtca agctgcgggg tttccggatc gagctcggtg    42660
agatcgaagc cgtgctgacc aggcacaacg acgtgtcgca agcagctgtg gtcgtgcgtg    42720
aggaccagcc aggagaccag cgcctggtgg cctacgtcgt cgcaccggcg ggcgatgtcg    42780
acggagccgg gctccgggag cacacggcgt cggcgttgcc ggagtacatg gttccctcgg    42840
cgatcgtggt cctcgacgag ctgccgctga cccgcacgg caagctcgac cgcaaggcgt    42900
tgctgcgcga ggagttcatc cccgccgtcg aggaaaccga agttgtcgcg cgcgggccgc    42960
gttcgccgca cgaggagatc ctctgtgccc tgttcgcgga agtgctcggc gtggccgagg    43020
tcagcatcga cgacgggttc ttcgacctgg gcggccactc cctgctcgcg atcaggctga    43080
tcagcaaggc tcgcagcgtt cttggcgtcg aactgccggt acgacagctg ttcgagacgc    43140
cgaccgtggc cggactggcg gcggtcgtca acgcggccgg gcgcgcacgg gaaggcgtca    43200
aggcagtcgt gccgaggccg gaccgtgtgc cggtttccca tgcgcaacgg cgtttgtggt    43260
tcctcaacca gttcgagaac ggtggcgcga cctacaacat cccggcggct ctccggctga    43320
cgggcgatct ggaccgcgtc gcactgcgtg ccgcgctcaa cgacgtcatc gccaggcacg    43380
agagcctgcg gacgatcttc gcggaggacg acaacggtcc gcaccagatc atcctcccgc    43440
tggagcacgc cgatctcgat gtcctggtgg tcccggcgac cgaagccgag ctggacgacc    43500
tggtcgacca agccgcccgg cacgagttcg acctggccgc cgagttgccg atgcgggtca    43560
cgttgttcga gctcgcgccg gacgaccacg tcttgctgct gctgatgcac cacatcgcga    43620
ccgacggctg gtccctggcg ccgctggcac gagacctggc caccgcctac cgcgctcgtc    43680
gcgctggtcg agcgccgtct tggtccgccc tgccggtcca gtacgcggac tacgcgctgt    43740
ggcagcagcg cgtgctggat tcggaggccg atcagatcgg ctactggcag gaggcgctgg    43800
ccggactgcc ggatgagctg ccgttgccgg tcgatcgtcc gcgcacggcg aatccgtcgt    43860
tccggggcgg tgtcgtccgg ttcgacgttc ccgccgatct gcaccgcggc ctggccggtc    43920
tggctcggga aagtcaggcg agcctgttca tggtggtgca gtccgcggtc tcggtgttgt    43980
tgtcacggct gggtgccggg gacgacgttc cgttgggcac accggtggcc ggccggaccg    44040
atgaggcggt ggcggacctc gtcgggttct tcctgaacac gctggtgctg cgcaccgact    44100
tgtccggtga tccggtgttc cgtgagctgg tcgggcgggt ccgggagacg gacctggccg    44160
cgtacgccaa ccaggacgtg ccgttcgagc gcctggtcga ggtgctcaac ccggatcggt    44220
cactggccag gcacccgctg ttccaggtga tgatcgtctt caacaacaac gaccaccagg    44280
```

```
aatctgtcga cgtgctggac cggctgcccg gcctcacggt cggcaaagcc atggcggaca    44340
cgcacatcgc caagttcgac ctgtcgttcc ggttctccga gctgttcgac gaggacggcg    44400
ggcacgccgg gctgtcgtgt ggtctcgagt tcgccgagga cctgttcgac cagtcgtcgg    44460
tcgaggttct ggtccagcgc ctgctggcag tgctggaagg tgttgtcgcc gatcctggtg    44520
tgcgggtctc cgccgtcgac gtgctggtga acggtgagcg cgagcggatt ctcaacgagt    44580
tcaacgacac ttcgcgcgag gttcggacgg tctcgttgcc ggagttgttc gccgagcagg    44640
ttctgcggac cccgtccgcg gtcgcggtgg agtgtgatgg cgttgagctg acgtacgccg    44700
agttggatga gcgggcgaat cggttggcgc gttacctgat ctcgcgtggt gtgggtgcgg    44760
agaagttcgt cgcggtgatg atgccacgga gtatcgatct tgtggtgtcg ttgttggcgg    44820
tgttgaagtc cggtggtgcc tacgtgccga tcgaccccgg ctaccggcg gatcgcatcg    44880 ctttcatggt ggcggacgcc gaaccggttc tggtcttgac ctccacggaa ggcgccgagg    44940
agttcgacgg ctcgcctctg tccgatgtgg aggtgtcgct cggtaacccg gcgtacatga    45000
tctacacgtc gggttcgacg ggccagccga agggcgtggt ggtcgaacac ggctcggtgg    45060
gtgcgtatgt ggagcgggcg cgtgaggtgt atccgtgggc gtcgggtgtg tcgttggtgc    45120
actctccggt ctcgttcgac ctcacggtca cggcgctcta ctcgccgctg gtttccggcg    45180
gacgtgtcgt cctgtccagc cttgaggatg cttcgggtcc gcggccgacg ttcatgaagg    45240
tcacgccgtc acaccttgct ctgttggacg cgttgcccga tgacgtctcg ccgagcggcg    45300
ctttggtcat cggtggtgag gcgcttcgcg gtgacgtgct tgatcgctgg cgttcacgtt    45360
tcccggacgt gaccgtgatc aacgcctacg gcccgaccga ggcgacggtc aactgtgccg    45420
aattccgtgt gcttcccgga gaggaaacgc ctgccggtgc ggtgccgatc ggccgtgcct    45480 tctgaacac gagggcttac gtcctcgacg cggcacttca gccggttccg caaggcgttg    45540
cgggagagct ctacgtctcc ggtgttgtgc tggcacgcgg ctactggcgc agggccggcc    45600
tcacctccga gcgtttcgtg gccgacccgt tcggtgggcc tggtgcccgg atgtaccgca    45660
cgggtgacat ggctcgctgg aatgccgatg gcagctgga attcgtgggt cgtgcggacg    45720
atcaggtcaa gctgcggggt ttccggatcg agctcggtga gatcgaagcc gtgctggcga    45780
agcacgtctc ccaggccgcc gtcatcgtcc gggaggacca gccaggcgac cagcgcctgg    45840
tggcttatgt cgtcgggaac gacgcggtt tgccggaccg cttggccgaa gccctgccgg    45900
agtacatggt tccctcggcg atcgtcgccc tcgacgaact gccactgaac ccgcacggca    45960
agctcgaccg gaaagccttg cggcgtgcgg actacgcccc ggccatcgac cgggaggcgg    46020
tggcccgcgg tccgcgtggg ccgcacgagg agatcctgtg cgacctgttc gccgaagtcc    46080
tcggtgttcc ccaggtcggt gtggacgacg gtttcttcca cctgggcggc cactcgctgc    46140
tcgcgacccg gttgatcagc aaggtccgcg ccgtgctgcg cgtcgaactg cctgtccggc    46200
aactgttcga cacccgacg gtccgccgcc tcgccgccgt gatcgaccgg ccgccggcg    46260 cacgggaagc ggtcgaggcc gttgtgccga ggccgggcac catcccgctg tcgcctgccc    46320
agcgcaggtt ctggttcctc aaccagttcg agcgcaacgg tgccgtgtac aacgtcccgg    46380
ccgcgctccg gctgctcggt gacctcgacc gggaagccct tcgagccgcg ctcaacgatc    46440
tggtcgtccg gcacgaaagc ctgcgcacac tgttctcaca ggacggtccg caccagatca    46500
tcctgccccg ggcggaggcc cgccttgacg ttgtcgaggc ggacgtgcgc gaagccgacc    46560
tcaacgacta cctcgacacc gccgcccggc aggagttcga cctggcacgg gatctgccga    46620
tccgcgcgca cctggcgaag atctcggccg aggaccacgt gctgctggtc gtcgtgcacc    46680
```

```
acatcgccac ggacggctgg tccatgccgt tgctggccaa ggacttcacc accgcgtacc    46740
aggcccgttg tgcgggccag gcgccgacct ggcctgacct gcttgtccag tacgcggact    46800
acaccttgtg gcagcagcgc gtgctgggcg ccgaggacga cccggacagc ctggcaagca    46860
agcaattggc ctattggacc gacgccttgg ccgggctgcc gggggaactg tccctgccca    46920
ccgaccggcc acgcccgcga accgcgtcct accagggcga gaccgtgttc ttcgacatcc    46980
cggcaggcct gcaggaacgc ctcgccaagc tggcgcgaga ggcgcaggtc agcctcttca    47040
tggtggtcca ggcggccgtg gcgaccatgc tcggcaggct gggcgcgggg gacgacatcc    47100
cgctcggcag cccgatcgcc ggccgcaccg acagctcgct cgaaagcgtt gtcgggctgt    47160
tcctgaacac cctggtcctg cgaaccgacc tgtccggcag gccgaccgtg aacgaactgc    47220
tgacccgggt cgggagacc aatctcgcgg cgtacgccaa ccaggacgtg ccgttcgagc    47280
gcctggtcga ggtgctcaac ccacagcggt cgctggccag gcacccgttg ttccaggtga    47340
tggtccagtt caacaacgca ggccagtacg gcgcctcgga aaccgtgcac gacctgcccg    47400
gcatgaccgc gaccctgcgg tcgccggaca ccggtgtggc gcggttcgac ctgttgttcg    47460
gcttcaccga gcgcacggtc ccggacggct cggctgccgg actgcgtggt gcgcttgaat    47520
tcgccacgga cctgttcgac cggacgaccg cggatgcgct ggtggcacgc ctgatccggg    47580
tgcttgaggc gttcgctgac cggcctgacc aggtcatcga cgacgtgaac gtgctcagtg    47640
cggacgagcg tgagcaggtc ttgcatgagt ggaacgacac cgcggtggtc gtgccgcagg    47700
ccggcgtgcc ggagttgttc gaacgccagg tcgcgagcac gcctgacgcg gtcgccgtga    47760
tctgcggtga gatcacgctc acgtatgccg agttgaacga acgggcggac aaactggctg    47820
gctacctggt ttcccagggt gccgggccgg aacgcttcgt cgcagtcggg ttgccgcgtg    47880
acgaacggct cgtggtcgcg ttgttggccg tgctcaaggc aggcgcggcg tacctgccac    47940
tggacctgga gtatccttcg gaccggatcg cgcacatgat cgcggacgcc tcgcctgtgc    48000
tcgcgctggc cacttcggac acctcgagcc tgattcccgg tgagctgccc agagttctgc    48060
ttgacgccc ggttcctgag gccgtgccgg tgaccgtcac gcggaaggcg gaccaggcgg    48120
cgtacgtgat ctacacgtcc ggctcgacgg gcaggccgaa gggcgtagtc gtgccgatgg    48180
cgccgatggt gaacttcctg gacagcatga ccgcaggtt cccccttgacc actcgcgaca    48240
gaatgctggc ggtcaccacg gtcggcttcg acatcgctgt gctggagttg ttcctgccgc    48300
tgctgcgcgg cgcaggggtg gtgctggcga ccgcgagac cactcgtgac ccggtggcgt    48360
tgcgggcgtt gatcgagcag tccggcgcca cgatcatgca ggcgacgccg agcctctggc    48420
gttccttggc ggcggaaggt gttccgtcgc tgcggatctt ggtgggtggc gaggctttgc    48480
ccgccgacct ggccagggaa ctggccgcgg acggccggga cgtgaccaac ctctacggac    48540
cgaccgaaac cacggtctgg tcgggcgcga cgcggatcag ccaggacgac gcgccgatcg    48600
gcgaaccgat cggcaacacc cggctgtacg tgctcgacgc cggacttcac cctgtaccag    48660
aaggtgttcc tggcgagctg tacatcgccg gtgccggtct ggcccgcggc tactggcaac    48720
ggtccgggct gaccgccgag aggttcgtgg cgtgtccgtt cggcgggccg ggcgagcgca    48780
tgtaccggac cggtgacttg gtcaaactcc gtgccgacgg gcggatcgac tatctcagcc    48840
gggtcgacaa ccaggtcaag ctgcggggtt tccggatcga gctcggcgag atcgaggccg    48900
tgctgtccgg cgtcgactcg gtcgaccagg cggttgtggt ggtccgtgag gaccgtgaac    48960
aggacaagcg tttggtcgcg tacacggtcg gttccacgcc ggacgccttg cgggcacacg    49020
```

```
cggcggcgca cctgccggag tacatggtgc cgtcggcgtt cgtggtcctc gacgagctac    49080
cgctgacgcc caacggaaag atcgatcgac gcgcgctgcc cgctccggag tacaccgctg    49140
cggccggtcg tgcgccgcgg acaccgcagg aggagatcct gtgcgagctg ttcgcggagg    49200
tgctcggcgt caccgatgtc ggcatcgacg actcgttctt cgcgctcggc gggcattcgc    49260
tgctggccac caagctggtc aaccggatcc ggtcgccct cggcgcggag atctcggtcc     49320
gcaccctgtt cgagacctcc accgtggccg gactggcccc gctgatgtcc ggcgacggca    49380
ggcgtaccgc actggttgcc ggacagcggc cagagcggct gccgttgtcg ttcgcccagc    49440
ggcggcagtg gttcctgcag cagctcgaag gcgccaacac ggcgtacaac atcccgagtg    49500
cactgcgtct gaccggtgat ctcgacgagg acgcgctgcg cgccgcgctg ttggacgtgg    49560
cggtccggca cgagtccctg cgaacggtct tcgcggagga cgacctcggc gcacgtcagg    49620
tcgtgctgcc cgaacaggct gctcggcctg cgatgacggt cgtggagacc accgagcccg    49680
agctgcggac gcggatggac gaggccgcgg cgtaccggtt cgacctgggc gccgagccgc    49740
cgctgcgggc ctgggtgttc cggctttccc agaccgagca cgtgctgttg gtgctgacgc    49800
accacatcgc cagcgacggc tggtcggtcc cggtgctgat gcgggatctg gccaccgcgt    49860
acgcggcacg tcgtggcggc caggcaccgg gctgggcgcc gttgcccgtg caatacgccg    49920
actacacgtt gtggcagcac gaaatcctcg gcgccgagga cgatcccgcc agcgagttcg    49980
cccgtcagat cggctactgg aagaccacat tggatggtct gccgcgcaa ctggacctgc     50040
cggccgaccg gccgcgcccg cggcaccgt cacaccgtgg cggcacggtg gagttcgatg      50100
tccccgccga actgcacggt gcactggttg cgttggcacg tcagcacaac gcgagtgtgt    50160
tcatggtcgt ccgtgctgcc gtggcggccc tgctgaaccg gcttggcgcg ggggaggaca    50220
tcccgctcgg cacggcgatc gcgggccggt ccgacgacgc actgcacgac ctggtcgggt    50280
tcttcgtcaa caccttggtg ctgcggaccg acctggcagg caacccgagc ttcagcgagc    50340
tggtcgaccg ggttcgtgag gccgacctgg ccgcgtacgc caaccaggac gtgccgttcg    50400
agcgcctggt ggaggtgctc agcccggctc ggtccatggc cagccacccg ctcttccaga    50460
ccatggtgac ctggcacaac accgaccgtc gcgccgccgt cgaggcacaa cgcgacctgc    50520
ctgggctggc cgtcagtccc tatgaggtgc ggaacgtgtc ggccaagttc gacctggcgt    50580
tctccttcac cgaaggcacg ggaatcagcg ccgagctcgg ctacagcgcc gacctgttcg    50640
accgggccac cgccgaggcc ttcgcgcagc gtctgcttcg agtgctggag acggtcgccg    50700
cggacccgga cgttctggtg agccggatca gcctggtcac cgaggacgag cgtgacctgg    50760
tgctgagggc gtggaacgac accgcgcaac cggtggccgg gaccacgttc accgaactgt    50820
tcgccaggca ggcccaggcc acgccggact ccgtcgcgt cgagtgcgac ggccggaccc     50880
tgacgtacgc cgagttggac acgcggtcca accagctggc gcattacctg gtcagcaacg    50940
gggtcgggcc ggagcggttc gtcgcgatcg tcatgaacaa gtcggtggac atggtggtcg    51000
ctctgctcgg tgtgctgaag tcgggcgccg cgtacgtgcc gatcgacccg gcctaccgc     51060
gcgatcgcat cgagttcatg ttctccgatg tggcgccggt cctcgtgctg acttcacggg    51120
atgcggcctc ggcattgccc gagtcggacc acgtgttcct ccaggacgtc gatttggccg    51180
cctacccgga cgccgccatt tcggaggcgt gcccggccaa cccggcgtac gtcatctaca    51240
cgtctggttc gaccggacgc ccgaagggtg tggtgatcga gcaccgggcg ctcggcgcct    51300
acctggaccg cgcccgcgag gcgtatccgt ggatgtccgg caccacctgg gtgcactcgc    51360
cgatctcgtt cgacctgacg gtcaccggcc tgttctcgcc gctggtgagt ggtggccggg    51420
```

-continued

| | | | | | |
|---|---|---|---|---|---|
| cgcggctggt | ggacctcgag | ggtggcgcgg | cgacggggga | gcggccgtcc | ttcgtcaagg | 51480 |
| gcactccgtc | gcacctcggt | ctgttggacg | tcctgccgga | caacgcttcg | ccttccggcg | 51540 |
| cgctgatgct | cggcggcgag | ttgctgatcg | gtgacgtgct | gcagcgctgg | cgggaccgca | 51600 |
| accccgatgc | ggtcgcgttc | aacgtctacg | gcgccactga | ggcgaccgtg | aactcggtgg | 51660 |
| agaaccggat | cctgccgggc | acgccgattc | cttcggggc | ggtgccggtg | ggcacaccgt | 51720 |
| tccgcaacac | ccggatctac | gtgctcgacg | agagcctgcg | gccggtgccg | ccgggtgttc | 51780 |
| ccggtgacgc | ctacatcgcg | agcaccggtc | tggcgcgtgg | ctactggcga | cggttcgggc | 51840 |
| tgaccgcgga | acggttcgtg | gcctgtccgt | acggcgagcc | aggcgagcgg | atgtaccgca | 51900 |
| ccggcgactt | gttgcgctgg | aacaagcagg | ggcaactgga | gttcgtcggc | cgggcggact | 51960 |
| cgcaggtcaa | ggtccggggc | ttccggatcg | aacccggcga | ggtcgagtcg | gcgctgacgc | 52020 |
| ggtgcgacgg | cgtgagccgg | gctgtggtcg | tggtccgcga | gggccggctg | gtcggctacc | 52080 |
| tccttggcga | tggcgtggac | ccggagacgg | tccgggcgac | ggcggcagag | ctgttgccgg | 52140 |
| gctacatggt | tccggccgct | ttcgtggttc | tcgacgagct | cccgctgacg | cccaacggaa | 52200 |
| agctcgacca | gcgggcgttg | cccgcaccgg | acttcggtgc | cgcgaccacg | gccaccgcac | 52260 |
| cgcgtgacgc | tgtggaggaa | ctcctcgccg | gactgttcgc | cgaggtcctc | gggctggaac | 52320 |
| aggtcggcgt | cgacgacggg | ttcttcgacc | tgggcggcga | cagcatcatg | tccattcagc | 52380 |
| tggtcagcag | ggctcgtcgg | gcgggtttga | cgatctcgcc | gcgtgacgtg | ttcgaccggc | 52440 |
| agacggtcgc | gggccttgcc | gctgtggcaa | aggcttccga | tgcggtgacg | gtcgaggaac | 52500 |
| cgggtgcggg | gatcggcgag | ttcccggcaa | cgcctgccat | cgcgcgattc | ctggagagcg | 52560 |
| gcgcccaggt | cgaccagttc | aaccagagcg | tcgtcgtgcg | cgtgccgtcc | ggacttggcg | 52620 |
| aggaccggct | tgtggccgcc | gtgcagaagc | tggtcgacca | ccacgatgcc | ctgcgtactc | 52680 |
| atctcaactc | ggtgctgtcg | gtgagtgcac | cgggcacagt | ggacgcacgg | gacctcgtgt | 52740 |
| cccgtgtgga | cgcggccggg | ctcgacgacg | aagcactggt | tccggtgatg | tcggagcacg | 52800 |
| ccgtcacggc | ccgtctgagg | ctggcgcccg | ccgacgggaa | ggtcatccag | ttcgtctggt | 52860 |
| tcgaccgcgg | tgacctgccg | ggacaactcg | tcgtggtcgc | acaccacctc | gtggtcgacg | 52920 |
| gcgtgtcctg | gcgtgtgctg | ttgccggatc | tcgcactggc | atggcagggc | gaagaactgg | 52980 |
| cacctgtggg | cacttcggtt | cgccgctggg | cccagcgcct | gaccgagctg | gcccgacgtt | 53040 |
| cgtccgagtt | ggggctgtgg | accgagatcc | tcggtgaccc | ggaaccggtt | ctcggttcgc | 53100 |
| gggcattgga | tccctctcgg | gacaacgctt | ccacggcacg | tcacctcacc | acgacattgc | 53160 |
| cggaggacgt | cacaggcgac | atcctcacga | ccgttccgtc | cgctttccac | gccgagatca | 53220 |
| acgacgtgct | cctggcgacc | ttcgccgtgg | cgttcgacga | atggcgcggc | gggagcgtcc | 53280 |
| tgatcgacct | ggaaggccac | ggccgcgagg | aacatctgct | cgacaacgtg | gacctgtcca | 53340 |
| ggaccgtcgg | ctggttcacc | aacctgtacc | cagtccggct | ggatcccggt | acgggcgaca | 53400 |
| tcggtgacgc | gctgaagcgg | atcaaggagc | agttgcgcgc | ggtcccggac | aagggcatgg | 53460 |
| gctacggcct | gctgcgctac | ctcaacccgg | gcaccgccgc | ccggttgcgt | gaactgcctg | 53520 |
| gcgcccaggt | caagttcaac | tacctcggcc | gggtcggcaa | cgcggaatca | ggcgactggg | 53580 |
| caccgggatc | cggcatcaac | ggcgtcggcg | ccggtcgcga | ccgcgccat | ccgttgtcgc | 53640 |
| acgcactgga | ggtcaacgcc | cggacgctcg | ggccggaact | cgtggtcagc | tggacgtggc | 53700 |
| cggacgaggt | cctgagtgcc | gacgaagtca | cgcggctgaa | cgagatctgg | ttccgggcac | 53760 |

```
tgcggtcgct gacccagtcg acagccggtg gcctcacccc gtcggacgtc tccttggcgg    53820
aactcagcca gagcgagatc gacctgctcg aatcggaatg gacggactag gcgcatggca    53880
cgatccgaca tcgcggacat cctgccgctg accccgctgc aggaagggct gctgttccac    53940
acgctctacg acgagcaggc ccgtgacgcc tacctcggcc agcacgcgtt cgagctggac    54000
ggggagctgg acgtcgaagc gttgcgcgcc gcggcggagg gcgtgttgcg caggcacgga    54060
aatctcaggg cttccttccg gtacaagggg ttgagccgga ccgtgcaggt gattccccgg    54120
cgggtcaccg ttccgtggca gtacatcgac ctgtccgacc ggccggagga ggctgagcgg    54180
gtcaccgcgg cggaccgcag tgcgcggttc gacgtcacca aaggcccgct gctgcggttc    54240
acggtcatca ggctcggggc gcgtcgtcac ctgttcctgc tgacgtatca ccacatcctc    54300
ctggatggct ggtcgacccc gttgctgctg cgtgagctga tgacgctgta ccagagcaag    54360
ggcgatccgt cgtcgctgcc cgcggtccgg ccgtacaagg actacctggg ctggctgtcc    54420
aaacaggacg tttcagtggc cgggcaggcc tggcgggaag cgatgtccgg gcttgcggag    54480
ccgactcgtg tcgccagtga cccgaacgcg gtcactgtcc cggagatgac cgagttcgca    54540
ctggacgatg ccgtgtgtca gcgcctgcgg acgcggggtg tcaccttgag cacggctgtc    54600
cagtgcgcgt gggcgttggt gctggctcag ctgaccggcc gtgacgacgt ggtgttcggc    54660
atgccggtgg ctggtcgccc gccggagttg ccgggtgtcg agcagatgat cgggctgttc    54720
atcaacaccg tgccggtccg gatccggttg cgcccggccg agacgctcgg cgagctgttg    54780
gccccgggtcc agggtgagca ggccgctttg ctgccgtacc agtacctggg gctctcggag    54840
atccagcgcg cgtgtggcat gggtgagctg ttcgacgcct cgatggcgtt cgagaactat    54900
cccgtgtccc cggacacagt ggacagtccg cgtggtgacg ccctgcgggt gcgcaagagg    54960
cgtggcgtgg acaccgggca ctaccgttg acgttgatcg cggtgtcccg ggccggcctg    55020
aggttccggc tcaaccggcg gcctgacgtc gtgcctggca tggacgtggc cgacctgctt    55080
gtgcgcaccc tgacagccat cgcggaccag cccgatctcc ggctggccca actgcctccg    55140
gccgctgagg tgcggcacgt cactcccgac ggcacgcctg ggttgtttc gcgtgacttc    55200
gaagaggtgg ctcggcaggc acctgacgcc atcgcggtga cgttcgatgc cgggaagctg    55260
acgtatcggc agctggatca gcgcgcgaac cggttggcac gttcgctgat ctcgcgcggt    55320
gtgcggcgag gtgacttcgt cgcggtggcg ctgccacggt cggctgacct cgtggtcgcc    55380
ttgctcgccg tgctgaaggc cggtgccgcg tacgttcccc tggatctcaa gaatccggcc    55440
gcgcggaccg atgcggtgct cgccgatgcc cgtcctgccg ttgtgctgtc cgaagtcggt    55500
gatcttgagg acttctccgg cgatgttctg acggatgcgg agatcggcgg tccgctgacg    55560
ccgaacgatg ccgcgtacat gatctacacc tcgggttcca ccggtgtgcc caagggcgtg    55620
ctcgtcgagc gggggtcgat cgaccggatc gcccgcggca tccctggcgt cgaactgacc    55680
gccgacgatg tcgtcgccca gttggccgcg gtcgccttcg acgcgacgac attcgaggtg    55740
tggggcgcat tgctgaacgg cgccacgctg gccgtcgcgc caccgtccgc gttgtcggta    55800
ggcgaactga ggaccttcct gaccgacgcc ggtgtgaccg cactctggct gacggccgga    55860
ctgttccacg aggtcgtcga gcaggacatc acggccttga cggggttgcg ttacctcctc    55920
gcaggtggcg acgtcctgtc gccaagcgct tgctcggccg tccgtgccgt gtacccggat    55980
cttcggctga tcaacggtta cggcccgacc gagaccacga cctttgccgc cacgcacgcg    56040
gtggatcgcg cggacacgac cgtgccgatc ggtgcgccgg tgaccgcgac tcgtcttcac    56100
gtcctggatg gctggctgcg gccggtgcct ccgggcgtca caggggagct gtacatcgca    56160
```

```
ggcacaggct tggcgcgtgg ataccacgat cggcgtggat tgaccgcgga acggttcgtc   56220
gcttgtccgt ccggtgggcg gatgtaccgc accggggatc tcgtccggtg gaactccgcc   56280
ggtgacctcg agttcctcgg ccgcgtcgac tcccaggtga aggtccgtgg tttccggatc   56340
gaactcggcg agatcgaggc cgcgttggtc gcgcacccgt cggtggacgc ggcggcggtg   56400
atcgtgcggg aggaccggcc ggatgacaag cggatcgtcg cctacgtgcg tcccaccatc   56460
gatcccgttg tgctgcgggc gcatctggcc tcgatcgtgc cggacttcat gatcccggca   56520
gcgttcgtgc cggtgacgca gttcccgctg accgccaacg aaagctcga ccgacgagcc   56580 ttgccggtgc cggactacgg cgacggccgg gcacacgcgg cggcacggtc cccgcgcgag   56640
gagatcctgt gtgagatctt cgccgacgtg ctcggtgtcg accgggtcgg tgtggacgcc   56700
agcttcttcg atctcggcgg ccattcgctg ctggcgactc gtctggtcag ccgggtccgc   56760
agcacgctcg gcgtggagat gtccatccgc cggctctacg actcgcctac cgtggctggg   56820
ctgtccgagg ccctcgatgc cctggcaggc gcccggaccc gggtgaccgc ggttcaacgg   56880
cccgagcggg tgccgctttc cttcgcgcag cagcggctgt ggttcatcga ccggctcgaa   56940
ggccccagcc ccagctacaa cgtgcccttcg gcgttgcggt tgcgtgggcc gctcgatgtg   57000
acggccttgc tggcggcgct cagggacgtg atcacgcggc acgagtcgtt gcggacgatc   57060
tacgccgagg accagcacgg accacaccag gtggtgctcg ccgaattctc gacaccccttt  57120 gccgtcatgg acgtgacgca ggacgagctg tccatggccc tgtccggagc cgccaggtac   57180
tcgttcgaca ccgcggccga aatccccatc cgggccaccc tgttccggct cggccccgag   57240
gaacacgtgc tgctgacggt cgtgcaccac atcgcgaccg atggctggtc gatgcccgtg   57300
ctggctcgtg acctcgcgca cgcgtacacc gcgcggcacg ccggtcacgc accgggctgg   57360
gctccgctgc cggtgcagta catcgactac acggtgtggc agcgggaagt ccttggttcc   57420
gaggacgatc cggacagcgt gatctcggcg gaactggcgt actggcagag accctggcc   57480 gggcttcccg aggagatcgc gctcccagtg gaccggccgc gtccgcgtac ggccagctat   57540
gcgggcgacg gaatccgctt cgccatcccg cccgagctgc atgggaagct ggcctcgatc   57600
gcccgtaagc ggcacgtcag cctgttcatg gtcgtccagg ccgccgtggc gacgttgctg   57660
caccgcctcg gcgcgggcga ggacatcgcg ctgggcagtc cgatcgccgg acggaccgac   57720
gacacgctgg attcactcgt cggggttcttc gtcaacacgt tggtgctgcg caacgacttg   57780
tccggcgatc cgtcgttcgc cgagctgctg acgcgggtca gggacaccga cttggcggcg   57840
tacgcgcacc agaacgtgcc gttcgagcgc ttggtcgagg tggtcaaccc ggagcggtcg   57900
ctggcccgtc accgctgtt ccaggtgatg ctcgcgtaca acaacaccga cttcggcact   57960
gcggacgagc cggcttccgg cctcgtgatc agccaggaac gcgtcgacac cggtacctcg   58020
aagttcgacc tgctgttcgc cttcaccgaa gggcaaggcg gcgggttgcg tggcgaactc   58080
cgcttcgcca cagcgttgtt cgaccggggcg accgcccagt cgattgtgga ccgtctgctg   58140
ctggttctcg attccgttgc cgctcagccg gacttgcccg tgtccgcggt gaacgtcctg   58200
gcggagcacg agcgggatct cgtggtcgac ggcggcgccc ggcaggtgcc ttcgtcacct   58260
gtgcctgctt tgttcgaaca gcaggccgtg ctcaggccgt ccgcggtcgc gctggagaca   58320
agttccggca cgctgacgta cgccgagctc aacgagcggg ccaaccacct ggcgtggcac   58380
ctgatcgccc aggggatcgg gccggaccac ctggtcgccg tgctgcttcc gcgtggcgag   58440
tggcttgcgg cggccatgct cggaatcctc aaggcaggcg ccgcgtacgt gccggtcgac   58500
```

```
gtcacctacc cggaagaccg ggtcgccgag atcctggcgg acgcttcacc ttcactcgtg   58560
gtgagcaccg ggtggcccgc cggtcgttcg gacaacccgc cgtacaccgc cgatgacgcg   58620
aacccgtcgt acgtgatcta cacgtccgga tcgacaggga agcccaaggg cgtggtgatg   58680
accaacctcg ccctgcgcaa cctgctggca tggcattcgt cggcggtgcc cggcgaaccc   58740
ggcgaccggg tctcgcagtt cacggcggtg agtttcgacg tgtcggtgca ggagatgctg   58800
tccaccttga ccactggcaa gaccctggtc gtcccggacg aggacacccg cgcgatccg    58860 gcgcagctcg ccgcgtggct cgaccggacg caggtcaacg agttctacgc gccgaacctg   58920
gtgatcaacg ccgtgttcga ggcgggactg ccgttgcctt cggtcaaaca cgtcgtccag   58980
ggcggcgagg cgttcgtgat cagcgaggcg atgcgcgccg cgcacatccc cggccgccgt   59040
ctgcacaacc actacggccc cagcgaaacc catgccatca ccggttacgt gctgcccgaa   59100
gaccccgggt cgtgggaacc ggtgacgccg atcggcaagc cgatcccgaa ctcccaggca   59160
cacatcctgg acactcggtt gcgtccagtc ccgcccggcg tgccagggga gctgtacctc   59220
gccggcgacg cgctggcgcg gggataccct aaccgtccgg cactgaccgc agaacgattc   59280
atcgccttcc ccaacgggca acgcgcctac cggacaggcg acatcgtccg tcgaacgcac   59340
accggtgacc tgatctacct cggccgcgcg gacaagcagg tgaaagtccg cggcttccgc   59400
atcgaacccg gtgagatcga agcccgcctc accgcgcacg tcgacgtcac ccaagccgcg   59460
gtcgtcgtgc gtgaggaccg ccccggcgat cgtcgcctgg tggcctatgt cgtgggtacg   59520
gcgtcggccg acgtgcttcg caagaccctg agtgacgcac tgcccaacta catggtcccg   59580
tccgcgttcg ttcacctcga cgaactcccg ttgacgccca acggcaaact cgactggcgc   59640
gccctgcccg cgccggactt caccgcggct cgggaaagcc gtcagccccg cacacccgt    59700 gaagagatcc tgtgtggcct gttcgccgaa atcctcggtg tggacagtgt ggggatcgac   59760
gacgacttct tcgaactcgg cggccattcc atcctggcgg cgaaactggc cggccggatc   59820
cgtgccgaac tcggcgagga actgacggtc cgcaacctct tcgaaacgcc ttccgtcgcg   59880
ggccttaccg gtgcttcggc ggacaaacgc gctccgctcg gcccgctgct ggccctgcgg   59940
cgcaacggtt gcgcccaacc ggtgttctgc atgcaccccg gcggtgggat cggctggtcg   60000
tatgcgcggc tcgtccggca cctcagcccg gacgtacccg tctacgcact ccaggcctcg   60060
ggtttctcga ccggctcggc actcccgtcc tcggttgagg aaatggccgc gtcctacgtg   60120
gcccggatgc tgtcggtaca gcctgaaggc ccgtaccgga tcatcggctg gtcttttcggc  60180 ggcctggtgg ctcacgccgt cgcgaccacc ctgcagtccc tggggcacga ggtgtcactg   60240
ctggccctgc tcgacgcctt cccacccacc acgtccgcgg gcgagctcga cccacacgcg   60300
gtgctcgccg cgaacatgcg ggcgtccggg ttctcgttcg acgaggacga gctgcgcaac   60360
gatgagcagg gcgtgctgaa ggcgttcacg gagttcctca ggcacgagaa catggcggtt   60420
tctctggcgt acctggacga ggaggaactg gtcaacgcca agaacgtcta cctgaacaac   60480
atccgcctga tgcgccggtt cacccccgcg gagttcgcgg cgacgtggt gttcttcgcg    60540 gccacgaagg tcgccaagga caagctcgac cgtgccaggc cggaagcgtg gaacccgcac   60600
atctcgggga cgctgaccgc ccacccgtg gccacgcgc acgagaagct gctggtggag     60660
ccggaagcgg tggcggaggt ggccagggtg ctcaactcac acctggacag gtcatgatgt   60720
cgtcgtcgaa gcccagcggg tcatggtgca tccggccgat gatgcgttcc gcttccccgg   60780
ccctgccgcc tgtgtgcagt gcggccacgg cgatcttgcg gcactttgcc agccgggcgg   60840
gcgaacccta gagccggacg tgccggtagg cctcgctgat cagttcgaga gcacgggcga   60900
```

```
acgagttccc gcggtagtgg aaatacgccg ctatcgacag cgtctcgccc agtgattcag    60960
gatgactggc cctgttgtgg gcgatgttct cgtccatcac ccgcagcgcc gcggcgctgt    61020
ctccgcgttt ggccagcatt tgcgcgaggt tggtcttgac ctggctcgtg taccgatgag    61080
cggcgtcacg ctcgaccatg acccagccgt cgcgcggaag cagctcgtcg gcgttgctga    61140
tggaatcgaa ggcttcccgg ggttcgccct gccggatgaa ggccagggcc gcaaggttcg    61200
cgaccagtgc gcacatcgtc atccgatcag ccggggagat cacataccgg ctctccgcgt    61260
cacacgcgcg gtgccgcagg cggtcgagga tctccagcgc ccggctcggc tcattccgtc    61320
gcttcagcac gaatgccgcg agccgcagct cggcgagcat ggaatccacg atggcaggcg    61380
ttgcctcggc agcgcggacg aagagctcct ccgcgtcgaa aaccgagtcg cgtcggatg    61440 ccatggccgc cgccgcgtag agcagggcga catgcgtgcc gagcggcttg gcggcagaga    61500
gcacagccgt tgtcagctca cgcgccatcg accagtttcc ggcgaaacac acgtgcgcgt    61560
cgatgagagc gcagaagtca tactcccggt actggccgtc ggcccagcgg gtggcccatt    61620
cgctcggctt catcggctgg atcgagtcgt cggcgtggga tgtgaggtcc tggatgcgta    61680
ggtgcccgtc aaggaacgcg gccgcctcgg tcatgccacg aacacccaga tcagtcaggt    61740
aattggtctg cacgggaagg cgggtgtgcg gcagtccggg cagtgccgcc gacctggccc    61800
tttcgaccag accgtaccgt gcggtcagcg tgccgcaggc ttccgcgtcg agaatcgtcc    61860
tggcggttcg ggtcgcccag aagacgtcat tcgtgctgtc catcgccatt cctgtcgggt    61920
atgggcggcg gcgcctgtcc gggcgccgcc actggtcatc gagcgtcgtt acctgggccc    61980
gtgcttccag ccgccgagca ggccgttgat cgtcgcgtcg gctgagtcca gctccgcgac    62040
gatctggtcc ggcgtgaccg tcgaggagtc cgtgctctgc gcgcttgcga cgcctgcggc    62100
cgtcagcaac gacgccagcg ccgccgcgga caccgccgcg gtcttcacga gaacattctt    62160
catgcacgtg accttctct gatttcgttt cacacaccca cagcgaaacg gtggacatca    62220
aggaactact tccgtcgagc gattgtgagc ccgtcaccga tgggcagcat caccggctcg    62280
acacggtcgt ccgcgagtac gtgctcgttg aattcgcgca gcgcactgcc actcgcgttc    62340
gacgggtcgt cgtcgacaac gccaccaaag ccgaagacgt tgtcgacaac gatcagtcca    62400
cccgcacggg tccgcgggac aagctcagtc cagtactgga cgtattcgtc cttgtcggca    62460
tcgacgaagg cgagatcgat cgtccgccgg cgcgggagtt cgcggagcgt gtcgagggcc    62520
cgccccagtt tcacggtgat gaggtgcgcc acgcccgccc gctccccgaa tgggcgcgcc    62580
accgcgatcg cggccgaact cgcctcgcaa caaagcaagc gcccttgacg tggcattccc    62640
ctggcaatgg ccatcgccga atatccggtg aaggtgccga cctcgaccgc gaatctgacc    62700
tccgccgtcc gtgccagcat tgtcagcagt gctgcctgca gcggcgtgac ctgcatcccc    62760
gaatactccg gacaaacccg ccttgttgtg gcgatgagat cccgctcgac ctcatccatc    62820
ggcgtactgt gatctgccgc gtacgtgacc aggtcagcac gcacggcgcc cgactggtgc    62880
accgagtatc aaccccccga ctcatcgatg tcagtgagtt tccgacaacg accgtaaaaa    62940
ccatgacagg agccgcttgc ggttttcttc cgccgatcgc cgtgaaatga ggagaagccg    63000
cgtgacgatg ccggtggacg agctgatcaa gccaggtggt gctggaaagc agaacgcgag    63060 cggggggttag ggtcgcagcg tggcagagac tgagccgttc tcggtgaaga agttcgtcgc    63120
ggggctgagc cgcaagcgga tggcgtcagg gatgctgttc cggacgacca ccggccgtgt    63180
ccttctggtg gagccctcct acaaggagca gtgggagatc ccgggcggtg cggtcgacga    63240
```

```
gaacgagtcc ccatgggcga cggtgtcccg cgagctgacc gaggaactgg gcatgcggcg   63300
gcccgtcggg cgcctgctgg tcgtcgacta cgtccaccg gagggcgact ggccggaggc    63360
ggtgatgttc gtgttcgacg gcggcgtcct ggcacagtct gatgtggacg cgatggtgtt   63420
cgccgacggg gagatcctct cggcaggctt ctacgacctc gcggaagccc ggaaactgct   63480
gaagccgcgg ctcgccggcc gggtcgaggc cgccatctcc gcgctgcggc agggcacgac   63540
ggtcctctgc gaacacggcc gccagatcac ttaggcgcac ctccccggat cctcaccacg   63600
cgggccggct gaaaaccggg tgcggacggc gggcgcgctg gtgtgtgatc aagggatggc   63660
gatcgtgatg ggcaagccgg gagtcgacgg gctgagcgcg gctgtgggcg tgctgcggga   63720
atggcagtac gaggggggcgc cgatgcaact gcatccgggg gacctgggct ggttctggcg   63780
gttcggtgcg gaggcgacgg ccgcggcggt ccggacctgg agccgggacg gacagattct   63840
cgccgtcggg ctgctggacg gtcccgagct gttgcggctg acgatcgcgc cggacgtcca   63900
gcaggacgag gagttggccc agcaactggt tgaggacgtg actgagccgg agcgcggtgt   63960
cctgccggcg ggaaaggtgt tcatcgaagc gccgatgggc gtgctggtcc aagatctgct   64020
gttcgagagc ggctggaagg tcgatgagcg gtggacgcca ctgcgccgcg acctcacgga   64080
accggtgaag gacccaggcg tgcggatcga ggtgatcgga ccggagcagg tgcacgtgcg   64140
gaccgccata cagcgggcat cgttcgacag ttcgacgttc acagacgagc gctggcacgc   64200
gatggcggcc ggattgccgt acgccgacgc ccggtgtctg gtcgcgtacg acgaccaggg   64260
caacggggtg gcggcggcga cagtgtggtc agccggtccg gggaagcccg ggttgctcga   64320
gccgatgggc gtacacccgg cacaccgcgg ccacggctac ggcaaggcga tcaccgtcgc   64380
cgccgcggcc gcactccagg agctgggctc gtcgagcgcg atcgtctaca ccccgagccg   64440
caatgtcggc gccgtcgcca cctacaagtc ggcaggcttc cagcagcgcc ctgagatccg   64500
ggaccaatgc cgggactagt cggagttggc gaacaccagc acagcggctt gatcacccgc   64560
gcgaacggga atccacgcct cggtgaggtc gtccagccgg tcgaagtcga ggctcagcag   64620
gacgcgtgcg tcggagtcgc cgtcgggcac gaagtaggcg accttctccc ggaccaggcg   64680
ctgcaggtgg tccaggtcgt cgacggtcca gttgaccggt ggccgcccgg cgaaccggcc   64740
gaagaagccg gtgaacggcg tcgcccggcc gaccacgacg aggtagccct caagcgactt   64800
ccgcaggcac gcaagacccc cgcactggtt ctcgtacacg accccggtcg cgcgcggcac   64860
gatcaggcac agcacctcgg ggaccgcgtc atgcgggttg aaatccacgc gtacctgcat   64920
ggactcaagc gtaacgccgg tactacatga ggcggacggg ctctcccatg ccacgacga    64980 tctcccgagg acccttgtac ggctcgacgg cgtgtgccat ccggatgttg tcgaccagca   65040
tgagatcgcc gtcctgccat ggctcacgga tggtgtgggc gtcgtagaca gcgttgatgg   65100
cgtcgacgct ctcgcggtcg agcggcgtgc catcgcctgc gaaggtgttg aacggcaggc   65160
cgccgtcgag cgccatggtc aggtagtccc ggacgtccgg atccatggtc cactcgttca   65220
ggaacgcgat ctggttgaac cagccaggac gccccgaaac cgggtgccgg acgaccgcag   65280
ggcgcgtctg agtcgtccgc aggctgccat ccggcccccca gttccaggaa atcccgtggg   65340
actcgcaata agcctccacg acgtccttgt cggcactgcc gaaggcatcc gccaacggaa   65400
cgccgaccag cgggttgtag ttgcggacca actgccaccc gtggccggag aaccgggaga   65460
ccaagtccgc ggggaggtcg tcgagacacag cctgcgagtc ggccaatgcc gtcacgccac   65520
ccgaagccgg tgcccgcaaa caggtgaagg ccagcacagt gggcacatcg ggcacgtagc   65580
tcagttcgtg gtgcatgcac atcggctggt ccgacggcca tttggtggac gagtacatgc   65640
```

```
cctgctcgag cgagtcgcgt ggggcgaagc cctcgcgctc gacgacgaac gagtcgatca    65700
aggcgtggct gacggccgcg gccgtggaca cgtccgcgat tcccagacca cgcaccagaa    65760
cagcgccatc ggtggcgagc agtgagcgga gttccgcacg gttccgggcc gcccaggcag    65820
ccgggtccgt tgtggacact gagaggatct tcaccggtca ccctccagtc gggtagcggc    65880
caggctgagg tacacgtcgt cgagcgtggg ctccccgatg gcgagctcgg ccggctcgat    65940
cagggcgtcg tccagtgccc gcaccacgat cgcgaggtcc gcggaccggt cgacgggcgc    66000
ggtgatcgtc agcccgtccg gtccgcggt ggcggtcaga ccggcgcgcc gcagtgcgtc    66060
cattgccggg gtggtgtggt tgacgtcgga caacgtcacg gtcgcggtcc gcttgcccac    66120
ggtcgccttg agctccgccg ttccgccggt cgccaccacc ttgcccgcgg acaacaccgt    66180
gatcgtgtcg gcaaggcggt cggcttcctc aaggtactgg gtggtcagca ggacggtcgt    66240
gccgtcggcg accagcttct ccaccgtctc ccacaggccg agacgactga ccggatccag    66300
tccggtcgtc ggctcgtcca ggaagatcac ctcggggttg ccgaccaggc tcgcggccag    66360
gtccagtctg cggcgcattc cgccggagta gtgctgcacc tgtttgcgtg ccgcgtccgt    66420
gaggtcgaac agctccagca gatcgtccgc gcgccggacc gctcacgct tgcccgcgcc    66480 cagcagcctg gcgatgagca cgaggttgtc ccgcccgttg agctgcccgt ccaccgaggc    66540
gaactggccg gtcaagccga tccgggaacg tacctgcctg ccctcgctgg ccacgtcgtg    66600
cccggcgacc ctggcctgcc cggcgtcgaa cggcagcatc gtggtgagga cgttgaccat    66660
tgtggtcttg ccggcgccgt tgtgccccaa cagaccgagc acagttcctc gcggcgcctc    66720
gagggacacg ccgtcgagca cggtcacgtc accgaacttc ttgctgacgt cccgtgcgtc    66780
gatcatcaac tcggtcacag acaaagccta tgaggtccgg gaccgtagat ctctagcgaa    66840
aaacccagaa tcaccaccgg tgccgcagtt cggccacctc gtgcaggacg tccgggttcc    66900
cggcgaacac gccactttcc cgtggccagt gcacaacgag gtgcgtgatg ccggtttcgg    66960
cgtaccgttc ggccatgtcc cggcaggccc gcgaagactt cagcggatca ccggcacgcg    67020
gagtggcgat gaagatccgg tcgatctcgg tgctgtcccg gcccgcttga gcacacgcct    67080
tgtcgagcaa ctcgttctgg acggcgacct gcgcggcgac ttcgtccggc gagatgtcgg    67140
tcgtccaggc cgccgggccg gtcgtgatcc acttggtccc gtagcgggcg acgagatcca    67200
tgccgcgtgg cccggtcgcc gcgatcgcca gcggacgcg gatctccggc agcatcaggg    67260
cctcggacac ggcgtagaac tgcccggagt acgaggtggc cggattgttc agcagttctg    67320
acgtcagctc gacgaactcc gcgaaccggt tcgcccgtgt gcgctgggac aacggagcgg    67380
agtcgagcac ggtcgcatcg gtcgtgcctg gtgaacccgc tccgacaccg agcacgaaac    67440
ggccgcctga gatgtcctga acggtcgccg cgtccttggc cagcacggcc gggtgccgga    67500
ggttcggcgt ggcgaccatg gtgccgatct cgatccgcct tgtcgttgcc gcgacggcgg    67560
aaagcactgg tacagcggag aaccacgggc cattggtgcg ccaccacaag tggtcgtagg    67620
tccaggccga gtcgaagccc agctcttcgg ccgtacgcca ccgttcgacg ttgtcctgcc    67680
acgacagctc aggcaggatc acgactccca aacgcatgcg ggccttcccc tcatcgacac    67740
atcattcgca cggcagctca gccgtgatca cggtgcgcgc cgagcaggat catcagcagc    67800
acacccgcgc cgagcccgcc ggccatccac cgcagcgcga gagaccggac agccaggaat    67860
cccgcttcga cgactgcggt cgcaccaccg agggcgactc cgacagtcgg acggcaggca    67920
cgaagcgcta actcacgccg gagaaaagac accgcgcagt gtatcgacca ccccgcaagc    67980
```

```
gaaattcact accggctcgt caacaccgcc ttcatcacgc tgccgttggc gacatcccgc    68040
aacgcggcgc cgtgctcggc gagcgggtac gtggtcacca ggctggccag gtcgaatcgt    68100
gcggccagcg cgggcagcag ttgtacgtac tcgatcaggt gcgcgccggt gaacgccac     68160 gatccgatca cgtcgagctg ccggtacacg atctggtgcg ggttcacggt cgcgtcaccg    68220
ctgtcggtgt actggccgac gacgagatac gacccgccac gccgagcgag cgcagacct    68280 tcaccgaacg cggacggcac accagcgcac tcgatcacca ggtcggcgcc gccaccaccg    68340
gtgagctcga ccacctcggc cagcgcgtcc cacgtctcca ccacgttcac gtggtggtcg    68400 ccgatcccg cctcggcggc cagcttgagc cgattcgccg gaccaccgc gaggatcacc     68460 ttgccagcgc cggagatgtg cgccagtgcg gccgcggcca agccgaccgg cccgctgcct    68520
tgcacgacaa cggttttcacc cagccggacc ggcctgcgtt cgaacaacgc gtgcaccatc   68580
gtcggacccg cacaggcgaa cgacatcgcg gcgaccggat cgatcccgtc cggcaccttg    68640
atcacggtgg tgccttcgcg cagcacgatg aagtcggccc atgacccgga aagtgcgggc    68700
tcggcggtgg tcggccggtt gacaccgtac gtctgacggt tggtgcacaa cgtcggctca    68760
cggtacgacc ggcacggcac acaccgtcca cacgcgatgg aagacgccca catgacccgg    68820
tcgccgacgt tcagcgcctg cccccttggcg tcagtcgcgg tggccagttc gacgatggtg    68880
ccgaatccct catgaccgag caccaacggg accggaacgt cgagatgccc ctgctgcagg    68940
tgcagatccg tgccgcacac gccgcgtac tcgctcgcca cgaccatccc gccgggcggt    69000
gcctgcggca ccgggaactc ccgcagccgg aggtcacggc cgaactcggt gagcaccacc    69060
gcgcgcccgt tcaccgggcg cgcgccgcgg caagcagcgg ttcgtcgacg atctccagtg    69120
cggtggtgtc ctgctcgacc aggtaccact cgcgcggcgc gcccagcggc acgttcgtgc    69180
tgtcgttgta cgtcaccagc agcagccgcc tgctgaacgg tgacatgttg gtggccgagc    69240
cgtgcacgat ctccgggtcg aagaagatca ccgacccggc ggcgcccttg ggctgtcca     69300 tgccgcaccg ccgacaagg ccggccatct cggtcgtggt cagctggatg tcatcccggt    69360
cgaggtgctg catggacttc atcgtgccgc tgcggtccga ccggatcaac ccgtgccggt    69420
gtgagccggg cacgaacatc agcggccgt tgaactcggt gacgtcgtcg aggaacagcc    69480
cgacgttgac cagcctcggc tcgggcaggc tgtcggcgat ctgccacgcg gcgaagtcct    69540
ggtgccacgc ccagccgccg ccgacgaacg cgggcttggc gttgatcttg aactggtaga    69600
cgtacacctt gtcggtcagc aactgctgga ccggtccgag cagcctgggg gagcggacca    69660
gccgggcgaa ctccggttgc cgtaagtgcg acgcgtagat cgcgcgcacg tccttgccgt    69720
cgttctcggc gatccgctgc tcaccgggga tctcgccgtc ccgcacgaac gcgtcgcgca    69780
gcgactcgac ctcgtcggtg ttgaacagcc gctcgacgac gaggtagccg ttctcccggt    69840
agctgttgat ctggtcttcg gtgagaatca tcgttcttcc ttcagttcac cgtgaaatgg    69900
atcgactggg atgccgtcgt cagcacgtcg accaagtcct ccccggctcgg cgcggtggcg    69960 atgacgtacc cgaggcggcc gtacgcgtcg actggcggag cgacctcgcg gcccggcttc    70020
gtggtcacga tcacctgctg cacgccggcc actgccttcg cgcgctccac gccggagatc    70080
tcggtgagca cgccggtgtc cggcgtggtc aggaactgga tcccggcgaa gcagccggtg    70140
cccgacggca ccgtgacggg cagcccgcag gcctgcctga cctgctgttc gagcaggtcg    70200
acgccgctgg cgaggcggat cagctcgggg atcatgccgc cggccagccg tgggttgatc    70260
tcgatgatga ccggccccgga ctcggtgatc ttgacctcgg tgtggctcgc gccccctggtc    70320 agcccggccg cccgcaacgc ggcgcgcacc acgtcggcga cctggccggc cacctcctct    70380
```

```
ggcacggacg cgggcacgat gtgccgcgac tccacgaaat tcggcgcacc catcaccgat   70440
ttccgcacca tcgcgaccag ttcgtggtca ccgtcggccg cgaacatctc cacgctgtac   70500
tcaaggccat ccacatagga ctcgatcagc gcgccgcgag cccggggcat gccgcggacg   70560
ttcgtcgtca cggcaaggac cgcctcgacc gcgtcgagtg cctgctcggc cgtgtcgcag   70620
cggaccacgc cggtcgaccc ggactcgtcg accggtttca ccacgcacgg caatcccacc   70680
ttgtccaccg cggcagccac ttccaaagcg ttgtcgacca gcacccacaa cggttgcggc   70740
aaccccgcct tgtcgaggcg atcacgcagc ctggccttgt cacgacagcc gtcgatcgcc   70800 tccgccgtt  cggccggcag cccgaactcg gccgccagcc tcgccgcggt ggacaggtag   70860
aactcgctgg tggtcgtcac cgcgctgatc cggcggcgcg gcacctgcga gtggagtgcc   70920
gcggccagcg caccgggatc tccgtgtcg  cagcgcaaca cccggcatcc ggtctccggc   70980
agtcccagat accgttcggg cttgttcgtc aggaaaatcg gctcgtagcc gaggcgctgg   71040
gcgatgccga tcgcggccat cccggtgccg gtcgtgttgg actccacgaa cgcgagcacc   71100
ggccgggccg tgtccgggtc ggtcagccgg gtgaacgccc agctgtgcac caccgtgccg   71160
ggcggaacct gacgaggccg cgtggccaac ggttgatcgg gcaggccgcg ttcgacccag   71220
tacgtcttgt tgtgcacggt ctcggcatag cgatcgccac gatcggggaa gatcccgaca   71280
atggtcgtgc caccgggctc gtgctcggcc aggtgcgtca tcaccggta  caccgagccg   71340 gacgtgttgc ccgcgaacag tttctgctct cgtgccaacg cgaccgacgc ctcgaaggcc   71400
tcccggtcgt tgagccagtg cacctcgtcg atctggccgt gatccaggtt cttcgggtgc   71460
atgctgttgc cgagcccgct ctgcagccgt tgcggccagt ccggctgtcc gaacaggaca   71520
ctgccgacgc agtcgatgcc gaccaccgcg aggtcgggca gggtctcgcg cagcgctcgt   71580
gccgtgccgc acaacgatcc gccgctgccg accgagccga ccaggatgtc gatccggcca   71640
aggtcgttga ccagttcgcc ggccagtgtc cggtatgccg ccgggttgtc cgggttctcg   71700
tactgccgtg gccagaacga gccggggttg gcggccatga tctcggccag ccgcttgagc   71760
cgggcgccct gccagccgtg ctcgtccatc tccggcacga catggacctc gcagcccagc   71820
gactccagtt tggccagcgt gatccggtcg atccgcgggt cggtgacgat gtgcaccggg   71880
tgccccatga gcgtgccgac gagtgccacg cccagcgcca tcgtgccgga cgagctctcc   71940
acgatcgggg cgccgtcggc cagtgcaccg cttt gcttgg cgcgcagcag gatgttgcgg   72000
gccacccggt ccttcatcgc gaacaggttc tggatctcca gcttggcgta gcaggcaggc   72060
gcgtccgcgc cgttgttcag cgccagccgg acgagcgggg tgttgccgat ggcgtcgagc   72120
aggttctcac tgatcacgcg ctggcctccg ggagatgggt cgatgcttcg gtgagcgcct   72180
tgagcagccg gtctgtctcg gcgtaggcct cggtgatccg ggcacggcgg gtggccacc   72240 gccgttccgc caggtcgaac gccgccgcct gttgatcgag catggtccgt acgctgtcct   72300
ggcccgcgga gcccgtcgtg cgtttcgccg acaacgcctt gtccacatcg aacgcccgcg   72360
tcagcaattg ctcggcgccg gacaccgcga acccgcgttc ctcagccacc tgcctcagca   72420
gtccggcgtc cggctcggcc ggggaaagtc ctttgtcgac agcggcgacg atgtagcggc   72480
ccgcgatcac ctgtgccgtg cgccaggcca caccgcgtt  cagacagagt ccgttggcca   72540
ggctgaaacc gccgaggtat tcggtggtgc agacgtcacg cagccgttcg gtccgtagcc   72600
gcaaggcatc aaggaccgct gtgaacagtc gcagcaccga gctcgcctgg tcgaacgcga   72660
gcgggacgtg tctgcccgct tccttggaca cttcgatggt gttgctgaag ggcgtcgccc   72720
```

```
gttggccgag cacaacgccc atgaaccccg ctgccagctg cgcggtccgg ccgcgcaggc    72780
gttcgagcac ggggaagttc ttcttctgcg gcatggccga ggagatgccg ctgaactcgt    72840
cgggcaggtc gatgaacccg taacccgcgc cgctccacgt cagcaggtcg gtgacgaacc    72900
ggctgagcgg cacgccgagc aggcacagct ccgcggtggc ctccagcgcc cagtcccgtg    72960
cggccacacc gatcagggcg tgcccgtcgc cggaactgaa gccgagcagc cgcgccatcc    73020
gtgtccggtc ccagtccagc tcgccccggg tcatcgcacc cgcacccatc ggcgaggcgt    73080
cgacgctggc gtacaccatg tcgaaccggt gcaaactgtg cagcacctgg gcggacaggg    73140
cggagaagta gaaaccggcg ctggccacct gggcgggctg ggagtgcgtg tacccggca    73200
tcagggtgtc gatctcgcgg ccggccagcc ggtgcgcggc cctgccgagg ccgatcagct    73260
cgtcgaccgt gctgagcacc cggtcacgtc cgtagatcgt ctgtgccgtg gcttgcaggt    73320
cgttgcggct gcgatccacg tgccatgcgt gcgcggcacc gccgatccgg tcggtgacgt    73380
accgctcgat ggtgaacgcg atgtcgctca tcgggcgtc ggccagctcc cggacgaccg    73440
agctgtccag ctcggacagg acggaagcga tcgcggcgac gtcagcggtg ccgagcaggc    73500
ccattcggtg gtactcgagc aacagcacct gttccagccg caggtagccg ggcagcaggt    73560
gctcggcctc gaagtccagc tgcggccgca gcacctcccg ccgcagcagt tcgtcggggc    73620
ccgcggtgat ccgcccggtc agttcggccg cggtgtcgtg ccggtccttt tccgcgcaca    73680
ccgatgaaac ctccctcgag gggtggaaat tcgccagatc ggcgccgaat gcgatcgatc    73740
gtgccagtgg cgcttctccg aaaggttcgc cggatttccc ggcggcccgc cttcccgctg    73800
gccgcaccgg ccgaaagcgc cggaacaacc cggcacaggc cccttcgtcc ggcactccca    73860
gcggaaaccc ggatcagccg aatgaaccca gcgaccttcc gagacgcacc actagtccgg    73920
cgggctgctt tgaattcctc tcaccttccc cagtaggctc gccggccccc agtcagccgt    73980
ggtcgagtcc gcacaagagt gcccagaccg gtgcgcggca gtcaaccgtg accgggctat    74040
gactagggt ttccccggcg ttgccgaatg ccgccggtga gagcggggcg agagcaccgt    74100
gagagcatgc tgttccactc tggacacctc acgatggcgc acagtgatgg gaggtttggt    74160
tggacgtcct agcgattcag tcttttggcg gccgtccgtt acggtccgct tcatcccagc    74220
gtcacctgcg gataccacac accatcgggc aggcgctcgc gctggttgtg gcctagatcg    74280
cggtcagcac tacggtcctg gtcaccgggg ttgtgacgcg ctgtcacacc ctgggagccc    74340
ttgcgtggcc gccggggtgg atggcattct caggccggta gtacgggtag ttggtgaact    74400
actgacgggg gttgctgcca gatatcacgt cgaagttcgt tgccattatg ggggaactac    74460
tttcggggga gtagcccgat gtcctgcgaa tcagtgatag acacgcacaa aaccttaagt    74520
gtattgagcg cgaaggttct cgaaggcgtc gctgccggtt cctcgacgat ccaactcgcg    74580
tccgaactgt acctcagccg acaaggagtg gaatatcacg ttaacgtaat gctgcggaag    74640
ttcaaggtgc ccaaccgtgt ggcactcgtg tccagggtgt actcgatggg gatgttcgac    74700
cacaccgcat ggccgcctgc cgtgctcccc gaatacatcc gctgacgggg ttctctaggg    74760
aattccccac ccgctgagct cgtagactcc gatgggagca gattcccgga caggaggagc    74820
gccgaccgtg agcaccaacc cgtttgaaga tcctgacggt acctaccacg tactcgtgaa    74880
cgacgaggga cagcactcac tgtggccctc gttcgtcgag gtgccgtccg gctggaccgt    74940
ggtggtgcgc gagacggacc gtcagtccgc gctcgactac gtcgagcaga actggacgga    75000
catgcgaccg aagagcctga tccgtgcgat ggaaggctca gcctgacagg ggggccggga    75060
cgaacccggg ccggtgcggt cgtgtgagac gactgggaac aactgggtg gatgcgaccc    75120
```

```
gtccggcacc tgccgggcgg gttcacctgt ttgccgtttg tggcgcgagg gcctcctttc   75180
ggtagatgtg gtacgtggtc cagatcgtgg gtcggaacta cgacccggat ccggcgggca   75240
cccgcgcacg cttccgtgcc atcctcgacc ggctgttgcc gaagctctcc ggcgacgaag   75300
cctcggacgg cgaagcctcg gacgacggtg gcgagctgat ccgaaacccc gtgcgccact   75360
atgaaagcgg caacctcgaa ctcgtcggcg gcggtatcgg cgagttcact gtagacggcg   75420
gcgttgacgt gatccggtgc atgaacgtgt tcatgtactt cgaccacccg ttccgcgaga   75480
aggcgttgtc atgggcgacg acgatgctgc gtcccggcgg gctgttgctc tgcggcaact   75540
ggatcgactc ggccgaggaa cgcgcccggt gcagttccat cctcgcctcg caactggacg   75600
atgagggctt cgtcggtgag gccgtcgacg tcctgcgccg atcaggacga catgcgtggc   75660
gcaatcacgt tggccacgtt gccatgcggc cgtgacacc gccaccgctg gcgccgtcgt   75720
cggtgctctg acggacgcgt tcggaccgga catgtccgtt acgatgaccg agtggccctt   75780
caacgcgcct gcaaccggcg cgagcgaccg gcgacgccgg tactgacgcg cgacgggacc   75840
gtcgcgaccg ccgtgtctgt catggggggcg gacgggcttg agcgggtgcc gatgcgccgc   75900
ctcgccgggg aactggacac cggccccgct tcgcttgacg tgtacgtcaa ggacaccgac   75960
gagtcgcacg gcgagatcct ggacgcgcca cttgacgaag tggatctgaa aaccgcgccg   76020
gattccggcg ctggtgactg gcgcgaacgc ctgtggacag tcctcggccg gtaccgcgaa   76080
gtgctcgtcg cgaacccgaa tctggccaag gtcgcgctgg tgacgcggct gaacgggccg   76140
aaccacctcg ccgtgacgga gaccgggccg gcgctgccgg ccgaaggcgg cgtgcctccg   76200
ggtcaagccg agtgggccgc ggacgtccta ttgttggtgt tcacggcgac cgcggtcgaa   76260
gccgggacga ggaaggggat gcctggtgcg acagaggaac acgatgcctt ggtcaacacc   76320
gtgctcgcgg catcggcgcg aacccacccc cacatcgcgg ccctaggcgc cgatctggtc   76380
tcgggacccg gcaccgcgcg cgcccggtgg gcgatcgacc tggtgctcga cagaatcctc   76440
agcgcccctt gccagtagtc gtccacgtga cgcgaccaga cgaaggtgac acatccatgg   76500
ccgatcacgc cgaactcatg cccattgcca ccagggccgt ttcgttggcc agacggatca   76560
tccaggagcg gacaccgtcc actgtgtccg ccaagggtga ccgagacatg gtgaccgacg   76620
tcgacctcgc cgtcgaggat gcggtacgcg acttcctcgc gaaggagacc cccgagatcg   76680
ggatgctcgc cgaggagcac gggcagtccg gagcgggcgg cgggctgttg aactgggtcc   76740
tcgacccgat cgacggaacc gccaacttcg cccgtggcat cccgttgtgc gcggtgtccc   76800
tcgcactggt cgacggtacg gaagccaggc tcgcggcgat cgacctgccg ttcctggaca   76860
cctggtacac cgcgcgggcc gagaacggcg cgtacgccaa cggtgagccg ctgcggtgct   76920
ccgcggtcac gcaggagtcc gacgccatga tctcgatcgg ggacttctcg gtcggcgagg   76980
actcgaccga gaagaaccgg atccggctcg cgctgctgac cgacctgggc gcccgtgtcc   77040
agcggatcag gatgatcggc accgccgcga tcgatctggc ctgggtcgcg cagggcaagc   77100
tggacgccac gatcaacctc tccaacatgc cttgggacac catggcgggc gcgctgatgg   77160
tgcgtgaggc gggcggcatg gtcgtcgact acgacggcac gccgcacacg tccgagtcga   77220
ccaatacgat cgctgtggcg ccgggactct acgatgtgct gatgaagagg ctggccgaag   77280
cccggctatg acacgtcgag tggtcgttct cggccttggc gggaccatcg cgatgaccgc   77340
cgacgccagt ggtggtgtgg ttccggcact gtccgccgag caactggtcg cggcggtgcc   77400
gggattggcc gagacgggca tcaccgtcga cgtggtggac ttccgccgcg tcccgggcgc   77460
```

```
ctcattgtcc tttgcggaca tccgcgcgct tgccgaggcc gtcgggcgac acctggccga    77520
gggagtggac ggtgtcgtgg tcacccaagg caccgacacc atcgaggaaa ccgcgtacct    77580
gctcgacctg acccatgcca gggacgaacc gcttgtggtg acgggcgcga tgcgcaatcc    77640
cacatcggcg ggcgcggatg gacccgccaa catattggcc gccgtgcaca ctgcggcctc    77700
cccggcggct cgtggactcg gtgcggttgt cgttttcgcc gacgagatcc acgccgcctc    77760
gcgcgtgcgc aagacgcaca ccacgagtgg gcatacgttc cagtccgtga acggcggccc    77820
gttgggctac gtggtcgaag gtacgccccg gatcgtcaac agaccgaatt cccgcgtcac    77880
ggttcccgct gtgcaaggcg aaccggttga ggtcgcagtt gtccccatgg tgttgggcga    77940
caacgggact gttctcgagg ccgtcgctga ccgggtggat ggtcttgtcg tggcggcgtt    78000
cggtgtgggg cacgtgcccg ccggggtcgt ggacgtcttg agtggactcg ccgaacggat    78060
cccggtcgtg ctggcctccc gcacgggttc cggctccgtg ctcgagcgga cgtactcctt    78120
cccagggtcc gaattggaca tgatcgggcg ggggctggtc ccagcgggtt tccttgaccc    78180
gttgaaggcg cggatcctgt tgtggcactt gctcagcagt ggccacgacc gcgcgagcat    78240
ccggcgcgtg ttcgccgcgg cgtcagtctg agtcgagcac gtcccgtacc gctgtgcacg    78300
gtccgcgccg ggttcttctg agtgaatccg gcccgccgcc cggtgcatca tctcctggaa    78360
cacggcttgt tcatccggac cgaggcccgc aagtacgaca tcttcgaccg cggcgacccg    78420
tcgttccgcc tcggtgagca ccttttccgt gatccgtttt gtccgcgccg cgacccagct    78480
caacaacgtc caggtgtcca gcaggcccac gttgtacggg tggtcctgga aggtcgccgc    78540
gtccagtccg gcggcctcgg tcagctccgc cagccccacc accgctcgg gtccttcgc    78600
cgacggcgtg atgaaggtgc ccagcaccag ggcatgaccg tagtcagtca tcccaaaccc    78660
cacttgtccg ttgccggacc ttctgtacga aatatgatat ttcgagcaac atggtcggtg    78720
gctggtcggg catcggccca gacggatctg tcacggcaga acccgggatg agcagactgt    78780
ccaccccgga cggcgagccg cgaagggtga cgtgcggtcc gacgcctgac gtggtcatca    78840
cgcgtgccga ctaggctggg aacgttctcg gcaggaaggc ggtatcgagc tatcgctggg    78900
ggaacggtga cggcagtgga gttcggtctg cttggcgcga tcgaggcgcg tatcgacggc    78960
catcaggtgg agctggggca tgcccggcag cgacacgttc tcgcggcgtt gctcgtcgac    79020
gccgaccggc tggtgcccat cgcggatctc gccgcccgca tctggggtga gcgcacgccg    79080
cacagtggcc tgaccccgct ttacggttac ctttcccgtc tgaggcaagc gttggcgcct    79140
gccgaacaga gcgtgcggat cgtcgtcag cccggtgggt acatggctgc ggtcaacccg    79200
gcgacggtgg atctgcacag tttccggcag ttgatggctc gcgccaggac aaccgacgaa    79260
ccgaccagcg cgatcggctt gttcaacgag gctctggcgt tgtggcgggg cgaaccgttc    79320
gccggggtcg acaacccgtg gttcaacgga caacgcgcgg cactgctgcg ggaacgggag    79380
tccgccgaga tcgatctgcg tgatctgcgg ctgcgctgcg gcatgcacgc cgaggtgttg    79440
accgaggtga ccggcgcgtt cgaggccgac ccgatgaacg aacgcgttgc cgggcaactg    79500
atgctcgcgt tgtaccggca ggggcgcccg gcagaggcgt tgacgtgcta cgaccggatg    79560
cgcgccggt tggccgagga actgggggtg ccgccgagct cgcagttgca gcggctttac    79620
ctgcgcatcc tggaagccga cccggaactg ctggcgaccg gtcagcctgc ggcgccggag    79680
cagcaggcca gcacgcaagc aagggcctgg tcggcaccgg cgttgctgcc gccgaaggtc    79740
gccgacttca ccggcaggct ggccgagacc gccgcgctga tcaagcactt gaccgacggc    79800
tgggggtcgt cgccggtcac caccatcgtc ggcatgggcg gcatcggcaa aaccgcgttg    79860
```

```
agcgtctacg tcgcgcacaa cgcagccgcc tcgtacacag acggccagtt atgggccaac  79920
ctgcacggcg cgagcgcgaa cccggcgaaa cccgccgacg tgttggcccg gttcctgcgc  79980
gcactcggcg tcccggaacg ggcgatcccc gccgacccgg acgagcgcgt cgagacatac  80040
cggacgctcg tcaacggcag gaagatcctg atcctgctgg acgacgccgc gtccgaagaa  80100
caggtaaggc cattgctgcc gggaactccc acgtgtgcgg tggtgatcac gagccgggcc  80160
aggctgatcg ggctcgaagg cgcacaccgc atcgacctcg acgtcttcgc cgcgaacgag  80220
gccatcgacc tgctcaccca gatcgtcggt gagaaccggg tcaccgccga gctgtccgcg  80280
gcgacggaga tcgtcgaact ctgcggcggc ctgccgctcg ccgtccggat cgcgggtgcc  80340
cgcctcgcgg ccagatccgc gtggcggctg gcacatctgg cgtcgatgct cagtgacgaa  80400
cggcgtcggc tggatcagtt gtccgcgggt gatctggccg tccgagcctc ggtcgcgttg  80460
agctaccgcg ggttggacga ccagccgcgc aggttgttcc gactgctcgg cttgttcagt  80520
gcgccggact tcccgccgtg gctggccgct gtgctgctgg agtgcccgct cgacgaggcc  80580
accgagtacg ccgaggcgtt ggtggacgcg cagctgctga ccacgtccgg cacggacgcc  80640
gccgccagt accggtaccg gttccacgat ctggtgcggc tgttcgcggc ggaacgagcc  80700
gcggaagagg agaccgggga aagccgcgcc cgtgcgctgg agcaaggctt gggcggctgg  80760
ctcagcctcg cggaacggat gtcggcctcg gtcccgggac cgtgcttcgc gccgatcagc  80820
agccccgcgc cacggccgcg gatggactat gtgctgcggg acttccggcc cgaatgggcc  80880
gccaactggt tcgacgccga acgcggcgcg ttgctgtccg cggtgcgcca ggcgtgccgc  80940
ctcggcatgg cggacctggc gttcgacctg gctgcccgca tggagaagta cttcgacgta  81000
cgcgggatgt acacggactg gatcgcgctc aacaccgagg tgctggcggt gtgccgggaa  81060
tccggcaacg ccttgggcga ggcgatcatg ctgcgcggcc tcatcgacgt cacgacgtgg  81120
gccacggagg gcacggacgg cgacgccatg gcacgccagt acgccgaagc cacgcggttg  81180
aaagagatgt tcaccgaact cggtctgcca caaggcagtg cggacgcggc actgatgtgc  81240
tcatggtccc tgaccgcgaa cggcgcgtac acggacgcga tcaccatggc caacgaggca  81300
ctcgaactcg ccacgcggtc cggtcacgtc ggcggccagg ccagggccga actctcactg  81360
gcgttggcgc acttcgagaa ccgcgatgtg atggtcgcga tcggccacgc cggcaacgcg  81420
ctcgaacgtg cccgtgagct cggcaacgcc cggtgttacg ccaccgcgct gcagttcgcc  81480
ggcatcggcc accgcgcact gggccatttc gacaccagca ggcagatgct cgacgagtcg  81540
ctggccatct cgcggtccta tcgcgacacc tacaccgagg tactgacgct cttggcgttg  81600
gcacggctgt acttcaggat cggtgacgag gccgcgcgac ccaccgccga ggccgcggtc  81660
tcgctgagcg gtgactacaa catgagccat cacctcgctg aggcactgga gatcctcggc  81720
tcgatcgaag tcgccgacgg caatccggcc aaggccatcc gcacctcga ggagtccgtc  81780
gcgttgtggc ggacgcgcgg ctggcacacg ttccacgcga tcgcgttgac cagtctgggc  81840
aaggcgtacg cggacagtga cccggcggcg gcgcgggagg ctttccgttc cgcacacgat  81900
ctcttcgtcc aggtgggaaa ctgggaccag gccgccgagg tcgcccggct cgcggagggg  81960
tgaacgcgtg aacgcaggac gtgtggtgct gatcctgacg tgcctggtcg tcgcaggtct  82020
tggcgtctgg ttcgtgctgg cccagtggga cgtggccaac cgtgcggcaa cagtgtcctc  82080
ggcgttgggc gcggtcgccg ctgtcggcgt ggcgatccgg gcggccctgc gcgacccgga  82140
cgggcaacgc gaccgcgtcc gacggcggtt cggcgaacac cggcatgtgg ctgacgagcc  82200
```

```
gcggccgccg ccccgcagga tcgaagcggg ccggacgggc cacgcgcggg ccgagtccgg    82260
gggatacgcc aacagcggcg tgcactcgga tcgatctact cctagcgcag gaggggggccg   82320 aaccccgcgg actcgatccg caggccgagt tgtgcctcgg tcaacccgag cgcggcggcg    82380
gcgttcccca ggtgccagtc gtgcccgcc agctgggtca gcaggtgccc gcggcggatc     82440
tggttctccg acagccggaa cgtcttcagg tacgccgtgc gcccgtgccg gtcggtgatc    82500
agctcgccga tgtggttctc ctgcttgagc tggaaaccag gcaggaaacg cgacagcgtg    82560
tagtcgccca tgcggtacac gcggcgcacg tcgtacgagg cgtccagcag tcctgacgcc    82620
atggtcgaat cgtggaaatc cggccacgcc agctgttgcc ttgtcgccgc cgccctgaga    82680
tccgacaggg tgttgatgtg ggtctcgttc agccgcacac ggaactgcgg tacgggcgag    82740
gcgaacatcg cgtactggta gaccaggtcg ccgtacagat cctggagcag cgtgtggtgc    82800
agtgcgcggt agtcgtccgg gtgcggcacg acgaacgcgg cggcgagggc atcggccacg    82860
tagaccaaca cgccgcactg gccagggtgg atttcgaaga tccgcaacgc gtccgccaga    82920
ccgtccacct cggcaccggt gtaggcctgc tcggcgcgcg gcgaaagccc gtgccggatc    82980
gcgcgctgcg accactccgc ccacacgacc tgcggcccac cgaagtgcag cgccaggtat    83040
ccctccatcg ccaggtgcat gggcagaaaa cgcaggcggg tcttgtcggt gcgccgtgcc    83100
atccgccggt ggaagtgcag cggcatgcag gacgcgggat cttcggcgat ttcagtgccg    83160 tacgccgcg cgggtgtgcc gtcacgcgtc cacgtcgcca caaacccgtg cgggatgtac      83220
gacatgtacg aggtacggcg atcgacgtcc accacaccca aggagcggta gatctcggcg    83280
tgcagccgca aggcgcggat cggttcgtcg cggaccagcg gcacgagccg gacaccgccc    83340
cacacctggg aaggccggac cgacagtccg gtcaggtcga agccgcccat catccctcca    83400
gaaaccgggc gatccggtcg tcgaagtgcg cgcgcagctc ggcaaggccg gtccggcccct   83460 cggtgaaccg ggcgaactcc accagggcag gcacgtcctc cgcgtcccgc acgcccactg    83520
tgggcacgtg cccgaggcgc ttcacgtcaa aggtgtccgc gtcgtactcc gggttcaggt    83580
ggacgacact gacctcgtgc cgcggatcca ccttggcccg ccacacccgc agcacctccg    83640
aggccagccc gtccggcgcg ttgtcccagc cgtcggacac gatcaccagc cggtcgggct    83700
tgtgctccaa cgcgtcgagg atccgctcac ccagcggcgt cacgccgtgc ggatgcgtca    83760
tcaacgcgtc ggtccgccct gacgtccaca gtggaacata gctgtccgcc agcgcctcga    83820
acaggtaatg gcaggcaagc gcgacggcca gcggacgcct gcgtttctgc cgagacccgg    83880
acgctgagaa gctgtcgtcg agcacggcca cgacccgtcc ccaacgtcct ggcgtacgcg    83940
aggccgcagc acgcagagcg cccgtcagct cgtcccgcct tgcggcacgc gccgacaacg    84000
gcaaggacag gacataagac gcgagccggg tcaacggcat ggccgagagg tccgcggcga    84060
cgtcgacgtc gtcgcggatt gccgattcct gcagtcgcag ccgttccacc ctggtcatcc    84120
ggggcgcgat gcgttcgagg aatgtggcac ggtcgaccct tgtgcttggcc gcgaaccctt   84180 ccgcgaccgt gtacggcagg tcgtagatcg ccgcgcgctc gtagtgcgcc cgccgccacg    84240
cctccaggat cggcgtgtca taacgggttt tcccggtgaa caggaacggc ccgagctcat    84300
cacccgcggg ggtgaggtgt gcgtgccgca cggccagctt gagcgtggtg cggtacttca    84360
cggcgtcgaa cgccggatca ggccggtgcg tcaaccagtc ccggatgatc gccctggtcc    84420
ggcggttgtt cacacgagac tgtgcagcc tgcggaaaag cccgtacacc cgttgcggcg     84480
ccacaagacg caaccgcttg ccgatcagct gcccttccag cgtcgttgt tgttcgtccg     84540 cgtccctgga tgtcgccagt agccggtacg cgatcaacgt ggcgttgtgg tcgttgatgt    84600
```

-continued

```
ccagtgccag tgccgcggcg tacagctccc ggtagttgcc gatcatgtac tcgtgcagga    84660
agtccagtga cagctgctgc tcctgcgccg cactgtggaa ctcacgctgt ccgctcgagg    84720
tgatcgcggc gttgacgaac atgagcatgt cgtcagcggt gacgcggtcc atgatttccc    84780
ccccgtgagc aggcgccggc cggggaaagg gggcacgaac tgcgaagcat cgcttcgagg    84840
gcgggttccg ggagtcgcac cgaagtccca cggccggcca gcgaacggta ccagcccatg    84900
atcccacgtg catcgaatta ggccgtgtat cgccggccctg cccgccatag cggggccgcc    84960
ccactgaatt ccggctccgg cctccggccg gggcaggctc tcgtcgaacg gagacttcga    85020
tacacgacct aagcgggtag ttgcgagtgc tcgtcgctgt ccgagcagag cgaggcgatg    85080
tagtccagcg agatgtcgag cacgtccgcg atcgcggcga ctgtgaagaa cgaggggctc    85140
gggatccggc ctgcctcgat cttgcgcaac gtctcgtgtg acaagcctgt ctccgtggcc    85200
agctgcacca ggctcatcga gccgcgtgcc gcacgcagta ccgcggccag ttgcttaccg    85260
cgttcccgtt cctggggtgt cagcggagcc cgcaccatgg atcaacggta acccagatcc    85320
tggtgcgagt cacctcaaga tggtgatgtg ctcaaggaca tcctcgagta cgtcgatgtc    85380
tccggtcacg atcgtgacgt cgccgaccga caccaagggc tgcgccgaag ccggtgcacc    85440
gatcaggatg acaggaacga caagggcggt gagcagtcgt ccgcgcatgt gaactcctgg    85500
agtgacgagg ggtttcttcc cagcgaacac ccgggtcgcg tgcttgttca atcgccggc    85560 gcgggaattc tcgttccatt ctggacacgc tgggccagcg gtccggccac gtgatgggcc    85620
gttcggttgg ccgatcgggt gatgtgggca gcgtccagat tgtcccgtcg agtttatttt    85680
tcaacagccc tgagctcgca cgacacgctc tggtgtgcgg gcgttgtgcg tcggctgtgc    85740
gggagtgatg tggtgggttt ggcacggtca tgccacgtcg ccgggagcga cggtgtggat    85800
ctctacagga ggagcatgac catgcgagtg ggcaagatga tggggttgc tgtcgccctg    85860 tcggccgcga ccatgctggg tggcggtatg gccgcggcag cggcccccgt gccgccggag    85920
gccgaggtcg cggacttcga ggacatcacg gcgttggagg agaccgagga cacgaccctc    85980
gcggccaagc cgaagttctc cgcgcccttc aagtgcaagc agaagtggaa gggcaccacg    86040
tacaacggtc actggccgaa cacgcacagc cgggacttct ggcggtccgg tgccaagacc    86100
aaggggtcac cggtgctggc cgcggccgcg ggcaaggtca tccacgccaa gttcggcagc    86160
cgtcagggct gggcgtgtc catggacaac ggcagtggtt acaagacgta ctacttccac    86220
ctgaccgcga agccgaaggt caagaatggc cagaaggtca agaagggcca gctgctcggc    86280
tacgccgggg acaccggcca ggccaagggc aacccgcacc tgcactacac ggtcacgttg    86340
aagaacaagg gcatcaagcc ggtcttcgac ggcaaggcgc acaaggccgg cacgacgatc    86400
accagcaaga acgttgctg accacggtg ggccccgcc atgcggccgg gcccacccct    86460
gctgaaaggc tctgacatga gagtgctttc cggactggtg gcgttgctgt gcggcctggt    86520
gctggccgcc gcgcccgcga gcgcgggat ccgtcgtgac tgggaaaacc ctggcggccg    86580
```

<210> SEQ ID NO 5
<211> LENGTH: 58
<212> TYPE: DNA
<213> ORGANISM: Artificial Sequence
<220> FEATURE:
<223> OTHER INFORMATION: chemically synthesized

<400> SEQUENCE: 5
caagcagaag acggcatacg agatgtgact ggagttcaga cgtgtgctct tccgatct    58

```
<210> SEQ ID NO 6
<211> LENGTH: 58
<212> TYPE: DNA
<213> ORGANISM: Artificial Sequence
<220> FEATURE:
<223> OTHER INFORMATION: chemically synthesized

<400> SEQUENCE: 6
aatgatacgg cgaccaccga gatctacact ctttccctac acgacgctct tccgatct        58
```

MALACIDINS AND METHODS OF USE

CROSS-REFERENCE TO RELATED APPLICATIONS

This application is a U.S. national phase application filed under 35 U.S.C. § 371 claiming priority to International Patent Application No. PCT/US18/34533, filed May 25, 2018, which is entitled to priority under 35 U.S.C. § 119(e) to U.S. Provisional Patent Application No. 62/511,981, filed May 27, 2017, the contents of each of which are incorporated by reference herein in their entireties.

STATEMENT OF GOVERNMENT FUNDING

This invention was made with government support under NIH U19AI109713, NIH F32AI24479 and NIH F32 AI11100029 awarded by the NIH. The government has certain rights in the invention.

BACKGROUND OF THE INVENTION

Despite the wide availability of antibiotics, infectious diseases remain a leading cause of death worldwide. In the absence of new therapies, mortality rates due to untreatable infections are predicted to rise more than tenfold by 2050. Natural products (NPs) made by cultured bacteria have been a major source of clinically useful antibiotics. In spite of decades of productivity, the use of bacteria in the search for new antibiotics was largely abandoned due to high rediscovery rates (Tringe, S. G. et al., 2005, Science 308, 554-557; Reddy, B. V. et al., 2012. Appl. Environ Microbiol. 78, 3744-3752).

Thus, there is a need in the art for new compositions and methods for treating infections. The present invention satisfies the need in the art.

SUMMARY OF THE INVENTION

In one aspect, the invention provides novel malacidin compounds. In one embodiment, the compound is represented by formula (I)

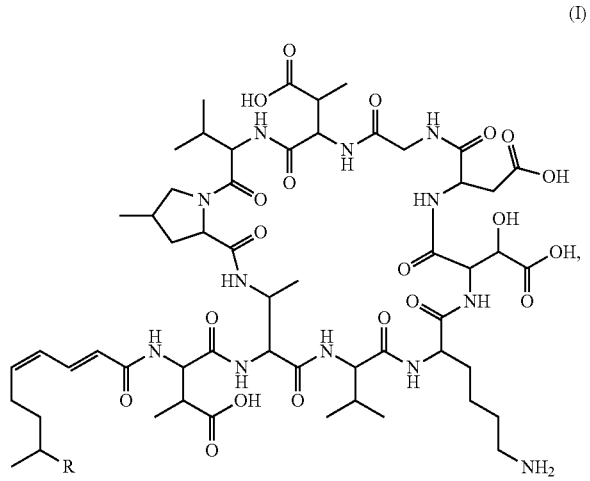

(I)

wherein R is a hydrogen alkyl, aryl or heteroaryl group.

In one embodiment, R is a $C_1$-$C_{10}$ alkyl. In one embodiment, R is selected from the group consisting of methyl and ethyl.

In one embodiment, the compound represented by formula (I) is a compound represented by formula (II):

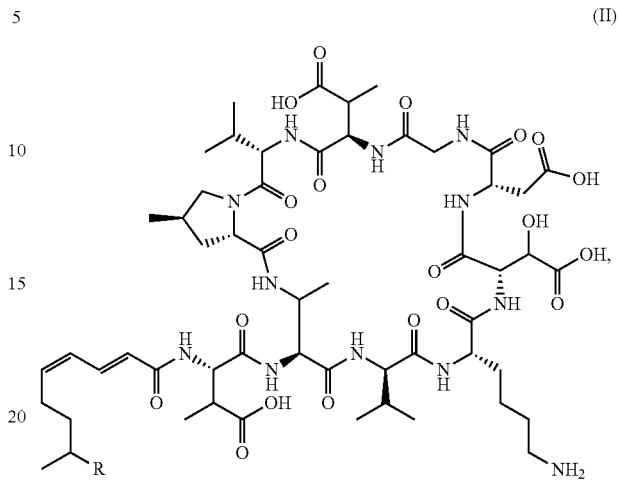

(II)

wherein R is a hydrogen, alkyl, aryl or heteroaryl group.

In one embodiment, R is a $C_1$-$C_{10}$ alkyl. In one embodiment, R is selected from the group consisting of methyl and ethyl.

In one embodiment, the invention provides a pharmaceutical composition comprising a compound of formula (I) or a compound of formula (H).

In one embodiment, the invention provides an isolated nucleic acid encoding a malacidin. In one embodiment, the nucleic acid comprises a sequence at least 90% homologous to SEQ ID NO:4. In one embodiment, the nucleic acid comprises the sequence set forth in SEQ ID NO:4.

In one embodiment, the invention provides a genetically engineered cell, wherein the cell expresses a malacidin. In one embodiment, the cell is transformed with a nucleic acid comprising a sequence at least 90% homologous to SEQ ID NO:4. In one embodiment, the cell is transformed with a nucleic acid comprising the sequence set forth in SEQ ID NO:4.

In one aspect, the invention provides a method for treating or preventing a bacterial infection in a subject. In one embodiment, the method comprises administering a composition comprising a compound of formula (I) or formula (II) to the subject. In one embodiment, the subject is exposed to or infected with a bacteria. In one embodiment, the bacteria is a gram positive bacteria. In one the bacteria is a drug resistant bacteria. In one embodiment, the method further comprises administering a second therapeutic. In one embodiment, the second therapeutic is an antibiotic.

In one aspect, the invention provides a method for inhibiting the growth of or killing a bacterial cell. In one embodiment, the method comprises contacting the bacterial cell with a composition comprising a compound of formulae (I) or (II).

In one aspect, the invention provides a method of biosynthesizing a malacidin. In one embodiment, the method comprises providing a heterologous nucleic acid of the invention to a host, incubating the host in a growth medium, and isolating a malacidin from the host or the growth medium. In one embodiment, the heterologous nucleic acid comprises a sequence at least 90% homologous to SEQ ID NO:4.

BRIEF DESCRIPTION OF THE DRAWINGS

The following detailed description of preferred embodiments of the invention will be better understood when read in conjunction with the appended drawings. For the purpose of illustrating the invention, there are shown in the drawings embodiments which are presently preferred. It should be understood, however, that the invention is not limited to the precise arrangements and instrumentalities of the embodiments shown in the drawings.

FIG. 1 depicts the generation of PCR amplicon pools containing homologous genes from BGCs present in an environmental DNA sample. Degenerate PCR primers targeting the conserved regions of adenylation domains found in non-ribosomal peptide synthetase genes were used to generate amplicons from an arrayed collection of eDNA isolated from 2,000 unique soils. The reads from these next-generation sequenced amplicons (NPSTs) were analysed by eSNaPD. A desert soil rich in AD NPSTs from the previously unknown malacidin clade was used to build an arrayed cosmid library. Cosmids harbouring all fragments of a targeted BGC were assembled and integrated into a heterologous host for production, extraction and characterization.

FIG. 2, comprising FIG. 2A depicts the three overlapping cosmid clones from which malacidin BGC was recovered. FIG. 2B depicts three overlapping clones in yeast using transformation-associated recombination (TAR) from which malacidin BGC was assembled. The resulting BAC was integrated into the S. albus genome for heterologous expression studies. FIG. 2C depicts a representative HPLC analysis of crude extracts derived from cultures of S. albus transformed with the malacidin BGC shows the presence of BGC-specific small molecules. The two primary malacidin peaks are highlighted with an asterisk. FIG. 2C depicts a representative HPLC analysis of four independent fermentations. FIG. 2D depicts a representative antibacterial activity of four independent fermentations. Unlike crude extracts of the S. albus host strain alone, only extracts from the S. albus harbouring the malacidin BGC showed antibacterial activity when applied to a lawn of S. aureus USA300. FIG. 2E depicts Malacidin A and Malacidin B structures. Malacidin A and B are cyclic lipopeptides containing eight-amino-acid macrocycles and polyunsaturated lipids. The malacidins do not contain the conserved DXDG motif seen in all known calcium-dependent antibiotics—incorporating a rare 3-hydroxyl aspartic acid (HyAsp, highlighted in violet) and lacking the spacer residue. Biosynthetic enzymes predicted to be involved in the production of non-proteinogenic amino acid (3-methyl aspartic acid, 4-methyl proline and 2,3-diamino 3-methyl propanoic acid) and fatty acid substrates required for the biosynthesis of the maladicins are shown and colour-coded according to their activities. Stereocentres in malacidin that were predicted bioinformatically, as opposed to through chemical and spectroscopic analysis, are denoted with an asterisk.

FIG. 3, comprising FIG. 3A depicts the MIC of malacidin A against MRSA assessed at various concentrations of calcium and the antibiosis of malacidin A was found to be calcium-dependent. The error bars represent the standard deviation across two replicates over three independent experiments (n=6). FIG. 3B depicts results demonstrating malacidin A is an effective treatment against MRSA in rat cutaneous wound infections. The error bars represent the standard deviation across replicate wounds (n=4). FIG. 3C depicts results demonstrating that unlike daptomycin, malacidin A activity against S. pneumoniae is largely unaffected by the presence of pulmonary surfactants. The error bars represent the standard deviation across two replicates over three independent experiments (n=6). FIG. 3D depicts results demonstrating that after 20 days of repeated exposure to 0.5×MIC of malacidin A (Mal.), malacidin-resistant S. aureus was not detected. Vancomycin (Van.), daptomycin (Dap.) and rifamycin (Rif.) were used as controls in this assay. The error bars represent the standard deviation across three replicates for MIC determination (n=3).

FIG. 4, comprising

FIG. 4A depicts a schematic diagram showing modes of action of daptomycin, friulimicin and malacidin. FIG. 4B depicts experimental results demonstrating that in contrast to daptomycin, malacidin A does not cause MRSA membrane leakage in a SYTOX green fluorescent assay. The error bars represent the standard deviation across three biological replicates (n=3). FIG. 4C depicts experimental results demonstrating that as seen with the cell wall biosynthesis inhibitor vancomycin, exposing MRSA to malacidin A results in the accumulation of the cell wall intermediate UDP-MurNAc-pentapeptide. The UDP-MurNAc-pentapeptide peak ([M−H]$^-$=1148.35) is indicated with a red asterisk on the UPLC-MS trace. The chromatograms are representative of at least three independent experiments. FIG. 4D depicts the interaction of malacidin A and daptomycin with purified cell wall precursors. An interaction is indicated by a reduction of the amount of free antibiotic (visible on the TLC by ultraviolet light). FIG. 4E depicts experimental results demonstrating that the interaction of malacidin A with cell wall precursor, lipid II, is calcium-dependent.

FIG. 5, comprising FIG. 5A depicts phylogenetic trees of NRPS AD domains from known reference calcium-dependent antibiotic BGCs using i) all NRPS AD domains, ii) Asp4 NRPS AD domains only, iii) Asp4 NRPS AD domains from references and Asp4-like eSNAPD-processed NRPS AD domains from soil metagenomes. FIG. 5B depicts phylogenetic trees including soil metagenomes NRPS AD domains with hits for Asp6 in the calcium-dependent DXDG motif. FIG. 5C depicts phylogenetic trees including soil metagenomes NRPS AD domains with hits for Gly7 in the calcium-dependent DXDG motif. FIG. 5D depicts geospatial distributions of specific molecule NPSTs from screened soil metagenomes.

FIG. 18A depicts results demonstrating each amino acid unit and fatty acid side chain were developed by COSY, TOCSY, and HMBC correlations. FIG. 18B depicts the key correlations between α protons of amino acid units and carbonyl carbons. Based on this data, five partial structures were determined.

FIG. 19, comprising FIG. 19A depicts that MS/MS analysis malacidins were reacted with propionic anhydride. FIG. 19B depicts five partial residues, which were determined from NMR were connected by MS/MS fragmentation major ion (highlighted in bold text). The MS spectrum is representative across two independent derivatizations and MS analysis. FIG. 19C depicts the sequential MS/MS fragmentation of malacidin A and B begins with the loss of Val between the MePro and MeAsp. The mass malacidin after the loss of each sequential residue is indicated and fragment units are noted by color. Other major MS/MS fragments present in (b) are MeAsp-Gly-Asp-HyAsp (*) and the 9-mer cyclic peptide core (#).

FIG. 28, comprising FIG. 28A depicts Malacidin A and B and their general motif. FIG. 28B depicts a comparison of Malacidin A and B to other previously characterized calcium-dependent antibiotics. FIG. 28C depicts a comparison of Malacidin A and B to other Lipid II-binding antibiotics.

FIG. 29, comprising FIG. 29A and FIG. 29B, depicts a comparison of malacidin BGC to other calcium-dependent antibiotic gene clusters. FIG. 29A depicts malacidin biosynthetic gene cluster compared to the gene clusters of other representative calcium-dependent antibiotics. The NRPS genes are indicated in light blue with the domain architecture and incorporated amino acids listed below. The rest of the genes are indicated by color: regulatory (green), transport (yellow), amino acid biosynthesis (purple), and fatty acid biosynthesis (red). FIG. 29B depicts a table of malacidin proteins and their homologs in other representative calcium-dependent antibiotics biosynthetic clusters. Percent identities of these proteins to malacidin are indicated in parenthesis.

FIG. 31, comprising FIG. 31A depicts the viability assay of two mammalian cell lines, HEK293 (epithelial morphology) and MRC5 (fibroblast morphology), when treated with vehicle or 0.1 mg/ml Malacidin A (100×MIC). Error bars represent the standard error across three biological replicates. FIG. 31B depicts results demonstrating malacidin A showed no hemolytic effects over 24 hours when assayed in red blood cell disc diffusion assays. Triton X-100 was used a positive control for lysis. Image of red blood cell plate is representative of three replicate experiments.

DETAILED DESCRIPTION

Figure 1:
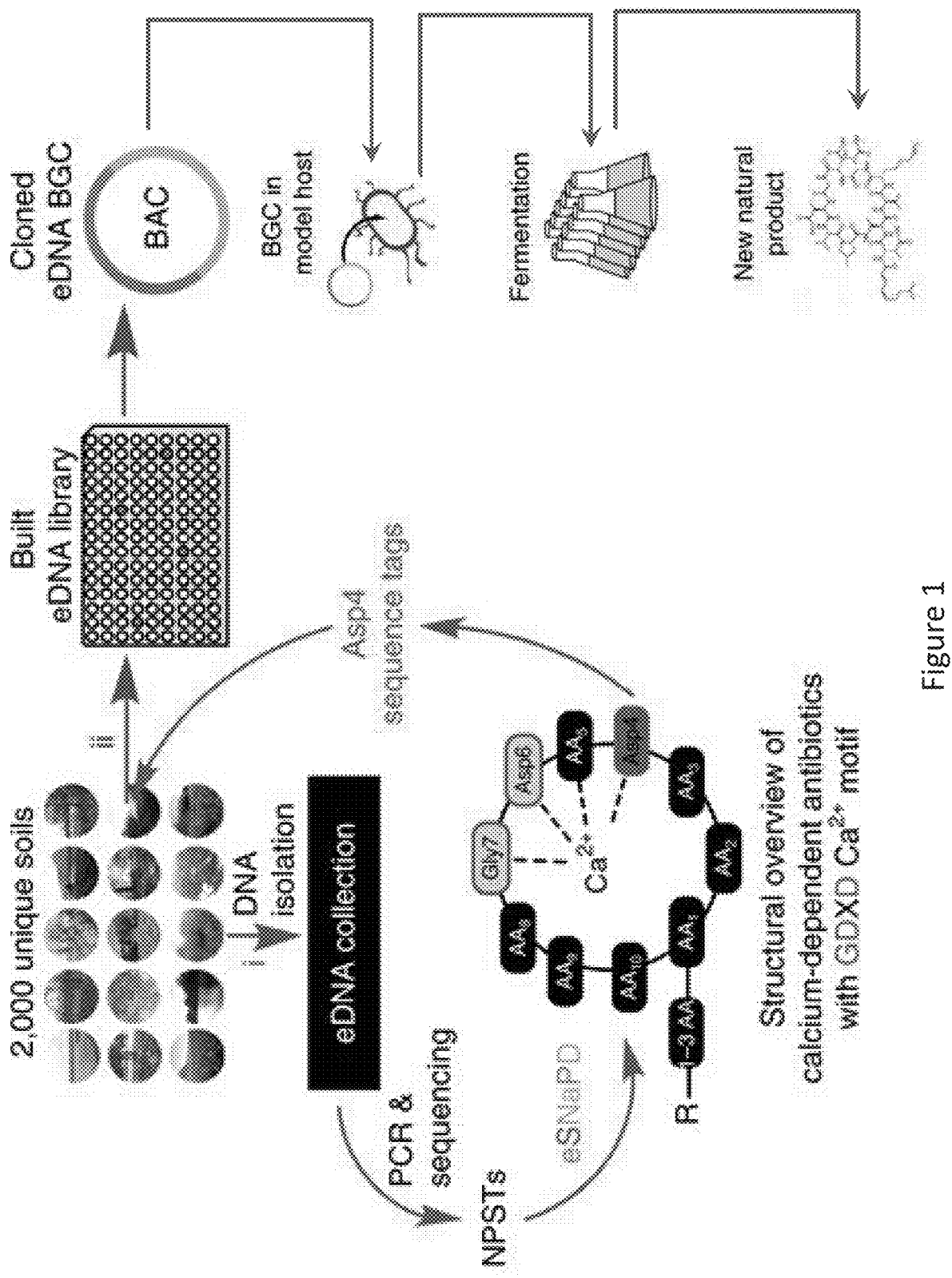
FIG. 1 depicts using a culture-independent strategy for the discovery of calcium-dependent antibiotics from the global microbiome.

The present invention is based, in part, on the unexpected discovery of malacidins as antibiotics which have activity against multidrug resistant pathogens. In one embodiment, the present invention provides compounds or a therapeutic compound comprising a desired activity. In one embodiment, the compound is an antibiotic. In embodiment, the antibiotic compound of the invention can be used in the treatment of bacterial infections. In embodiment, the antibiotic compound of the invention can be used in the treatment of gram positive bacterial infections. In certain embodiments, the use of the antibiotic compound of the invention in the treatment of bacterial infections optionally includes a pharmaceutically acceptable carrier, excipient or adjuvant.

In one embodiment, the compound can be biosynthesized via heterologous expression of a biosynthetic gene. Thus, in one aspect, the invention provides compounds and methods for synthesizing a malacidin compound. In one embodiment, the invention provides a nucleic acid encoding a malacidin. In one embodiment, the nucleic is an isolated nucleic acid. In one embodiment, the nucleic acid is transformed into a cell.

Definitions

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are described.

As used herein, each of the following terms has the meaning associated with it in this section.

The articles "a" and "an" are used herein to refer to one or to more than one (i.e., to at least one) of the grammatical object of the article. By way of example, "an element" means one element or more than one element.

"About" as used herein when referring to a measurable value such as an amount, a temporal duration, and the like, is meant to encompass variations of ±20%, ±10%, ±5%, ±1%, or 0.1% from the specified value, as such variations are appropriate to perform the disclosed methods.

The term "abnormal" when used in the context of organisms, tissues, cells or components thereof, refers to those organisms, tissues, cells or components thereof that differ in at least one observable or detectable characteristic (e.g., age, treatment, time of day, etc.) from those organisms, tissues, cells or components thereof that display the "normal" (expected) respective characteristic. Characteristics which are normal or expected for one cell or tissue type, might be abnormal for a different cell or tissue type.

An "amino terminus modification group" refers to any molecule that can be attached to the amino terminus of a polypeptide. Similarly, a "carboxy terminus modification group" refers to any molecule that can be attached to the carboxy terminus of a polypeptide. Terminus modification groups include but are not limited to various water soluble polymers, peptides or proteins such as serum albumin, or other moieties that increase serum half-life of peptides.

A "disease" is a state of health of an animal wherein the animal cannot maintain homeostasis, and wherein if the disease is not ameliorated then the animal's health continues to deteriorate.

In contrast, a "disorder" in an animal is a state of health in which the animal is able to maintain homeostasis, but in which the animal's state of health is less favorable than it would be in the absence of the disorder. Left untreated, a disorder does not necessarily cause a further decrease in the animal's state of health.

A disease or disorder is "alleviated" if the severity of a sign or symptom of the disease or disorder, the frequency with which such a sign or symptom is experienced by a patient, or both, is reduced.

The term, "biologically active" or "bioactive" can mean, but is in no way limited to, the ability of an agent or compound to effectuate a physiological change or response. The response may be detected, for example, at the cellular level, for example, as a change in growth and/or viability, gene expression, protein quantity, protein modification, protein activity, or combination thereof; at the tissue level; at the systemic level; or at the organism level. For example, as used herein, biologically active molecules include but are not limited to any substance intended for diagnosis, cure, mitigation, treatment, or prevention of disease in humans or other animals, or to otherwise enhance physical or mental well-being of humans or animals. Examples of biologically active molecules include, but are not limited to, peptides, proteins, enzymes, small molecule drugs, dyes, lipids, nucleosides, oligonucleotides, cells, viruses, liposomes, microparticles and micelles. Classes of biologically active agents that are suitable for use with the invention include, but are not limited to, antibiotics, fungicides, anti-viral agents, anti-inflammatory agents, anti-tumor agents, cardiovascular agents, anti-anxiety agents, hormones, growth factors, steroidal agents, and the like.

The term "conservative mutations" refers to the substitution, deletion or addition of nucleic acids that alter, add or delete a single amino acid or a small number of amino acids in a coding sequence where the nucleic acid alterations result in the substitution of a chemically similar amino acid. Amino acids that may serve as conservative substitutions for each other include the following:

Basic: Arginine (R), Lysine (K), Histidine (H);
Acidic: Aspartic acid (D), Glutamic acid (E);
Neutral: Asparagine (N), Cysteine (C), Glutamine (Q), Methionine (M), Serine (S), Threonine (T);
Aliphatic: Alanine (A), Valine (V), Leucine (L), Isoleucine (I), Glycine (G);
Hydrophobic—Aromatic: Phenylalanine (F), Tyrosine (Y), Tryptophan (W);
Sulfur-containing: Methionine (M), Cysteine (C)
Hydroxyl: Serine (S), Threonine (T);
Aminde: Asparagine (N), Glutamine (Q).

In addition, sequences that differ by conservative variations are generally homologous. In some instances, the following eight groups each contain amino acids that are conservative substitutions for one another: 1) Alanine (A), Glycine (G); 2) Aspartic acid (D), Glutamic acid (E); 3) Asparagine (N), Glutamine (Q); 4) Arginine (R), Lysine (K); 5) Isoleucine (I), Leucine (L), Methionine (M), Valine (V); 6) Phenylalanine (F), Tyrosine (Y), Tryptophan (W); 7) Serine (S), Threonine (T); and 8) Cysteine (C), Methionine (M).

As used herein, "derivatives" are compositions formed from the native compounds either directly, by modification, or by partial substitution. As used herein, "analogs" are compositions that have a structure similar to, but not identical to, the native compound.

"Encoding" refers to the inherent property of specific sequences of nucleotides in a polynucleotide, such as a gene, a cDNA, or an mRNA, to serve as templates for synthesis of other polymers and macromolecules in biological processes having either a defined sequence of nucleotides (i.e., rRNA, tRNA and mRNA) or a defined sequence of amino acids and the biological properties resulting therefrom. Thus, a gene encodes a protein if transcription and translation of mRNA corresponding to that gene produces the protein in a cell or other biological system. Both the coding strand, the nucleotide sequence of which is identical to the mRNA sequence and is usually provided in sequence listings, and the non-coding strand, used as the template for transcription of a gene or cDNA, can be referred to as encoding the protein or other product of that gene or cDNA.

An "effective amount" or "therapeutically effective amount" of a compound is that amount of compound which is sufficient to provide a beneficial effect to the subject to which the compound is administered. An "effective amount" of a delivery vehicle is that amount sufficient to effectively bind or deliver a compound.

"Expression vector" refers to a vector comprising a recombinant polynucleotide comprising expression control sequences operatively linked to a nucleotide sequence to be expressed. An expression vector comprises sufficient cis-acting elements for expression; other elements for expression can be supplied by the host cell or in an in vitro expression system. Expression vectors include all those known in the art, such as cosmids, plasmids (e.g., naked or contained in liposomes) and viruses (e.g., lentiviruses, retroviruses, adenoviruses, and adeno-associated viruses) that incorporate the recombinant polynucleotide.

"Homologous" refers to the sequence similarity or sequence identity between two polypeptides or between two nucleic acid molecules. When a position in both of the two compared sequences is occupied by the same base or amino acid monomer subunit, e.g., if a position in each of two DNA molecules is occupied by adenine, then the molecules are homologous at that position. The percent of homology between two sequences is a function of the number of matching or homologous positions shared by the two sequences divided by the number of positions compared× 100. For example, if 6 of 10 of the positions in two sequences are matched or homologous then the two sequences are 60% homologous. By way of example, the DNA sequences ATTGCC and TATGGC share 50% homology. Generally, a comparison is made when two sequences are aligned to give maximum homology.

"Isolated" means altered or removed from the natural state. For example, a nucleic acid or a peptide naturally present in a living animal is not "isolated," but the same nucleic acid or peptide partially or completely separated from the coexisting materials of its natural state is "isolated." An isolated nucleic acid or protein can exist in substantially purified form, or can exist in a non-native environment such as, for example, a host cell.

In the context of the present invention, the following abbreviations for the commonly occurring nucleic acid bases are used. "A" refers to adenosine, "C" refers to cytosine, "G" refers to guanosine, "T" refers to thymidine, and "U" refers to uridine.

Unless otherwise specified, a "nucleotide sequence encoding an amino acid sequence" includes all nucleotide sequences that are degenerate versions of each other and that encode the same amino acid sequence. The phrase nucleotide sequence that encodes a protein or an RNA may also include introns to the extent that the nucleotide sequence encoding the protein may in some version contain an intron(s).

In the context of the invention, term "natural amino acid" means any amino acid which is found naturally in vivo in a living being. Natural amino acids therefore include amino acids coded by mRNA incorporated into proteins during translation but also other amino acids found naturally in vivo which are a product or by-product of a metabolic process, such as for example ornithine which is generated by the urea production process by arginase from L-arginine. In the invention, the amino acids used can therefore be natural or not. Namely, natural amino acids generally have the L configuration but also, according to the invention, an amino acid can have the L or D configuration.

A "non-naturally encoded amino acid" refers to an amino acid that is not one of the 20 common amino acids or pyrolysine or selenocysteine. The term "non-naturally encoded amino acid" includes, but is not limited to, amino acids that occur naturally by modification of a naturally encoded amino acid (including but not limited to, the 20 common amino acids or pyrolysine and selenocysteine) but are not themselves incorporated into a growing polypeptide chain by the translation complex. Examples of naturally-occurring amino acids that are not naturally-encoded include, but are not limited to, N-acetylglucosaminyl-L-serine, N-acetylglucosaminyl-L-threonine, and O-phospho-tyrosine.

The terms "patient," "subject," "individual," and the like are used interchangeably herein, and refer to any animal, or cells thereof whether in vitro or in situ, amenable to the methods described herein. In certain non-limiting embodiments, the patient, subject or individual is a human.

"Parenteral" administration of a composition includes, e.g., subcutaneous (s.c.), intravenous (i.v.), intramuscular (i.m.), or intrasternal injection, or infusion techniques.

The term "polynucleotide" as used herein is defined as a chain of nucleotides. Furthermore, nucleic acids are polymers of nucleotides. Thus, nucleic acids and polynucleotides as used herein are interchangeable. One skilled in the art has the general knowledge that nucleic acids are polynucleotides, which can be hydrolyzed into the monomeric "nucleotides." The monomeric nucleotides can be hydrolyzed into nucleosides. As used herein polynucleotides include, but are not limited to, all nucleic acid sequences which are obtained by any means available in the art, including, without limitation, recombinant means, i.e., the cloning of nucleic acid sequences from a recombinant library or a cell genome, using ordinary cloning technology and PCR™, and the like, and by synthetic means.

Unless otherwise specified, a "nucleotide sequence encoding an amino acid sequence" includes all nucleotide sequences that are degenerate versions of each other and that encode the same amino acid sequence. The phrase nucleotide sequence that encodes a protein or an RNA may also include introns to the extent that the nucleotide sequence encoding the protein may in some version contain an intron(s).

As used herein, the terms "peptide," "polypeptide," and "protein" are used interchangeably, and refer to a compound comprised of amino acid residues covalently linked by peptide bonds. A protein or peptide must contain at least two amino acids, and no limitation is placed on the maximum number of amino acids that can comprise a protein's or peptide's sequence. Polypeptides include any peptide or protein comprising two or more amino acids joined to each other by peptide bonds. As used herein, the term refers to both short chains, which also commonly are referred to in the art as peptides, oligopeptides and oligomers, for example, and to longer chains, which generally are referred to in the art as proteins, of which there are many types. "Polypeptides" include, for example, biologically active fragments, substantially homologous polypeptides, oligopeptides, homodimers, heterodimers, variants of polypeptides, modified polypeptides, derivatives, analogs, fusion proteins, among others. The polypeptides include natural peptides, recombinant peptides, synthetic peptides, or a combination thereof. Furthermore, peptides of the invention may include amino acid mimetics, and analogs. Recombinant forms of the peptides can be produced according to standard methods and protocols which are well known to those of skill in the art, including for example, expression of recombinant proteins in prokaryotic and/or eukaryotic cells followed by one or more isolation and purification steps, and/or chemically synthesizing peptides or portions thereof using a peptide synthesizer.

Conventional notation is used herein to portray polypeptide sequences: the left-hand end of a polypeptide sequence is the amino-terminus; the right-hand end of a polypeptide sequence is the carboxyl-terminus.

As used herein, a "peptidomimetic" is a compound containing non-peptidic structural elements that is capable of mimicking the biological action of a parent peptide. A peptidomimetic may or may not comprise peptide bonds.

The term "recombinant polypeptide" as used herein is defined as a polypeptide produced by using recombinant DNA methods. A host cell that comprises a recombinant polynucleotide is referred to as a "recombinant host cell." A gene which is expressed in a recombinant host cell wherein the gene comprises a recombinant polynucleotide, produces a "recombinant polypeptide."

The term "pharmacological composition," "therapeutic composition," "therapeutic formulation" or "pharmaceutically acceptable formulation" can mean, but is in no way limited to, a composition or formulation that allows for the effective distribution of an agent provided by the invention, which is in a form suitable for administration to the physical location most suitable for their desired activity, e.g., systemic administration.

Non-limiting examples of agents suitable for formulation with the, e.g., compounds provided by the instant invention include: cinnamoyl, PEG, phospholipids or lipophilic moieties, phosphorothioates, P-glycoprotein inhibitors (such as Pluronic P85) which can enhance entry of drugs into various tissues, for example the CNS (Jolliet-Riant and Tillement, 1999, Fundam. Clin. Pharmacol., 13, 16-26); biodegradable polymers, such as poly (DL-lactide-coglycolide) microspheres for sustained release delivery after implantation (Emerich, D F et al, 1999, Cell Transplant, 8, 47-58) Alkermes, Inc. Cambridge, Mass.; and loaded nanoparticles, such as those made of polybutylcyanoacrylate, which can deliver drugs across the blood brain barrier and can alter neuronal uptake mechanisms (Prog Neuropsychopharmacol Biol Psychiatry, 23, 941-949, 1999).

The term "pharmaceutically acceptable" or "pharmacologically acceptable" can mean, but is in no way limited to, entities and compositions that do not produce an adverse, allergic or other untoward reaction when administered to an animal, or a human, as appropriate.

The term "pharmaceutically acceptable carrier" or "pharmacologically acceptable carrier" can mean, but is in no way limited to, any and all solvents, dispersion media, coatings, antibacterial and antifungal agents, isotonic and absorption delaying agents, and the like, compatible with pharmaceutical administration. Suitable carriers are described in the most recent edition of Remington's Pharmaceutical Sciences, a standard reference text in the field, which is incorporated herein by reference. Preferred examples of such carriers or diluents include, but are not limited to, water, saline, finger's solutions, dextrose solution, and 5% human serum albumin. Liposomes and non-aqueous vehicles such as fixed oils may also be used. The use of such media and agents for pharmaceutically active substances is well known in the art. Except insofar as any conventional media or agent is incompatible with the active compound, use thereof in the compositions is contemplated. Supplementary active compounds can also be incorporated into the compositions.

A "therapeutic" treatment is a treatment administered to a subject who exhibits signs of pathology, for the purpose of diminishing or eliminating those signs.

As used herein, "treating a disease or disorder" means reducing the frequency with which a symptom of the disease or disorder is experienced by a patient. Disease and disorder are used interchangeably herein.

The phrase "therapeutically effective amount," as used herein, refers to an amount that is sufficient or effective to prevent or treat (delay or prevent the onset of, prevent the progression of, inhibit, decrease or reverse) a disease or condition, including alleviating symptoms of such diseases.

To "treat" a disease as the term is used herein, means to reduce the frequency or severity of at least one sign or symptom of a disease or disorder experienced by a subject.

A "vector" is a composition of matter which comprises an isolated nucleic acid and which can be used to deliver the isolated nucleic acid to the interior of a cell. Numerous vectors are known in the art including, but not limited to, linear polynucleotides, polynucleotides associated with ionic or amphiphilic compounds, plasmids, and viruses. Thus, the term "vector" includes an autonomously replicating plasmid or a virus. The term should also be construed to include non-plasmid and non-viral compounds which facilitate transfer of nucleic acid into cells, such as, for example, polylysine compounds, liposomes, and the like. Examples of viral vectors include, but are not limited to, adenoviral vectors, adeno-associated virus vectors, retroviral vectors, and the like.

The term "compound," as used herein, unless otherwise indicated, refers to any specific chemical compound disclosed herein. In one embodiment, the term also refers to stereoisomers and/or optical isomers (including racemic mixtures) or enantiomerically enriched mixtures of disclosed compounds.

As used herein, the term "alkyl," by itself or as part of another substituent means, unless otherwise stated, a straight or branched chain hydrocarbon having the number of carbon atoms designated (i.e. $C_{1-6}$ means one to six carbon atoms) and including straight, branched chain, or cyclic substituent groups. Examples include methyl, ethyl, propyl, isopropyl, butyl, isobutyl, tert-butyl, pentyl, neopentyl, hexyl, and cyclopropylmethyl. Most preferred is $(C_1-C_6)$alkyl, particularly ethyl, methyl, isopropyl, isobutyl, n-pentyl, n-hexyl and cyclopropylmethyl.

As used herein, the term "substituted alkyl" means alkyl as defined above, substituted by one, two or three substituents selected from the group consisting of halogen, —OH, alkoxy, —$NH_2$, —$N(CH_3)_2$, —C(=O)OH, trifluoromethyl, —C≡N, —C(=O)O($C_1$-$C_4$)alkyl, —C(=O)$NH_2$, —$SO_2NH_2$, —C(=NH)$NH_2$, and —$NO_2$, preferably containing one or two substituents selected from halogen, —OH, alkoxy, —$NH_2$, trifluoromethyl, —$N(CH_3)_2$, and —C(=O)OH, more preferably selected from halogen, alkoxy and —OH. Examples of substituted alkyls include, but are not limited to, 2,2-difluoropropyl, 2-carboxycyclopentyl and 3-chloropropyl.

As used herein, the term "alkoxy" employed alone or in combination with other terms means, unless otherwise stated, an alkyl group having the designated number of carbon atoms, as defined above, connected to the rest of the molecule via an oxygen atom, such as, for example, methoxy, ethoxy, 1-propoxy, 2-propoxy (isopropoxy) and the higher homologs and isomers. Preferred are (C₁-C₃) alkoxy, particularly ethoxy and methoxy.

As used herein, the term "halo" or "halogen" alone or as part of another substituent means, unless otherwise stated, a fluorine, chlorine, bromine, or iodine atom, preferably, fluorine, chlorine, or bromine, more preferably, fluorine or chlorine.

As used herein, the term "cycloalkyl" refers to a mono cyclic or polycyclic non-aromatic radical, wherein each of the atoms forming the ring (i.e. skeletal atoms) is a carbon atom. In one embodiment, the cycloalkyl group is saturated or partially unsaturated. In another embodiment, the cycloalkyl group is fused with an aromatic ring. Cycloalkyl groups include groups having from 3 to 10 ring atoms. Illustrative examples of cycloalkyl groups include, but are not limited to, the following moieties:

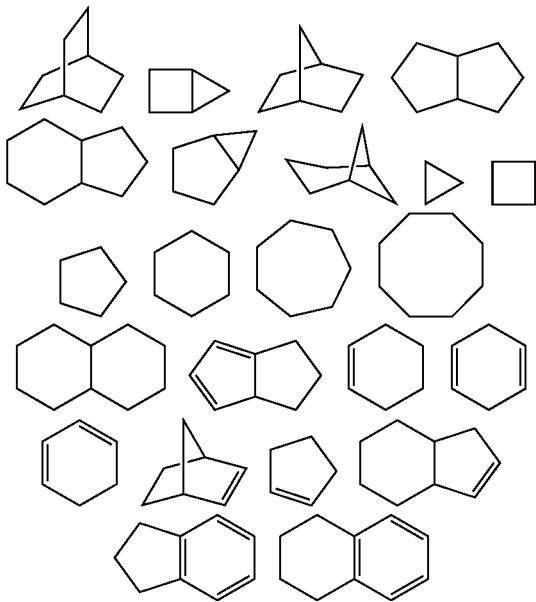

Monocyclic cycloalkyls include, but are not limited to, cyclopropyl, cyclobutyl, cyclopentyl, cyclohexyl, cycloheptyl, and cyclooctyl. Dicyclic cycloalkyls include, but are not limited to, tetrahydronaphthyl, indanyl, and tetrahydropentalene. Polycyclic cycloalkyls include adamantine and norbornane. The term cycloalkyl includes "unsaturated nonaromatic carbocyclyl" or "nonaromatic unsaturated carbocyclyl" groups, both of which refer to a nonaromatic carbocycle as defined herein, which contains at least one carbon carbon double bond or one carbon carbon triple bond.

As used herein, the term "aryl," employed alone or in combination with other terms, means, unless otherwise stated, a carbocyclic aromatic system containing one or more rings (typically one, two or three rings) wherein such rings may be attached together in a pendent manner, such as a biphenyl, or may be fused, such as naphthalene. Examples include phenyl, anthracyl, and naphthyl.

As used herein, the term "heterocycle" or "heterocyclyl" or "heterocyclic" by itself or as part of another substituent means, unless otherwise stated, an unsubstituted or substituted, stable, mono- or multi-cyclic heterocyclic ring system that consists of carbon atoms and at least one heteroatom selected from the group consisting of N, O, and S, and wherein the nitrogen and sulfur heteroatoms may be optionally oxidized, and the nitrogen atom may be optionally quaternized. The heterocyclic system may be attached, unless otherwise stated, at any heteroatom or carbon atom that affords a stable structure. A heterocycle may be aromatic or non-aromatic in nature.

As used herein, the term "heteroaryl" or "heteroaromatic" refers to a heterocycle having aromatic character. A polycyclic heteroaryl may include one or more rings that are partially saturated. Examples include tetrahydroquinoline and 2,3-dihydrobenzofuryl.

Examples of non-aromatic heterocycles include monocyclic groups such as aziridine, oxirane, thiirane, azetidine, oxetane, thietane, pyrrolidine, pyrroline, imidazoline, pyrazolidine, dioxolane, sulfolane, 2,3-dihydrofuran, 2,5-dihydrofuran, tetrahydrofuran, thiophane, piperidine, 1,2,3,6-tetrahydropyridine, 1,4-dihydropyridine, piperazine, morpholine, thiomorpholine, pyran, 2,3-dihydropyran, tetrahydropyran, 1,4-dioxane, 1,3-dioxane, homopiperazine, homopiperidine, 1,3-dioxepane, 4,7-dihydro-1,3-dioxepin and hexamethyleneoxide.

Examples of heteroaryl groups include pyridyl, pyrazinyl, pyrimidinyl (particularly 2- and 4-pyrimidinyl), pyridazinyl, thienyl, furyl, pyrrolyl (particularly 2-pyrrolyl), imidazolyl, thiazolyl, oxazolyl, pyrazolyl (particularly 3- and 5-pyrazolyl), isothiazolyl, 1,2,3-triazolyl, 1,2,4-triazolyl, 1,3,4-triazolyl, tetrazolyl, 1,2,3-thiadiazolyl, 1,2,3-oxadiazolyl, 1,3,4-thiadiazolyl and 1,3,4-oxadiazolyl.

Examples of polycyclic heterocycles include indolyl (particularly 3-, 4-, 5-, 6- and 7-indolyl), indolinyl, quinolyl, tetrahydroquinolyl, isoquinolyl (particularly 1- and 5-isoquinolyl), 1,2,3,4-tetrahydroisoquinolyl, cinnolinyl, quinoxalinyl (particularly 2- and 5-quinoxalinyl), quinazolinyl, phthalazinyl, 1,8-naphthyridinyl, 1,4-benzodioxanyl, coumarin, dihydrocoumarin, 1,5-naphthyridinyl, benzofuryl (particularly 3-, 4-, 5-, 6- and 7-benzofuryl), 2,3-dihydrobenzofuryl, 1,2-benzisoxazolyl, benzothienyl (particularly 3-, 4-, 5-, 6-, and 7-benzothienyl), benzoxazolyl, benzothiazolyl (particularly 2-benzothiazolyl and 5-benzothiazolyl), purinyl, benzimidazolyl (particularly 2-benzimidazolyl), benztriazolyl, thioxanthinyl, carbazolyl, carbolinyl, acridinyl, pyrrolizidinyl, and quinolizidinyl.

As used herein, the term "substituted" means that an atom or group of atoms has replaced hydrogen as the substituent attached to another group. The term "substituted" further refers to any level of substitution, namely mono-, di-, tri-, tetra-, or penta-substitution, where such substitution is permitted. The substituents are independently selected, and substitution may be at any chemically accessible position. In one embodiment, the substituents vary in number between one and four. In another embodiment, the substituents vary in number between one and three. In yet another embodiment, the substituents vary in number between one and two.

Ranges: throughout this disclosure, various aspects of the invention can be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 2.7, 3, 4, 5, 5.3, and 6. This applies regardless of the breadth of the range.

Compounds of the Invention

In one aspect, the present invention provides novel malacidin compounds. In one embodiment, the compounds can be biosynthesized via heterologous expression of a biosynthetic gene. Alternatively, the compounds of the present invention may be synthesized using techniques well-known in the art of organic synthesis. The starting materials and intermediates required for the synthesis may be obtained from commercial sources or synthesized according to methods known to those skilled in the art.

In one embodiment, the invention provides a malacidin compound or malacidin derivative.

In one embodiment, the malacidin compound is a compound of general formula (I):

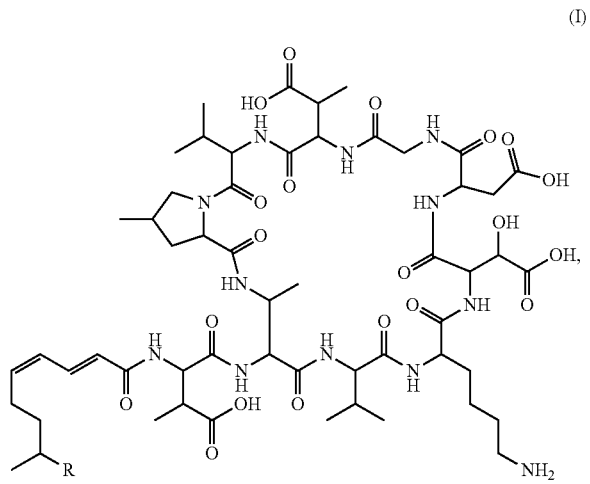

(I)

Wherein R is a hydrogen, alkyl, aryl or heteroaryl group.
In one embodiment R is a $C_1$-$C_{10}$ alkyl.
In one embodiment, R is methyl. In one embodiment, R is ethyl.

In one embodiment, the malacidin compound is a compound of general formula (II):

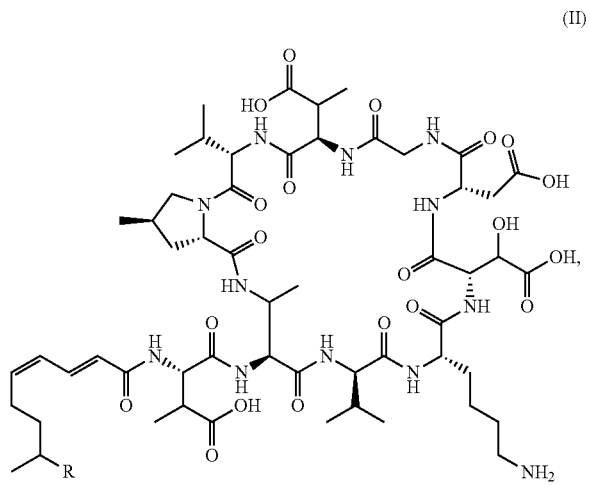

(II)

wherein R is a hydrogen, alkyl, aryl or heteroaryl group.
In one embodiment R is a $C_1$-$C_{10}$ alkyl.
In one embodiment, R is methyl. In one embodiment, R is ethyl.

The compounds described herein may form salts with acids or bases, and such salts are included in the present invention. The term "salts" embraces addition salts of free acids or free bases that are compounds of the invention.

Nucleic Acids

In one embodiment, the present invention provides isolated nucleic acids and vectors encoding a malacidin. In one embodiment, when the nucleic acids and vectors are administered to a subject, they produce a malacidin. In one embodiment, when the nucleic acids and vectors are administered to a subject, they produce an antibacterial effect.

In one embodiment, the nucleic acid comprises a sequence at 90% homologous to SEQ ID NO:1 or a fragment of SEQ ID NO:1. In one embodiment, the nucleic acid comprises a sequence at 95% homologous to SEQ ID NO:1. In one embodiment, the nucleic acid comprises a sequence at 96% homologous to SEQ ID NO:1. In one embodiment, the nucleic acid comprises a sequence at 97% homologous to SEQ ID NO:1. In one embodiment, the nucleic acid comprises a sequence at 98% homologous to SEQ ID NO:1. In one embodiment, the nucleic acid comprises a sequence at 99% homologous to SEQ ID NO:1. In one embodiment, the nucleic acid comprises a sequence at 99.5% homologous to SEQ ID NO:1. In one embodiment, the nucleic acid comprises SEQ ID NO:1.

In one embodiment, the nucleic acid comprises a sequence at 90% homologous to SEQ ID NO:2 or a fragment of SEQ ID NO:2. In one embodiment, the nucleic acid comprises a sequence at 95% homologous to SEQ ID NO:2. In one embodiment, the nucleic acid comprises a sequence at 96% homologous to SEQ ID NO:2. In one embodiment, the nucleic acid comprises a sequence at 97% homologous to SEQ ID NO:2. In one embodiment, the nucleic acid comprises a sequence at 98% homologous to SEQ ID NO:2. In one embodiment, the nucleic acid comprises a sequence at 99% homologous to SEQ ID NO:2. In one embodiment, the nucleic acid comprises a sequence at 99.5% homologous to SEQ ID NO:2. In one embodiment, the nucleic acid comprises SEQ ID NO:2.

In one embodiment, the nucleic acid comprises a sequence at 90% homologous to SEQ ID NO:3 or a fragment of SEQ ID NO:3. In one embodiment, the nucleic acid comprises a sequence at 95% homologous to SEQ ID NO:3. In one embodiment, the nucleic acid comprises a sequence at 96% homologous to SEQ ID NO:3. In one embodiment, the nucleic acid comprises a sequence at 97% homologous to SEQ ID NO:3. In one embodiment, the nucleic acid comprises a sequence at 98% homologous to SEQ ID NO:3. In one embodiment, the nucleic acid comprises a sequence at 99% homologous to SEQ ID NO:3. In one embodiment, the nucleic acid comprises a sequence at 99.5% homologous to SEQ ID NO:3. In one embodiment, the nucleic acid comprises SEQ ID NO:3.

In one embodiment, the nucleic acid comprises a sequence at 90% homologous to SEQ ID NO:1 or a fragment of SEQ ID NO:1; a sequence at 90% homologous to SEQ ID NO:2 or a fragment of SEQ ID NO:2; and a sequence at 90% homologous to SEQ ID NO:3 or a fragment of SEQ ID NO:3.

In one embodiment, the nucleic acid comprises a sequence at least 90% homologous to SEQ ID NO:4 or a fragment of SEQ ID NO:4. In one embodiment, the nucleic acid comprises a sequence at 90% homologous to SEQ ID NO:4 or a fragment of SEQ ID NO:4. In one embodiment, the nucleic acid comprises a sequence at 95% homologous to SEQ ID NO:4. In one embodiment, the nucleic acid comprises a sequence at 96% homologous to SEQ ID NO:4.

In one embodiment, the nucleic acid comprises a sequence at 97% homologous to SEQ ID NO:4. In one embodiment, the nucleic acid comprises a sequence at 98% homologous to SEQ ID NO:4. In one embodiment, the nucleic acid comprises a sequence at 99% homologous to SEQ ID NO:4. In one embodiment, the nucleic acid comprises a sequence at 99.5% homologous to SEQ ID NO:4. In one embodiment, the nucleic acid comprises SEQ ID NO:4.

The nucleic acid sequences include both the DNA sequence that is transcribed into RNA and the RNA sequence that is translated into a polypeptide. According to other embodiments, the polynucleotides of the invention are inferred from the amino acid sequence of the polypeptides of the invention. As is known in the art several alternative polynucleotides are possible due to redundant codons, while retaining the biological activity of the translated polypeptides.

It is to be understood explicitly that the scope of the present invention encompasses homologs, analogs, variants, fragments, derivatives and salts, including shorter and longer polynucleotides as well as polynucleotide analogs with one or more nucleic acid substitution, as well as nucleic acid derivatives, non-natural nucleic acids and synthetic nucleic acids as are known in the art, with the stipulation that these modifications must preserve the activity of the original molecule. The invention should be construed to include any and all isolated nucleic acids which are homologous to the nucleic acids described and referenced herein.

The skilled artisan would understand that the nucleic acids of the invention encompass a RNA or a DNA sequence comprising a sequence of the invention, and any modified forms thereof, including chemical modifications of the DNA or RNA which render the nucleotide sequence more stable when it is cell free or when it is associated with a cell. Chemical modifications of nucleotides may also be used to enhance the efficiency with which a nucleotide sequence is taken up by a cell or the efficiency with which it is expressed in a cell. Any and all combinations of modifications of the nucleotide sequences are contemplated in the present invention.

Vectors include, but are not limited to, plasmids, expression vectors, recombinant viruses, any form of recombinant "naked DNA" vector, and the like. A "vector" comprises a nucleic acid which can infect, transfect, transiently or permanently transduce a cell. It will be recognized that a vector can be a naked nucleic acid, or a nucleic acid complexed with protein or lipid. The vector optionally comprises viral or bacterial nucleic acids and/or proteins, and/or membranes (e.g., a cell membrane, a viral lipid envelope, etc.). Vectors include, but are not limited to replicons (e.g., RNA replicons, bacteriophages) to which fragments of DNA may be attached and become replicated. Vectors thus include, but are not limited to RNA, autonomous self-replicating circular or linear DNA or RNA (e.g., plasmids, viruses, and the like, see, e.g., U.S. Pat. No. 5,217,879), and include both the expression and non-expression plasmids. Where a recombinant microorganism or cell culture is described as hosting an "expression vector" this includes both extra-chromosomal circular and linear DNA and DNA that has been incorporated into the host chromosome(s). Where a vector is being maintained by a host cell, the vector may either be stably replicated by the cells during mitosis as an autonomous structure, or is incorporated within the host's genome.

In one embodiment, the vector is a plasmid. The plasmid may comprise one or more sequences encoding malacidins described herein. The plasmid may further comprise an initiation codon, which may be upstream of the coding sequence, and a stop codon, which may be downstream of the coding sequence. The initiation and termination codon may be in frame with the coding sequence.

The plasmid may also comprise a promoter that is operably linked to the coding sequence The promoter operably linked to the coding sequence may be a promoter from simian virus 40 (SV40), a mouse mammary tumor virus (MMTV) promoter, a human immunodeficiency virus (HIV) promoter such as the bovine immunodeficiency virus (BIV) long terminal repeat (LTR) promoter, a Moloney virus promoter, an avian leukosis virus (ALV) promoter, a cytomegalovirus (CMV) promoter such as the CMV immediate early promoter, Epstein Barr virus (EBV) promoter, or a Rous sarcoma virus (RSV) promoter. The promoter may also be a promoter from a human gene such as human actin, human myosin, human hemoglobin, human muscle creatine, or human metalothionein. The promoter may also be a tissue specific promoter, such as a muscle or skin specific promoter, natural or synthetic. Examples of such promoters are described in US patent application publication no. US20040175727, the contents of which are incorporated herein in its entirety.

The plasmid may also comprise a polyadenylation signal, which may be downstream of the coding sequence. The polyadenylation signal may be a SV40 polyadenylation signal, LTR polyadenylation signal, bovine growth hormone (bGH) polyadenylation signal, human growth hormone (hGH) polyadenylation signal, or human β-globin polyadenylation signal. The SV40 polyadenylation signal may be a polyadenylation signal from a pCEP4 plasmid (Invitrogen, San Diego, Calif.).

The plasmid may also comprise an enhancer upstream of the coding sequence. The enhancer may be human actin, human myosin, human hemoglobin, human muscle creatine or a viral enhancer such as one from CMV, FMDV, RSV or EBV. Polynucleotide function enhances are described in U.S. Pat. Nos. 5,593,972, 5,962,428, and WO94/016737, the contents of each are fully incorporated by reference.

The plasmid may also comprise a mammalian origin of replication in order to maintain the plasmid extrachromosomally and produce multiple copies of the plasmid in a cell. The plasmid may be pVAX1, pCEP4 or pREP4 from Invitrogen (San Diego, Calif.), which may comprise the Epstein Barr virus origin of replication and nuclear antigen EBNA-1 coding region, which may produce high copy episomal replication without integration. The backbone of the plasmid may be pAV0242. The plasmid may be a replication defective adenovirus type 5 (Ad5) plasmid.

The plasmid may also comprise a regulatory sequence, which may be well suited for gene expression in a cell into which the plasmid is administered. The coding sequence may comprise a codon that may allow more efficient transcription of the coding sequence in the host cell. In one embodiment, the plasmid may be pTARa (Invitrogen, San Diego, Calif.) plasmid.

Also provided herein is a linear nucleic acid vaccine, or linear expression cassette ("LEC"). The LEC may be any linear DNA devoid of any phosphate backbone. The DNA may encode one or more malacidins. The LEC may contain a promoter, an intron, a stop codon, a polyadenylation signal. The expression of the antigen may be controlled by the promoter. The LEC may not contain any antibiotic resistance genes and/or a phosphate backbone. The LEC may not contain other nucleic acid sequences unrelated to the desired malacidin expression.

The LEC may be derived from any plasmid capable of being linearized. The plasmid may be capable of expressing the malacidin. The plasmid may be any expression vector capable of expressing the DNA.

In one embodiment, viral vectors are provided herein which are capable of delivering a nucleic acid of the invention to a cell. The expression vector may be provided to a cell in the form of a viral vector. Viral vector technology is well known in the art and is described, for example, in Sambrook et al. (2001), and in Ausubel et al. (1997), and in other virology and molecular biology manuals. Viruses, which are useful as vectors include, but are not limited to, retroviruses, adenoviruses, adeno-associated viruses, herpes viruses, and lentiviruses. In general, a suitable vector contains an origin of replication functional in at least one organism, a promoter sequence, convenient restriction endonuclease sites, and one or more selectable markers. (See, e.g., WO 01/96584; WO 01/29058; and U.S. Pat. No. 6,326,193. Viral vectors, and especially retroviral vectors, have become the most widely used method for inserting genes into mammalian, e.g., human cells. Other viral vectors can be derived from lentivirus, poxviruses, herpes simplex virus I, adenoviruses and adeno-associated viruses, and the like. See, for example, U.S. Pat. Nos. 5,350,674 and 5,585,362.

Cells

In one aspect, the present invention provides an engineered cell that expresses a malacidin. The genetically modified cell according to the invention may be constructed from any suitable host cell. The host cell may be an unmodified cell or may already be genetically modified. The cell may be a prokaryote cell, a eukaryote cell, a plant cell or an animal cell.

In one embodiment, the engineered cell is modified by way of introducing genetic material into the cell in order for the cell to produce a malacidin. In one embodiment, the engineered cell is modified by way of transforming a nucleic acid of the invention into the cell. In one embodiment, the engineered cell is modified by way of transforming a nucleic acid that is at least 90% homologous, at least 95% homologous, at least 96% homologous, at least 97% homologous, at least 98% homologous, at least 99% homologous, or at least 99.5% homologous to SEQ ID NO: 1, SEQ ID NO: 2, SEQ ID NO: 3, or SEQ ID NO: 4.

In one embodiment, the engineered cell produces a compound of formula (I). In one embodiment, the engineered cell produces a compound of formula (II).

In one embodiment, the cell is a eukaryotic cell. In one embodiment, the cell may be a human cell, a non-human mammalian cell, a non-mammalian vertebrate cell, an invertebrate cell, an insect cell, a plant cell, a yeast cell, or a single cell eukaryotic organism. In one embodiment, the cell may be an adult cell or an embryonic cell (e.g., an embryo). In one embodiment, the cell may be a stem cell. Suitable stem cells include without limit embryonic stem cells, ES-like stem cells, fetal stem cells, adult stem cells, pluripotent stem cells, induced pluripotent stem cells, multipotent stem cells, oligopotent stem cells, unipotent stem cells and others.

In one embodiment, the cell is a cell line cell. Non-limiting examples of suitable mammalian cells include Chinese hamster ovary (CHO) cells, baby hamster kidney (BHK) cells; mouse myeloma NS0 cells, mouse embryonic fibroblast 3T3 cells (NIH3T3), mouse B lymphoma A20 cells; mouse melanoma B16 cells; mouse myoblast C2C12 cells; mouse myeloma SP2/0 cells; mouse embryonic mesenchymal C3H-10T1/2 cells; mouse carcinoma CT26 cells, mouse prostate DuCuP cells; mouse breast EMT6 cells; mouse hepatoma Hepa1c1c7 cells; mouse myeloma J5582 cells; mouse epithelial MTD-1A cells; mouse myocardial MyEnd cells; mouse renal RenCa cells; mouse pancreatic RIN-5F cells; mouse melanoma X64 cells; mouse lymphoma YAC-1 cells; rat glioblastoma 9L cells; rat B lymphoma RBL cells; rat neuroblastoma B35 cells; rat hepatoma cells (HTC); buffalo rat liver BRL 3A cells; canine kidney cells (MDCK); canine mammary (CMT) cells; rat osteosarcoma D17 cells; rat monocyte/macrophage DH82 cells; monkey kidney SV-40 transformed fibroblast (COS7) cells; monkey kidney CVI-76 cells; African green monkey kidney (VERO-76) cells; human embryonic kidney cells (HEK293, HEK293T); human cervical carcinoma cells (HELA); human lung cells (W138); human liver cells (Hep G2); human U2-OS osteosarcoma cells, human A549 cells, human A-431 cells, human SW48 cells, human HCT116 cells, and human K562 cells. An extensive list of mammalian cell lines may be found in the American Type Culture Collection catalog (ATCC, Manassas, Va.).

In one embodiment, the cell can be a prokaryotic cell or a eukaryotic cell. In one embodiment, the cell is a prokaryotic cell. In one embodiment, the cell is a genetically engineered bacteria cell.

In one embodiment, the genetically engineered bacteria cell is a non-pathogenic bacteria cell. In some embodiments, the genetically engineered bacteria cell is a commensal bacteria cell. In some embodiments, the genetically engineered bacteria cell is a probiotic bacteria cell. In some embodiments, the genetically engineered bacteria cell is a naturally pathogenic bacteria cell that is modified or mutated to reduce or eliminate pathogenicity. Exemplary bacteria include, but are not limited to *Bacillus, Bacteroides, Bifidobacterium, Brevibacteria, Clostridium, Enterococcus, Escherichia coli, Lactobacillus, Lactococcus, Saccharomyces*, and *Staphylococcus*, e.g., *Bacillus coagulans, Bacillus subtilis, Bacteroides fragilis, Bacteroides subtilis, Bacteroides thetaiotaomicron, Bifidobacterium bifidum, Bifidobacterium infantis, Bifidobacterium lactis, Bifidobacterium longum, Clostridium butyricum, Enterococcus faecium, Lactobacillus acidophilus, Lactobacillus bulgaricus, Lactobacillus casei, Lactobacillus johnsonii, Lactobacillus paracasei, Lactobacillus plantarum, Lactobacillus reuteri, Lactobacillus rhamnosus, Lactococcus lactis*, and *Saccharomyces boulardii*.

In some embodiments, the genetically engineered bacteria are *Escherichia coli* strain Nissle 1917 (*E. coli* Nissle), a Gram-negative bacterium of the Enterobacteriaceae family that "has evolved into one of the best characterized probiotics" (Ukena et al., 2007). The strain is characterized by its complete harmlessness (Schultz, 2008), and has GRAS (generally recognized as safe) status (Reister et al., 2014, emphasis added). Genomic sequencing confirmed that *E. coli* Nissle lacks prominent virulence factors (e.g., *E. coli* α-hemolysin, P-fimbrial adhesins) (Schultz, 2008). In addition, it has been shown that *E. coli* Nissle does not carry pathogenic adhesion factors, does not produce any enterotoxins or cytotoxins, is not invasive, and not uropathogenic (Sonnenborn et al., 2009). As early as in 1917, *E. coli* Nissle was packaged into medicinal capsules, called Mutaflor, for therapeutic use. *E. coli* Nissle has since been used to treat ulcerative colitis in humans in vivo (Rembacken et al., 1999), to treat inflammatory bowel disease, Crohn's disease, and pouchitis in humans in vivo (Schultz, 2008), and to inhibit enteroinvasive *Salmonella, Legionella, Yersinia*, and *Shigella* in vitro (Altenhoefer et al., 2004). It is commonly accepted that *E. coli* Nissle's therapeutic efficacy and safety have convincingly been proven (Ukena et al., 2007).

One of ordinary skill in the art would appreciate that the genetic modifications disclosed herein may be modified and adapted for other species, strains, and subtypes of bacteria.

Methods of Biosynthesis

In one aspect, the invention provides methods of biosynthesizing malacidins. In one embodiment, the method comprises providing a heterologous nucleic acid of the invention to a host, incubating the host in a growth medium, and isolating a malacidin from the host or the growth medium. In one embodiment, the malacidin is isolated from the growth medium. In one embodiment, providing a heterologous nucleic acid to the host comprises transforming the host with the heterologous nucleic acid. In one embodiment, the heterologous nucleic acid comprises a sequence at least 90% homologues to SEQ ID NO:4. In one embodiment, the heterologous nucleic acid comprises SEQ ID NO:4.

The term "heterologous nucleic acid" as used herein refers to a nucleic acid sequence, which has been introduced into the host organism, wherein said host does not endogenously comprise said nucleic acid. For example, said heterologous nucleic acid may be introduced into the host organism by recombinant methods. Thus, the genome of the host organism has been augmented by at least one incorporated heterologous nucleic acid sequence. It will be appreciated that typically the genome of a recombinant host described herein is augmented through the stable introduction of one or more heterologous nucleic acids encoding one or more malicidins.

Suitable host organisms include microorganisms, plant cells, and plants. The microorganism can be any microorganism suitable for expression of heterologous nucleic acids. In one embodiment the host organism of the invention is a eukaryotic cell. In another embodiment the host organism is a prokaryotic cell. In one embodiment, the host organism is a fungal cell such as a yeast or filamentous fungus. In one embodiment the host organism may be a yeast cell.

The host organism may also be a plant, plant or plant cell can be transformed by having a heterologous nucleic acid integrated into its genome, i.e., it can be stably transformed. Stably transformed cells typically retain the introduced nucleic acid with each cell division. A plant or plant cell can also be transiently transformed such that the recombinant gene is not integrated into its genome. Transiently transformed cells typically lose all or some portion of the introduced nucleic acid with each cell division such that the introduced nucleic acid cannot be detected in daughter cells after a certain number of cell divisions.

In one embodiment, the host cell is a non-pathogenic bacteria cell. Exemplary bacteria include, but are not limited to *Streptomyces albus, Bacillus, Bacteroides, Bifidobacterium, Brevibacteria, Clostridium, Enterococcus, Escherichia coli, Lactobacillus, Lactococcus, Saccharomyces*, and *Staphylococcus*, e.g., *Bacillus coagulans, Bacillus subtilis, Bacteroides fragilis, Bacteroides subtilis, Bacteroides thetaiomaomicron, Bifidobacterium bifidum, Bifidobacterium infantis, Bifidobacterium lactis, Bifidobacterium longum, Clostridium butyricum, Enterococcus faecium, Lactobacillus acidophilus, Lactobacillus bulgaricus. Lactobacillus casei, Lactobacillus johnsonii, Lactobacillus paracasei, Lactobacillus plantarum, Lactobacillus reuteri, Lactobacillus rhamnosus, Lactococcus lactis*, and *Saccharomyces boulardii*.

In one embodiment, the host is a *Streptomyces albus* cell.

Treatment Methods

In one aspect, the invention provides methods of treating or preventing an infection in a subject in need thereof. In some embodiments, the method comprises administering to the subject an effective amount of a composition comprising at least one compound of the invention. In some embodiments, the method comprises administering to the subject an effective amount of a composition comprising at least one nucleic acid of the invention In some embodiments, the method treats or prevents a bacterial infection. In one embodiment, the method treats or prevents a gram-positive bacterial infection. In one embodiment, the bacterial infection is resistant to antibiotics. For example, in one embodiment, the bacterial infection is resistant to one or more of, beta-lactams, including methicillin, oxacillin, or penicillin, tetracyclines, gentamicin, kanamycin, erythromycin, spectinomycin, and vancomycin.

Exemplary bacterial infections that may be treated by way of the present invention includes, but is not limited to, infections caused by bacteria from the taxonomic genus of *Bacillus, Bartonella, Bordetella, Borrelia, Brucella, Campylobacter, Chlamydia, Chlamydophila, Clostridium, Corynebacterium, Enterococcus, Escherichia, Francisella, Haemophilus, Helicobacter, Legionella, Leptospira, Listeria, Mycobacterium, Mycoplasma, Neisseria, Pseudomonas, Rickettsia, Salmonella, Shigella, Staphylococcus, Streptococcus, Treponema, Ureaplasma, Vibrio*, and *Yersinia*. In some embodiments, the bacterial infection is an infection of *Bacillus anthracis, Bacillus cereus, Bartonella henselae, Bartonella quintana, Bordetella pertussis, Borrelia burgdorferi, Borrelia garinii, Borrelia afzelii, Borrelia recurrentis, Brucella abortus, Brucella canis, Brucella melitensis, Brucella suis, Campylobacter jejuni, Chlamydia pneumoniae, Chlamydia trachomatis, Chlamydophila psittaci, Clostridium botulinum, Clostridium difficile, Clostridium perfringens, Clostridium tetani, Corynebacterium diphtheriae, Enterococcus faecalis, Enterococcus faecium, Escherichia coli, Francisella tularensis, Haemophilus influenzae, Helicobacter pylori, Klebsiella species, Legionella pneumophila, Leptospira interrogans, Leptospira santarosai, Leptospira weilii, Leptospira noguchii, Listeria monocytogenes, Morexella species, Mycobacterium leprae, Mycobacterium tuberculosis, Mycobacterium ulcerans, Mycoplasma pneumoniae, Neisseria gonorrhoeae, Neisseria meningitidis, Proteus species, Pseudomonas aeruginosa, Rickettsia rickettsii, Salmonella typhi, Salmonella typhimurium, Shigella sonnei, Staphylococcus aureus, Staphylococcus epidermidis, Staphylococcus saprophyticus, Streptococcus agalactiae, Streptococcus pneumoniae, Streptococcus pyogenes, Treponema pallidum, Ureaplasma urealyticum, Vibrio cholerae, Yersinia pestis, Yersinia enterocolitica*, or *Yersinia pseudotuberculosis*. In one embodiment, the bacterial infection is a *Listeria monocytogenes* infection.

In one embodiment, the bacterial infection is an infection of *S. aureus* USA300, *S. aureus* COL, *S. aureus* BAA-42, *S. aureus* NRS100, *S. aureus* NRS108, *S. aureus* NRS140, *S. aureus* NRS146, *E. faecium* VRE, *E. faecium* Com15, *S. pneumoniae, S. mutans, B. subtilis, L. rhamnosus, E. coli, C. albicans*, or *C. neoformans*.

Exemplary diseases caused by bacterial infections which may be treated using compositions of the present invention, include but are not limited to, bacterially mediated meningitis, sinus tract infections, pneumonia, endocarditis, pancreatitis, appendicitis, gastroenteritis, biliary tract infections, soft tissue infections, urinary tract infections, cystitis, pyelonephritis, osteomyelitis, bacteremia, Actinomycosis, Whooping cough, Secondary bacterial pneumonia, Lyme disease (*B. burgdorferi*), Relapsing fever, Brucellosis, Enteritis, bloody diarrhea, Guillain-Barre syndrome, Atypical pneumonia, Trachoma, Neonatal conjunctivitis, Neonatal pneumonia, Nongonococcal urethritis (NGU), Urethritis, Pelvic inflammatory disease, Epididymitis, Prostatitis, Lymphogranuloma venereum (LGV), Psittacosis, Botulism: Mainly muscle weakness and paralysis, Pseudomembranous colitis, Anaerobic cellulitis, Gas gangrene Acutefood poisoning, Tetanus, and Diphtheria.

However, the invention should not be limited to only treating bacterial infection. The invention encompasses compounds having an antimicrobial activity including but not limited to antibacterial, antimycobacterial, antifungal, antiviral and the likes.

In one aspect, the invention provides methods of killing a bacterial cell or inhibiting the grown of a bacterial cell. In some embodiments, the method comprises administering to the cell an effective amount of a composition comprising at least one compound of the invention. In some embodiments, the method comprises administering to the cell an effective amount of a composition comprising at least one nucleic acid of the invention. In one embodiment the bacterial cell is a gram positive bacterial cell. In one embodiment, the bacterial cell is resistant to antibiotics. For example, in one embodiment, the bacterial cell is resistant to one or more of beta-lactams, including methicillin, oxacillin, or penicillin, tetracyclines, gentamicin, kanamycin, erythromycin, spectinomycin, and vancomycin.

In another aspect, the invention provides compositions and methods for treating and/or preventing a disease or disorder related to the detrimental growth and/or proliferation of a bacterial cell in vivo, ex vivo or in vitro. In certain embodiments, the method comprises administering a composition comprising an effective amount of a composition provided by the invention to a subject, wherein the composition is effective in inhibiting or preventing the growth and/or proliferation of a bacterial cell. In certain embodiments, the bacterial cell is a Gram-positive bacterial cell, e.g., a bacteria of a genera such as *Staphylococcus, Streptococcus, Enterococcus*, (which are cocci) and *Bacillus, Corynebacterium, Nocardia, Clostridium*, Actinobacteria, and *Listeria* (which are rods and can be remembered by the mnemonic obconical), Mollicutes, bacteria-like *Mycoplasma*, Actinobacteria.

In certain embodiments, the bacterial cell is a Gram-bacteria cell, e.g., a bacteria of a genera such as *Citrobacter, Yersinia, Pseudomonas* and *Escherichia, Hemophilus, Neisseria, Klebsiella, Legionella, Helicobacter*, and *Salmonella*. The compounds as described herein and compositions comprising them may thus be for use in the treatment of bacterial infections by the above-mentioned Gram+ or Gram-bacteria.

In one embodiment, the method further comprises administering a second therapeutic agent. In one embodiment, the second therapeutic agent is an antibiotic agent. In one embodiment, the compound of the invention and the at least one additional antibiotic agent act synergistically in preventing, reducing or disrupting microbial growth.

Non-limiting examples of the at least one additional antibiotic agents include levofloxacin, doxycycline, neomycin, clindamycin, minocycline, gentamycin, rifampin, chlorhexidine, chloroxylenol, methylisothizolone, thymol, α-terpineol, cetylpyridinium chloride, hexachlorophene, triclosan, nitrofurantoin, erythromycin, nafcillin, cefazolin, imipenem, astreonam, gentamicin, sulfamethoxazole, vancomycin, ciprofloxacin, trimethoprim, rifampin, metronidazole, clindamycin, teicoplanin, mupirocin, azithromycin, clarithromycin, ofoxacin, lomefloxacin, norfloxacin, nalidixic acid, sparfloxacin, pefloxacin, amifloxacin, gatifloxacin, moxifloxacin, gemifloxacin, enoxacin, fleroxacin, minocycline, linexolid, temafloxacin, tosufloxacin, clinafloxacin, sulbactam, clavulanic acid, amphotericin B, fluconazole, itraconazole, ketoconazole, nystatin, penicillins, cephalosporins, carbepenems, beta-lactams antibiotics, aminoglycosides, macrolides, lincosamides, glycopeptides, tetracylines, chloramphenicol, quinolones, fucidines, sulfonamides, trimethoprims, rifamycins, oxalines, streptogramins, lipopeptides, ketolides, polyenes, azoles, echinocandines, and any combination thereof.

In one embodiment, the compositions of the invention find use in removing at least a portion of or reducing the number of microorganisms and/or biofilm-embedded microorganisms attached to the surface of a medical device or the surface of a subject's body (such as the skin of the subject, or a mucous membrane of the subject, such as the vagina, anus, throat, eyes or ears). In one embodiment, the compositions of the invention find further use in coating the surface of a medical device, thus inhibiting or disrupting microbial growth and/or inhibiting or disrupting the formation of biofilm on the surface of the medical device. The compositions of the invention find further use in preventing or reducing the growth or proliferation of microorganisms and/or biofilm-embedded microorganisms on the surface of a medical device or on the surface of a subject's body. However, the invention is not limited to applications in the medical field. Rather, the invention includes using a malacidin compound or an analog thereof as an antimicrobial and/or antibiofilm agent in any setting.

The composition of the invention may be administered to a patient or subject in need in a wide variety of ways, including by aerosol inhalation, injection, ingestion, transfusion, implantation or transplantation. The compositions described herein may be administered to a patient subcutaneously, intradermally, intratumorally, intranodally, intramedullary, intramuscularly, by intravenous (i.v.) injection, or intraperitoneally. In one embodiment, the composition is administered systemically to the subject. In one embodiment, the compositions of the present invention are administered to a patient by i.v. injection. In one embodiment, the composition is administered locally to the subject. In one embodiment, the compositions of the present invention are administered to a patient topically. Any administration may be a single application of a composition of invention or multiple applications. Administrations may be to single site or to more than one site in the individual to be treated. Multiple administrations may occur essentially at the same time or separated in time.

In one aspect, the compositions of the invention may be in the form of a coating that is applied to the surface of a medical device or the surface of a subject's body. In one embodiment, the coating prevents or hinders microorganisms and/or biofilm-embedded microorganisms from growing and proliferating on at least one surface of the medical device or at least one surface of the subject's body. In another embodiment, the coating facilitates access of antimicrobial agents to the microorganisms and/or biofilm-embedded microorganisms, thus helping prevent or hinder the microorganisms and/or biofilm-embedded microorganisms from growing or proliferating on at least one surface of the medical device or at least one surface of the subject's body. The compositions of the invention may also be in the form of a liquid or solution, used to clean the surface of medical device or the surface of a subject's body, on which microorganisms and/or biofilm-embedded microorganisms live and proliferate. Such cleaning of the medical device or body surface may occur by flushing, rinsing, soaking, or any additional cleaning method known to those skilled in the art, thus removing at least a portion of or reducing the number of microorganisms and/or biofilm-embedded microorganisms attached to at least one surface of the medical device or at least one surface of the subject's body.

Subjects to which administration of the pharmaceutical compositions of the invention is contemplated include, but are not limited to, humans and other primates, mammals including but not limited to non-human mammals such as non-human primates, cattle, pigs, horses, sheep, cats, and dogs.

Pharmaceutical compositions of the present invention may be administered in a manner appropriate to the disease to be treated (or prevented). The quantity and frequency of administration will be determined by such factors as the condition of the subject, and the type and severity of the subject's disease, although appropriate dosages may be determined by clinical trials.

When "therapeutic amount" is indicated, the precise amount of the compositions of the present invention to be administered can be determined by a physician with consideration of individual differences in age, weight, disease type, extent of disease, and condition of the patient (subject).
Dosage and Formulation (Pharmaceutical Compositions)

The invention also encompasses the use of pharmaceutical compositions comprising a compound of the invention, a nucleic acid of the invention, or salts thereof. Such a pharmaceutical composition may comprise of at least one a compound of the invention, a nucleic acid of the invention, or salts thereof in a form suitable for administration to a subject, or the pharmaceutical composition may comprise at least one a compound of the invention, a nucleic acid of the invention, or salts thereof, and one or more pharmaceutically acceptable carriers, one or more additional ingredients, or some combination of these. The compound or nucleic acid of the invention may be present in the pharmaceutical composition in the form of a physiologically acceptable salt, such as in combination with a physiologically acceptable cation or anion, as is well known in the art.

Administration of the therapeutic agent in accordance with the present invention may be continuous or intermittent, depending, for example, upon the recipient's physiological condition, whether the purpose of the administration is therapeutic or prophylactic, and other factors known to skilled practitioners. The administration of the agents of the invention may be essentially continuous over a preselected period of time or may be in a series of spaced doses. Both local and systemic administration is contemplated. The amount administered will vary depending on various factors including, but not limited to, the composition chosen, the particular disease, the weight, the physical condition, and the age of the subject, and whether prevention or treatment is to be achieved. Such factors can be readily determined by the clinician employing animal models or other test systems which are well known to the art The formulations may, where appropriate, be conveniently presented in discrete unit dosage forms and may be prepared by any of the methods well known to pharmacy. Such methods may include the step of bringing into association the therapeutic agent with liquid carriers, solid matrices, semi-solid carriers, finely divided solid carriers or combinations thereof, and then, if necessary, introducing or shaping the product into the desired delivery system.

In one embodiment, the pharmaceutical compositions useful for practicing the methods of the invention may be administered to deliver a dose of between 1 ng/kg/day and 100 mg/kg/day. In another embodiment, the pharmaceutical compositions useful for practicing the invention may be administered to deliver a dose of between 1 ng/kg/day and 500 mg/kg/day.

Typically, dosages which may be administered in a method of the invention to a mammal, preferably a human, range in amount from 0.5 µg to about 50 mg per kilogram of body weight of the mammal, while the precise dosage administered will vary depending upon any number of factors, including but not limited to, the type of mammal and type of disease state being treated, the age of the mammal and the route of administration. Preferably, the dosage of the compound will vary from about 1 µg to about 10 mg per kilogram of body weight of the mammal. More preferably, the dosage will vary from about 3 µg to about 5 mg per kilogram of body weight of the mammal.

The relative amounts of the active ingredient, the pharmaceutically acceptable carrier, and any additional ingredients in a pharmaceutical composition of the invention will vary, depending upon the identity, size, and condition of the subject treated and further depending upon the route by which the composition is to be administered. By way of example, the composition may comprise between 0.1% and 100% (w/w) active ingredient.

The composition may be administered to a mammal as frequently as several times daily, or it may be administered less frequently, such as once a day, once a week, once every two weeks, once a month, or even less frequently, such as once every several months or even once a year or less. The frequency of the dose will be readily apparent to the skilled artisan and will depend upon any number of factors, such as, but not limited to, the type and severity of the disease being treated, the type and age of the mammal, etc.

When the therapeutic agents of the invention are prepared for administration, they are preferably combined with a pharmaceutically acceptable carrier, diluent or excipient to form a pharmaceutical formulation, or unit dosage form. The total active ingredients in such formulations include from 0.1 to 99.9% by weight of the formulation. A "pharmaceutically acceptable" is a carrier, diluent, excipient, and/or salt that is compatible with the other ingredients of the formulation, and not deleterious to the recipient thereof. The active ingredient for administration may be present as a powder or as granules; as a solution, a suspension or an emulsion.

Pharmaceutical formulations containing the therapeutic agents of the invention can be prepared by procedures known in the art using well known and readily available ingredients. The therapeutic agents of the invention can also be formulated as solutions appropriate for parenteral administration, for instance by intramuscular, subcutaneous or intravenous routes.

The pharmaceutical formulations of the therapeutic agents of the invention can also take the form of an aqueous or anhydrous solution or dispersion, or alternatively the form of an emulsion or suspension.

Thus, the therapeutic agent may be formulated for parenteral administration (e.g., by injection, for example, bolus injection or continuous infusion) and may be presented in unit dose form in ampules, pre-filled syringes, small volume infusion containers or in multi-dose containers with an added preservative. The active ingredients may take such forms as suspensions, solutions, or emulsions in oily or aqueous vehicles, and may contain formulatory agents such as suspending, stabilizing and/or dispersing agents. Alternatively, the active ingredients may be in powder form, obtained by aseptic isolation of sterile solid or by lyophilization from solution, for constitution with a suitable vehicle, e.g., sterile, pyrogen-free water, before use.

It will be appreciated that the unit content of active ingredient or ingredients contained in an individual aerosol dose of each dosage form need not in itself constitute an effective amount for treating the particular indication or disease since the necessary effective amount can be reached by administration of a plurality of dosage units. Moreover, the effective amount may be achieved using less than the dose in the dosage form, either individually, or in a series of administrations.

The pharmaceutical formulations of the present invention may include, as optional ingredients, pharmaceutically acceptable carriers, diluents, solubilizing or emulsifying agents, and salts of the type that are well-known in the art. Specific non-limiting examples of the carriers and/or diluents that are useful in the pharmaceutical formulations of the present invention include water and physiologically acceptable buffered saline solutions, such as phosphate buffered saline solutions pH 7.0-8.0.

The compounds and polypeptides (active ingredients) of this invention can be formulated and administered to treat a variety of disease states by any means that produces contact of the active ingredient with the agent's site of action in the body of the organism. They can be administered by any conventional means available for use in conjunction with pharmaceuticals, either as individual therapeutic active ingredients or in a combination of therapeutic active ingredients. They can be administered alone, but are generally administered with a pharmaceutical carrier selected on the basis of the chosen route of administration and standard pharmaceutical practice.

In general, water, suitable oil, saline, aqueous dextrose (glucose), and related sugar solutions and glycols such as propylene glycol or polyethylene glycols are suitable carriers for parenteral solutions. Solutions for parenteral administration contain the active ingredient, suitable stabilizing agents and, if necessary, buffer substances. Antioxidizing agents such as sodium bisulfate, sodium sulfite or ascorbic acid, either alone or combined, are suitable stabilizing agents. Also used are citric acid and its salts and sodium Ethylenediaminetetraacetic acid (EDTA). In addition, parenteral solutions can contain preservatives such as benzalkonium chloride, methyl- or propyl-paraben and chlorobutanol. Suitable pharmaceutical carriers are described in Remington's Pharmaceutical Sciences, a standard reference text in this field.

The active ingredients of the invention may be formulated to be suspended in a pharmaceutically acceptable composition suitable for use in mammals and in particular, in humans. Such formulations include the use of adjuvants such as muramyl dipeptide derivatives (MDP) or analogs that are described in U.S. Pat. Nos. 4,082,735; 4,082,736; 4,101,536; 4,185,089; 4,235,771; and 4,406,890. Other adjuvants, which are useful, include alum (Pierce Chemical Co.), lipid A, trehalose dimycolate and dimethyldioctadecylammonium bromide (DDA), Freund's adjuvant, and IL-12. Other components may include a polyoxypropylene-polyoxyethylene block polymer (Pluronic®), a non-ionic surfactant, and a metabolizable oil such as squalene (U.S. Pat. No. 4,606,918).

Additionally, standard pharmaceutical methods can be employed to control the duration of action. These are well known in the art and include control release preparations and can include appropriate macromolecules, for example polymers, polyesters, polyamino acids, polyvinyl, pyrolidone, ethylenevinylacetate, methyl cellulose, carboxymethyl cellulose or protamine sulfate. The concentration of macromolecules as well as the methods of incorporation can be adjusted in order to control release. Additionally, the agent can be incorporated into particles of polymeric materials such as polyesters, polyamino acids, hydrogels, poly (lactic acid) or ethylenevinylacetate copolymers. In addition to being incorporated, these agents can also be used to trap the compound in microcapsules.

Accordingly, the pharmaceutical composition of the present invention may be delivered via various routes and to various sites in a mammal body to achieve a particular effect (see, e.g., Rosenfeld et al., 1991; Rosenfeld et al., 1991a; Jaffe et al., supra; Berkner, supra). One skilled in the art will recognize that although more than one route can be used for administration, a particular route can provide a more immediate and more effective reaction than another route. Local or systemic delivery can be accomplished by administration comprising application or instillation of the formulation into body cavities, inhalation or insufflation of an aerosol, or by parenteral introduction, comprising intramuscular, intravenous, peritoneal, subcutaneous, intradermal, as well as topical administration.

The active ingredients of the present invention can be provided in unit dosage form wherein each dosage unit, e.g., a teaspoonful, tablet, solution, or suppository, contains a predetermined amount of the composition, alone or in appropriate combination with other active agents. The term "unit dosage form" as used herein refers to physically discrete units suitable as unitary dosages for human and mammal subjects, each unit containing a predetermined quantity of the compositions of the present invention, alone or in combination with other active agents, calculated in an amount sufficient to produce the desired effect, in association with a pharmaceutically acceptable diluent, carrier, or vehicle, where appropriate. The specifications for the unit dosage forms of the present invention depend on the particular effect to be achieved and the particular pharmacodynamics associated with the pharmaceutical composition in the particular host.

In one embodiment, the compositions of the invention are formulated using one or more pharmaceutically acceptable excipients or carriers. In one embodiment, the pharmaceutical compositions of the invention comprise a therapeutically effective amount of a compound or conjugate of the invention and a pharmaceutically acceptable carrier. Pharmaceutically acceptable carriers that are useful, include, but are not limited to, glycerol, water, saline, ethanol and other pharmaceutically acceptable salt solutions such as phosphates and salts of organic acids. Examples of these and other pharmaceutically acceptable carriers are described in Remington's Pharmaceutical Sciences (1991, Mack Publication Co., New Jersey).

The carrier may be a solvent or dispersion medium containing, for example, water, ethanol, polyol (for example, glycerol, propylene glycol, and liquid polyethylene glycol, and the like), suitable mixtures thereof, and vegetable oils. The proper fluidity may be maintained, for example, by the use of a coating such as lecithin, by the maintenance of the required particle size in the case of dispersion and by the use of surfactants. Prevention of the action of microorganisms may be achieved by various antibacterial and antifungal agents, for example, parabens, chlorobutanol, phenol, ascorbic acid, thimerosal, and the like. In many cases, it will be preferable to include isotonic agents, for example, sugars, sodium chloride, or polyalcohols such as mannitol and sorbitol, in the composition. Prolonged absorption of the injectable compositions may be brought about by including in the composition an agent that delays absorption, for example, aluminum monostearate or gelatin. In one embodiment, the pharmaceutically acceptable carrier is not DMSO alone.

The present invention also provides pharmaceutical compositions comprising one or more of the compositions described herein. Formulations may be employed in admixtures with conventional excipients, i.e., pharmaceutically acceptable organic or inorganic carrier substances suitable for administration to subject. The pharmaceutical compositions may be sterilized and if desired mixed with auxiliary agents, e.g., lubricants, preservatives, stabilizers, wetting agents, emulsifiers, salts for influencing osmotic pressure buffers, coloring, and/or aromatic substances and the like. They may also be combined where desired with other active agents, e.g., other analgesic agents.

As used herein, "additional ingredients" include, but are not limited to, one or more of the following: excipients; surface active agents; dispersing agents; inert diluents; granulating and disintegrating agents; binding agents; lubricating agents; coloring agents; preservatives; physiologically degradable compositions such as gelatin; aqueous vehicles and solvents; oily vehicles and solvents; suspending agents; dispersing or wetting agents; emulsifying agents, demulcents; buffers; salts; thickening agents; fillers; emulsifying agents; antioxidants; antibiotics; antifungal agents; stabilizing agents; and pharmaceutically acceptable polymeric or hydrophobic materials. Other "additional ingredients" that may be included in the pharmaceutical compositions of the invention are known in the art and described, for example in Genaro, ed. (1985, Remington's Pharmaceutical Sciences, Mack Publishing Co., Easton, Pa.), which is incorporated herein by reference.

The composition of the invention may comprise a preservative from about 0.005% to 2.0% by total weight of the composition. The preservative is used to prevent spoilage in the case of exposure to contaminants in the environment. Examples of preservatives useful in accordance with the invention included but are not limited to those selected from the group consisting of benzyl alcohol, sorbic acid, parabens, imidurea and combinations thereof. A particularly preferred preservative is a combination of about 0.5% to 2.0% benzyl alcohol and 0.05% to 0.5% sorbic acid.

In an embodiment, the composition includes an antioxidant and a chelating agent that inhibits the degradation of one or more components of the composition. Preferred antioxidants for some compounds are BHT, BHA, alpha-tocopherol and ascorbic acid in the preferred range of about 0.01% to 0.3% and more preferably BHT in the range of 0.03% to 0.1% by weight by total weight of the composition. Preferably, the chelating agent is present in an amount of from 0.01% to 0.5% by weight by total weight of the composition. Particularly preferred chelating agents include edetate salts (e.g. disodium edetate) and citric acid in the weight range of about 0.01% to 0.20% and more preferably in the range of 0.02% to 0.10% by weight by total weight of the composition. The chelating agent is useful for chelating metal ions in the composition that may be detrimental to the shelf life of the formulation. While BHT and disodium edetate are the particularly preferred antioxidant and chelating agent respectively for some compounds, other suitable and equivalent antioxidants and chelating agents may be substituted therefore as would be known to those skilled in the art.

Liquid suspensions may be prepared using conventional methods to achieve suspension of the HMW-HA or other composition of the invention in an aqueous or oily vehicle. Aqueous vehicles include, for example, water, and isotonic saline. Oily vehicles include, for example, almond oil, oily esters, ethyl alcohol, vegetable oils such as arachis, olive, sesame, or coconut oil, fractionated vegetable oils, and mineral oils such as liquid paraffin. Liquid suspensions may further comprise one or more additional ingredients including, but not limited to, suspending agents, dispersing or wetting agents, emulsifying agents, demulcents, preservatives, buffers, salts, flavorings, coloring agents, and sweetening agents. Oily suspensions may further comprise a thickening agent. Known suspending agents include, but are not limited to, sorbitol syrup, hydrogenated edible fats, sodium alginate, polyvinylpyrrolidone, gum tragacanth, gum acacia, and cellulose derivatives such as sodium carboxymethylcellulose, methylcellulose, hydroxypropylmethylcellulose. Known dispersing or wetting agents include, but are not limited to, naturally-occurring phosphatides such as lecithin, condensation products of an alkylene oxide with a fatty acid, with a long chain aliphatic alcohol, with a partial ester derived from a fatty acid and a hexitol, or with a partial ester derived from a fatty acid and a hexitol anhydride (e.g., polyoxyethylene stearate, heptadecaethyleneoxycetanol, polyoxyethylene sorbitol monooleate, and polyoxyethylene sorbitan monooleate, respectively). Known emulsifying agents include, but are not limited to, lecithin, and acacia. Known preservatives include, but are not limited to, methyl, ethyl, or n-propyl-para-hydroxybenzoates, ascorbic acid, and sorbic acid.

Powdered and granular formulations of a pharmaceutical preparation of the invention may be prepared using known methods. Such formulations may be administered directly to a subject, used, for example, to form tablets, to fill capsules, or to prepare an aqueous or oily suspension or solution by addition of an aqueous or oily vehicle thereto. Each of these formulations may further comprise one or more of dispersing or wetting agent, a suspending agent, and a preservative. Additional excipients, such as fillers and sweetening, flavoring, or coloring agents, may also be included in these formulations.

A pharmaceutical composition of the invention may also be prepared, packaged, or sold in the form of oil-in-water emulsion or a water-in-oil emulsion. The oily phase may be a vegetable oil such as olive or arachis oil, a mineral oil such as liquid paraffin, or a combination of these. Such compositions may further comprise one or more emulsifying agents such as naturally occurring gums such as gum acacia or gum tragacanth, naturally-occurring phosphatides such as soybean or lecithin phosphatide, esters or partial esters derived from combinations of fatty acids and hexitol anhydrides such as sorbitan monooleate, and condensation products of such partial esters with ethylene oxide such as polyoxyethylene sorbitan monooleate. These emulsions may also contain additional ingredients including, for example, sweetening or flavoring agents.

Methods for impregnating or coating a material with a chemical composition are known in the art, and include, but are not limited to methods of depositing or binding a chemical composition onto a surface, methods of incorporating a chemical composition into the structure of a material during the synthesis of the material (i.e., such as with a physiologically degradable material), and methods of absorbing an aqueous or oily solution or suspension into an absorbent material, with or without subsequent drying.

The regimen of administration may affect what constitutes an effective amount. The therapeutic formulations may be administered to the subject either prior to or after a diagnosis of disease. Further, several divided dosages, as well as staggered dosages may be administered daily or sequentially, or the dose may be continuously infused, or may be a bolus injection. Further, the dosages of the therapeutic formulations may be proportionally increased or decreased as indicated by the exigencies of the therapeutic or prophylactic situation.

Administration of the compositions of the present invention to a subject, preferably a mammal, more preferably a human, may be carried out using known procedures, at dosages and for periods of time effective to prevent or treat disease. An effective amount of the therapeutic compound necessary to achieve a therapeutic effect may vary according to factors such as the activity of the particular compound employed; the time of administration; the rate of excretion of the compound; the duration of the treatment; other drugs, compounds or materials used in combination with the compound; the state of the disease or disorder, age, sex, weight, condition, general health and prior medical history of the subject being treated, and like factors well-known in the medical arts. Dosage regimens may be adjusted to provide the optimum therapeutic response. For example, several divided doses may be administered daily or the dose may be proportionally reduced as indicated by the exigencies of the therapeutic situation. A non-limiting example of an effective dose range for a therapeutic compound of the invention is from about 1 and 5,000 mg/kg of body weight/per day. One of ordinary skill in the art would be able to study the relevant factors and make the determination regarding the effective amount of the therapeutic compound without undue experimentation.

The compound may be administered to a subject as frequently as several times daily, or it may be administered less frequently, such as once a day, once a week, once every two weeks, once a month, or even less frequently, such as once every several months or even once a year or less. It is understood that the amount of compound dosed per day may be administered, in non-limiting examples, every day, every other day, every 2 days, every 3 days, every 4 days, or every 5 days. For example, with every other day administration, a 5 mg per day dose may be initiated on Monday with a first subsequent 5 mg per day dose administered on Wednesday, a second subsequent 5 mg per day dose administered on Friday, and so on. The frequency of the dose will be readily apparent to the skilled artisan and will depend upon any number of factors, such as, but not limited to, the type and severity of the disease being treated, the type and age of the animal, etc.

Actual dosage levels of the active ingredients in the pharmaceutical compositions of this invention may be varied so as to obtain an amount of the active ingredient that is effective to achieve the desired therapeutic response for a particular subject, composition, and mode of administration, without being toxic to the subject.

A medical doctor, e.g., physician or veterinarian, having ordinary skill in the art may readily determine and prescribe the effective amount of the pharmaceutical composition required. For example, the physician or veterinarian could start doses of the compounds of the invention employed in the pharmaceutical composition at levels lower than that required in order to achieve the desired therapeutic effect and gradually increase the dosage until the desired effect is achieved.

In particular embodiments, it is especially advantageous to formulate the compound in dosage unit form for ease of administration and uniformity of dosage. Dosage unit form as used herein refers to physically discrete units suited as unitary dosages for the subjects to be treated; each unit containing a predetermined quantity of therapeutic compound calculated to produce the desired therapeutic effect in association with the required pharmaceutical vehicle. The dosage unit forms of the invention are dictated by and directly dependent on (a) the unique characteristics of the therapeutic compound and the particular therapeutic effect to be achieved, and (b) the limitations inherent in the art of compounding/formulating such a therapeutic compound for the treatment of a disease in a subject.

In one embodiment, the compositions of the invention are administered to the subject in dosages that range from one to five times per day or more. In another embodiment, the compositions of the invention are administered to the subject in range of dosages that include, but are not limited to, once every day, every two, days, every three days to once a week, and once every two weeks. It will be readily apparent to one skilled in the art that the frequency of administration of the various combination compositions of the invention will vary from subject to subject depending on many factors including, but not limited to, age, disease or disorder to be treated, gender, overall health, and other factors. Thus, the invention should not be construed to be limited to any particular dosage regime and the precise dosage and composition to be administered to any subject will be determined by the attending physical taking all other factors about the subject into account.

Compounds of the invention for administration may be in the range of from about 1 mg to about 10,000 mg, about 20 mg to about 9,500 mg, about 40 mg to about 9,000 mg, about 75 mg to about 8,500 mg, about 150 mg to about 7,500 mg, about 200 mg to about 7,000 mg, about 3050 mg to about 6,000 mg, about 500 mg to about 5,000 mg, about 750 mg to about 4,000 mg, about 1 mg to about 3,000 mg, about 10 mg to about 2,500 mg, about 20 mg to about 2,000 mg, about 25 mg to about 1,500 mg, about 50 mg to about 1,000 mg, about 75 mg to about 900 mg, about 100 mg to about 800 mg, about 250 mg to about 750 mg, about 300 mg to about 600 mg, about 400 mg to about 500 mg, and any and all whole or partial increments there between.

In some embodiments, the dose of a compound of the invention is from about 1 mg and about 2,500 mg. In some embodiments, a dose of a compound of the invention used in compositions described herein is less than about 10,000 mg, or less than about 8,000 mg, or less than about 6,000 mg, or less than about 5,000 mg, or less than about 3,000 mg, or less than about 2,000 mg, or less than about 1,000 mg, or less than about 500 mg, or less than about 200 mg, or less than about 50 mg. Similarly, in some embodiments, a dose of a second compound (i.e., a drug used for treating the same or another disease as that treated by the compositions of the invention) as described herein is less than about 1,000 mg, or less than about 800 mg, or less than about 600 mg, or less than about 500 mg, or less than about 400 mg, or less than about 300 mg, or less than about 200 mg, or less than about 100 mg, or less than about 50 mg, or less than about 40 mg, or less than about 30 mg, or less than about 25 mg, or less than about 20 mg, or less than about 15 mg, or less than about 10 mg, or less than about 5 mg, or less than about 2 mg, or less than about 1 mg, or less than about 0.5 mg, and any and all whole or partial increments thereof.

In one embodiment, the present invention is directed to a packaged pharmaceutical composition comprising a container holding a therapeutically effective amount of a compound or conjugate of the invention, alone or in combination with a second pharmaceutical agent; and instructions for using the compound or conjugate to treat, prevent, or reduce one or more symptoms of a disease in a subject.

The term "container" includes any receptacle for holding the pharmaceutical composition. For example, in one embodiment, the container is the packaging that contains the pharmaceutical composition. In other embodiments, the container is not the packaging that contains the pharmaceutical composition, i.e., the container is a receptacle, such as a box or vial that contains the packaged pharmaceutical composition or unpackaged pharmaceutical composition and the instructions for use of the pharmaceutical composition. Moreover, packaging techniques are well known in the art. It should be understood that the instructions for use of the pharmaceutical composition may be contained on the packaging containing the pharmaceutical composition, and as such the instructions form an increased functional relationship to the packaged product. However, it should be understood that the instructions may contain information pertaining to the compound's ability to perform its intended function, e.g., treating or preventing a disease in a subject, or delivering an imaging or diagnostic agent to a subject.

Routes of administration of any of the compositions of the invention include oral, nasal, rectal, parenteral, sublingual, transdermal, transmucosal (e.g., sublingual, lingual, (trans)buccal, (trans)urethral, vaginal (e.g., trans- and perivaginally), (intra)nasal, and (trans)rectal), intravesical, intrapulmonary, intraduodenal, intragastrical, intrathecal, subcutaneous, intramuscular, intradermal, intra-arterial, intravenous, intrabronchial, inhalation, and topical administration.

Suitable compositions and dosage forms include, for example, tablets, capsules, caplets, pills, gel caps, troches, dispersions, suspensions, solutions, syrups, granules, beads, transdermal patches, gels, powders, pellets, magmas, lozenges, creams, pastes, plasters, lotions, discs, suppositories, liquid sprays for nasal or oral administration, dry powder or aerosolized formulations for inhalation, compositions and formulations for intravesical administration and the like. It should be understood that the formulations and compositions that would be useful in the present invention are not limited to the particular formulations and compositions that are described herein.

These methods described herein are by no means all-inclusive, and further methods to suit the specific application will be apparent to the ordinary skilled artisan. Moreover, the effective amount of the compositions can be further approximated through analogy to compounds known to exert the desired effect.

EXPERIMENTAL EXAMPLES

The invention is further described in detail by reference to the following experimental examples. These examples are provided for purposes of illustration only, and are not intended to be limiting unless otherwise specified. Thus, the invention should in no way be construed as being limited to the following examples, but rather, should be construed to encompass any and all variations which become evident as a result of the teaching provided herein.

Without further description, it is believed that one of ordinary skill in the art can, using the preceding description and the following illustrative examples, make and utilize the present invention and practice the claimed methods. The following working examples therefore, specifically point out the preferred embodiments of the present invention, and are not to be construed as limiting in any way the remainder of the disclosure.

Example 1: Culture-Independent Discovery of the Malacidins as Calcium-Dependent Antibiotics with Activity Against Multidrug-Resistant Gram-Positive Pathogens In an effort to access bacterial natural products (NPs), a culture-independent NP discovery platform was developed that involves sequencing, bioinformatic analysis and heterologous expression of biosynthetic gene clusters captured on DNA extracted from environmental samples. The data presented herein describes the application of this platform to the discovery of the malacidins, a distinctive class of antibiotics that are commonly encoded in soil microbiomes but have never been reported in culture-based NP discovery efforts. The malacidins are active against multidrug-resistant pathogens, sterilize methicillin-resistant *Staphylococcus aureus* skin infections in an animal wound model and did not select for resistance under laboratory conditions.

Calcium-dependent antibiotics are a small family of N-acylated cyclic peptides that require calcium for antibacterial activity. Known members of this family contain a conserved Asp-X-Asp-Gly motif that is thought to facilitate calcium binding (Strieker and Marahiel, 2009, *ChemBioChem* 10, 607-616; Jung, et al., 2004, Chem. Biol. 11, 949-957; Bunkoczi et al., 2005, *Acta Crystallogr. Sect. D.* 61, 1160-1164). One example, daptomycin, has proved useful clinically in the treatment of multidrug-resistant bacteremia. Calcium-dependent antibiotics are of particular interest to because individual family members have been shown to have discrete modes of action, targeting either cell wall biosynthesis or cell membrane integrity. It is hypothesized herein that the conserved Asp-X-Asp-Gly calcium-binding motif might be indicative of a broader collection of uncharacterized, bacterially encoded antibiotics with diverse mechanisms of action and therapeutic potential.

To test this hypothesis, a sequence-guided screen of diverse soils was performed for biosynthetic gene clusters (BGCs) that encode calcium-binding motifs. Due to the complexity of soil metagenomes, it remains challenging to shotgun sequence deep enough to generate data that are broadly useful for BGC discovery (Katz et al., 2016, *J. Ind. Microbiol. Biotechnol.* 43, 129-141). Sequencing strategies have been developed that rely on the barcoding of biosynthetic genes using degenerate polymerase chain reaction (PCR) primers to parse mixtures of BGCs present in environmental samples (Katz et al., 2016, *J. Ind. Microbiol. Biotechnol* 43, 129-141; Owen et al., 2013, PNAS 110, 11797-11802). In this approach, primers targeting conserved NP biosynthetic genes are used to generate PCR amplicon pools containing homologous genes from BGCs present in an environmental DNA (eDNA) sample (FIG. 1A). Individual next-generation sequencing reads derived from these amplicons (NP sequence tags, NPSTs) are used to predict BGCs present in a sample by comparing them to a database of sequences from characterized BGCs. This analysis is carried out using the bioinformatics platform eSNaPD (environmental Surveyor of Natural Product Diversity: http://esnapd2.rockefeller.edu) that was developed to evaluate metagenome-derived NPSTs (Owen et al., 2013, PNAS 110, 11797-11802; Reddy et al., 2014, *Chem. Biol.* 21, 1023-1033).

Known calcium-dependent antibiotics are biosynthesized by non-ribosomal peptide synthetases (NRPS). Accordingly, primers targeting NRPS adenylation domains (ADs) were used to track this family of NPs across diverse soil microbiomes. For this study, and as part of this ongoing soil metagenome-driven NP discovery efforts, the soil collection was expanded to more than 2,000 soils from ecologically and geographically diverse environments (Owen et al., 2013, PNAS 110, 11797-11802). Even using a conservative estimate of $10^3$ unique bacterial species per gram of soil (Tringe, S. G. et al., 2005, Science 308, 554-557), the diversity of bacteria present in this collection is expected to rival that of the largest culture collections. Initially, primers targeting NRPS ADs were used to screen eDNA isolated from small aliquots of each soil to identify environments predicted to contain gene clusters that encode for unidentified calcium-dependent antibiotics.

Three-quarters of sequenced soils had NPSTs that mapped to at least one AD from a known calcium-dependent antibiotic BGC (FIG. 5). Only 13% of these identified NPSTs cluster at ≥95% nucleotide identity to ADs found in characterized calcium-dependent antibiotics and less than 30% of them are found in more than one soil metagenome. Taken together, this indicates that the majority of lipopeptides encoded by the global soil metagenome are probably uncharacterized and that even within the large soil collection, only a fraction of the biosynthetic diversity that exists within the calcium-dependent antibiotic family has been captured.

Figure 5A:
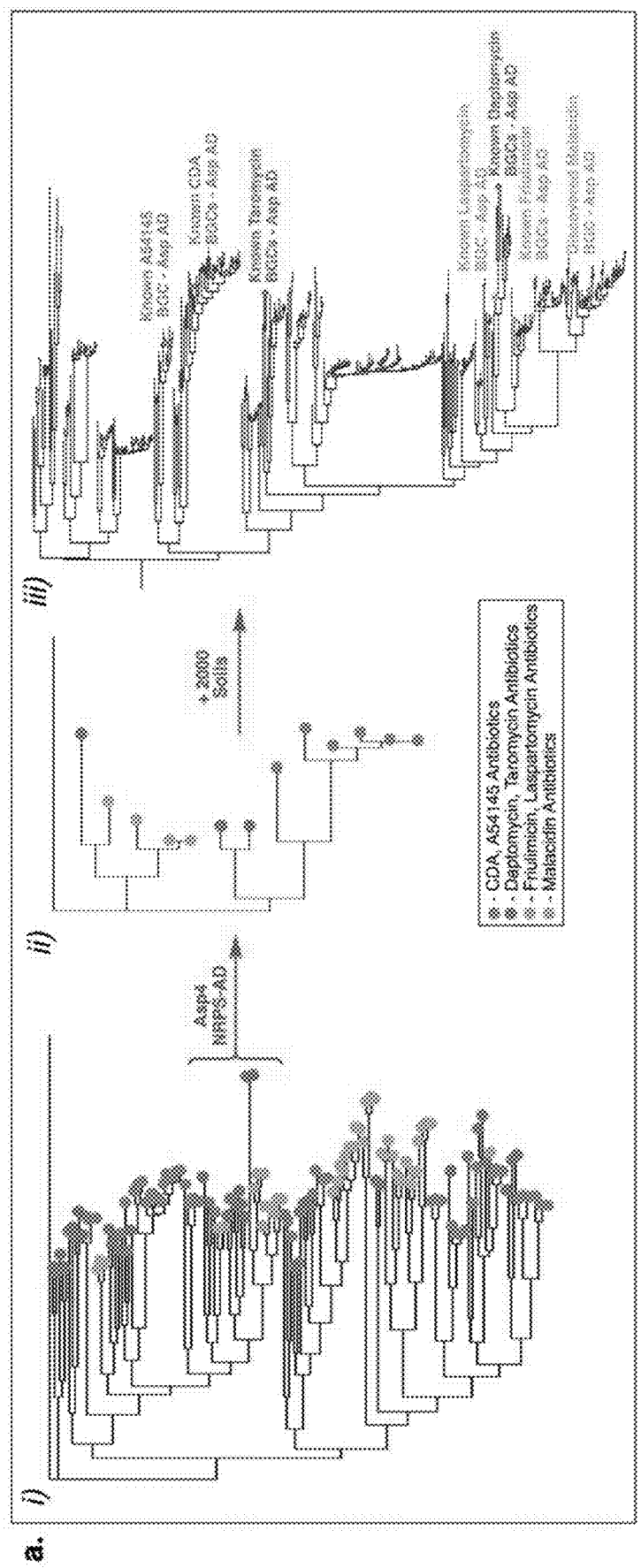
FIG. 5A through FIG. 5D, depicts additional bioinformatic analysis of calcium-dependent antibiotics.
Figure 5B:
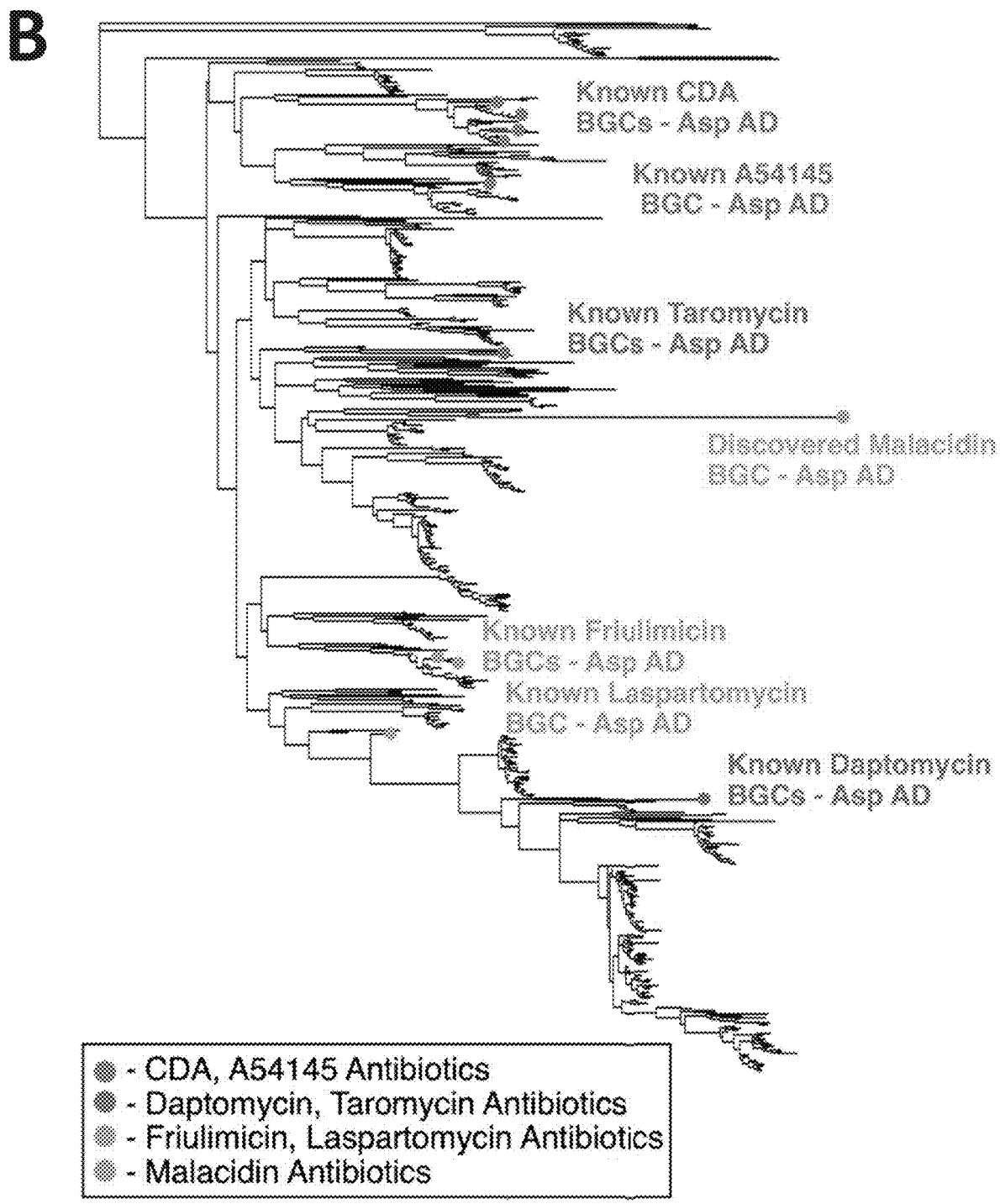

Phylogenetic analysis of AD sequences from characterized calcium-dependent antibiotics indicated that the domain responsible for incorporating the first aspartic acid (Asp4) in the conserved Asp-X-Asp-Gly motif most closely mapped to functional divergence of BGCs in this family (FIG. 5B). Therefore, eSNaPD data was focused on for this domain to track calcium-dependent antibiotic BGCs. A phylogenetic tree derived from tags associated with this domain showed numerous clades not associated with known BGCs, indicating the existence of uncharacterized calcium-dependent antibiotics in soil microbiomes. One distinct, eDNA-specific clade was found in 19% of metagenomes (FIG. 5B), suggesting that the BGCs associated with these tags belong to an abundant and yet uncharacterized family of antibiotics, which are called herein malacidins (metagenomic acidic lipopeptide antibiotic-cidins).

Figure 5C:
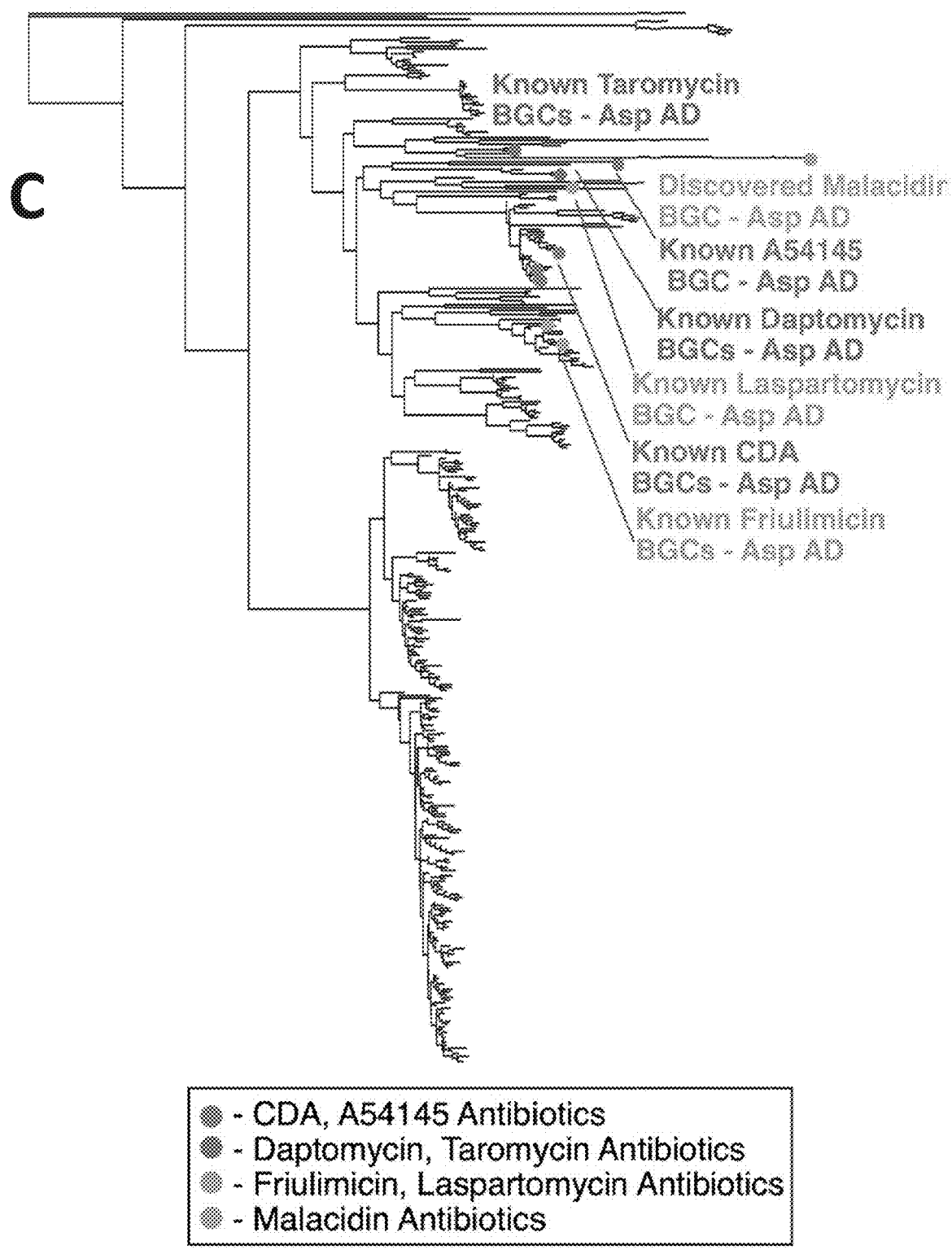
Figure 5D:
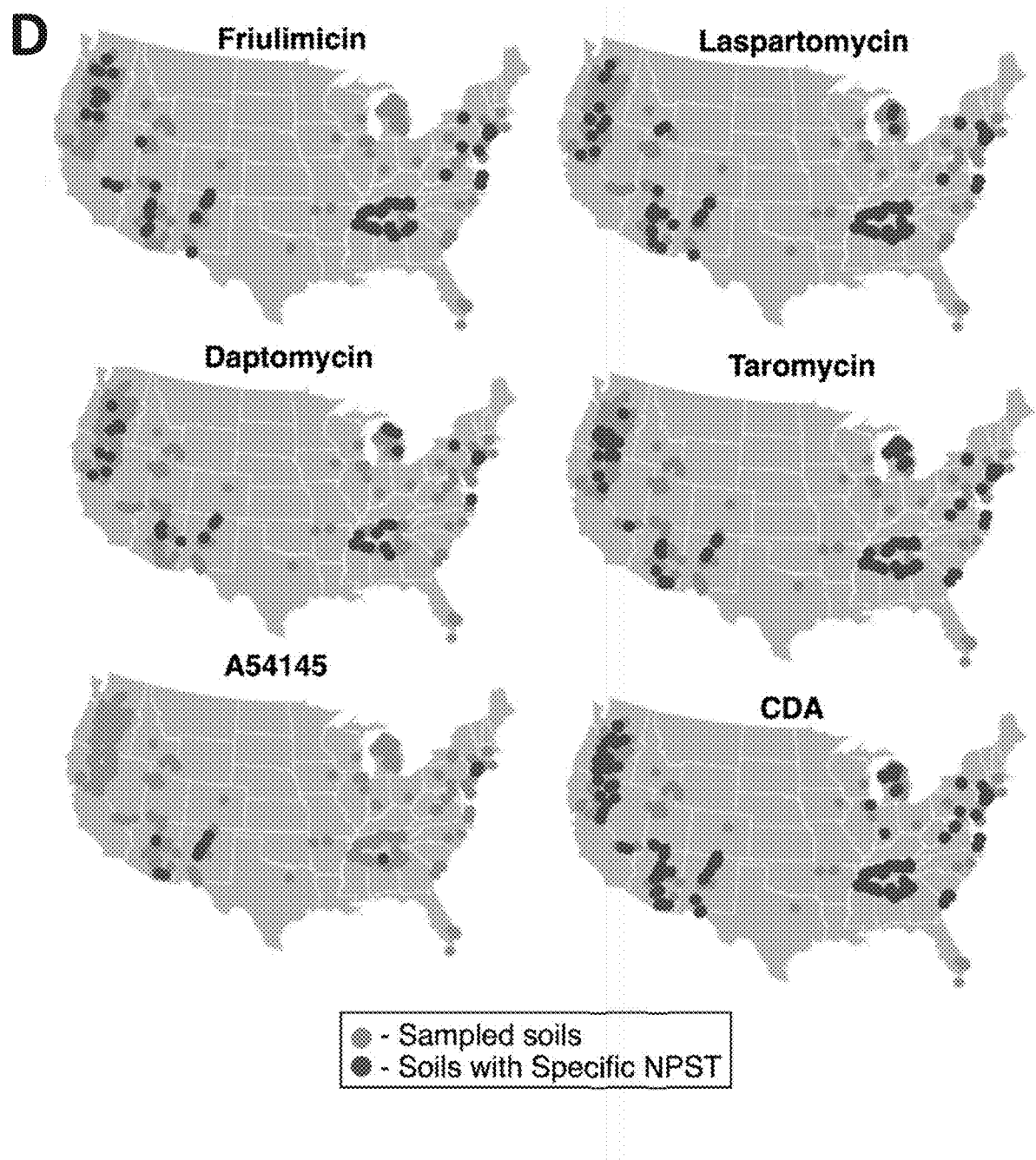
Figure 6:
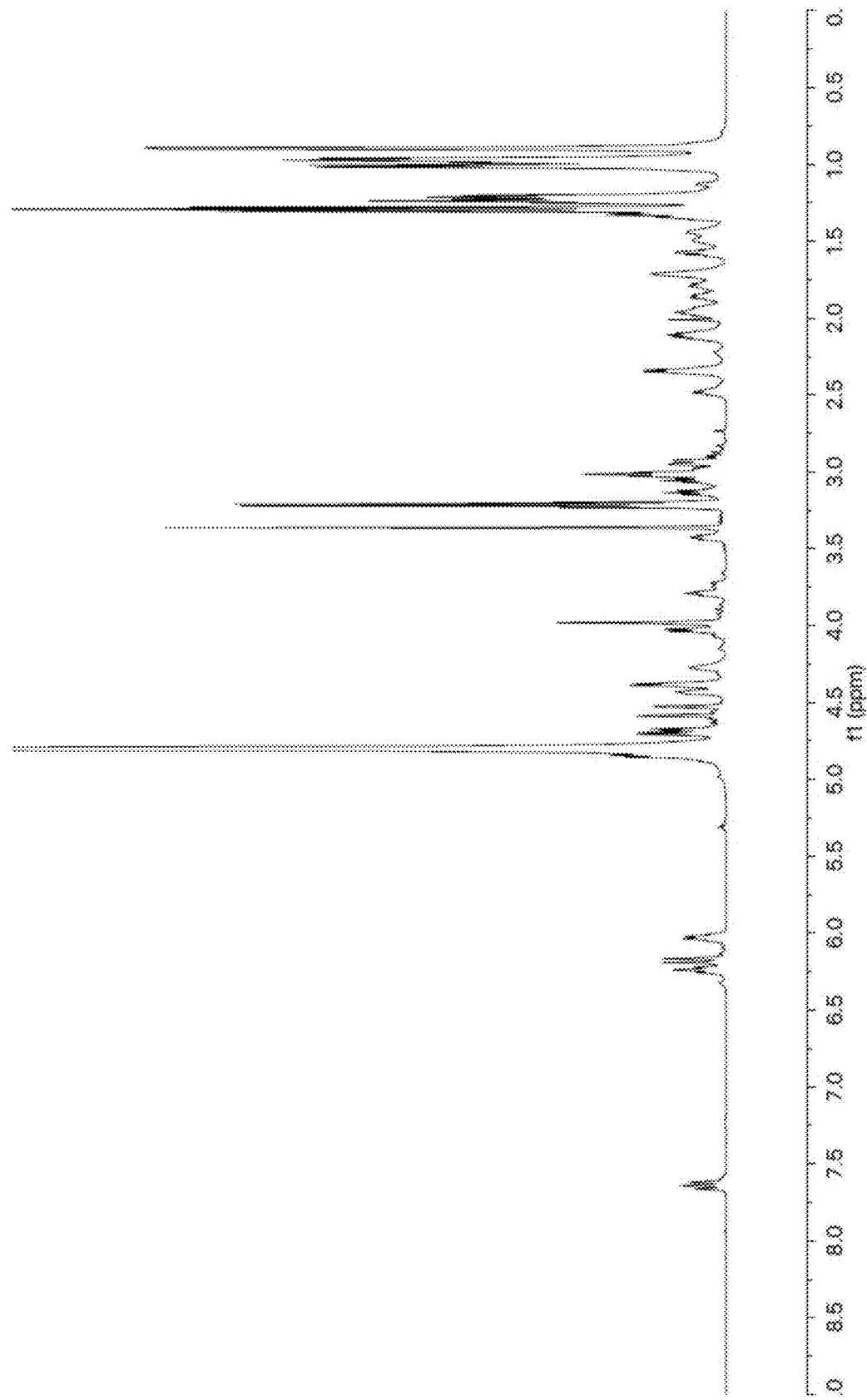
FIG. 6 depicts $^1$H NMR spectrum of malacidin A in $D_2O$. Representative NMR spectrum of malacidin from 4 independent fermentations and isolations.
Figure 7:
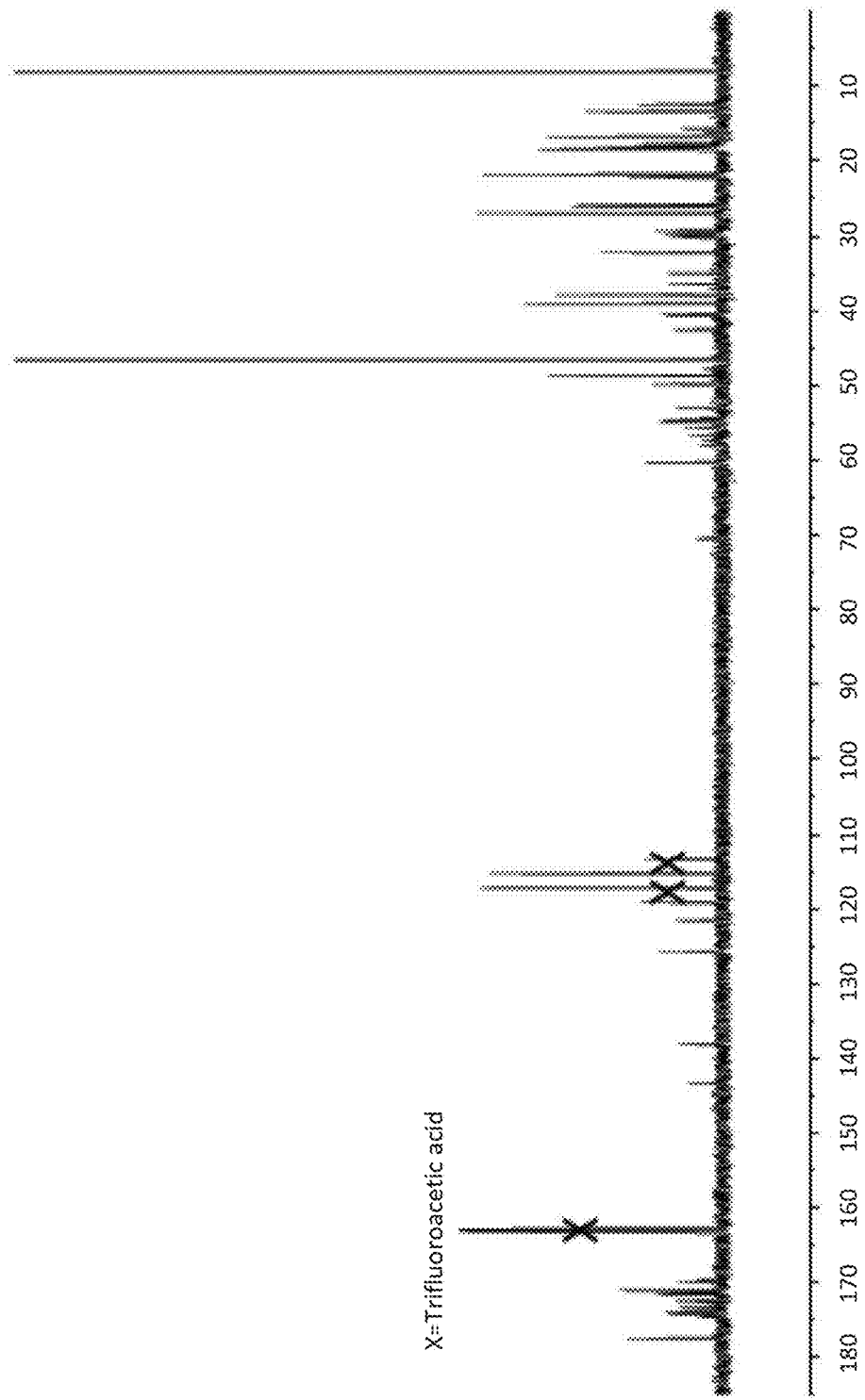
FIG. 7 depicts $^{13}$C NMR spectrum of malacidin A in $D_2O$. Representative NMR spectrum of malacidin from 4 independent fermentations and isolations. Chemical shifts of trifluoroacetic acid are indicated by an X.
Figure 8:
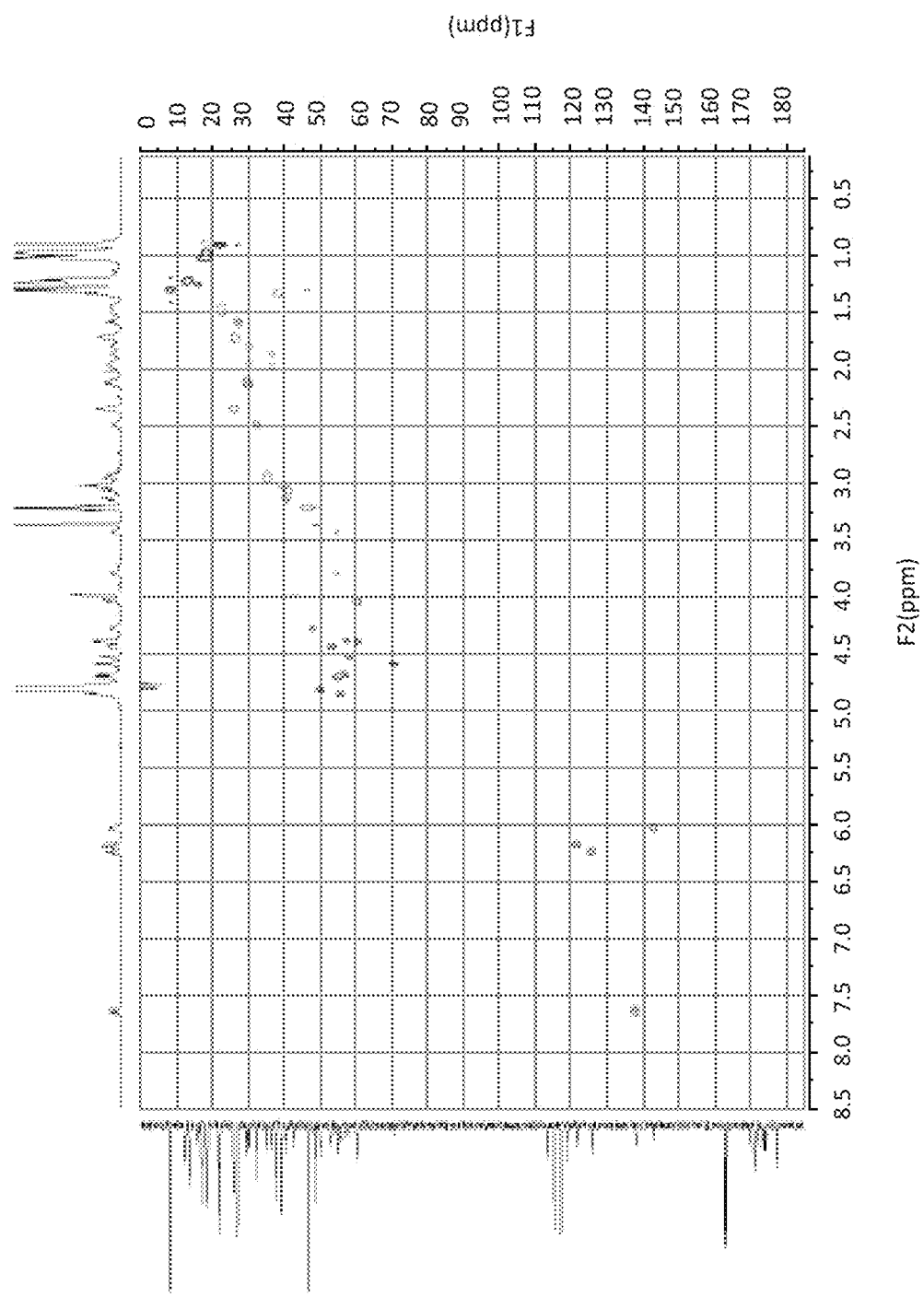
FIG. 8 depicts HSQC NMR spectrum of malacidin A. Representative NMR spectrum of malacidin from 4 independent fermentations and isolations.
Figure 9:
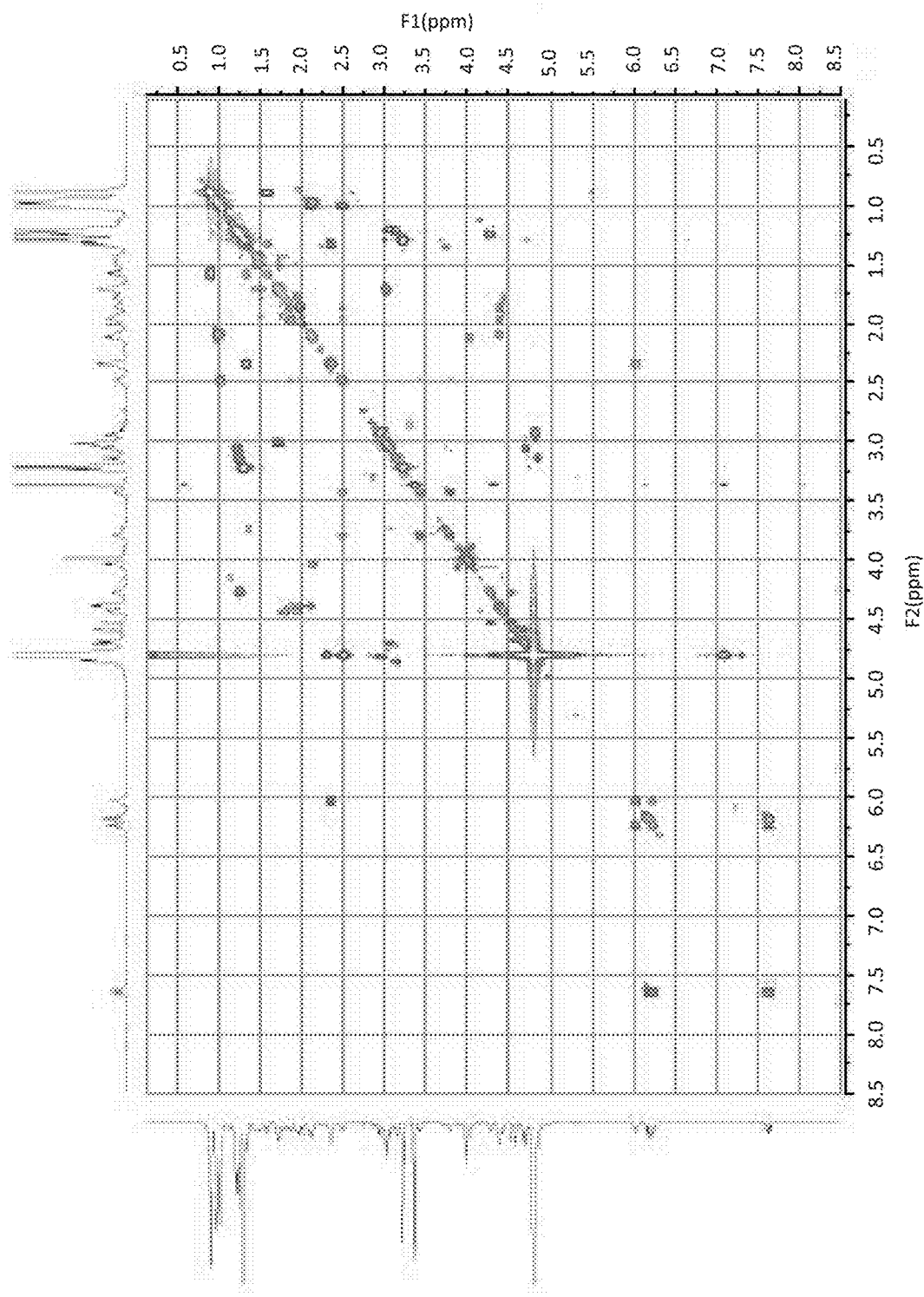
FIG. 9 depicts COSY NMR spectrum of malacidin A. Representative NMR spectrum of malacidin from 4 independent fermentations and isolations.
Figure 10:
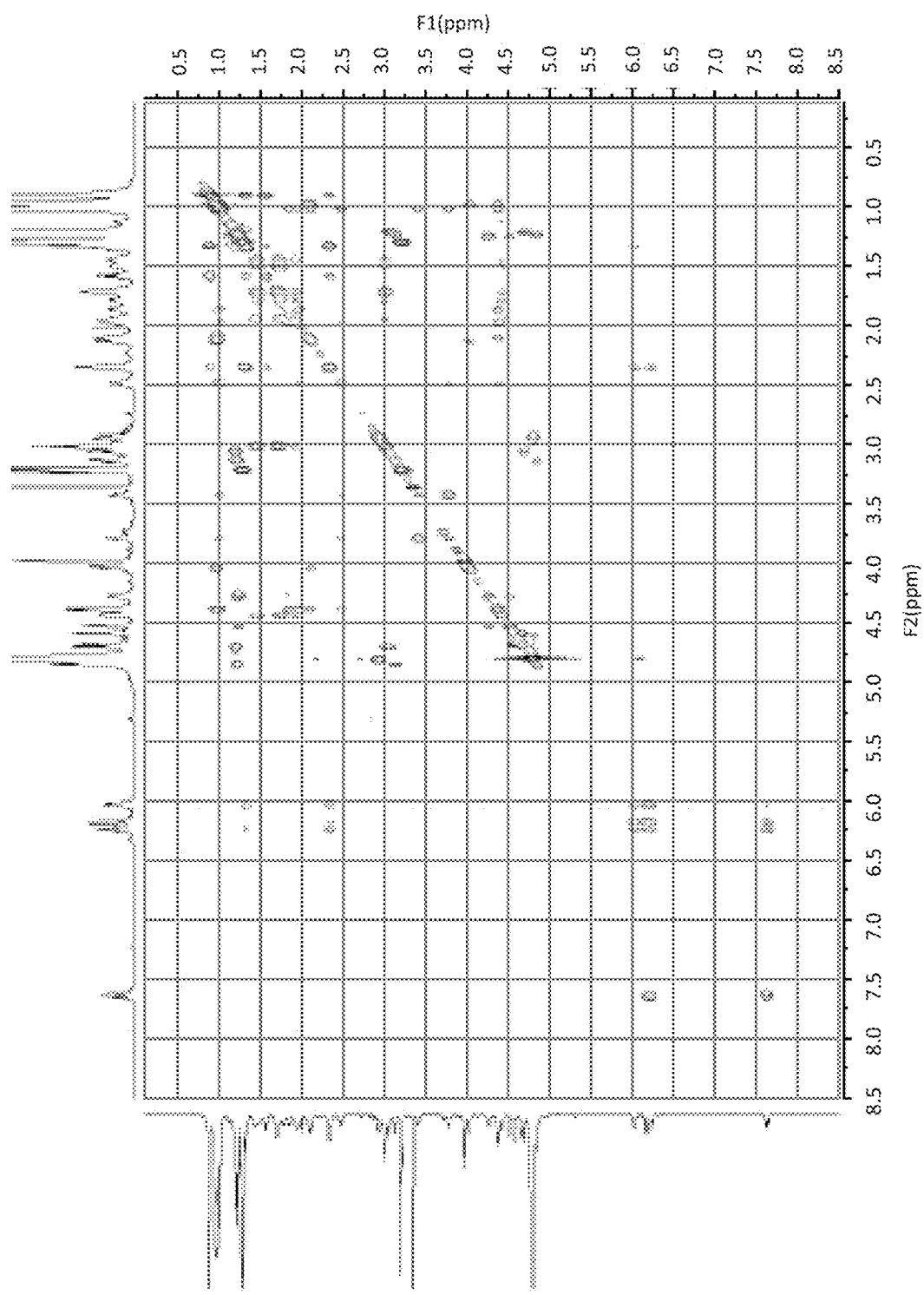
FIG. 10 depicts TOCSY NMR spectrum of malacidin A. Representative NMR spectrum of malacidin from 4 independent fermentations and isolations.
Figure 11:
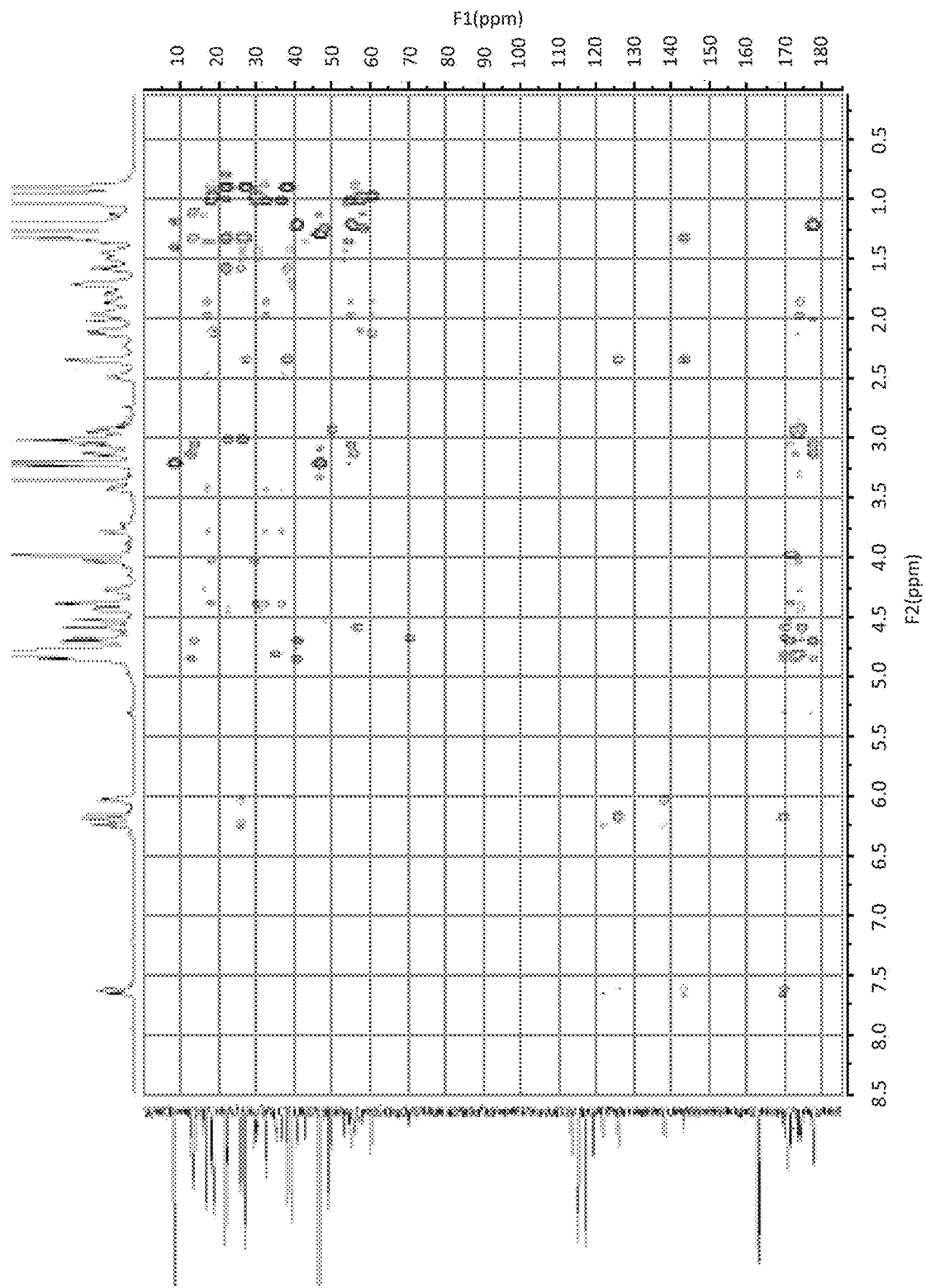
FIG. 11 depicts HMBC NMR spectrum of malacidin A. Representative NMR spectrum of malacidin from 4 independent fermentations and isolations.
Figure 12:
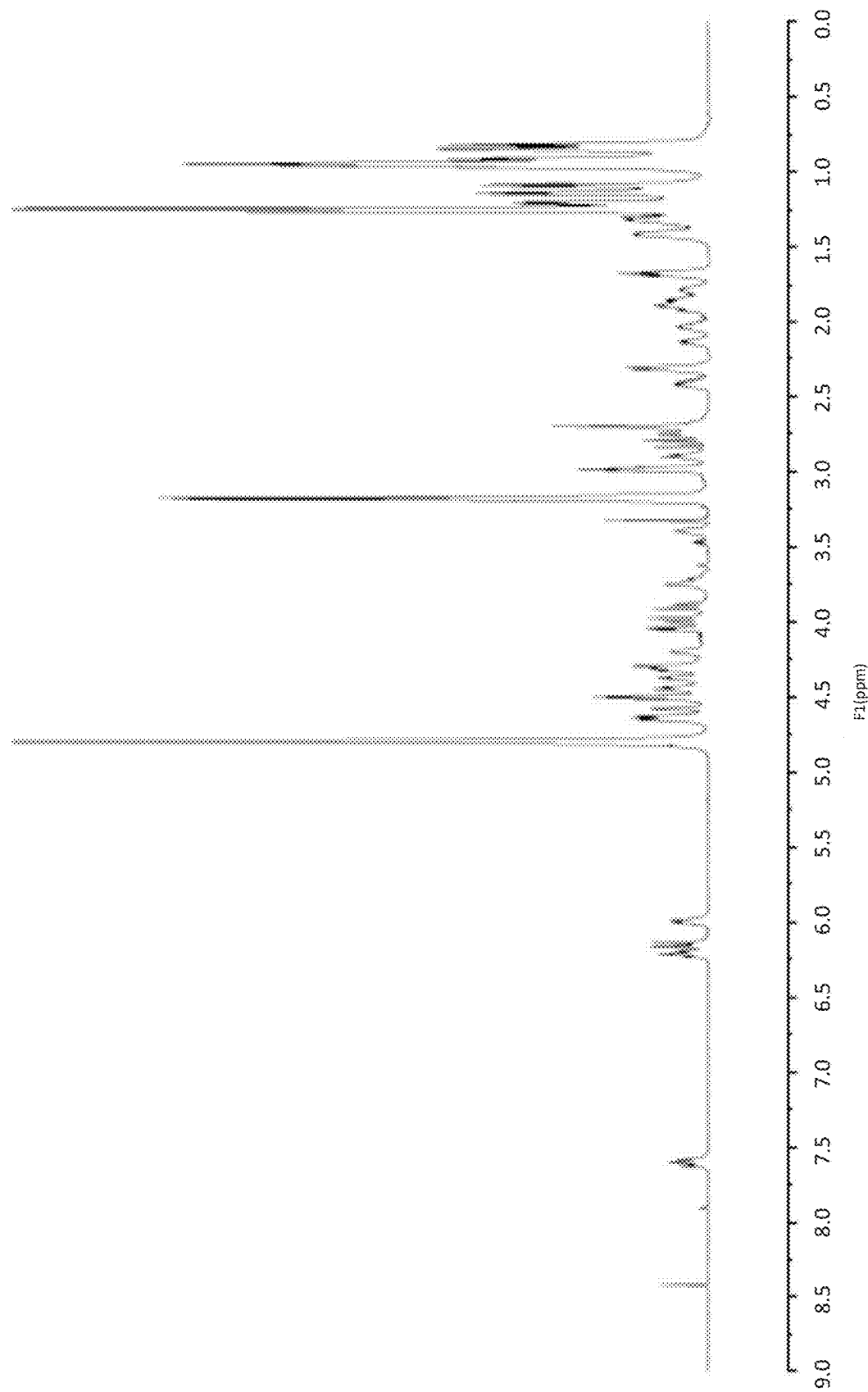
FIG. 12 depicts $^1$H NMR spectrum of malacidin B in $D_2O$. Representative NMR spectrum of malacidin from 4 independent fermentations and isolations.
Figure 13:
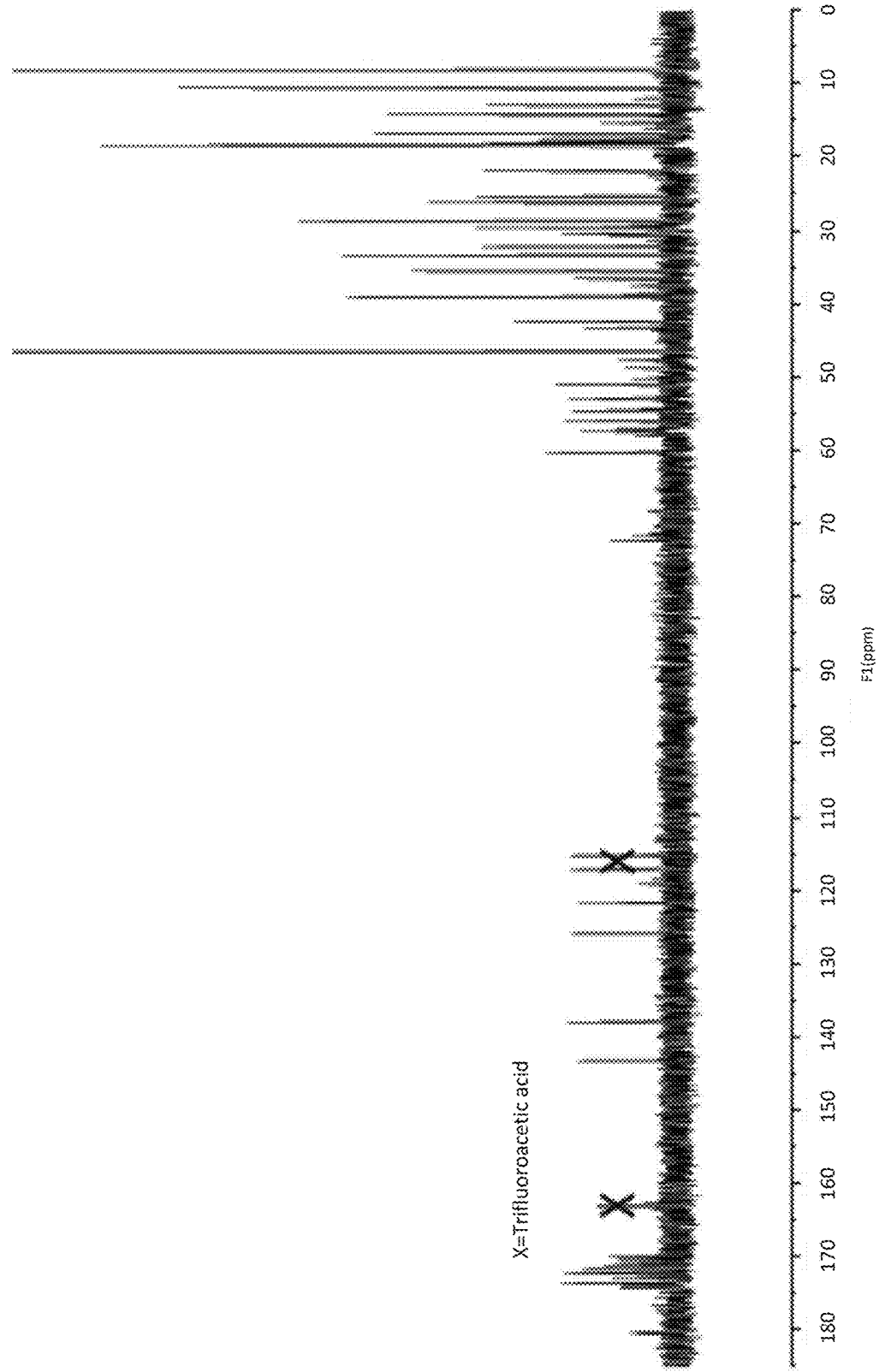
FIG. 13 depicts $^{13}$C NMR spectrum of malacidin B in $D_2O$. Representative NMR spectrum of malacidin from 4 independent fermentations and isolations. Chemical shifts of trifluoroacetic acid are indicated by an X.
Figure 14:
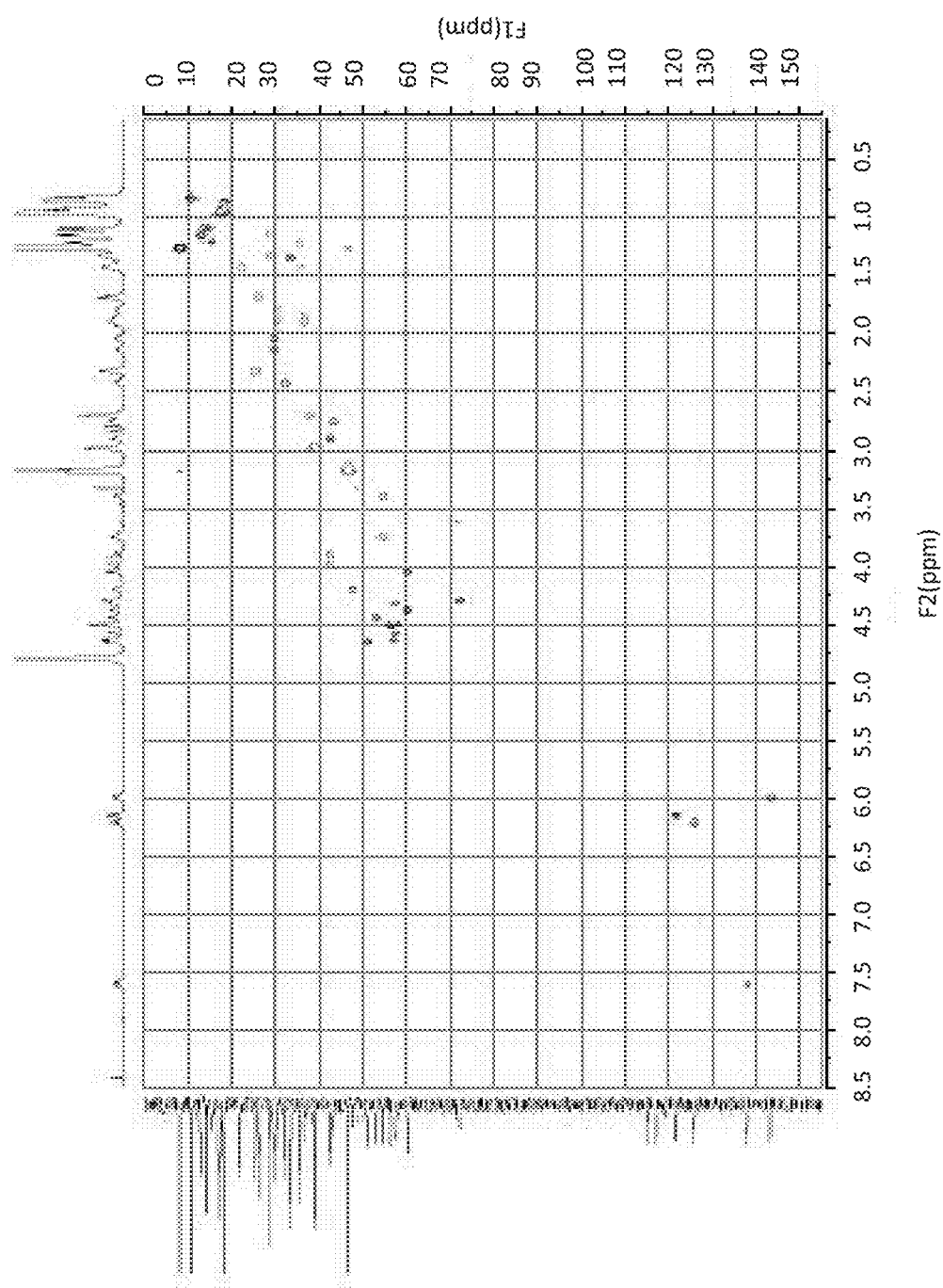
FIG. 14 depicts HSQC NMR spectrum of malacidin B. Representative NMR spectrum of malacidin from 4 independent fermentations and isolations.
Figure 15:
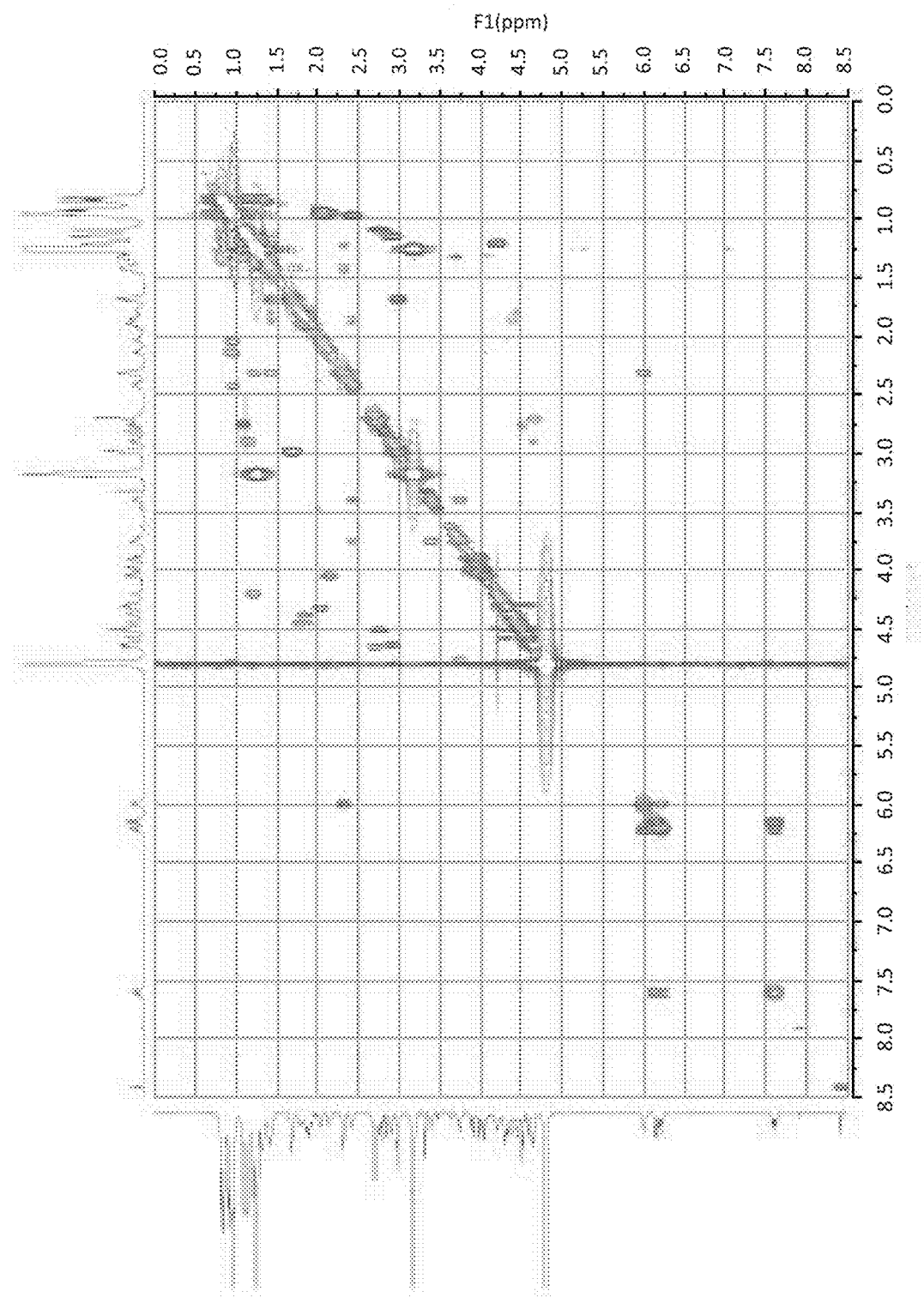
FIG. 15 depicts COSY NMR spectrum of malacidin B. Representative NMR spectrum of malacidin from 4 independent fermentations and isolations.
Figure 16:
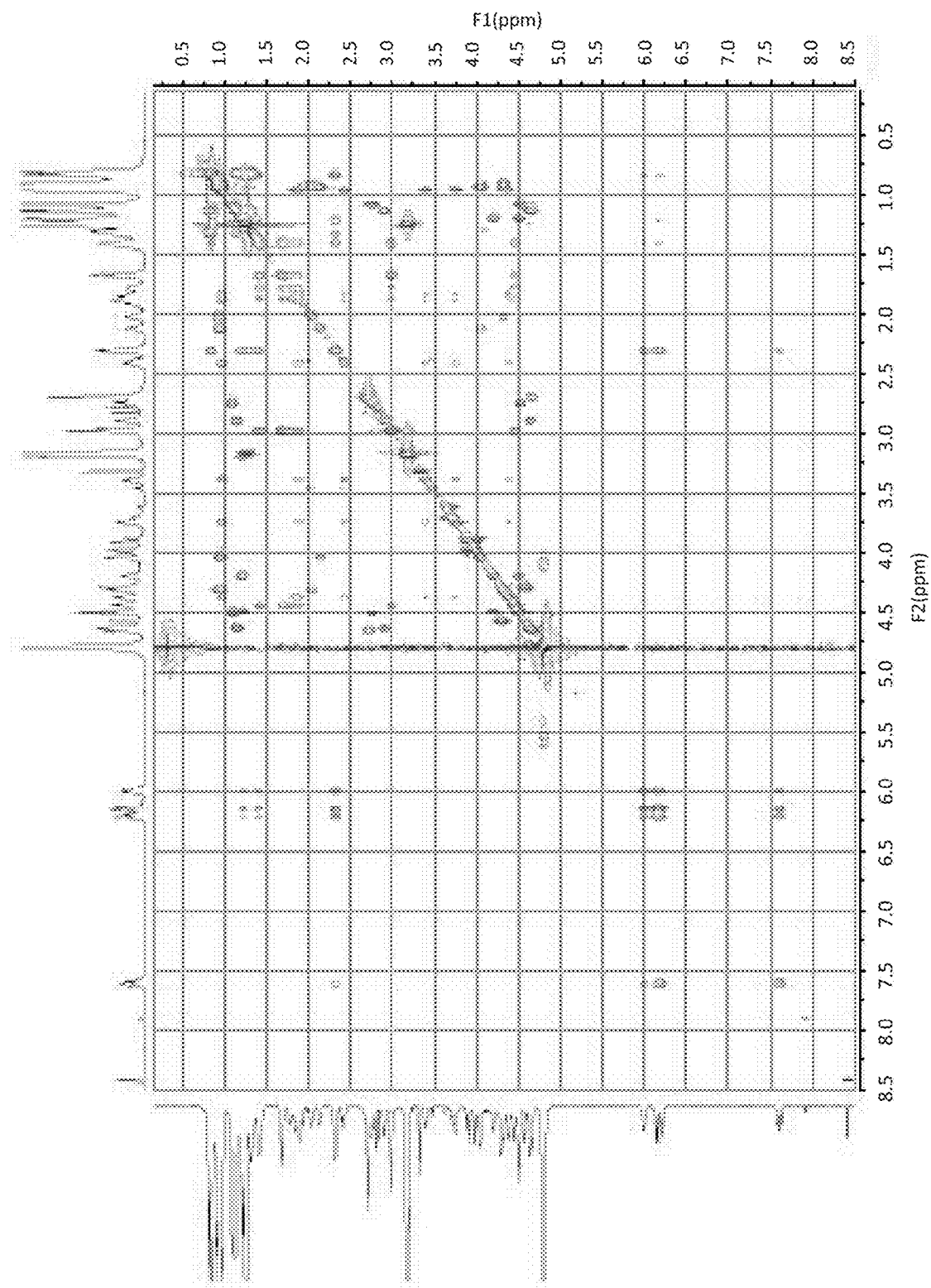
FIG. 16 depicts TOCSY NMR spectrum of malacidin B. Representative NMR spectrum of malacidin from 4 independent fermentations and isolations.
Figure 17:
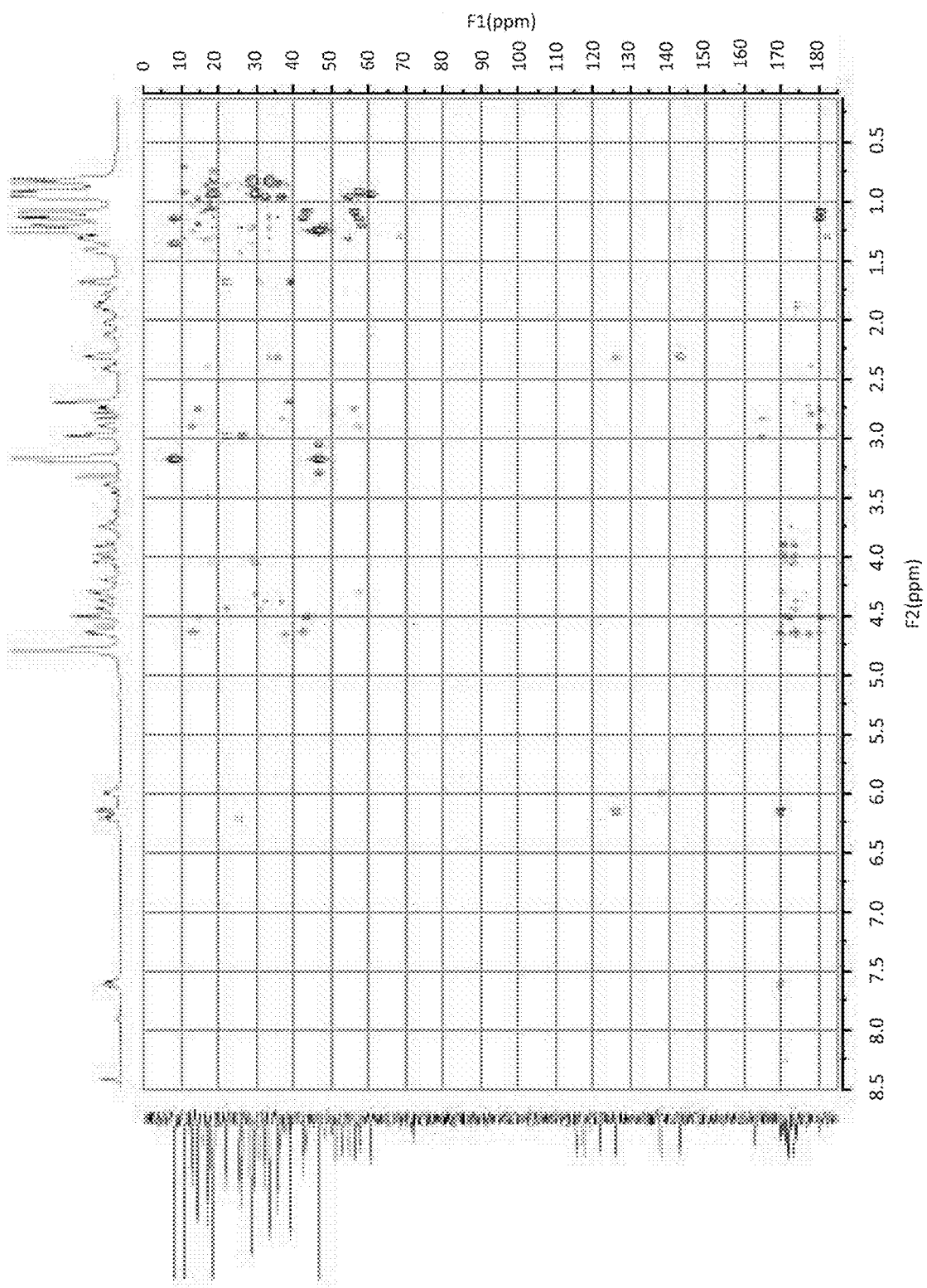
FIG. 17 depicts HMBC NMR spectrum of malacidin B. Representative NMR spectrum of malacidin from 4 independent fermentations and isolations FIG. 18, comprising
Figure 18A:
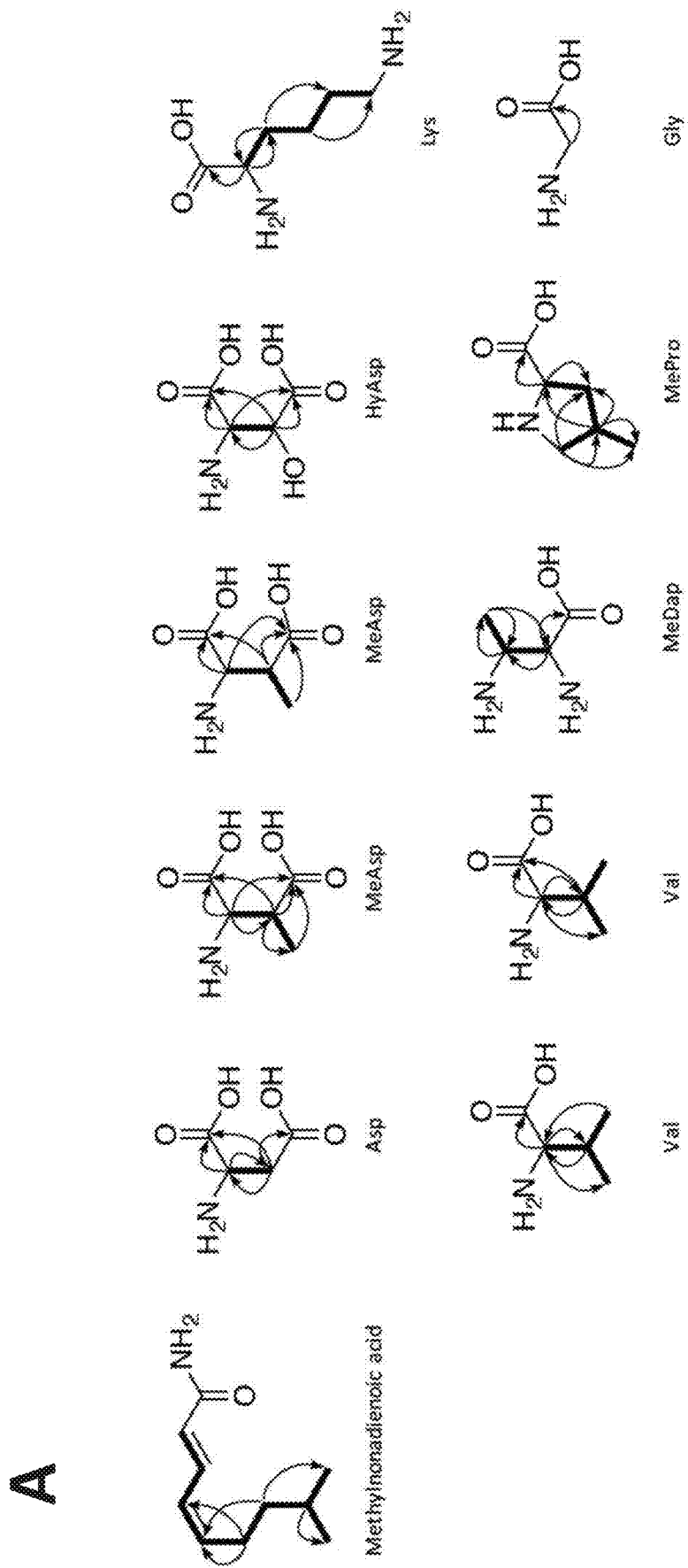
FIG. 18A and FIG. 18B, depicts the partial structures of malacidin A from NMR analysis.
Figure 18B:
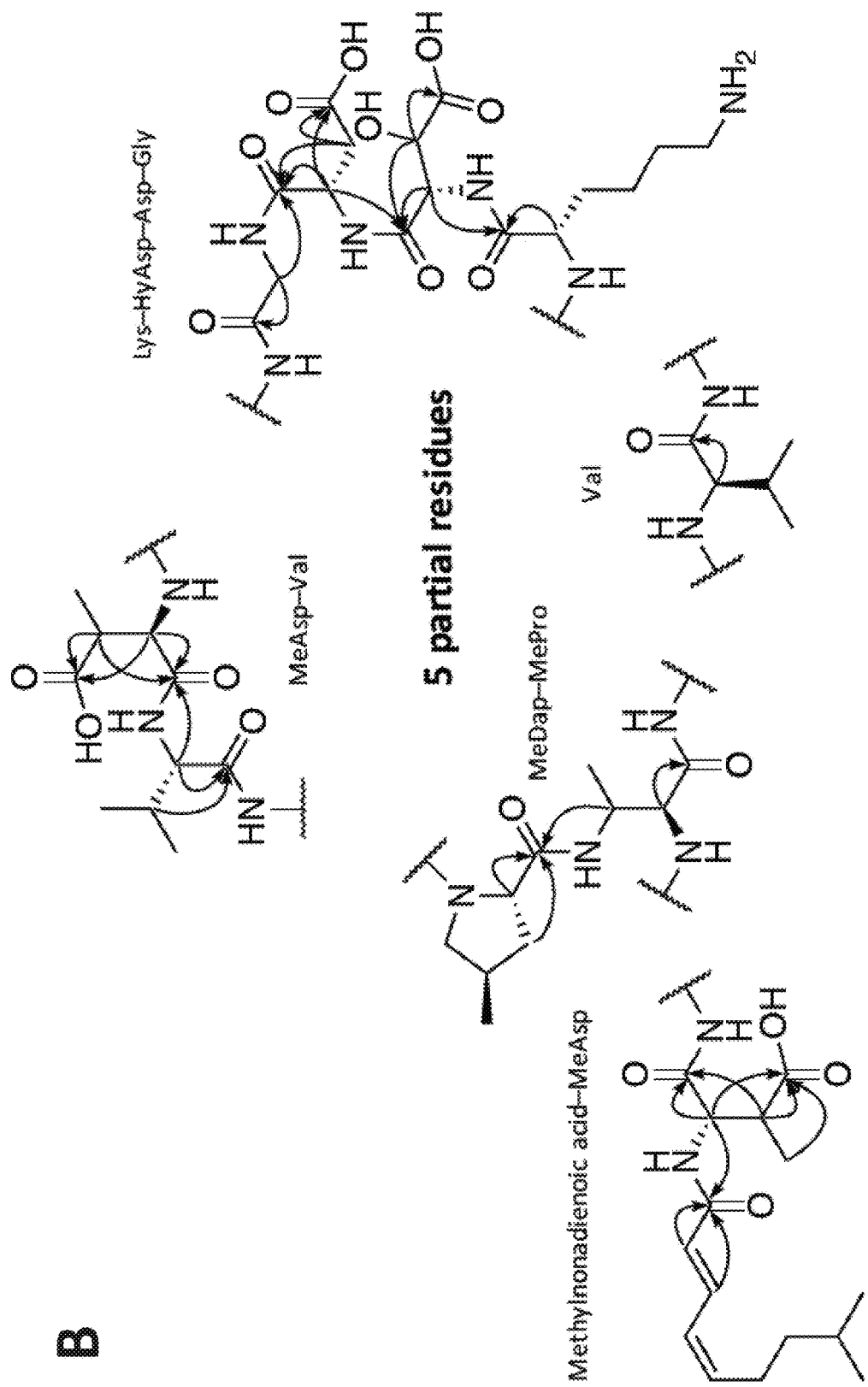
Figure 19A:
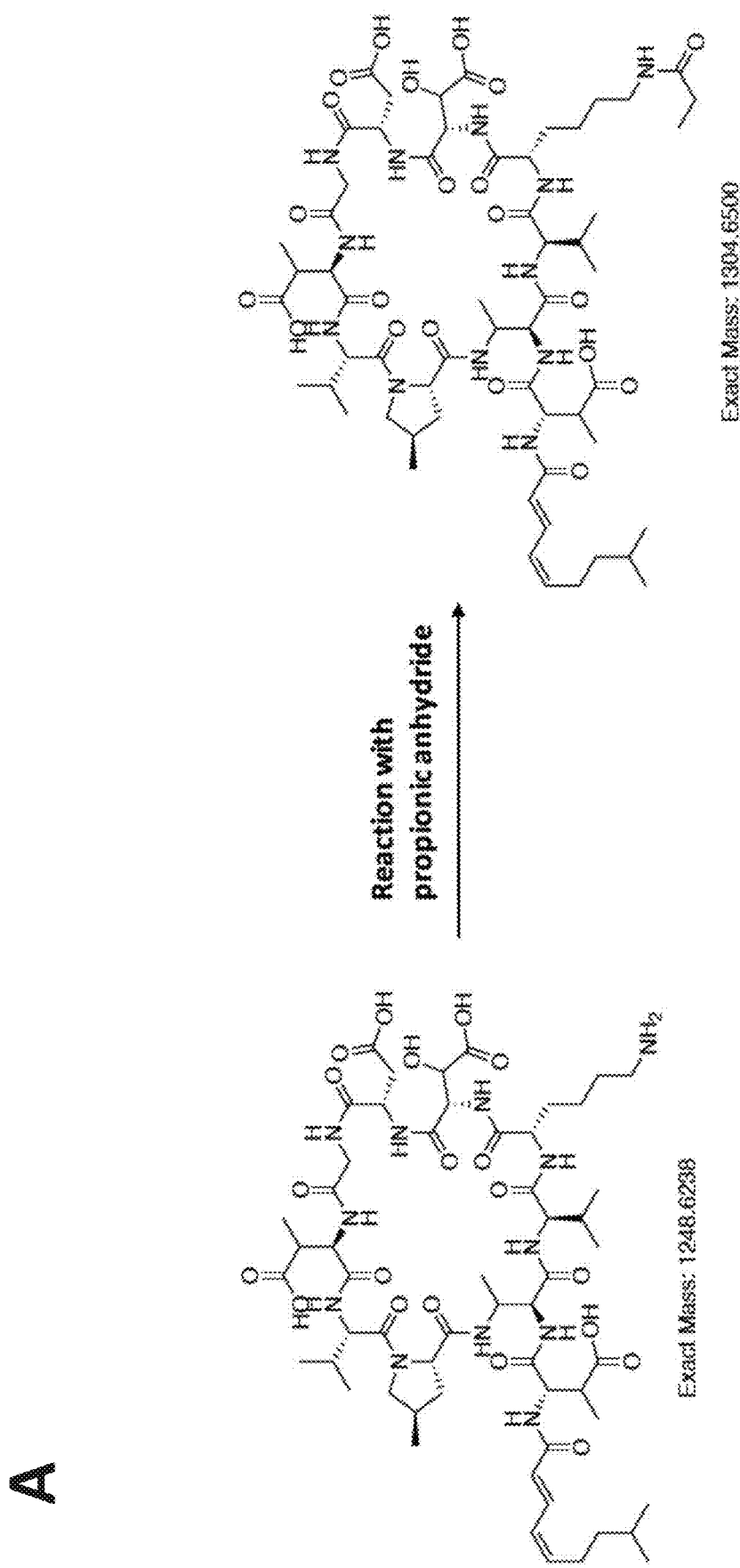
FIG. 19A through FIG. 19C, depicts ESI-MS/MS fragmentation patterns of propionate malacidin A.
Figure 19B:
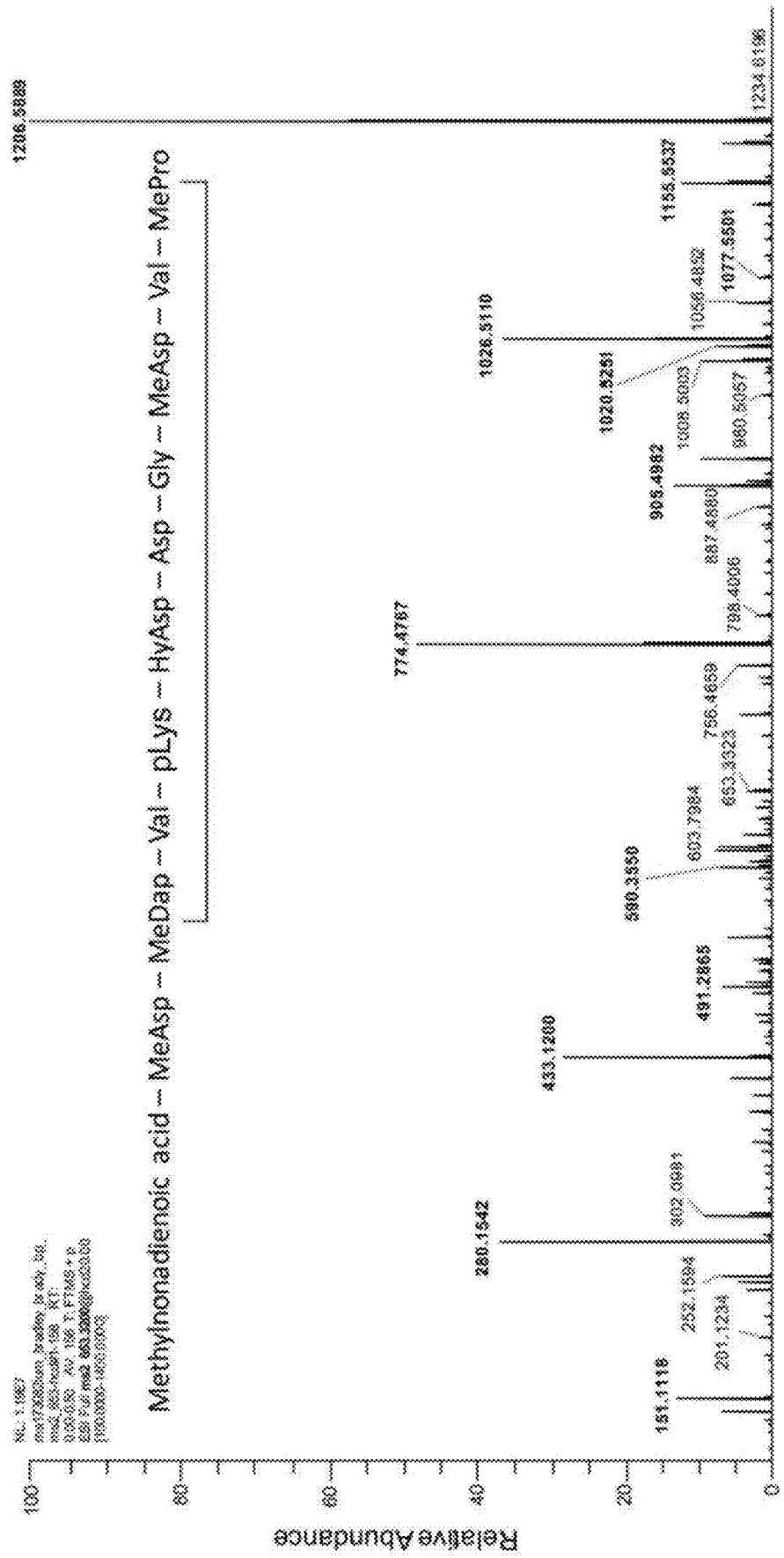
Figure 19C:
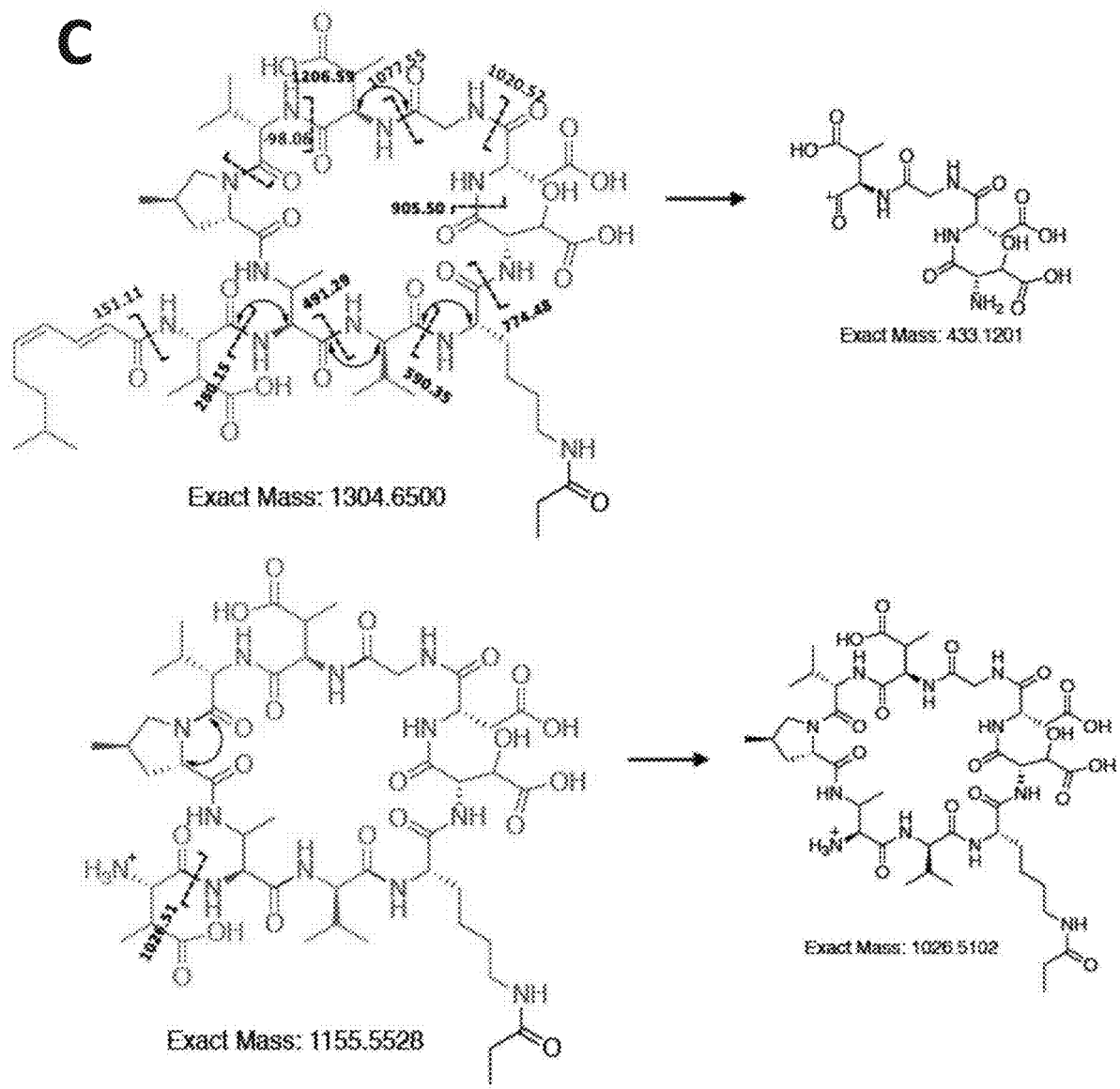
Figure 20:
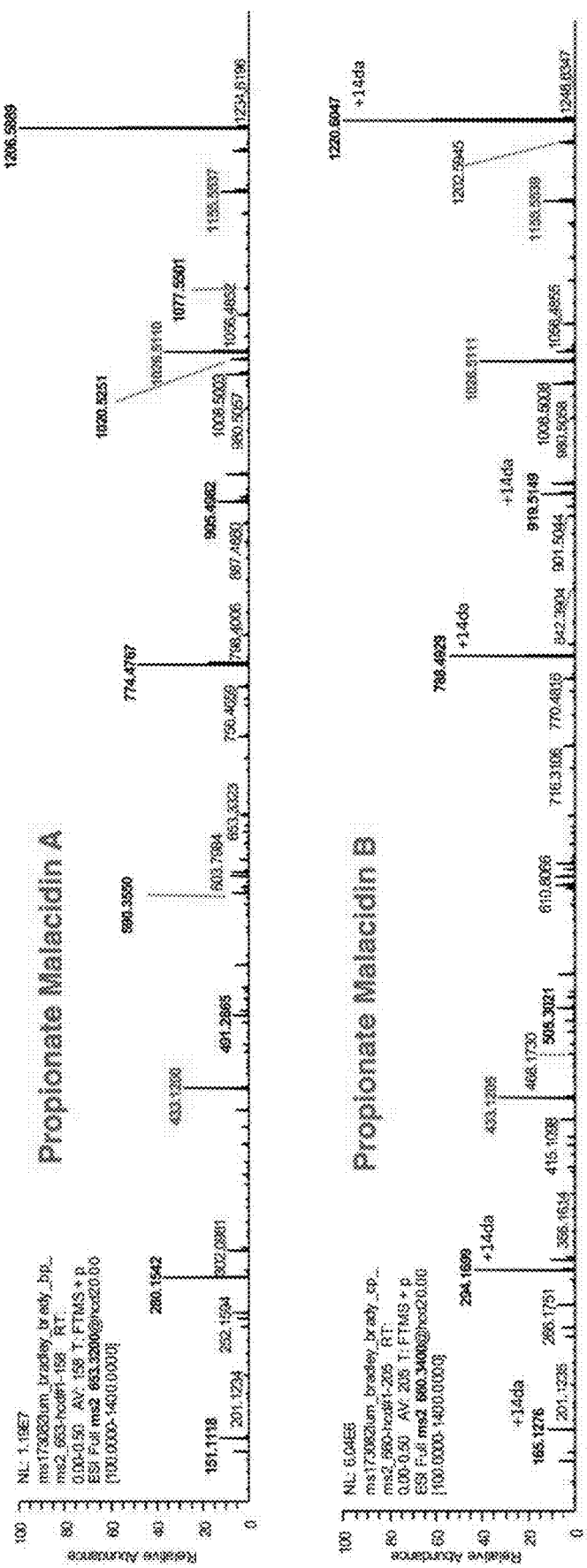
FIG. 20 depicts a comparison of MS/MS fragmentation patterns of propionate malacidins A and B. Red labeled exact mass ions were originated from the core cyclic peptide of malacidins A and B. Spectra are representative across two independent derivatizations and MS analysis.
Figure 21:
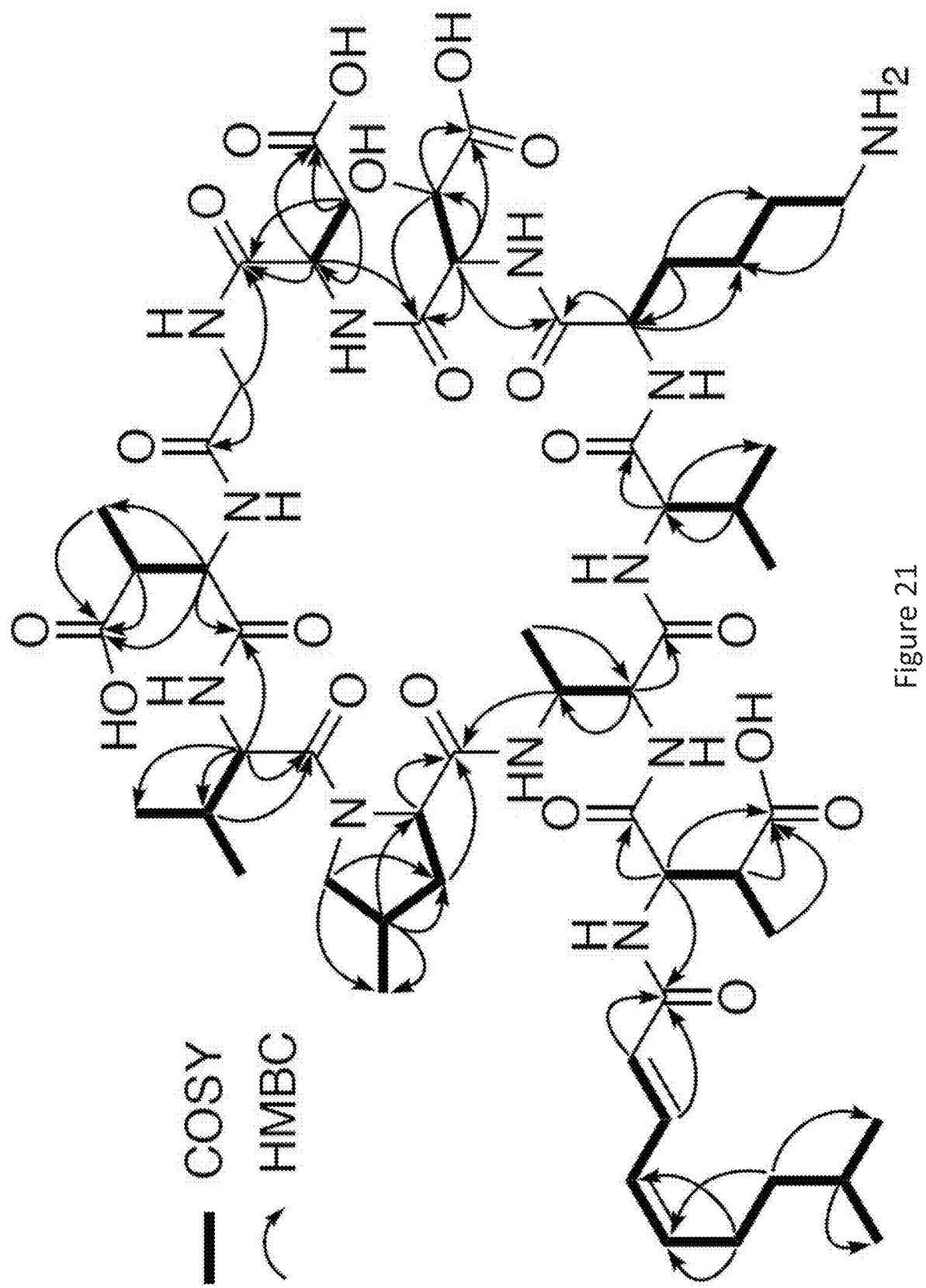
FIG. 21 depicts the key HMBC and COSY correlations of malacidin A.
Figure 22:
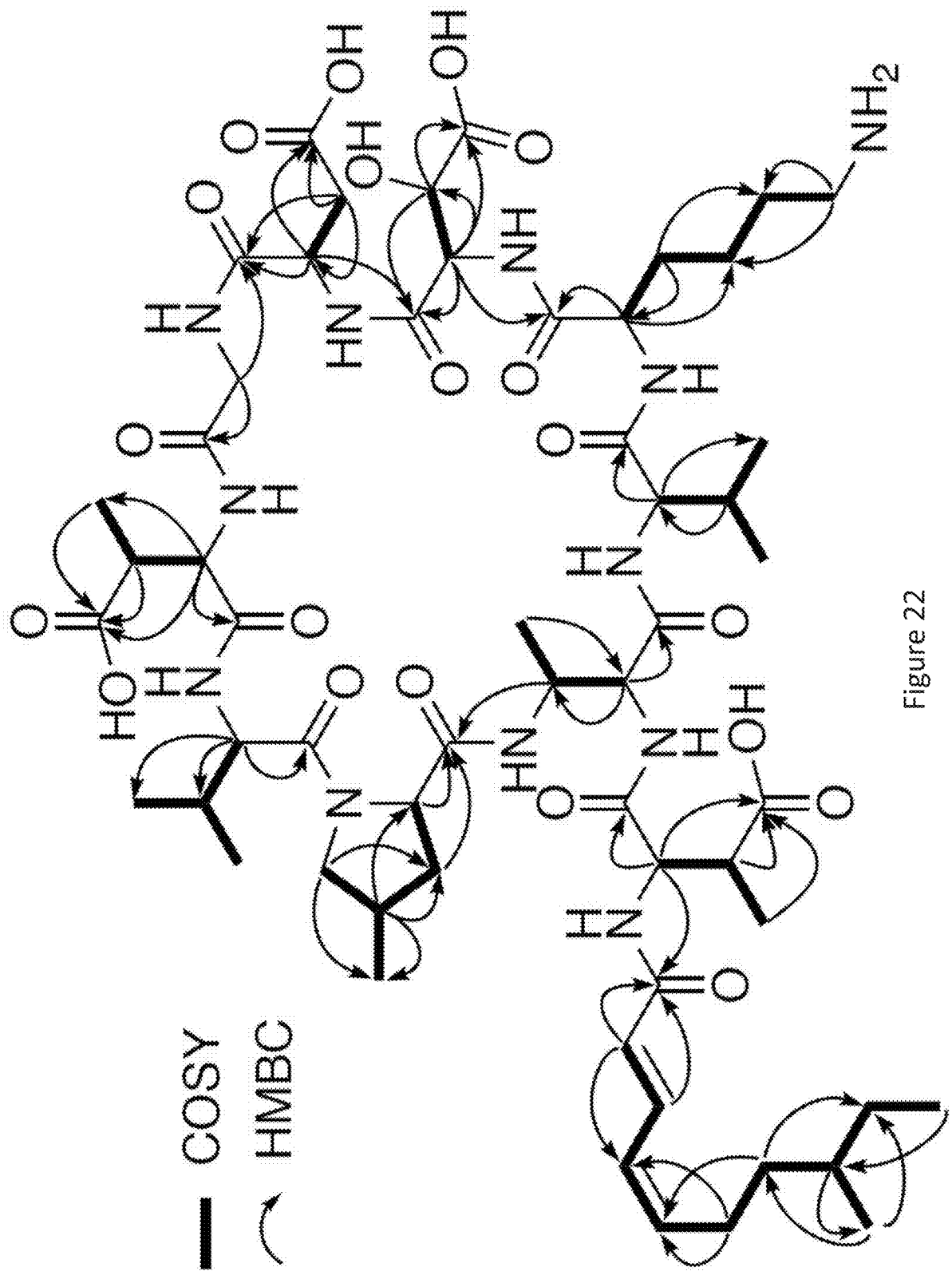
FIG. 22 depicts the key HMBC and COSY correlations of malacidin B.

To recover a complete malacidin BGC for use in heterologous expression studies, a desert soil (DFD0097) was retrieved from the soil archive that was rich in NPSTs from the malacidin branch of the AD phylogenetic tree (FIG. 5C). Employing standard soil metagenome cloning methods, a saturating cosmid library was constructed using DNA extracted from DFD0097 soil (Brady et al., 2007, Nat. Protoc. 2, 1297-1305). This 20-million-membered library was archived as purified cosmid DNA and *Escherichia coli* glycerol stocks arrayed in 96-well format, with each library well containing ~20,000 unique clones (Brady et al., 2007, Nat. Protoc. 2, 1297-1305; Kim et al., 2010, Biopolymers 93, 833-844). To expedite the recovery of BGCs, each well of the library was individually screened by PCR using the barcoded AD-targeting primers used to profile soils. Library-derived NPST data were analyzed by eSNaPD to generate a map of BGC information across the arrayed library.

Figures 2A, 2B, 2C, 2D, 2E:
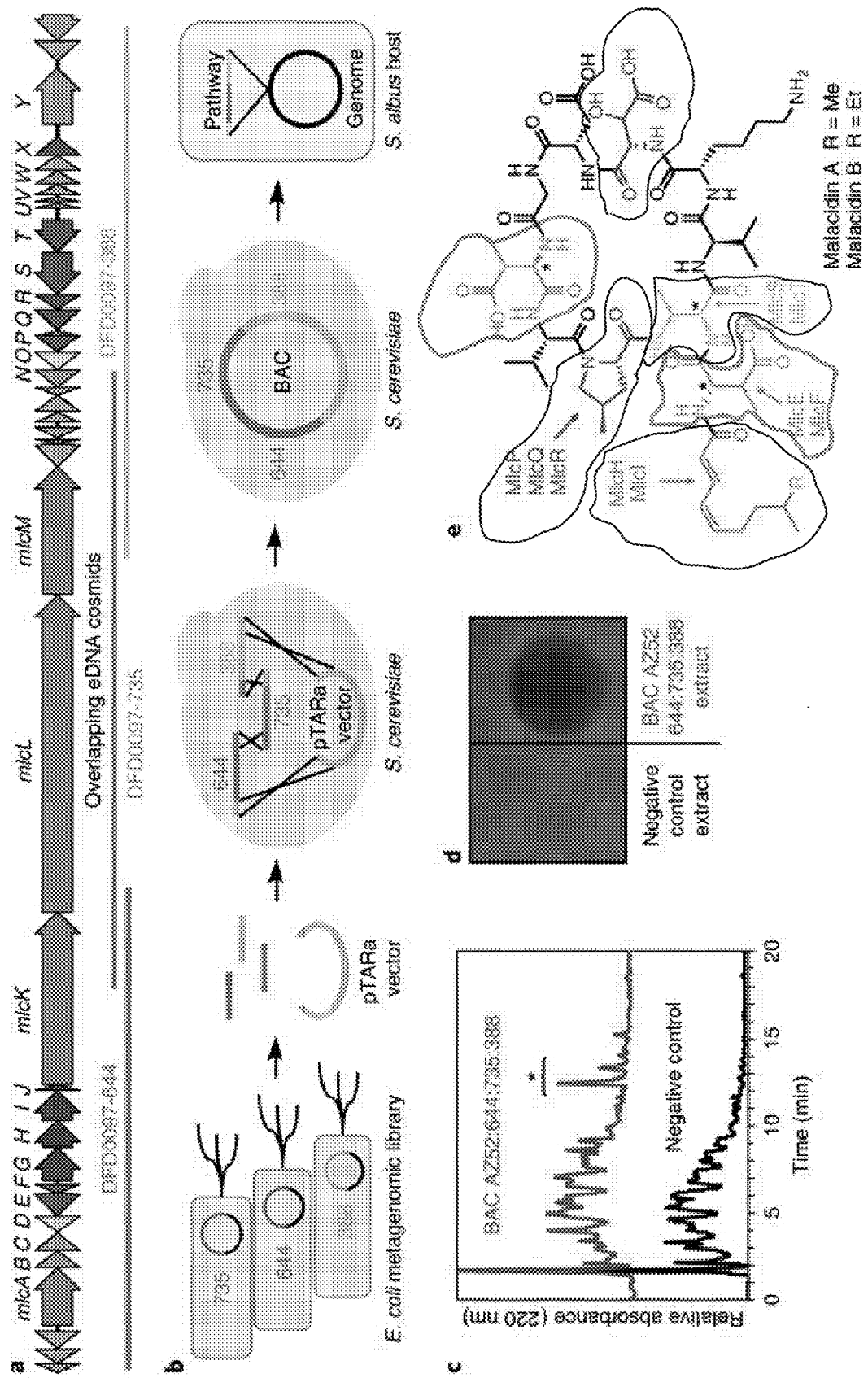
FIG. 2A through FIG. 2E, depicts maladicin biosynthesis, heterologous expression and structure.

Using this BGC prediction map, overlapping cosmid clones predicted to contain the malacidin BGC were recovered from the library. Sequencing and in silico analysis of these clones suggested that the malacidin BGC spanned 72 kilobases across 3 cosmids (DFD0097-644, DFD0097-735 and DFD0097-388) (FIG. 2A and Table 2 GenBank Accession KY654519). For the purposes of heterologous expression, these three overlapping cosmids were assembled into a contiguous fragment of DNA using transformation-associated recombination in yeast and the *E. coli*:yeast:*Streptomyces* shuttle vector, pTARa (FIG. 2B) (Kim et al., 2010, Biopolymers 93, 833-844). The resulting bacterial artificial chromosome (DFD0097-644:735:388) and the empty pTARa vector were separately conjugated into *Streptomyces albus* J 1074. Extracts from cultures of *S. albus* harbouring DFD0097-644:735:388 were found to exhibit antibacterial activity against *Staphylococcus aureus* and contain clone-specific metabolites (FIG. 2C and FIG. 2D). The major clone-specific metabolites, malacidin A and B, were isolated from cultures of *S. albus* DFD0097-644:735:388 and their structures were elucidated using a combination of mass spectrometry and NMR data. The malacidin structures were supported by a detailed bioinformatic analysis of the BGC (FIG. 2E, FIG. 6-FIG. 29, Tables 3 and 4.

TABLE 2

Malacidin biosynthetic gene cluster analysis. 39 predicted ORFs constituted the malacidin BGC (ORFS 1-39) - 26 of which (mlcA-Z) have similarities to genes found in characterized NRPS BGCs

| ORF | Gene Size (bp) | Gene Name | Proposed Function | Protein [Organism], NCBI Gene Bank Accession Number Corresponding to Gene with Sequence Similarity | E-value | Protein ID % |
|---|---|---|---|---|---|---|
| 1 | 459 | orf1 | Unknown | hypothetical protein [Amycolatopsis taiwanensis] WP_027945115 | 1.0E-62 | 89% |
| 2 | 774 | orf2 | Unknown | Nucleoside-diphosphate-sugar epimerase [Saccharopolyspora shandongensis], SDW57388 | 3.0E-146 | 87% |
| 3 | 927 | orf3 | Unknown | RNA polymerase, sigma subunit, ECF family Saccharopolyspora shandongensis], SDW57388 | 9.0E-177 | 90% |
| 4 | 3132 | mlcA | Peptide Synthesis | non-ribosomal peptide synthetase [Actinoplanes friuliensis], WP_023362349 | 0 | 54% |
| 5 | 897 | mlcB | Peptide Synthesis | GHMP kinase [Actinoplanes friuliensis], WP 023362350 | 2.0E-114 | 65% |
| 6 | 939 | mlcC | Regulation | SyrP [Streptomyces ambofaciens] WP_053138577 | 2.0E-157 | 72% |

TABLE 2-continued

Malacidin biosynthetic gene cluster analysis. 39 predicted ORFs constituted the malacidin BGC (ORFS 1-39) - 26 of which (mlcA-Z) have similarities to genes found in characterized NRPS BGCs

| ORF | Gene Size (bp) | Gene Name | Proposed Function | Protein [Organism], NCBI Gene Bank Accession Number Corresponding to Gene with Sequence Similarity | E-value | Protein ID % |
| --- | --- | --- | --- | --- | --- | --- |
| 7 | 816 | mlcD | Transport/Resistance | ABC transporter permease [Streptomyces ambofaciens] WP_063484561 | 1.0E-76 | 56% |
| 8 | 1218 | mlcE | 3-Methylaspartic Acid Biosynthesis | methylaspartate mutase, E-chain [Streptomyces sp. NRRL S-350], WP_030245251 | 2.0E-163 | 63% |
| 9 | 474 | mlcF | 3-Methylaspartic Acid Biosynthesis | methylaspartate mutase, S-chain [Streptomyces sp. NRRL S-350], WP_030245253 | 4.0E-41 | 57% |
| 10 | 1764 | mlcG | Acyl-CoA/AMP Synthesis | acyl-CoA synthase [Actinoplanes friuliensis] WP_023362355 | 7.0E-180 | 52% |
| 11 | 1434 | mlcH | Desaturation of Acyl Chain | acyl-CoA dehydrogenase [Streptomyces sp. MBT76] WP_058042025 | 7.0E-151 | 54% |
| 12 | 1596 | mlcI | Desaturation of Acyl Chain | acyl-CoA dehydrogenase [Streptomyces ambofaciens] WP_064384562 | 0 | 55% |
| 13 | 270 | mlcJ | Attachemnt of Acyl Chain | acyl carrier protein [Streptomyces sp. DvalAA-43], SCD55195 | 1.0E-19 | 54% |
| 14 | 9195 | mlcK | Peptide Synthesis | non-ribosomal peptide synthetase B [Actinoplanes friuliensis], CAJ18237 | 0 | 50% |
| 15 | 16887 | mlcL | Peptide Synthesis | non-ribosomal peptide synthetase C [Actinoplanes friuliensis] WP_023362360 | 0 | 52% |
| 16 | 6843 | mlcM | Peptide Synthesis | non-ribosomal peptide synthetase D [Actinoplanes friuliensis DSM 7358], AGZ41988 | 0 | 51% |
| 17 | 1218 | orf17 | Unknown | hypothetical protein [Frigoribacterium sp. Leaf186], WP_056257329 | 3.0E-27 | 31% |
| 18 | 195 | orf18 | Unknown | none | | |
| 19 | 594 | orf19 | Possible O-Me Transferase | caffeoyl-CoA O-methyltransferase [Actinopolyspora alba] SFE37636 | 1.0E-64 | 54% |
| 20 | 495 | orf20 | Unknown | NUDIX pyrophosphate hydrolase [Kibdelosporangium aridum] WP_051897132 | 3.0E-72 | 85% |
| 21 | 864 | orf21 | Possible N-acetyltransferase | N-acetyltransferase [Streptomyces yerevanensis] WP_033322847 | 7.0E-170 | 89% |
| 22 | 405 | orf22 | Unknown | hypothetical protein [Kibdelosporangium aridum] WP_033390436 | 4.0E-75 | 83% |
| 23 | 912 | mlcN | Regulation | regulatory protein B [Streptomyces viridochromogenes], AEF16019 | 2.0E-122 | 61% |

TABLE 2-continued

Malacidin biosynthetic gene cluster analysis. 39 predicted
ORFs constituted the malacidin BGC (ORFS 1-39) - 26 of which
(mlcA-Z) have similarities to genes found in characterized NRPS BGCs

| ORF | Gene Size (bp) | Gene Name | Proposed Function | Protein [Organism], NCBI Gene Bank Accession Number Corresponding to Gene with Sequence Similarity | E-value | Protein ID % |
|---|---|---|---|---|---|---|
| 24 | 936 | mlcO | Transport/Resistance | daunorubicin resistance protein DrrA family ABC transporter ATP-binding protein [Lechevalieria aerocolonigenes], WP_045314983 | 9.0E-125 | 70% |
| 25 | 867 | mlcP | 5-methylproline biosynthesis | Coenzyme F420-dependent N5,N10-methylene tetrahydromethanopterin reductas [Streptomyces sp. WMMB 322], SCK14243 | 1.0E-72 | 47% |
| 26 | 216 | orf26 | Unknown | None | | |
| 27 | 1086 | mlcQ | 5-methylproline biosynthesis | alcohol dehydrogenase [Streptomyces sp. CFMR 7], WP_053560816 | 1.0E-170 | 75% |
| 28 | 801 | mlcR | 5-methylproline biosynthesis | L-proline 4-hydroxylase [Dactylosporangium sp.], BAA20094 | 2.0E-56 | 43% |
| 29 | 2256 | mlcS | 2 3-Diaminobutyric acid biosynthesis | cysteine synthase [Saccharopolyspora spinosa], WP_010696131 | 0 | 64% |
| 30 | 1722 | mlcT | 2 3-Diaminobutyric acid biosynthesis | argininosuccinate lyase, partial [Streptomyces sp. Termitarium-T10T-6], SCD57198 | 0 | 61% |
| 31 | 267 | mlcU | Regulation | LuxR family transcriptional regulator [Streptomyces sp. AW19M42], CEL20147 | 5.0E-46 | 93% |
| 32 | 219 | mlcV | Unknown NRPS Function | MbtH family protein [Kibdelosporangium sp. MJ126-NF4], WP_042191548 | 9.0E-41 | 89% |
| 33 | 546 | orf33 | Unknown | hypothetical protein [Kibdelosporangium sp. MJ126-NF4], WP_042191551 | 1.0E-51 | 74% |
| 34 | 687 | mlcW | Regulation | regulatory protein, tetR family [Amycolatopsis pretoriensis] SEF37903 | 8.0E-76 | 63% |
| 35 | 795 | orf35 | Unknown | inositol monophosphatase [Kibdelosporangium sp. MJ126-NF4], WP_042191557 | 1.0E-143 | 76% |
| 36 | 984 | mlcX | Amino aicd synthesis/catabolism | L-asparaginase [Kibdelosporangium sp. MJ126-NF4], WP_042191561 | 4.0E-142 | 75% |
| 37 | 3048 | mlcY | Regulation | AfsR/SARP family transcriptional regulator [Kibdelosporangium sp. MJ126-NF4], WP_042191568 | 0 | 83% |

TABLE 2-continued

Malacidin biosynthetic gene cluster analysis. 39 predicted
ORFs constituted the malacidin BGC (ORFS 1-39) - 26 of which
(mlcA-Z) have similarities to genes found in characterized NRPS BGCs

| ORF | Gene Size (bp) | Gene Name | Proposed Function | Protein [Organism], NCBI Gene Bank Accession Number Corresponding to Gene with Sequence Similarity | E-value | Protein ID % |
|---|---|---|---|---|---|---|
| 38 | 1092 | orf38 | Unknown | hypothetical protein [Kibdelosporangium sp. MJ126-NF4], WP_042192840 | 0 | 77% |
| 39 | 1383 | orf39 | Unknown | hypothetical protein [Kibdelosporangium phytohabitans WP_054290662 | 0 | 77% |

Figures 3A, 3B, 3C, 3D:
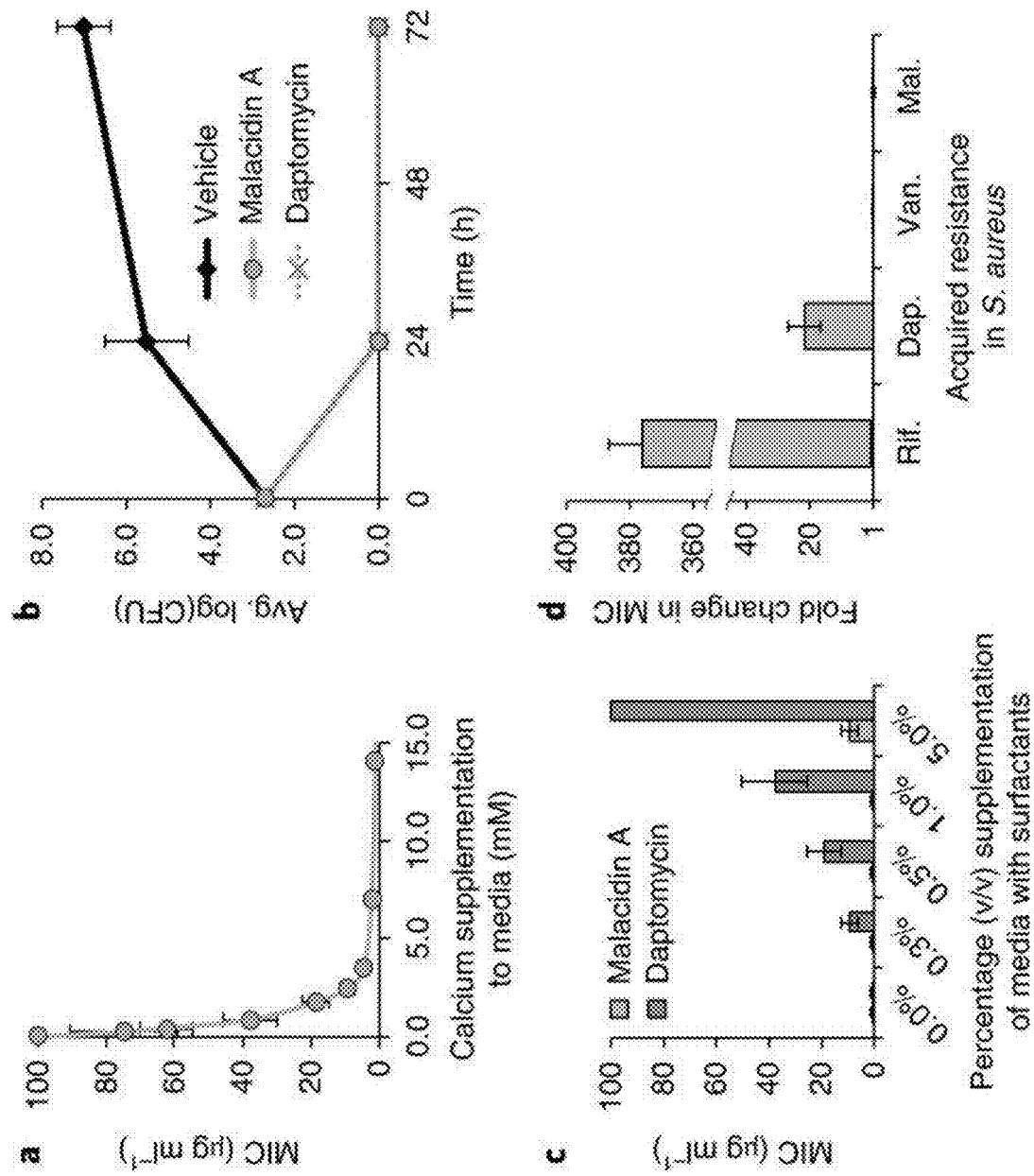
FIG. 3A through FIG. 3D, depicts experimental results demonstrating the calcium-dependent antibiotic activity of malacidin.
Figures 28A, 28B, 28C:
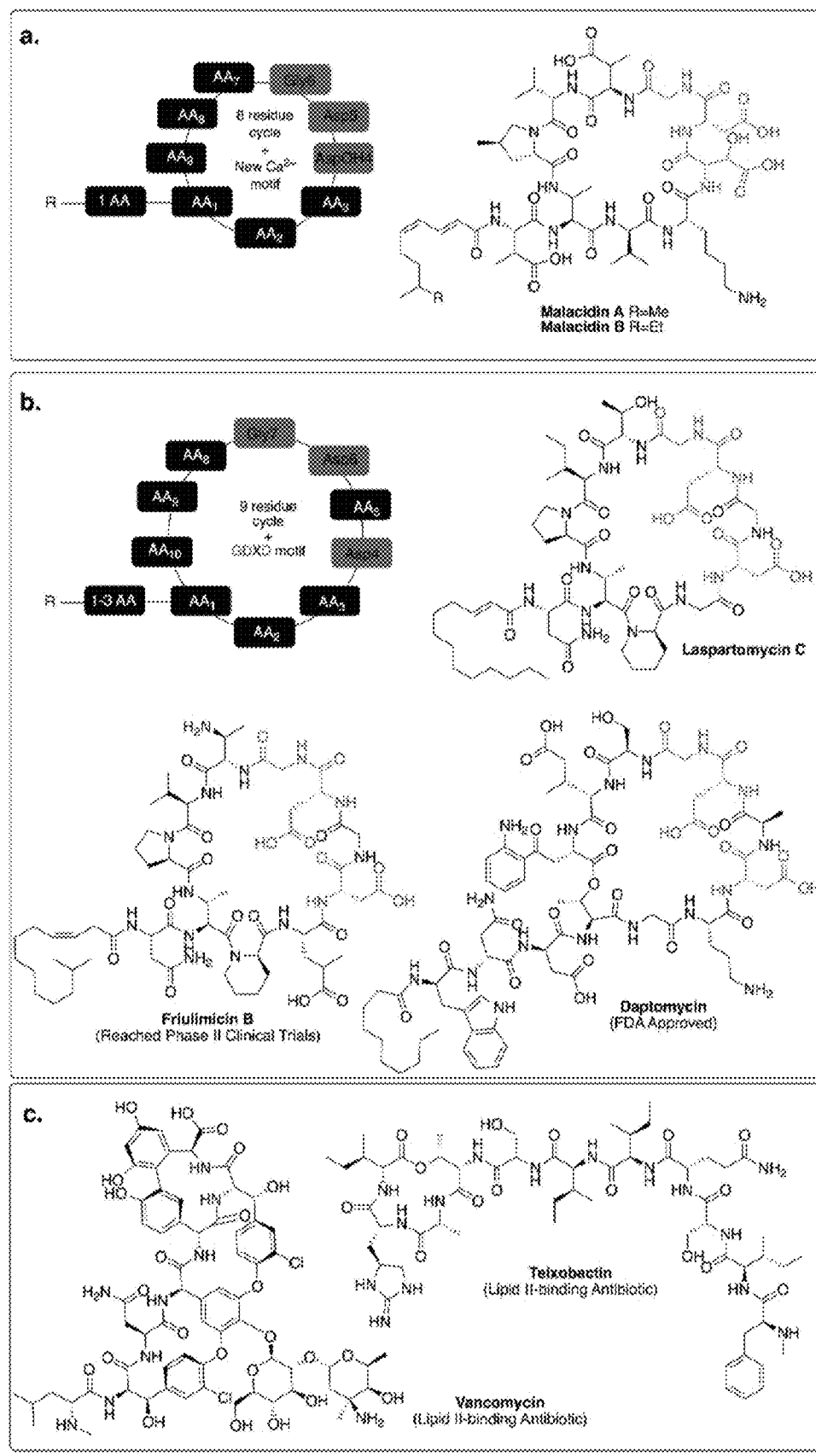
FIG. 28A through FIG. 28C, depicts a structural comparison of malacidin to other calcium-dependent antibiotics.
Figure 30:
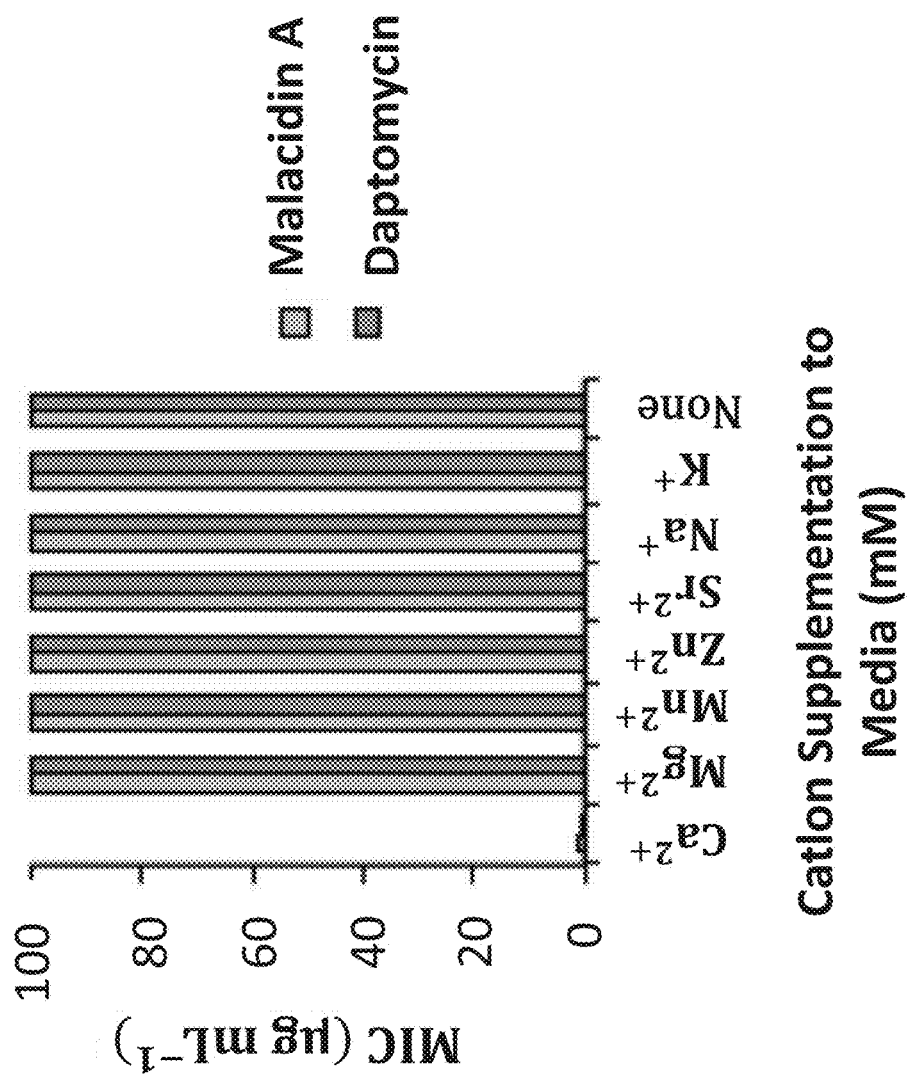
FIG. 30 depicts the effects of mono- and divalent cations on malacidin activity. Results of serial dilution MIC assays against *S. aureus* USA300 using media supplemented with 15 mM of various mono- and divalent cations. 0.1 mg/mL was the highest concentration tested. Error bars represent the standard error across three replicate experiments.
Figure 31A:
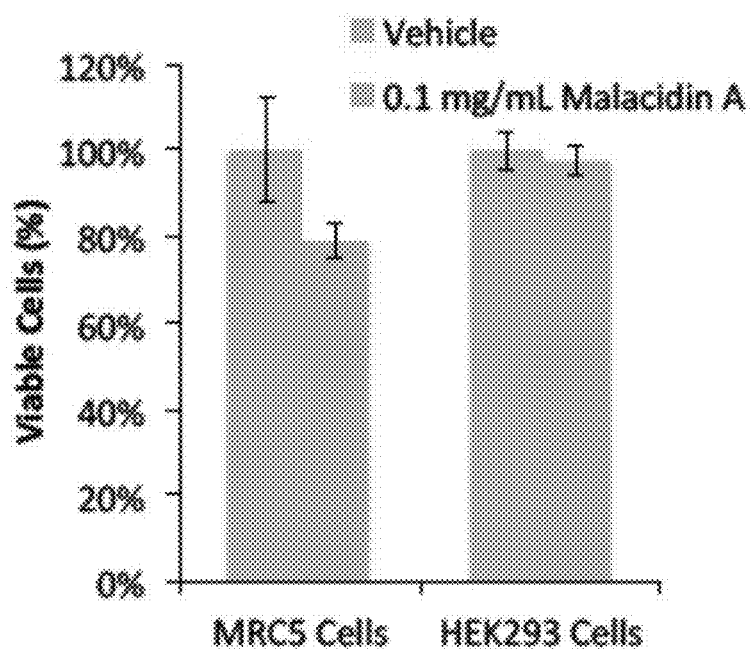
FIG. 31A and FIG. 31B, depicts experimental results assessing malacidin A mammalian toxicity.
Figure 31B:
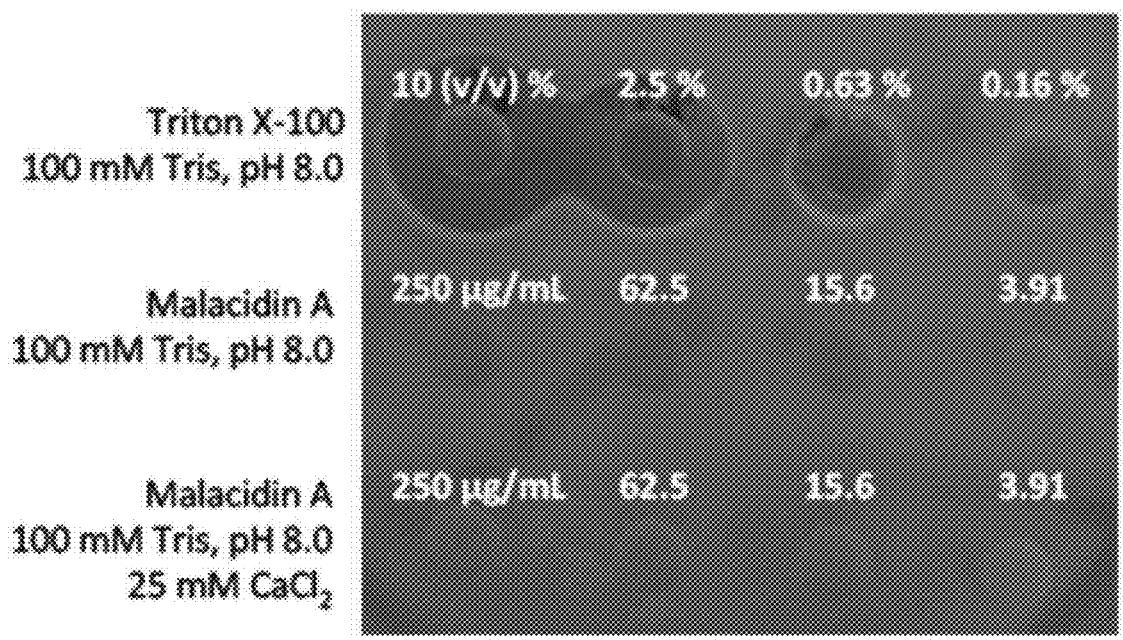
Figure 32:
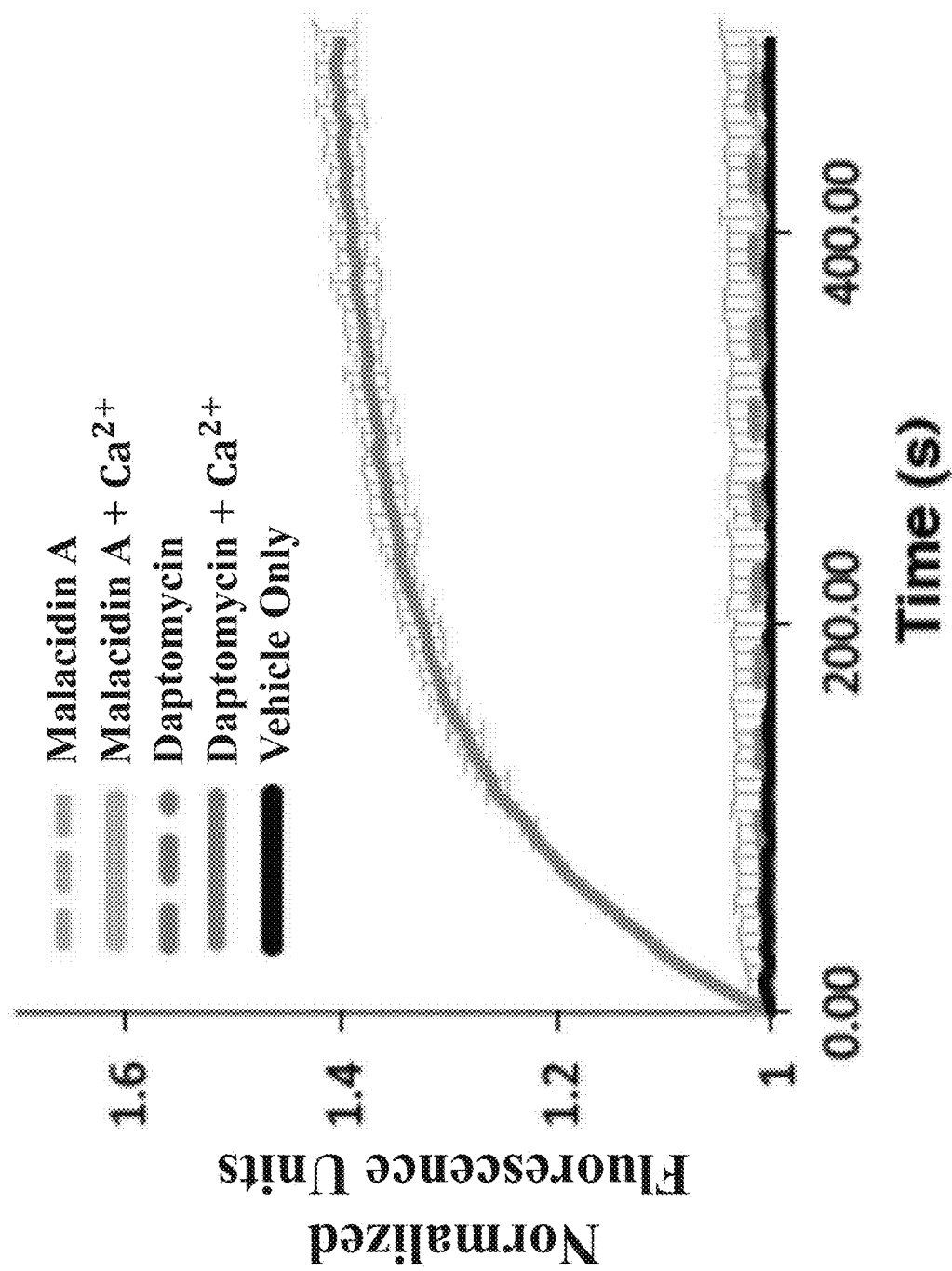
FIG. 32 depicts experimental results demonstrating malacidin does not induce membrane depolarization. In a similar experiment to the SYTOX membrane leakage experiments, the effects of malacidin on membrane depolarization were assessed using the membrane potential probe, DiBAC4 (Bis-(1,3-Dibutylbarbituric Acid)Trimethine Oxonol). Malacidin, in contrast to daptomycin, demonstrated no significant loss of membrane potential when testing against *S. aureus* cells pretreated with DiBAC4. These data along with the SYTOX green assays suggest that malacidin does not cause either significant membrane disruption or leakage of ions. Error bars represent the standard error across three biological replicates.

The malacidins at 10-membered cyclic lipopeptides that differ only by a methylene on the branch at the terminus of their lipid tails. Their peptide cores include four non-proteinogenic amino acids (FIG. 2E). Calcium-dependent antibiotics characterized from culture-based discovery programmes contain larger, 11- to 13-amino-acid rings and completely distinct peptide sequences (FIG. 28). The malacidins do not contain the canonical Asp-X-Asp-Gly calcium-binding motif found in known calcium-dependent antibiotics (Stricker and Marahiel, 2009. ChemBioChem 10, 607*-616). They lack the variable spacer residue found in this canonical motif and contain an ASP-OH, suggesting that they either no longer bind calcium or may represent a different calcium-binding motif (Strieker and Marahiel, 2009, ChemBioChem 10, 607-616; Jung, et al., 2004, Chem. Biol. 11, 949-957; Bunkoczi et al., 2005, Acta Crystallogr. Sect. D. 61, 1160-1164). To determine the requirement of calcium for the antibacterial activity of the malacidins, antibiosis against methicillin-resistant Staphylococcus aureus (MRSA) was tested across a range of calcium concentrations. In these assays, a clear dependence on calcium for antibiosis was observed, indicating that although the malacidins do not contain a canonical Asp-X-Asp-Gly motif, their antibacterial activity remains calcium-dependent (FIG. 3A). Similar experiments using cations other than calcium showed no antibiosis (FIG. 30). The malacidins are broadly active against Gram-positive bacteria including multidrug-resistant pathogens and bacteria resistant to mechanistically diverse, clinically used antibiotics (Table 1 and Table 5). As the most common form of Staphylococcus infection occurs on the skin, the in vivo efficacy of the malacidins was tested using an animal wound model. Topical administration of malacidin A was successful in sterilizing MRSA-infected wounds in a rat model (FIG. 3B). At 24 and 72 hours post infection, malacidin A treatment resulted in no observed bacterial burdens in the wounds. The vehicle-treated controls had an average of 5.5 log and 7.0 log of MRSA at 24 hours and 72 hours, respectively (Kruskal-Wallis P value<0.0001). Likewise, the malacidins showed no significant toxicity or haemolytic activity against mammalian cells at the highest concentrations tested (100-250 µg ml$^{-1}$, >100 minimal inhibitory concentration, MIC) (FIG. 31 and Table 4). Unlike daptomycin, which is unable to treat severe community-acquired pneumonia due to loss of activity in the presence of pulmonary surfactants (Silverman et al., 2005, J. Infect. Dis. 191, 2149-2152), malacidin A does not share this liability (FIG. 3C). Experimental efforts to induce resistance to malacidin in the laboratory have so far been unsuccessful. Even after 20 days of exposure to sublethal levels of malacidin A, malacidin-resistant S. aureus was not detected (FIG. 3D). Whether resistance can arise through horizontal gene transfer from environmental bacteria remains to be seen.

TABLE 1

Spectrum of activity of malacidin A

| Organism | Acquired Resistance | MIC (µg ml$^{-1}$) | IC$_{50}$ (µg ml$^{-1}$) |
|---|---|---|---|
| S. aureus USA300 | β-lactams (methicillin, oxacillin, penicillin) | 0.2-0.8 | |
| S. aureus USA300 + 10% serum | β-lactams (methicillin, oxacillin, penicillin) | 0.2-0.8 | |
| S. aureus COL | β-lactams | 0.2-0.8 | |
| S. aureus BAA-42 | β-lactams | 0.2-0.8 | |
| S. aureus NRS100 | β-lactams, tetracycline | 0.2-0.8 | |
| S. aureus NRS 108 | β-lactams, gentamicin, kanamycin | 0.2-0.8 | |
| S. aureus NRS140 | β-lactams, erythromycin, spectinomycin | 0.4-0.8 | |
| S. aureus NRS146 | β-lactams, vancomycin (VISA) | 0.4-0.8 | |
| E. faecium VRE | Vancomycin (VRE) | 0.4-0.8 | |
| E. faecium Com15 | | 0.8-2.0 | |
| S. pneumoniae | | 0.8-2.0 | |
| S. mutans | | 0.1-0.2 | |
| B. subtills | | 0.2-0.4 | |
| L. rhamnosus | | 0.1-0.2 | |
| E. coil | | >100 | |
| C. albicans | | >100 | |
| C. neofformans | | >100 | |
| HEK293 | | | >100 |
| MRC5 | | | >100 |

Figure 4A:
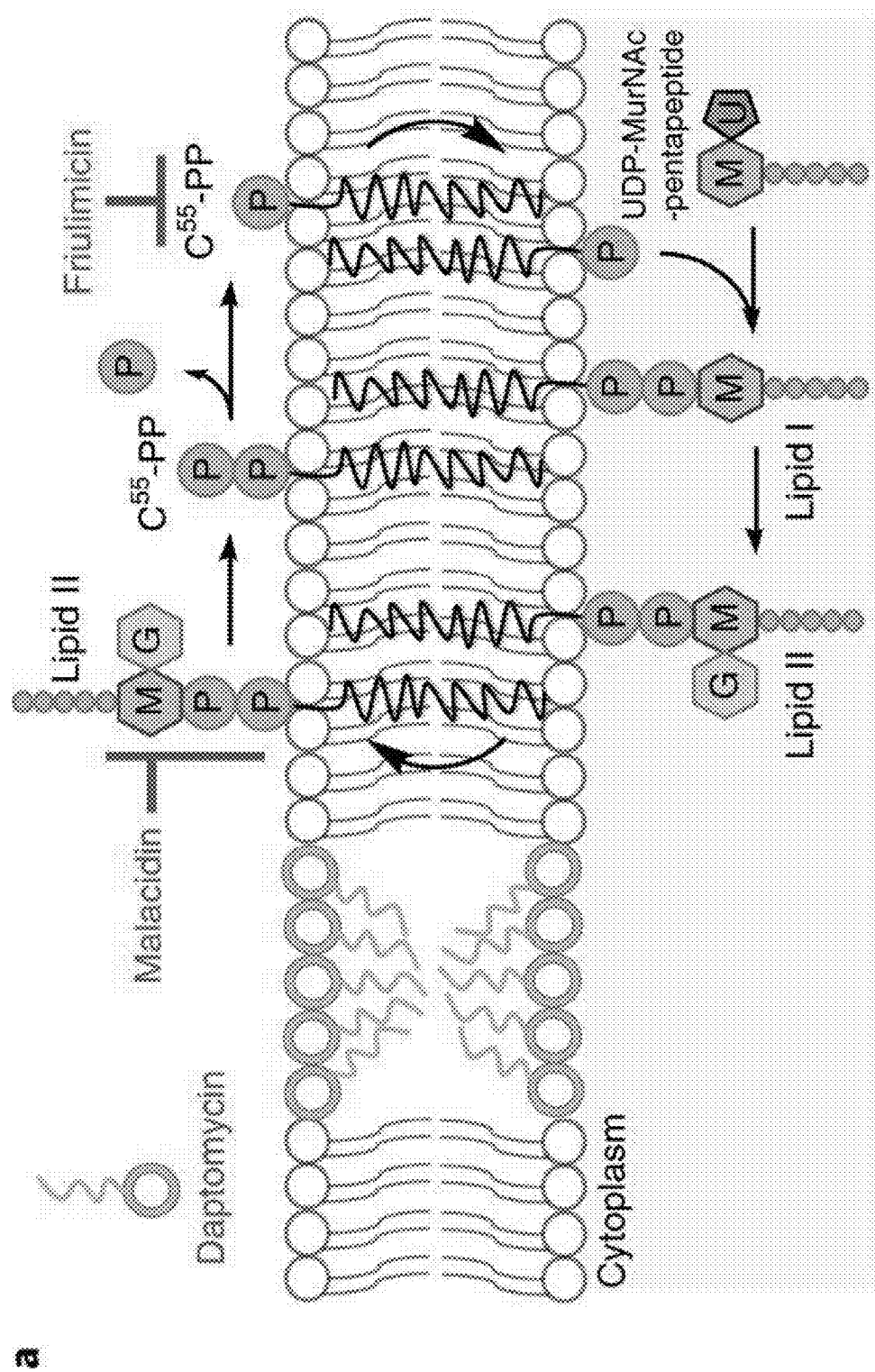
FIG. 4A through FIG. 4E, depicts experimental results demonstrating the malacidin mode of action.
Figures 4B, 4C, 4D, 4E:
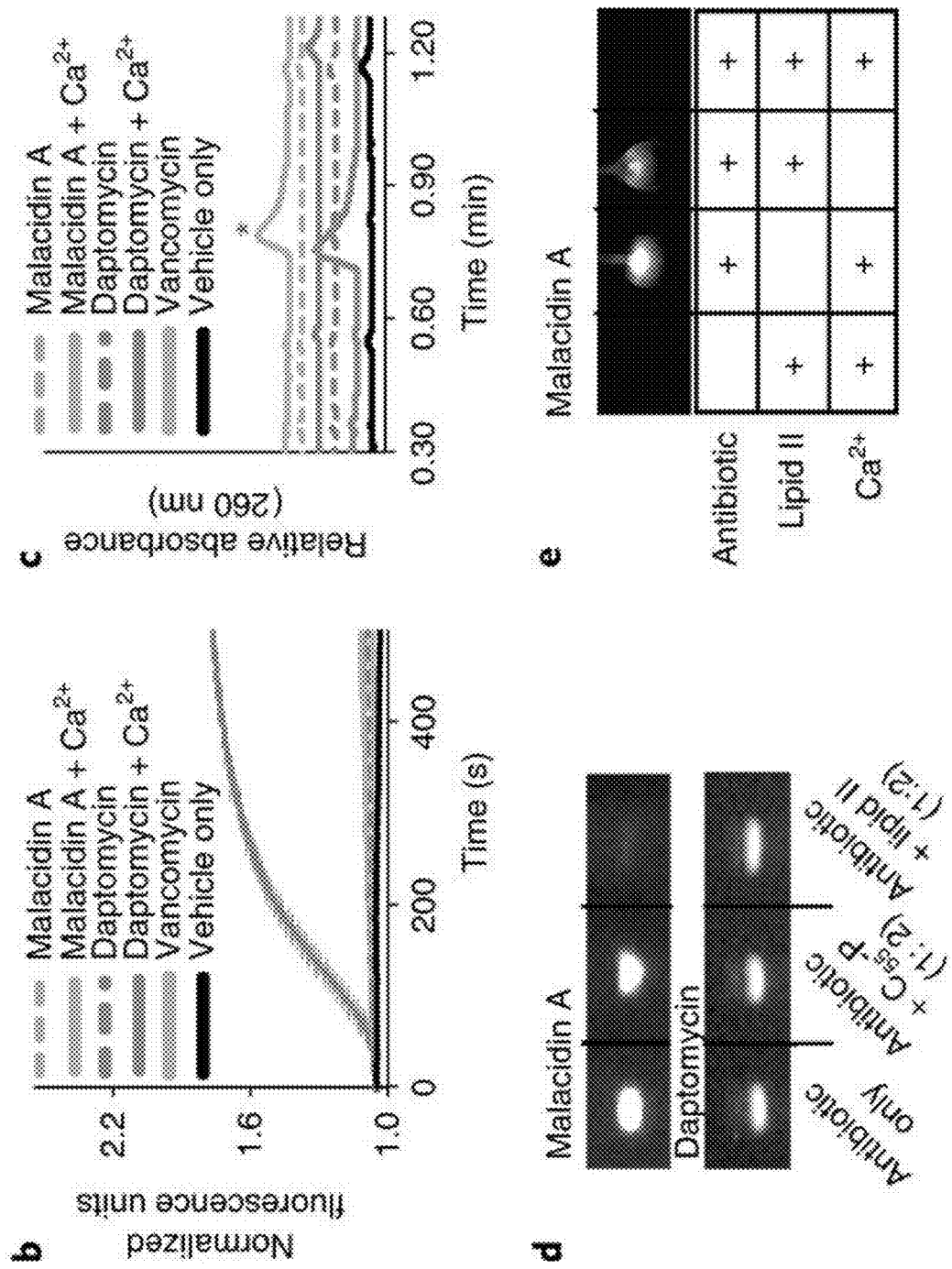

Characterized calcium-dependent antibiotics function by one of two distinct modes of action (FIG. 4A). Daptomycin displays rapid bactericidal activity by binding cytoplasmic membrane phospholipids and oligomerizing in the membrane (Zhang et al., 2016, Biophys. J. 111, 1267-1277; Straus and Hankcock, 2006, Biochim. Biophys. Aca 1758, 1215-1223). This affects phospholipid synthesis and overall membrane fluidity, ultimately leading to decreased membrane integrity and cell death (Muller, et al., 2016. PNAS 113, E7077-E7086). The potent antibacterial activity of friulimicin and its structural relatives is due to inhibition of bacterial cell wall biosynthesis through binding of the lipid 11 precursor, undecaprenyl phosphate ($C_{55}$-P) (Schneider et al., 2009, Antimicrob. Agents Ch. 53, 1610-1618; Kleinj et al., 2016, J. Med. Chem. 59, 3569-3574). As the malacidins are structurally distinct from other calcium-dependent antibiotics, it was next determined whether they function by one of these known mechanisms or a third distinct mode of action. First, the effect of malacidin on membrane integrity was assessed (FIG. 4B ). No membrane leakage was observed when *S. aureus* cells pretreated with SYTOX green or DiBAC4 were exposed to either daptomycin or malacidin in the absence of calcium supplementation. With the addition of calcium, daptomycin-treated *S. aureus* showed a rapid increase in fluorescence, which is indicative of a loss of membrane integrity. Malacidin, however, did not demonstrate the same effect, indicating that malacidin and daptomycin have distinct modes of action.

TABLE 3

Structures and $^1$H and $^{13}$C chemical shifts of malacidins A and B in D$_2$O$^3$

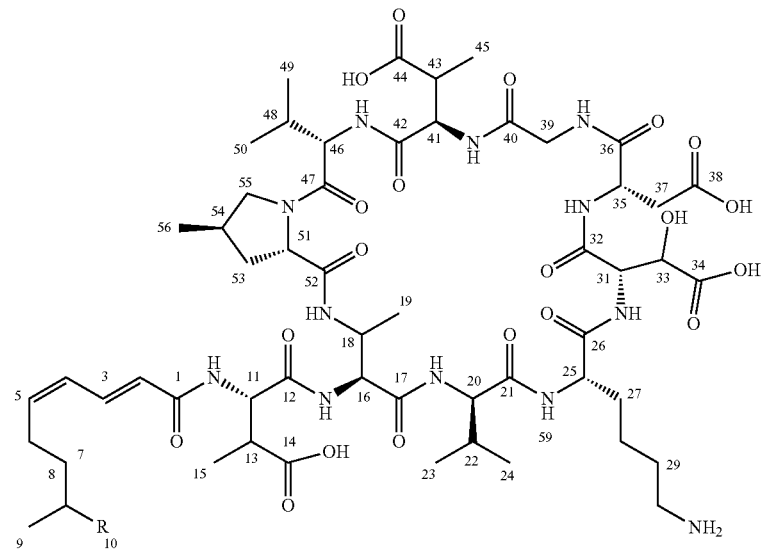

Malacidin A R = Me
Malacidin B R = Et

| Position | | Malacidin A | | | Malacidin B | | |
|---|---|---|---|---|---|---|---|
| Atom | Type | $\delta_C$ | $\delta_H$ mult. (J in Hz) | | $\delta_C$ | $\delta_H$ mult. (J in Hz) | |
| | | methyl-nonadienoic acid | | | methyl-nonadienoic acid | | |
| 1 | C | 169.5 | | | 169.8 | | |
| 2 | CH | 121.6 | 6.18 | d (15.0) | 121.7 | 6.19 | d (15.0) |
| 3 | CH | 138.1 | 7.64 | dd (15.0, 11.0) | 137.9 | 7.64 | dd (15.0, 11.0) |
| 4 | CH | 125.7 | 6.24 | dd (11.0, 11.0) | 125.8 | 6.25 | dd (11.0, 11.0) |
| 5 | CH | 143.3 | 6.03 | ddd (11.0, 7.5, 7.5) | 143.2 | 6.03 | ddd (11.0, 7.5, 7.5) |
| 6 | CH$_2$ | 25.7 | 2.35 | m | 25.4 | 2.35 | m |
| 7 | CH$_2$ | 37.9 | 1.33 | m | 35.5 | 1.45, 1.25 | m |
| 8 | CH | 27.0 | 1.58 | m | 33.3 | 1.38 | m |
| 9 | CH$_3$ | 21.7 | 0.90 | d (6.5) | 18.4 | 0.89 | d (6.5) |
| 10 | — | 21.7 | 0.90 | d (6.5) | 28.7 | 1.36, 1.16 | m |
| 10-Me | CH$_3$ | | | | 10.6 | 0.86 | 1 (7.0) |
| | | L-MeAsp$^1$ | | | | | |
| 11 | CH | 55.7 | 4.85 | d (7.0) | 57.1 | 4.67 | m |
| 12 | C | 172.6 | | | 173.7 | | |
| 13 | CH | 40.5 | 3.13 | M | 42.4 | 2.94 | m |
| 14 | C | 177.4 | | | 180.3 | | |
| 15 | CH$_3$ | 12.4 | 1.23 | d (7.0) | 12.9 | 1.18 | d (7.0) |
| | | L-MeDap$^2$ | | | | | |
| 16 | CH | 58.1 | 4.53 | d (3.5) | 57.9 | 4.54 | m |
| 17 | C | 171.0 | | | 171.6 | | |
| 18 | CH | 47.8 | 4.27 | M | 47.7 | 4.24 | m |
| 19 | CH$_3$ | 15.7 | 1.24 | d (6.5) | 15.3 | 1.24 | d (6.5) |
| | | D-Val$^3$ | | | | | |
| 20 | CH | 57.3 | 4.38 | m | 57.3 | 4.35 | d (8.0) |
| 21 | C | 171.6 | | | 171.1 | | |
| 22 | CH | 29.7 | 2.11 | m | 29.6 | 2.07 | m |
| 23 | CH$_3$ | 17.7 | 0.97 | m | 17.7 | 1.00 | m |
| 24 | CH$_3$ | 18.3 | 1.01 | m | 18.4 | 0.99 | m |

TABLE 3-continued

Structures and $^1$H and $^{13}$C chemical shifts of malacidins A and B in $D_2O^3$

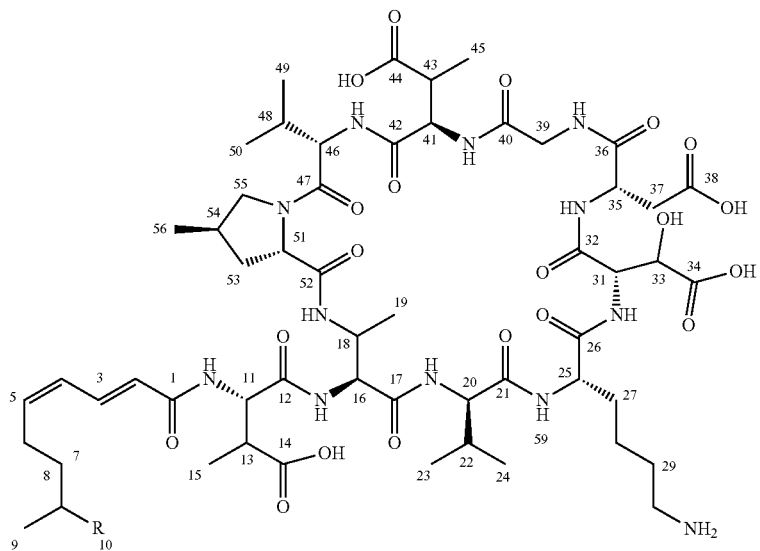

Malacidin A R = Me
Malacidin B R = Et

| | | Malacidin A | | | Malacidin B | | |
|---|---|---|---|---|---|---|---|
| Position | | $\delta_C$ | $\delta_H$ muilt. (J in Hz) | | $\delta_C$ | $\delta_H$ muilt. (J in Hz) | |
| Atom | Type | methyl-nonadienoic acid | | | methyl-nonadienoic acid | | |
| L-Lys$^4$ | | | | | | | |
| 25 | CH | 53.1 | 4.43 | dd (10.0, 5.0) | 53.0 | 4.48 | dd (7.5, 6.0) |
| 26 | C | 173.8 | | | 173.5 | | |
| 27 | CH$_2$ | 30.1 | 1.94, 1.79 | m | 30.4 | 1.92, 1.83 | m |
| 28 | CH$_2$ | 22.1 | 1.49, 1.44 | m | 21.8 | 1.45, 1.45 | m |
| 29 | CH$_2$ | 26.1 | 1.71, 1.71 | m | 26.2 | 1.72, 1.72 | m |
| 30 | CH$_2$ | 39.0 | 3.02, 3.02 | t (7.5) | 39.0 | 3.02, 3.02 | m |
| L-Hy Asp$^5$ | | | | | | | |
| 31 | CH | 56.6 | 4.68 | d (5.5) | 57.4 | 4.62 | d (4.5) |
| 32 | C | 169.9 | | | 170.1 | | |
| 33 | CH | 70.5 | 4.58 | d (5.5) | 72.2 | 4.34 | d (4.5) |
| 34 | C | 174.5 | | | 176.6 | | |
| L-Asp$^6$ | | | | | | | |
| 35 | CH | 49.8 | 4.81 | overlapped | 51.0 | 4.69 | m |
| 36 | C | 172.4 | | | 173.4 | | |
| 37 | CH$_2$ | 35.0 | 2.94, 2.94 | dd (13.0, 6.5) | 37.5 | 2.74, 2.74 | m |
| 38 | C | 174.2 | | | 177.3 | | |
| Gly$^7$ | | | | | | | |
| 39 | CH$_2$ | 42.6 | 3.98, 3.98 | s | 42.4 | 4.03, 3.93 | d (17.0) |
| 40 | C | 171.0 | | | 170.7 | | |
| D-MeAsp$^8$ | | | | | | | |
| 41 | CH | 54.9 | 4.70 | d (7.5) | 56.1 | 4.55 | m |
| 42 | C | 171.4 | | | 172.1 | | |
| 43 | CH | 40.7 | 3.06 | m | 43.3 | 2.79 | m |
| 44 | C | 177.4 | | | 180.5 | | |
| 45 | CH$_3$ | 13.4 | 1.21 | d (7.5) | 14.2 | 1.13 | d (7.0) |
| L-Val$^9$ | | | | | | | |
| 46 | CH | 60.3 | 4.03 | d (8.0) | 60.2 | 4.08 | d (8.0) |
| 47 | C | 173.3 | | | 172.7 | | |
| 48 | CH | 29.3 | 2.12 | m | 29.6 | 2.17 | m |

TABLE 3-continued

Structures and $^1$H and $^{13}$C chemical shifts of malacidins A and B in D$_2$O$^3$

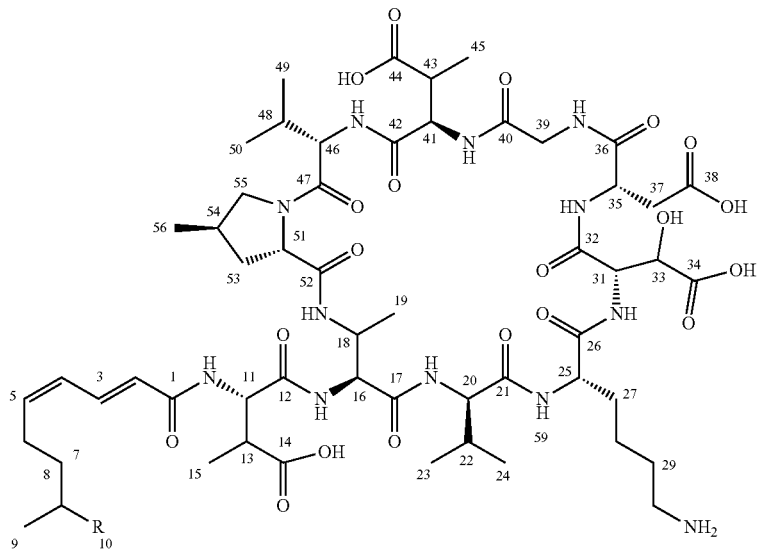

Malacidin A R = Me
Malacidin B R = Et

| | | Malacidin A | | | Malacidin B | | |
|---|---|---|---|---|---|---|---|
| Position | | $\delta_C$ | $\delta_H$ muilt. (J in Hz) | | $\delta_C$ | $\delta_H$ muilt. (J in Hz) | |
| Atom | Type | methyl-nonadienoic acid | | | methyl-nonadienoic acid | | |
| 49 | CH$_3$ | 18.5 | 0.98 | d (7.0) | 18.5 | 0.96 | m |
| 50 | CH$_3$ | 18.1 | 0.97 | d (6.5) | 18.1 | 0.98 | m |
| | | | | L-MePro$^{10}$ | | | |
| 51 | CH | 60.3 | 4.39 | m | 60.2 | 4.41 | dd (8.0, 5.5) |
| 52 | C | 173.8 | | | 174.1 | | |
| 53 | CH$_2$ | 36.4 | 1.96, 1.89 | m | 36.5 | 1.93, 1.89 | m |
| 54 | CH | 32.2 | 2.48 | m | 32.2 | 2.45 | m |
| 55 | CH$_2$ | 54.6 | 3.79, 3.43 | t (9.0, 6.5) | 54.6 | 3.79, 3.43 | m |
| 56 | CH$_3$ | 16.8 | 1.01 | d (6.5) | 16.8 | 1.00 | m |

$^1$H and $^{13}$C NMR were obtained at 600 and 150 MHz, respectively. These chemical shifts are representative of 4 independent fermentations and isolations of malacidin, and were referenced to the methyl group of triethylamine in D2O ($\delta_C$, 8.189, $\delta_H$ 1.292). The triethylamine concentrations in D2O are 3.59 mM for malacidins A and B. Each molar concentration of malacidins A and B was 11.21 mM and 7.92 mM.

As seen with friulimicin and other cell-wall-intermediate binding antibiotics, *S. aureus* treated with malacidin accumulates the cell wall precursor undecaprenyl-N-acetylmuramic acid-pentapeptide (UDP-MurNAc-pentapeptide) (FIG. 4C) (Schneider et al., 2009, *Antimicrob. Agents Ch.* 53, 1610-1618; Kleinj et al., 2016, *J. Med. Chem.* 59, 3569-3574). This signalled that the target of malacidin, like that of friulimicin, lies downstream of LDP-MurNAc-pentapeptide formation. Surprisingly, in a thin-layer chromatography (TLC) mobility shift assay, malacidin did not sequester $C_{55}$-P, the target of friulimicin (FIG. 4D) (Schneider et al., 2009, *Antimicrob. Agents Ch.* 53, 1610-1618; Kleinj et al., 2016, *J. Med. Chem.* 59, 3569-3574). Lipid II is the key downstream intermediate of MurNAc-pentapeptide. Therefore, malacidin was tested for lipid-II-binding activity. In this TLC-based mobility shift assay, lipid-II-dependent disappearance of the malacidin band was observed (FIG. 4D and FIG. 4E). Unlike previously characterized calcium-dependent antibiotics, malacidin neither depolarizes the membrane nor binds $C_{55}$-P but instead appears to interact with lipid 11 in a calcium-dependent manner. Fortuitously, despite the fact that vancomycin also binds lipid 11, the malacidins are active against both vancomycin-intermediate- and vancomycin-resistant pathogens.

The malacidins exhibited potent antibacterial activity against Gram-positive pathogens resistant to clinically used antibiotics, including the antibiotic of last resort vancomycin, and did not select for resistance in the laboratory under the conditions of these experiments. The discovery of the malacidins supports the hypothesis that the calcium-dependent antibiotics are a larger than previously thought family of NPs with low susceptibility to resistance and diverse modes of action. Environmental microbes are in a continuous antibiotic arms race that is likely to select for antibiotic variants capable of circumventing existing resistance mechanisms. The sequence-guided metagenomic discovery pipeline outlined here provides a means to interrogate complex environmental metagenomes for these uncharacterized antibiotics by tracking NPSTs that differ from those associated with known antibiotic BGCs. While metagenome-based antibiotic discovery methods are still in their infancy, the scaling and automation of the pipeline described here should permit the systematic discovery of NP antibiotics that have until now remained hidden in the global metagenome, providing a potentially powerful approach for combating antibiotic resistance.

TABLE 4

Results of Marfey's Analysis of malacidin A and B.

|  | $t_{RL}$ (min) | $t_{RD}$ (min) | Elution order | $\Delta t$ ($t_{RD}$-$t_{RL}$, min) |
|---|---|---|---|---|
| Amino acids of malacidin A |  |  |  |  |
| $_D$-valine | 27.1 | 22.2 | D → L | −4.9 |
| $_L$-lysine(di) | 28.7 | 30.6 | L → D | 1.9 |
| $_L$-hydroxyl aspartic acid | 16.0 | 15.0 | D → L | −1.0 |
| $_L$-aspartic acid | 13.4 | 14.4 | L → D | 1.0 |
| $_L$-valine | 22.3 | 27.0 | L → D | 4.7 |
| $_L$-(4R) methyl proline | 21.2 | 22.7 | L → D | 1.5 |
| (2S,4R)-4-methylpyrrolidine-2-carboxylic acid | 20.9 | 22.4 | L → D | 1.5 |
| Amino acids of malacidin B |  |  |  |  |
| $_D$-valine | 27.0 | 22.2 | D → L | −4.8 |
| $_L$-lysine(di) | 28.8 | 30.9 | L → D | 2.1 |
| $_L$-hydroxyl aspartic acid | 14.7 | 14.4 | D → L | −0.3 |
| $_L$-aspartic acid | 13.0 | 14.3 | L → D | 1.3 |
| $_L$-valine | 22.2 | 26.9 | L → D | 4.7 |
| $_L$-(4R) methyl proline | 21.2 | 22.6 | L → D | 1.4 |

TABLE 5

Full Spectrum of Activity of Malacidin Antibiotics and Daptomycin. The values are representative of the range of MICs determined in at least three independent experiments.

| Organism |  | Acquired Resistance | Malacidin A MIC (µg mL$^{-1}$) | Malacidin B MIC (µg mL$^{-1}$) | Daptomycin MIC (µg mL$^{-1}$) |
|---|---|---|---|---|---|
| *Acinetobacter baumannii* | ATCC 17978 |  | >100 | >100 | >100 |
| *Bacillus subtilis* | 168 IAI |  | 0.2-0.4 | N.D. | 0.2-0.4 |
| *Candida albicans* | ATCC 1884 |  | >100 | >100 | >100 |
| *Cryptococcus neoformans* | ATCC 32045 |  | >100 | >100 | >100 |
| *Enterococcus faecium* | Com15 |  | 0.8-2.0 | 0.8-2.0 | 0.4-2.0 |
| *Enterococcus faecium* | VRE | Vancomycin (VRE) | 0.8-2.0 | N.D. | 0.4-2.0 |
| *Escherichia coli* | DH5α |  | >100 | >100 | >100 |
| *Escherichia coli* | BAS849 |  | >100 | N.D. | 50-100 |
| Human embryonic kidney cells | HEK293 |  | >100a | N.D. | >100a |
| Human lung fibroblast cells | MRC5 |  | >100a | N.D. | N.D. |
| *Klebsiella pneumonia* | ATCC 10031 |  | >100 | >100 | >100 |
| *Lactobacillus rhamnosus* | NCTC 13031 |  | 0.1-0.2 | N.D. | N.D. |
| *Pseudomonas aeruginosa* | PAO1 |  | >100 | >100 | >100 |
| *Salmonella enterica* | IR 715 |  | >100 | >100 | >100 |
| *Staphylococcus aureus* | USA300 | β-lactams (Methicillin, Oxacillin, Penicillin) | 0.2-0.8 | 0.4-0.8 | 0.2-0.8 |
| *Staphylococcus aureus* + 10% Serum | USA300 | β-lactams (Methicillin, Oxacillin, Penicillin) | 0.2-0.8 | N.D. | N.D. |
| *Staphylococcus aureus* | COL | β-lactams (Methicillin, Oxacillin, Penicillin) | 0.2-0.8 | N.D. | 0.2-0.8 |
| *Staphylococcus aureus* | BAA-42 | β-lactams (Methicillin, Oxacillin, Penicillin) | 0.2-0.8 | N.D. | 0.2-0.8 |
| *Staphylococcus aureus* | NRS100 | β-lactams, Tetracycline | 0.2-0.8 | N.D. | 0.2-0.8 |
| *Staphylococcus aureus* | NRS108 | β-lactams, Gentamicin, Kanamycin | 0.2-0.8 | N.D. | 0.2-0.8 |

TABLE 5-continued

Full Spectrum of Activity of Malacidin Antibiotics and
Daptomycin. The values are representative of the range of MICs
determined in at least three independent experiments.

| Organism | | Acquired Resistance | Malacidin A MIC (μg mL$^{-1}$) | Malacidin B MIC (μg mL$^{-1}$) | Daptomycin MIC (μg mL$^{-1}$) |
|---|---|---|---|---|---|
| Staphylococcus aureus | NRS140 | β-lactams, Erythromycin, Spectinomycin | 0.4-2.0 | N.D. | 0.2-0.8 |
| Staphylococcus aureus | NRS146 | β-lactams, Vancomycin (VISA) | 0.4-0.8 | N.D. | 0.2-0.8 |
| Streptococcus mutans | UA159 | | 0.1-0.2 | N.D. | N.D. |
| Streptococcus pneumoniae | TCH8431 | | 0.1-0.2 | N.D. | 0.1-0.2 |

N.D. = Not determined/tested
a = Viability assessed by ATP release assay

NPST Generation and Sequencing

To add to the diversity of the 185 previously collected soil samples (Owen et al., 2013, PNAS 110:11797-802; Owen et al., 2015, PNAS 112:4221-26), an additional 1,800 soils were collected for this study from sites throughout the United States. Crude eDNA was extracted from each of these following established protocols (Brady, 2007, Nat Protoc 2:1297-1305; Owen et al., 2015, PNAS 112:4221-26). Briefly, 25 g of soil was heated (70° C.) in lysis buffer (100 mM Tris.HCl, 100 mM EDTA, 1.5 M NaCl, 1%/i (w/v) CTAB, 2% (w/v) SDS, pH 8.0) for 2 h. Soil particulates were removed from the crude lysate by centrifugation, and eDNA was precipitated from the resulting supernatant with the addition of 0.7 volumes of isopropanol. Crude eDNA was collected by centrifugation, washed with 70% ethanol and resuspended in TE. Crude eDNA was then spin-column-purified (PowerMax soil DNA kit) and employed as a template in PCR experiments targeting ADs as follows: AD fragments (~795 bp) were amplified using primers: 5'-GCSTACSYSATSTACACSTCSGG-3' and 5'-SASGTCVCCSGTSCGGTA-3'. These primers are designed to recognize the conserved regions in NRPS ADs (Owen et al., 2013, PNAS 110:11797-802; Owen et al., 2015, PNAS 112:4221-26). The 5' ends of the primers were augmented with MiSeq sequencing adapters followed by unique 8 bp barcode sequences identifying the soil metagenome from which they were amplified. PCR conditions: 12 μl reaction, 1×Buffer G (Epicentre), 50 pmol of each primer, 2.5 units Omni Klentaq polymerase (DNA Polymerase Technology) and 100 ng eDNA. Cycle conditions for AD amplification: 95° C.; 4 min. (95° C. 30 s, 63.5° C. 30 s, 72° C. 45 s)×34 cycles, 72° C. 5 min. First-round amplicons contained incomplete Illumina adaptors and therefore required a second round of PCR to append the remainder of the adaptor sequence. Amplicons were pooled as collections of 96 samples and cleaned using Agencourt Ampure XP magnetic beads (Beckman Coulter). Cleaned, pooled amplicons were used as a template in a second 20-μl PCR using the following reaction conditions: 10 μl of FailSafe Buffer G (Epicentre), 5.8 μl of water, 0.4 μl of each primer (100 μM) (MiSeqForward, CAAGCAGAAGACGGCATACGAGATGTGACTTCGAGITCAGACGTGTGCTCTTCCGATCT (SEQ ID NO:5); MiSeq Reverse AATGATACGGCTGACCACCGAGATCTACACTCTTTCCCTACACiACGCTCT TCCGATCT (SEQ ID NO:6)), 0.4 μl of Taq and 3 μl of cleaned amplicon (50 ng to 100 ng). Amplification proceeded as follows: 95° C. for 5 min, 6 cycles of 95° C. for 30 s, 70° C. for 30 s and 72° C. for 45 s, and, finally, 72° C. for 5 min. Prior to sequencing, all PCR amplicons were quantified by gel electrophoresis and mixed in an equal molar ratio. The resulting pool was fluorometrically quantified with an HS D1000 ScreenTape (Agilent 2200 TapeStation; Agilent Technologies) and sequenced on an Illumina MiSeq instrument using Reagent Kit v3 (MS-102-3003, Illumina).

Biosynthetic Profiling of NPSTs

Amplicon sequences were analysed and organized using the eSNaPD (environmental Surveyor of Natural Product Diversity) web-based tool as previously described (Owen et al., 2015, PNAS 112:4221-26; Owen et al., 2013, PNAS 110, 11797-11802; Reddy et al., 2014, Chem. Biol. 21, 1023-1033). The NRPS ADs from sequenced and known calcium-dependent antibiotic gene clusters (daptomycin, friulimicin, CDA, laspartomycin, A54145 and taromycin) were added to the eSNaPD reference database of domains from annotated and functionally characterized natural product gene clusters. NPSTs whose closest relatives among all reference ADs were one of these known lipopeptide domains were identified and mapped to soil locations and/or library wells. This analysis, in brief, was completed as previously described (Charlop-Powers et al., 2016, PNAS 113:14811-6) by debarcoding samples using a paired-end 2×8 bp barcode strategy. Debarcoded reads were filtered for quality and 240 bp of the forward reads, a single 'N' spacer and 175 bp of the reverse-complemented reverse read were concatenated to generate a synthetic amplicon of 416 bp. The reads from each sample were clustered using UCLUST (Edgar, 2010, Bioinformatics 26:2460-1) to generate the 95% identity centroid sequences (that is, NPST). Location information was used to map NPSTs back to soil collection locations and/or library wells. The forward read component (the first 240 bp) of each NPST was then searched using BlastN (Altschul et al., 1990, J Mol Biol 215:403-10) against a manually curated database of NRPS AD sequences. NPSTs that returned one of the known calcium-dependent antibiotics as a top match were considered hits. The resulting set of unique hits was used to generate geographic and phylogenetic distribution figures. A multiple sequence alignment of all sequences was generated using MUSCLE (Edgar, 2004, NAR 32:1792-7), and the resulting alignment file was used to generate a maximum-likelihood tree with FastTree (Price et al., 2009, Mol Biol Evol 26:1641-50).

Construction and Arraying of Metagenomic Cosmid Libraries eDNA cosmid libraries were constructed from soil using established protocols (Brady et al., 2007, Nat. Protoc. 2, 1297-1305). Briefly, crude eDNA was isolated from ~0.5 kg of soil as outlined above, and further purified by preparative agarose gel electrophoresis to yield pure high-molecular-weight eDNA. High-molecular-weight eDNA was blunt-ended (Epicentre, End-It), ligated into pWEB-TNC (Epicentre), packaged into lambda phage and transfected into E. coli EC100 (Epicentre). Following recovery, transfected cells were inoculated into 8 ml LB with selective antibiotic (12.5 µg ml$^{-1}$ chloramphenicol) in 24-well plates at a density of ~25,000 clones per well and grown overnight. Matching glycerol stocks and cosmid DNA minipreps were prepared from each well, and arrayed as 768 pools of ~25,000 unique cosmid clones. NPST data were prepared from each library pool by amplifying and sequencing ADs as described above.

Recovery of Biosynthetic Gene Clusters from eDNA Libraries

Calcium-dependent antibiotic-like NPST sequences identified within metagenomic libraries were automatically assigned to library wells by the barcode parsing functionality of the eSNaPD software package as described above. Specific primers targeting each unique sequence of interest were designed by hand. To recover single clones from library wells, a serial dilution PCR strategy (Owen et al., 2015, PNAS 112:4221-26) was used as follows: library wells containing targets as 1 of ~25,000 unique cosmids were grown overnight to confluence in LB (12.5 µg ml$^{-1}$ chloramphenicol, 100 µg ml$^1$ carbenicillin) and diluted to a concentration of 3,000 colony-forming units (CFUs) ml$^{-1}$ as judged by OD$_{600\ nm}$. Then, 384-well plates were inoculated with 100 µl (300 CFU) of the resulting dilution per well, grown to confluence, and screened using real-time PCR, to identify wells containing target clones as 1 of ~300 clones. Target positive wells were then diluted to a concentration of ~50 CFU ml and the process was repeated to identify wells containing targets as 1 of ~5 clones. Five clone pools were then plated on solid medium, and target clones were identified by colony PCR.

In Silico Analysis of Recovered Gene Clusters

Recovered single cosmid clones were pooled and sequenced using ion PGM technology. Reads were assembled into contigs using an assembler program, such as Newbler (Zhang et al., 2012, BMC Res Notes 5:567). Overlapping cosmids spanning a single pathway were initially sequenced separately and subsequently assembled into larger contigs. Assembled contigs were then annotated using an in-house pipeline consisting of open-reading-frame predictions with MetaGeneMark (Zhu et al., 2010, NAR 38:e132), BLAST search (Altschul et al., 1990, J Mol Biol 215:403-10) and AntiSMASH predictions (Medema et al., 2011, NAR 39:W339-46). The AntiSMASH predictions employ three prediction algorithms to call the amino acid substrate specificity of an adenylation domain (NRPSPredictor2, Stachelhaus code and Minowa). These amino acid predictions were used in the initial bioinformatic characterization of clusters to predict chemical structures. Putative functions for new tailoring enzymes in eDNA pathways were assigned on the basis of the predicted function of the closest characterized relative identified by Blast in NCBI.

Assembly of DFD0097-735 pTARa BAC for Heterologous Expression

For assembly of the DFD0097-735 pTARa bacterial artificial chromosome (BAC), transformation-associated recombination (TAR) in yeast was employed (Kim et al., 2010, Biopolymers 93:833-44; Kallifidas & Brady, 2012, Methods Enzymol 517:225-39). Initially, the three overlapping cosmids (DFD0097-644, DFD0097-735 and DFD0097-388) containing the full biosynthetic pathway were digested and linearized with DraI. A custom E. coli:yeast:Streptomyces shuttle capture vector, pTARa, containing two 500 bp homology arms to the terminal overlapping cosmid clones was constructed as previously described (Kim et al., 2010, Biopolymers 93:833-44; Kallifidas & Brady, 2012, Methods Enzymol 517:225-39). This vector was subsequently linearized with PmeI and gel-purified. The linearized cosmids and capture vector were then co-transformed into Saccharomyces cerevisiae(BY4727 Δdn14) using a standard LiAc/ss carrier DNA/PEG yeast transformation protocol (Gietz & Schiestl, 2007, Nat Protoc 2:38-41) Briefly, yeast were grown overnight in 50 ml of YPD medium containing G418 (200 µg ml$^{-1}$) at 30° C. In the morning, 2 ml of the overnight culture was reinoculated into 50 nil of fresh YPD medium containing G418 (200 µg ml$^{-1}$) and grown for ~4 h (OD$_{600\ nm}$=2.0). This culture was harvested by centrifugation (10 min, 3,200 g), washed twice with sterile 4° C. water and resuspended in 1 ml of sterile 4° C. water. For each transformation 100 µl of washed cells was transferred to a Microfuge tube. The cells were collected by centrifugation (30 s, 18,000 g) and resuspended in a transformation mix containing 36 µl of 1 M LiAc solution, 50 µl of 2 mg ml$^{-1}$ carrier DNA (salmon sperm DNA) solution, 240 µl of 50% (wt/vol) PEG 3350 solution, and 34 µl of Tris-EDTA containing 2 µg of each cosmid and 1 µg of vector. This transformation mix was incubated at 42° C. for 40 min. Cells were then collected by centrifugation (30 s, 18,000 g), resuspended in 100 µl of water and plated on appropriate synthetic composite dropout medium agar plates. Agar plates were incubated at 30° C. until colonies appeared. Colonies were checked by PCR. DNA was isolated from PCR-positive yeast clones, transferred into E. coli ET12567/pUZ8002 cells and then moved into Streptomyces spp. by intergeneric conjugation for heterologous expression.

Heterologous Expression

The assembled BAC, DFD0097-735 pTARa and an empty pTARa vector control were separately integrated into the chromosome of Streptomyces albus J1074. Spore suspensions of these recombinant strains were used to seed starter cultures in 50 ml trypticase soy broth (Oxoid). These cultures were grown for 48 h (30° C./200 rpm) and 0.4 ml of the resulting confluent culture was used to inoculate 50 ml flasks of production medium, R5a medium: 100 g l$^{-1}$ sucrose, 0.25 g l$^{-1}$ K$_2$SO$_4$, 10.12 g l$^{-1}$ MgCl$_2$, 10.0 g l$^{-1}$ D-glucose, 0.1 g l$^{-1}$ casamino acids, 21 g l$^{-1}$ MOPS, 2 g l$^{-1}$ NaOH, 40 µg l$^{-1}$ ZnCl$_2$, 20 µg l$^{-1}$ FeCl$_3$ 6H$_2$O, 10 µg l$^{-1}$ MnCl$_2$, 10 µg l$^{-1}$ (NH$_4$)$_6$Mo$_7$O$_{24}$ 4H$_2$O. Fifty-millilitre liquid cultures were grown in 125 ml baffled flasks (22° C., 220 rpm) for 14 days.

Isolation of Malacidin A and B

After 14 days, 41 of cultures were combined, and mycelia were removed by centrifugation at 4,000 g for 20 min. The mycelium-free medium supernatant was applied to 150 g of pre-equilibrated Diaion HP-20 resin packed in a column (40×220 mm). The HP-20 column was subsequently washed with 21 of H$_2$O, and then eluted with 21 of 100% methanol. The methanolic elution was concentrated by rotary evaporation, and then combined with 2 g octadecyl-functionalized silica resin (Sigma-Aldrich) per 10 ml concentrate. This resin/concentrate mixture was dried overnight on a Savant Speedvac Concentrator (Thermo-Fisher). The dried loaded resin was used to dry-load a 100 g Gold HP C18 column for medium-pressure reversed-phase chromatography (Teledyne Isco Combiflash Rf150). This chromatography was performed using a linear gradient of 0.1% acetic acid-acetonitrile from 10% to 100% over 20 min at 60 ml min. To identify column fractions containing active compound, aliquots of 10 ml fractions were analysed by ultra-performance liquid chromatography-mass spectrometry (UPLC-MS). Fractions containing the malacidins were pooled, re-dried on resin, and subjected to a second-round medium-pressure, narrow-range reversed-phase chromatography. Using a 100 g Gold HP C18 column, chromatography was performed with a linear gradient of 0.1% acetic acid-acetonitrile from 30% to 60% over 20 min at 60 ml min$^{-1}$. This enabled the initial separation of malacidin-A-containing and malacidin-B-containing fractions. Combined fractions containing either malacidin A or B were subsequently cleaned up individually using preparative high-performance liquid chromatography (HPLC; XBridge Prep C18, 10×150 mM, 5 µM, Agilent HPLC System) using a linear gradient of 0.1% trifloroacetic acid-acetonitrile from 30% to 50% over 30 min at a flow rate of 4 ml min$^{-1}$. Malacidin A and B had a retention time of 12 min and 16 min, respectively. For analysis of purity and detection of fractions by UPLC-MS throughout the isolation process, 5 µl was injected onto a UPLC-MS system (Waters Corporation) and analysed by a linear gradient of 0.1% formic acid-acetonitrile from 30% to 50% over 3.4 min.

Structural Determination by NMR and ESI-MS/MS $^1$H and $^{13}$C NMR spectra were obtained at 600 and 150 MHz, respectively, on a Bruker Avance DMX600 NMR. Spectra were taken at 298 K using either 11.21 mM malacidin A or 7.92 mM malacidin B in 3.59 mM triethylamine in D$_2$O, unless otherwise noted. The chemical shifts were referenced to the methyl group of triethylamine in D$_2$O ($\delta_C$ 8.189, $\delta_H$ 1.292). For electrospray ionization with tandem mass spectrometry (ESI-MS/MS), samples in methanol were diluted 1:50 with 50% methanol/0.1% formic acid and infused (5 µl min) for analysis by high-resolution (60,000 at m/z 200)/high-mass-accuracy MS, MS2 and MS3 (Fusion Lumos, ThermoFischer Scientific). In addition, each sample was diluted 1:1 with 0.1 M ammonium bicarbonate for propionylation of primary amines followed by a 1:25 dilution in methanol/0.1% formic acid and analysis by ESI-MS, MS2 and MS3. Positive-ion ESI conditions: 3.9 kV, heated capillary set at 300° C. and sheath gas setting of '1'. Both ion-trap-based collision-induced dissociation (CID) and beam-type fragmentation (HCD) were used. For fragmentation experiments, ions were isolated using a window of 2.0 m/z.

NMR and MS Analysis

Malacidin A was isolated as a white powder at a yield of 6 mg L$^{-1}$ of S. albus DFD0097-644:735:388 culture. The molecular formula was obtained as C56H88N12O20 by HRESIMS (experimental [M+H]$^+$=1249.6295, calculated [M+H]+ for C56H89N12O20=1249.6316), and confirmed by $^1$H and $^{13}$C and edited HSQC NMR spectra. Through COSY, TOCSY, and HMBC NMR analysis, the partial structures of 10 amino acids and an unsaturated fatty acid were developed. The ten amino acid groups were an aspartic acid, two 3-methyl aspartic acids (MeAsp), a 3-hydroxyl aspartic acid (HyAsp), a 2,3-diamino 3-methyl propanoic acid (MeDap), a 4-methyl proline (MePro), two valines (Val), a lysine (Lys), and a glycine (Gly). Based on $^1$H NMR and edited HSQC NMR spectra, 4 deshielded olefinic protons, 10 amide alpha protons from $\delta_H$ 4.85 to $\delta_H$ 3.98 coupled with $\delta_C$ 60.3 to $\delta_C$ 42.6, an oxymethine proton $\delta_H$ 4.58, 7 methyl methine protons, 9 methylene protons, and 10 methyl protons were revealed. The $^{13}$C NMR spectrum indicated 15 carbonyl carbons ($\delta_C$ 177.4~169.5), 4 olefinic carbons ($\delta_C$ 143.3~121.6), and 10 methyl carbons. The HMBC correlations from $\delta_H$ 3.13 and 1.23 to $\delta_C$ 177.4 and from $\delta_H$ 3.06 and 1.21 to $\delta_C$ 177.4, indicating the connections of carboxyl acids, established two methyl aspartic acids. The hydroxyl aspartic acid was developed by the HMBC correlation between $\delta_H$ 4.58 (connected with $\delta_C$ 70.5) and $\delta_C$ 174.5. The β methine carbon of diamino methyl propanoic acid was developed by the empirical $^1$H-$^{13}$C chemical shift of $\delta_H$ 4.27-$\delta_C$ 47.8 indicating a nearby nitrogen atom. The 4-methyl proline amino acid was supported by HMBC correlations between $\delta_H$ 3.79, 3.43, 2.48, 1.96, and 1.86 and $\delta_C$ 16.8. The valine and lysine amino acids were also established by HMBC correlations. The COSY correlations of olefinic protons between $\delta_H$ 7.64, 6.24, 6.18, and 6.03 indicated a diene functional group and the HMBC correlations between $\delta_H$ 6.18 and $\delta_C$ 169.5 supported an α,β-unsaturated carbonyl functional group. Through further COSY and HMBC analysis, methyl nonadienoic acid was fully determined. The geometries of methyl nonadienoic acid were determine by measuring coupling constants, $\delta_H$ 6.18 (d, J=15 Hz), $\delta_H$ 7.64 (dd, J=15, 11 Hz), $\delta_H$ 6.24 (dd, J=11, 11 Hz), and $\delta_H$ 6.03 (ddd, J=11, 7.5, 7.5 Hz) in sequence.

Based on the structures of 10 partial amino acids and a fatty acid, the five connected partial structures were developed by HMBC correlations between the α proton of amino acids and two carbonyl carbons of neighboring two amino acids. The HMBC correlations from $\delta_H$ 6.18 and 4.85 to $\delta_C$ 169.5 indicated the connection between methyl nonadienoic acid and MeAsp. The HMBC correlations from $\delta_H$ 4.39, 1.97, 1.86, and 4.27 to $\delta_C$ 173.8 indicated a MeDap-MePro residue. The MeAsp-Val residue was developed by HMBC correlations between $\delta_H$ 4.70, 4.03 and $\delta_C$ 171.4. The Lys-HyAsp-Asp-Gly residue was also constructed by HMBC correlations. To overcome the missing HMBC correlation among 5 residues and confirm the planar structure of malacidin A, the propionate derivative of malacidin A was made by reaction with propionic anhydride. The existence of a lysine was confirmed by more than 56 Da of a primary amine. The structure of propionic malacidin A was deduced by HRESI-MS/MS fragmentation experiments. Through MS/MS fragmentation analysis, the major ion value 433.1200 indicated the sequence connection of HyAsp-Asp-Gly-MeAsp including a Lys-HyAsp-Asp-Gly block, which was developed by HMBC. The major ion value 774.4767 supported the connection of two blocks between Lys-HyAsp-Asp-Gly and MeAsp-Val. The major fragment ion 280.1542 was confirmed as a Methylnonadienoic acid-MeAsp block. The major fragment ion 1026.5110 possessed the total value of 4 building blocks. Through fragmentation analysis, 774.4767, 590.3550, and 491.2865 ions were deduced to be a sequence from methylnonadienoic acid to propionate lysine. Malacidin B was isolated as white powder at a yield of 2.5 mg L-1 of S. albus DFD0097-644:735:388 culture. Its molecular formula was determined to be C57H90N12O20 by HRESIMS (found m/z 1263.6484, calcd for C57H91N12O20, 1263.6473). The 14 Dalton difference of molecular formula between 1 and 2 suggested that malacidin B was an analogue of A. The COSY, TOCSY, and HMBC analysis of malacidin B illustrated an additionally CH2 bond on the unsaturated fatty acid moiety. The triplet ($\delta_H$ 0.86) and doublet ($\delta_H$ 0.89) methyl proton signals suggests methyl decadienoic acid as the N-terminal fatty acid of malacidin B. Through HRESIMS/MS fragmentation experiments, malacidins A and B were confirmed to possess the same cyclic core peptide, strongly supporting the proposal that malacidin B is only different on the fatty acid side chain compared to malacidin A.

Bioinformatic Analysis

Figure 27:
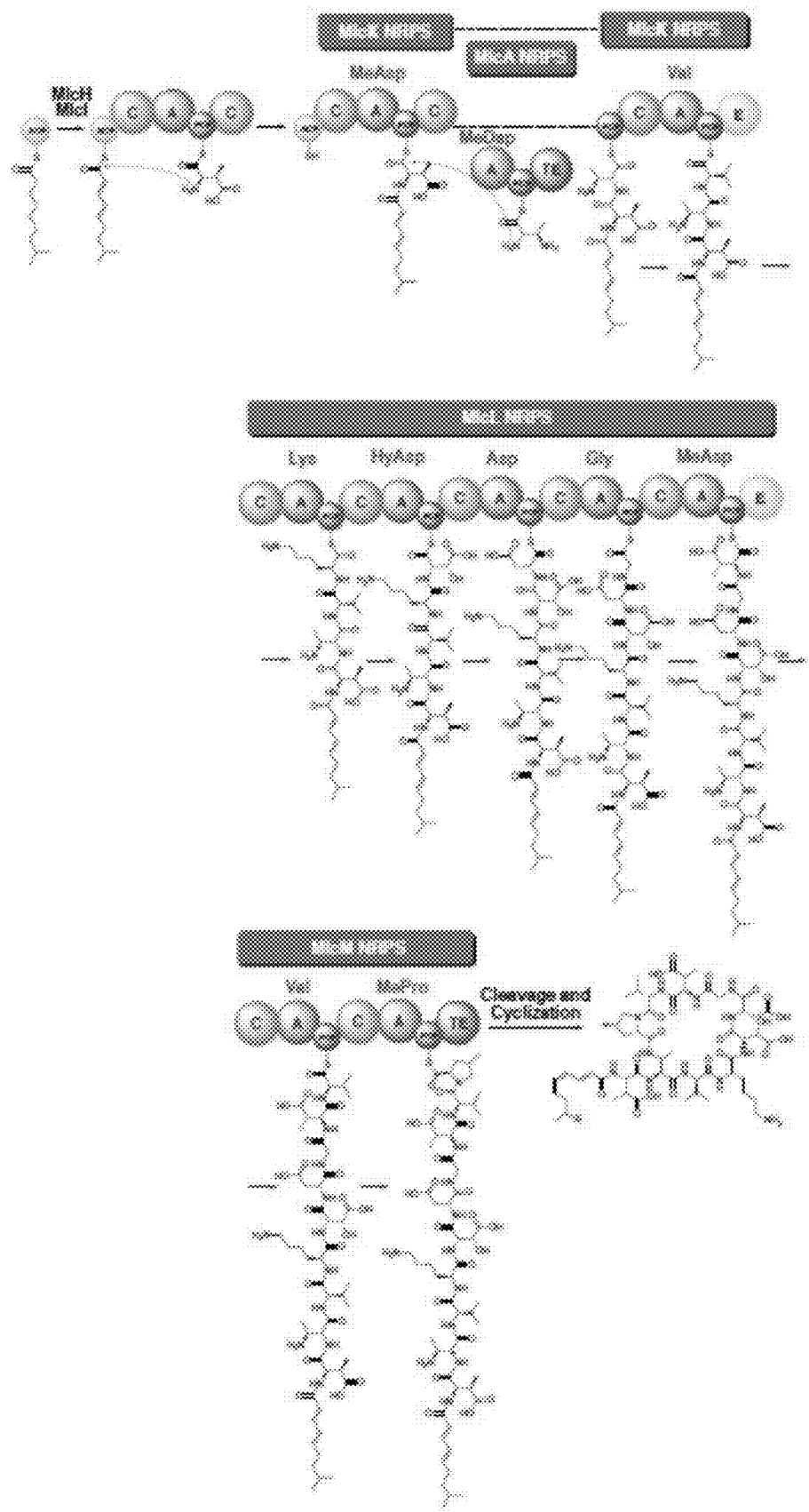
FIG. 27 depicts the proposed biosynthesis of malacidin A
Figure 29A:
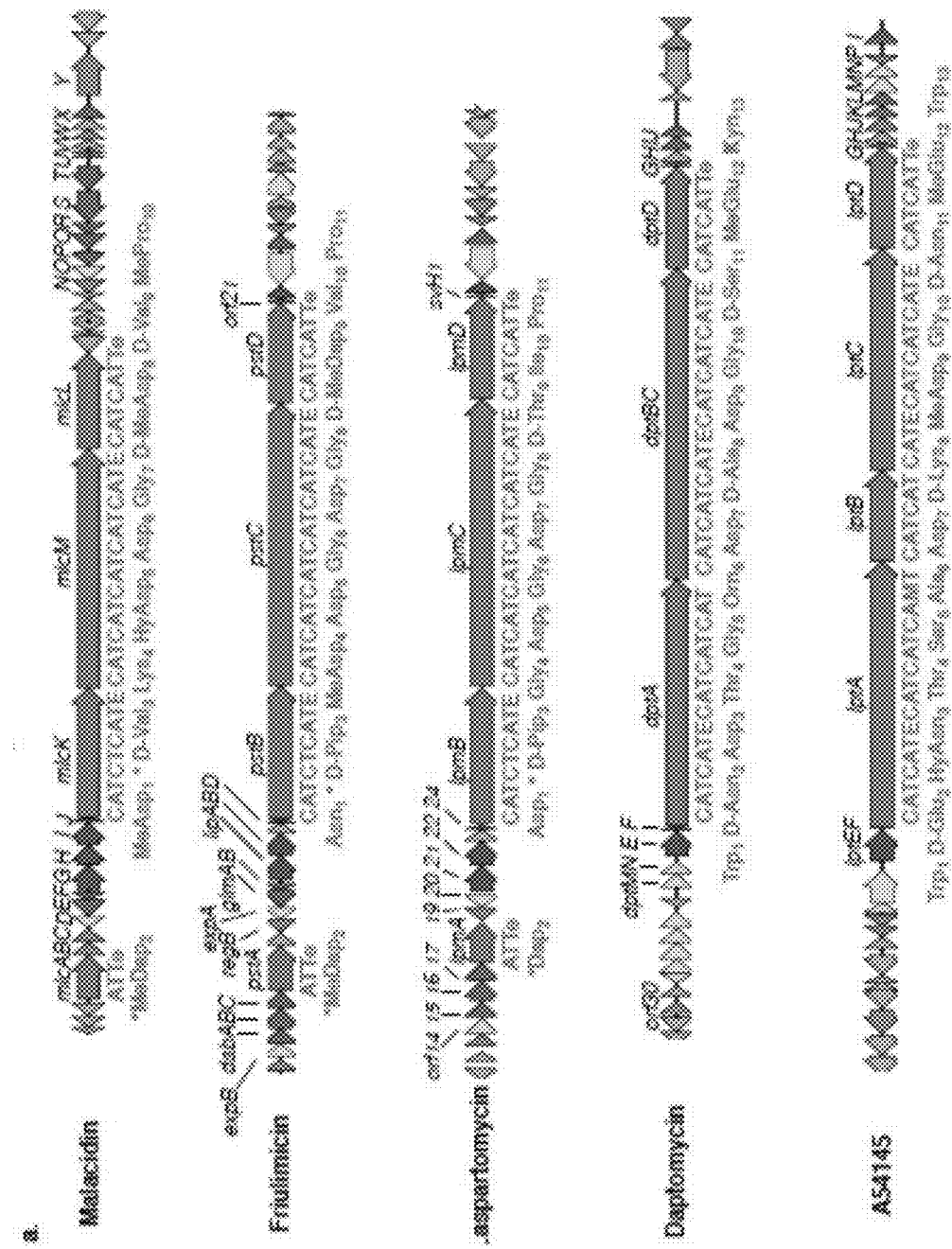

Support for the general structure of the malacidins was provided by a detailed bioinformatics analysis of the malacidin BGC (GenBank Accession KY654519). Four genes of the malacidin BGC are predicted to encode for nonribosomal peptide synthetases (MlcA and MlcK-M). Within this collection of NRPSs, there are a total of 10 adenylation domains, corresponding to the production of a 10-amino acid peptide (FIGS. 27-29). Genes predicted to encode the biosynthesis of three of the four non-proteinogenic amino acids present in the malacidins were easily identified in the malacidin BGC (Table 4, FIGS. 27-29). Only the origin of the 3-hydroxyl aspartic acid is not immediately obvious from the gene prediction analyses. The 3-methyl aspartic acids are likely produced by MlcE and MlcF, which show high sequence similarity to proteins GlmA and GlmB from the cobalamindependent glutamate mutase complex used to produce the same amino acid in friulimicin biosynthesis (Heinzelmann et al., 2003, Antimicrob Agents Ch 47:447-57). MlcPR are related to GriH, GriF/nosE and GriE, which are responsible for 4-methyl proline production in griselimycin and nostopeptolide biosynthesis (Liu et al., 2014, ACS Chem Biol 9:2646-55; Leusch et al., 2003, J Org Chem 68:83-91). Similarly, MlcT and MlcS share high sequence similarity to DabB and a fused DabC-A protein from *Actinoplanes friuliensis*, which are essential for 2,3-diamino 3-methyl propanoic acid. 4 Additionally, MlcG-J are predicted to be involved in the synthesis (MlcG), desaturation (MlcHI), and incorporation (MlcJ) of the N-terminal fatty acid component to malacidin A (Muller et al., 2007, Antimicrob Agents Ch 51:1028-37: Strieker & Marahiel, 2009, Chembiochem 10:607-16).

Stereochemical Analysis

Figure 23:
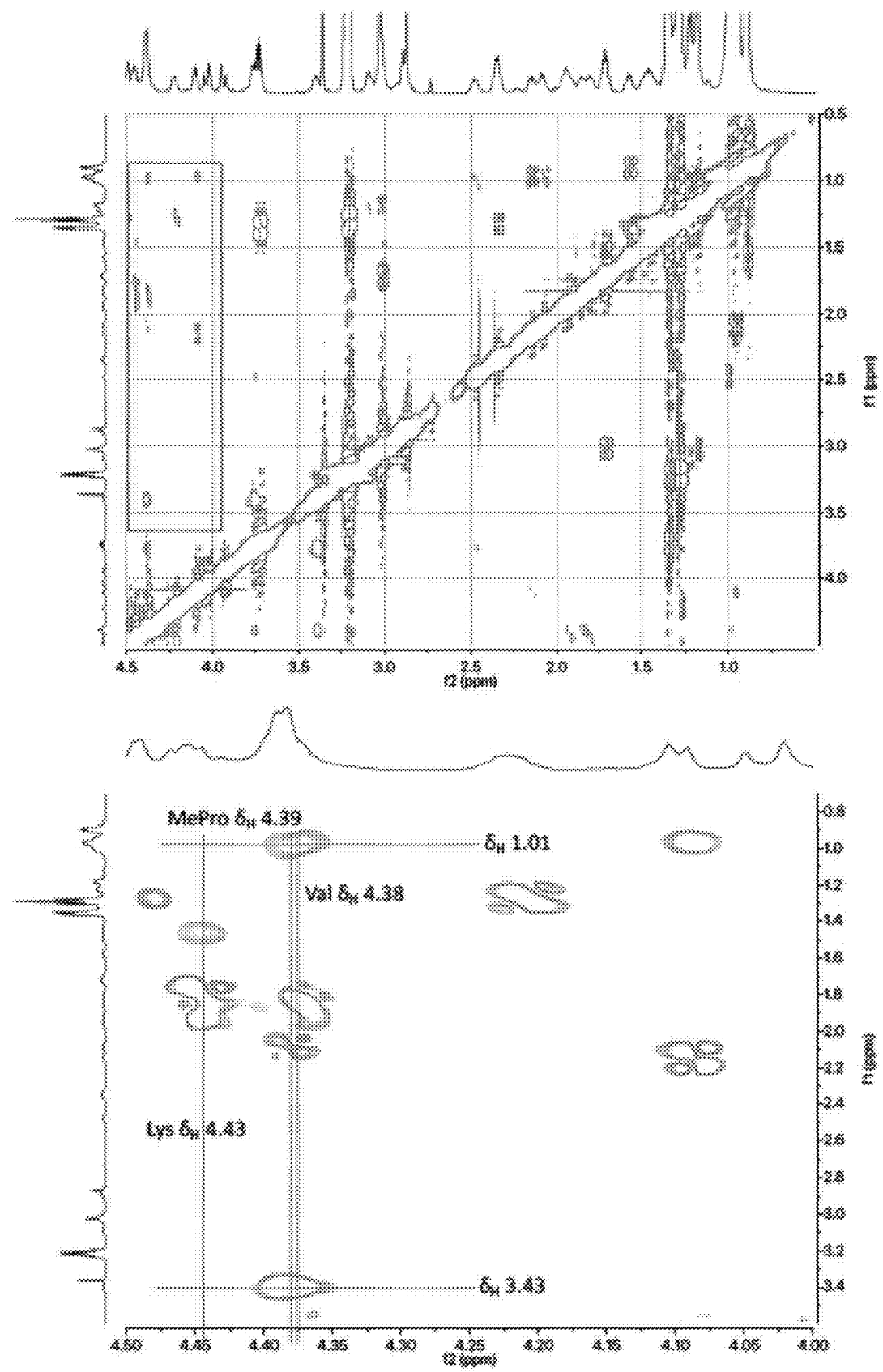
FIG. 23 depicts the ROESY NMR spectrum of malacidin A. Representative NMR spectrum of malacidin from 4 independent fermentations and isolations. Key correlations are highlighted in the red box, and zoomed in below the main spectrum.
Figure 24:
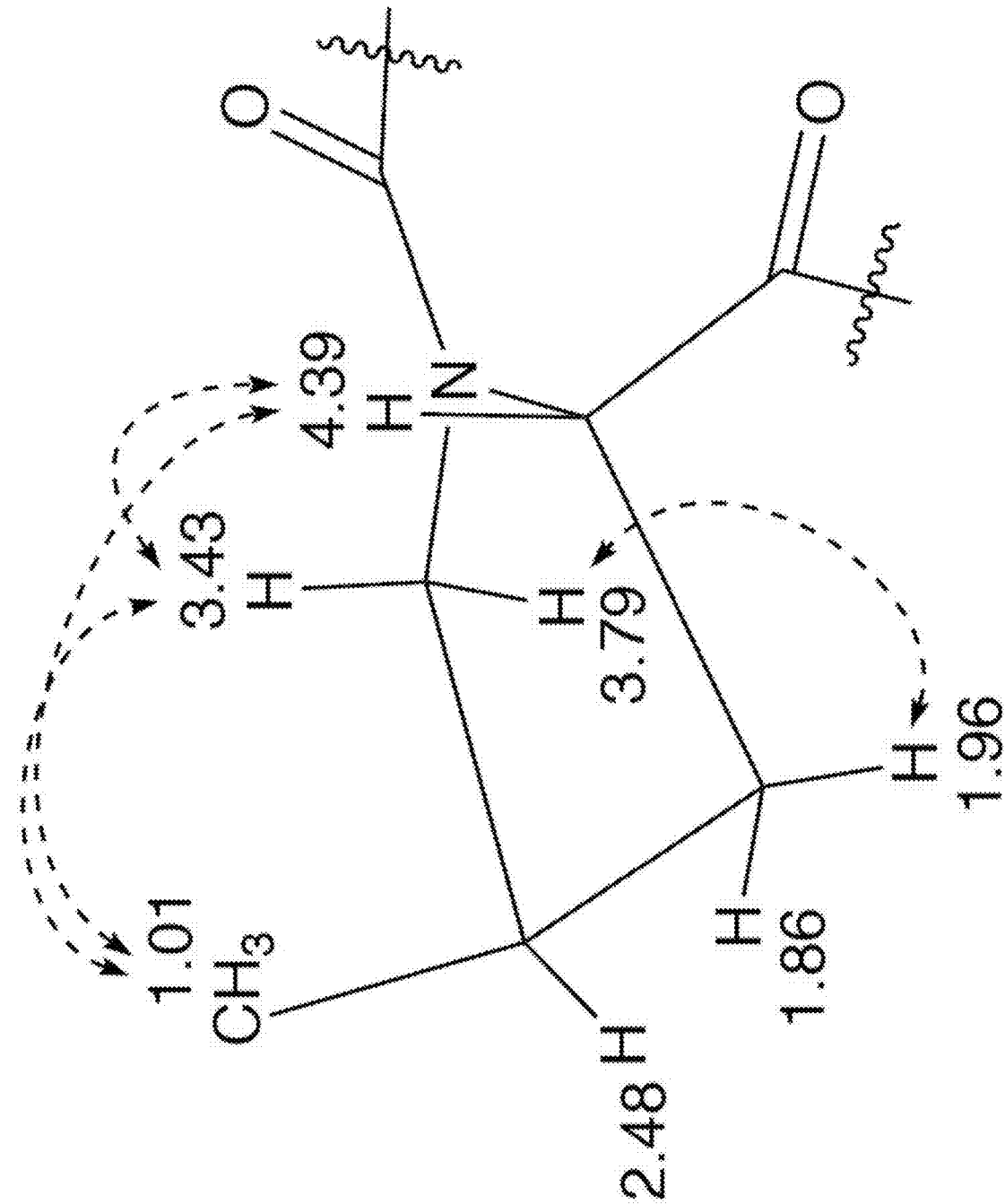
FIG. 24 depicts the key ROESY correlations of methyl proline of malacidin A.
Figure 25:
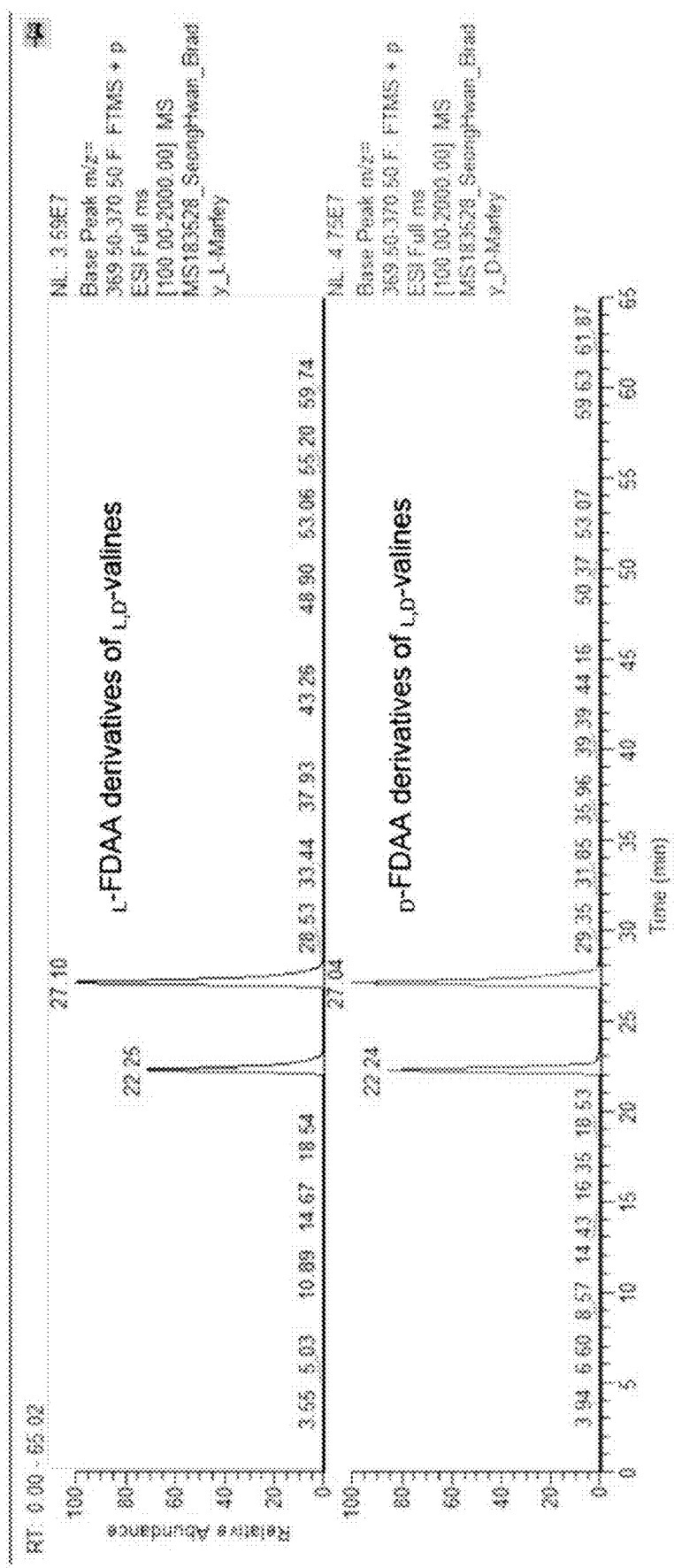
FIG. 25 depicts LC-MS charts of L, D-FDAA derivatives of malacidin A Chromatograms are representative across two independent derivatizations.
Figure 25:
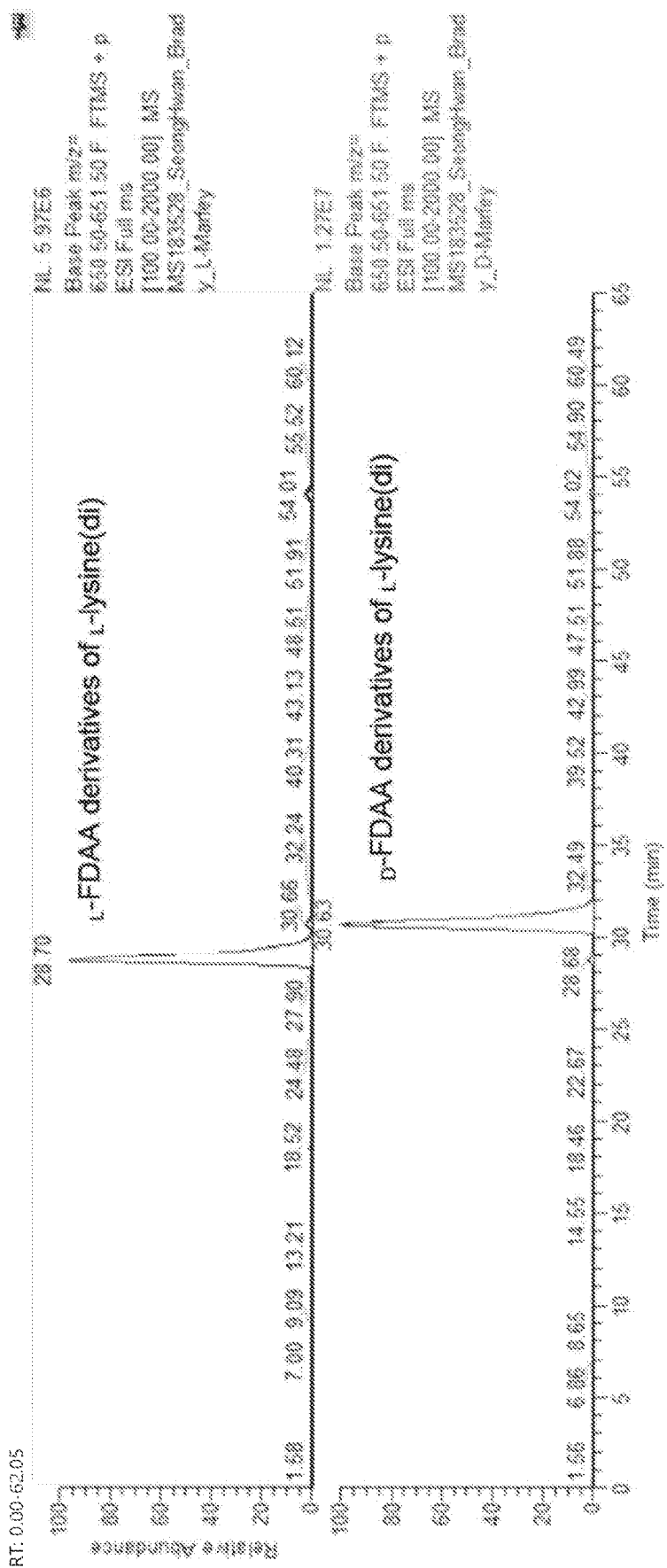
Figure 25:
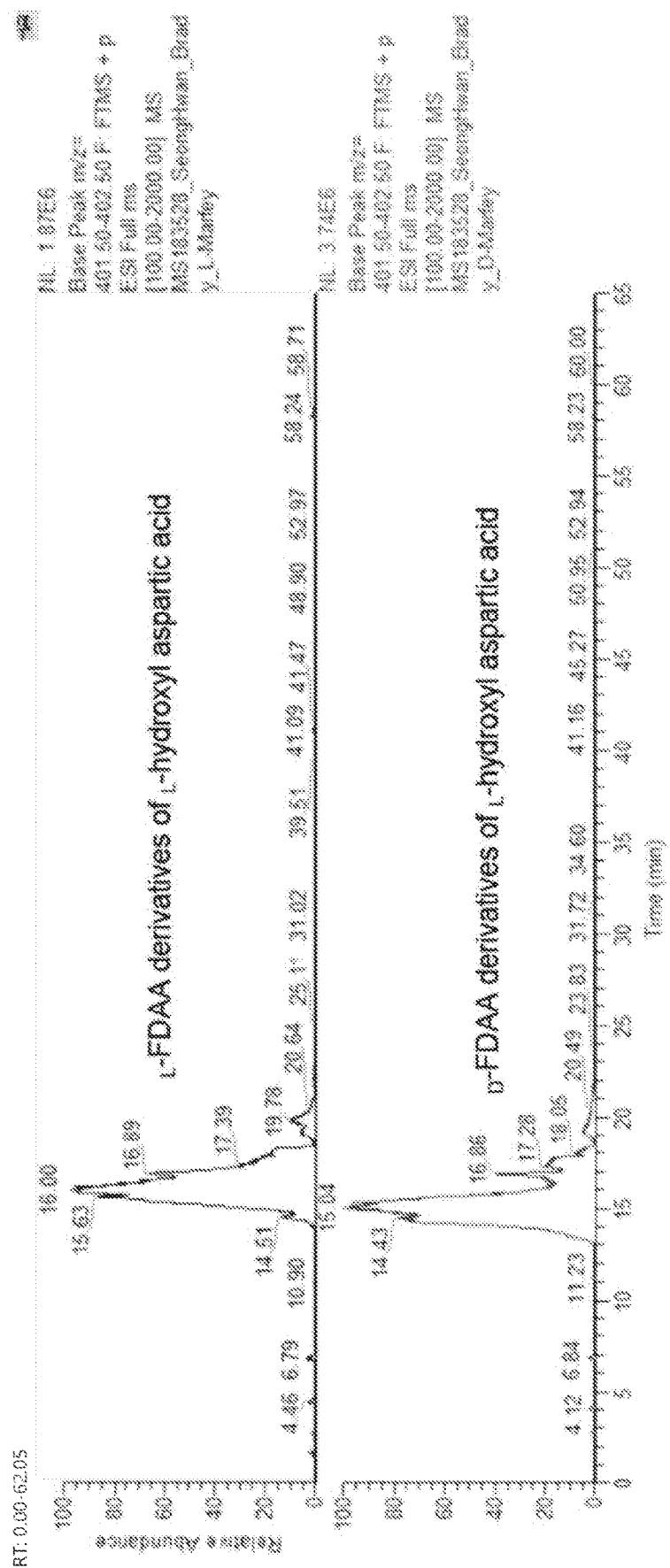
Figure 25:
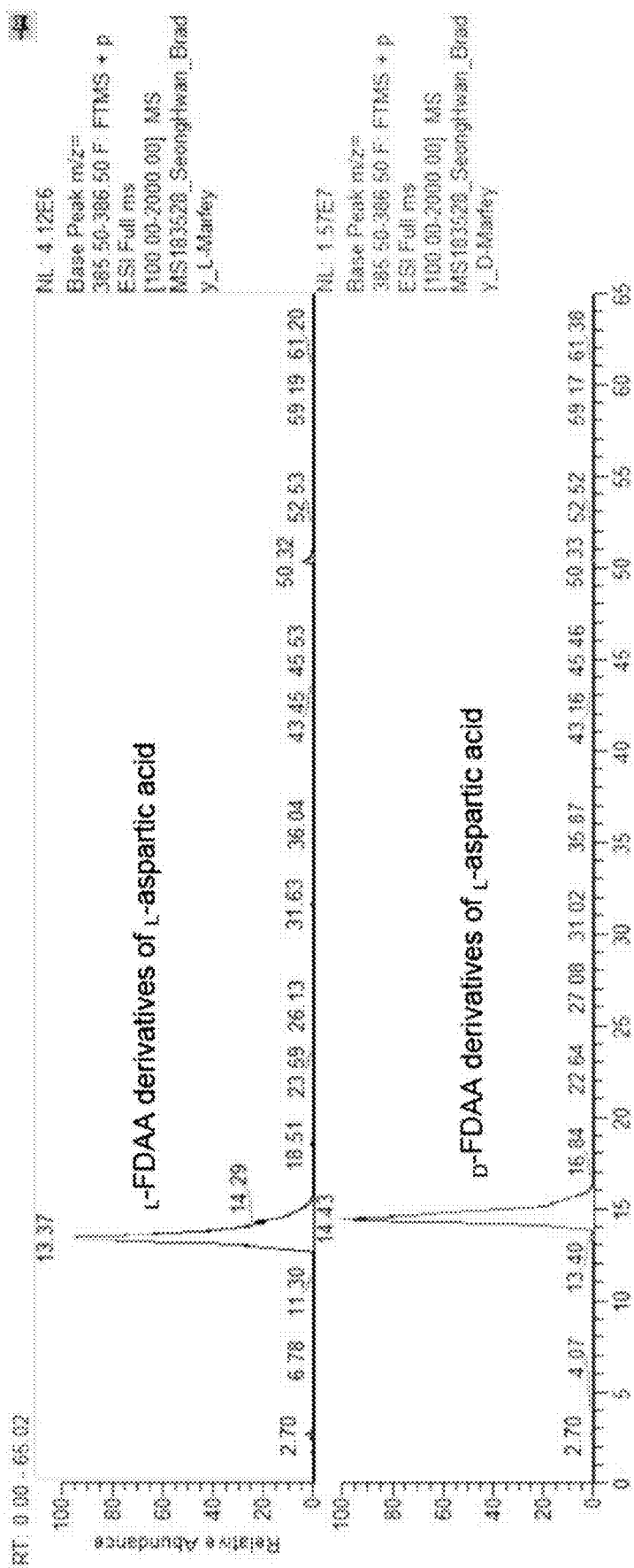
Figure 25:
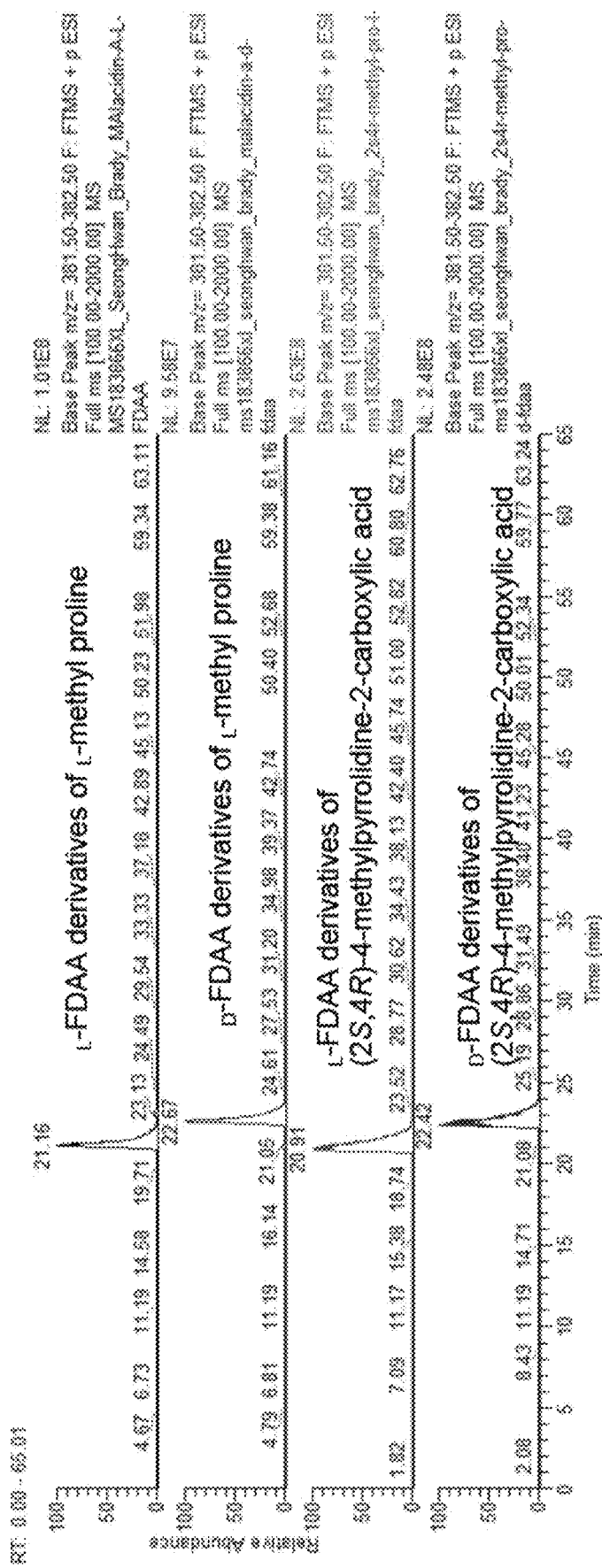
Figure 26:
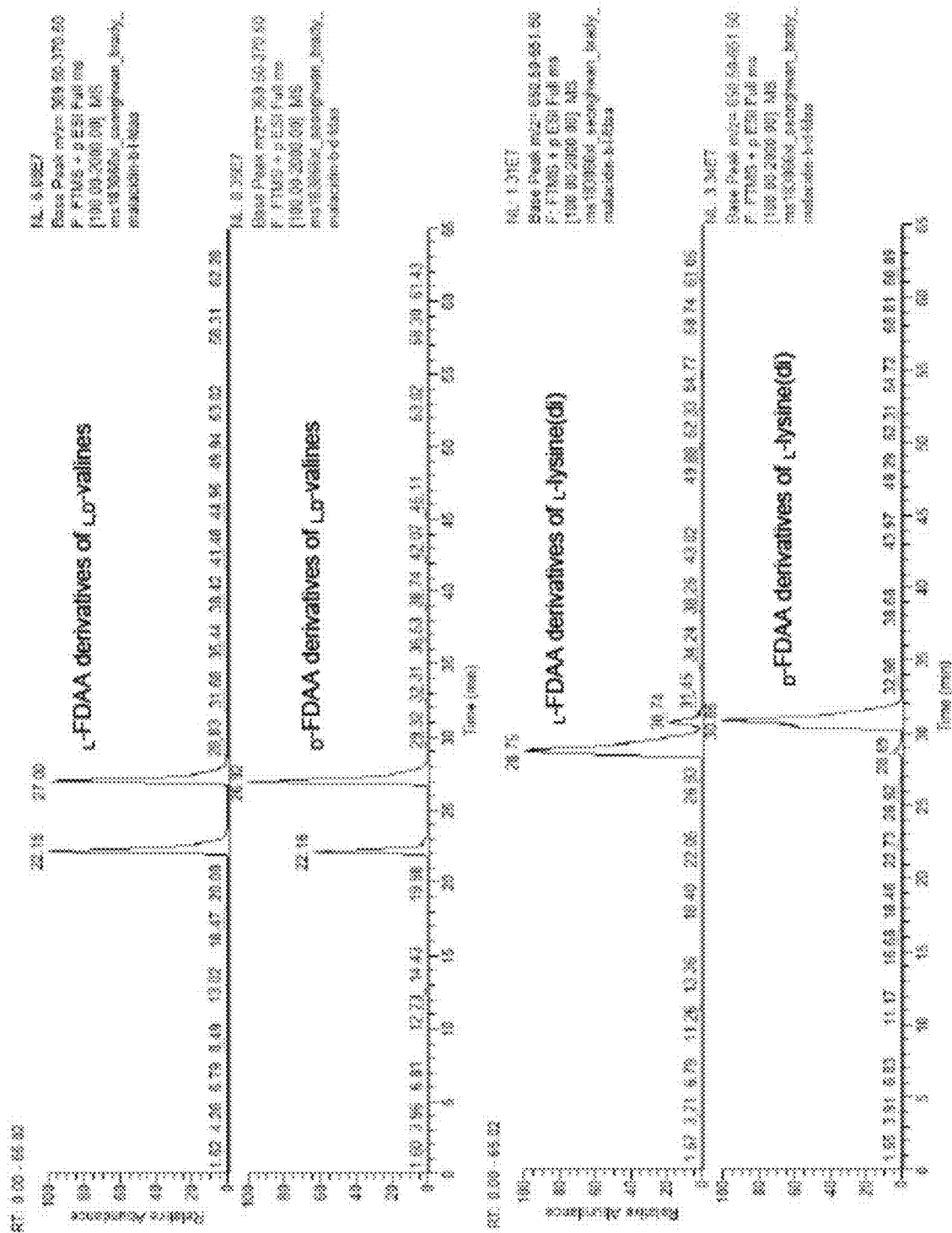
FIG. 26 depicts LC-MS charts of L, D-FDAA derivatives of malacidin B. Chromatograms are representative across two independent derivatizations.
Figure 26:
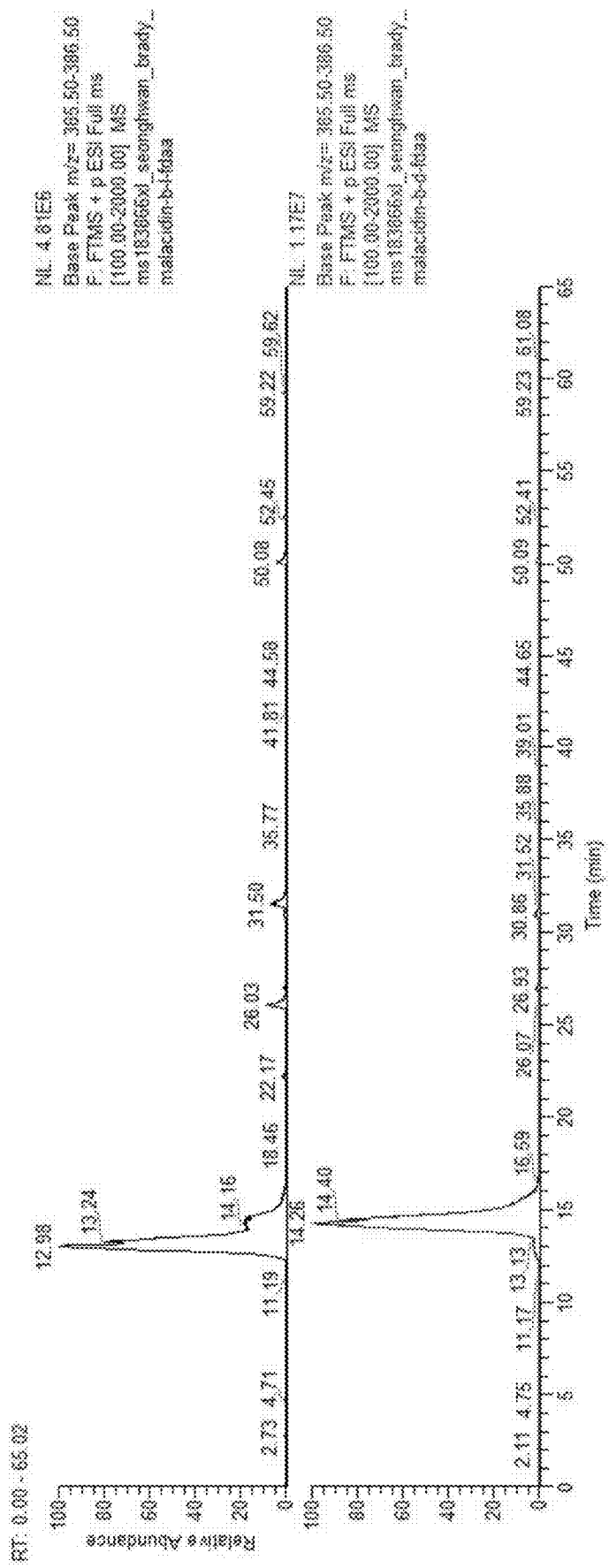
Figure 26:
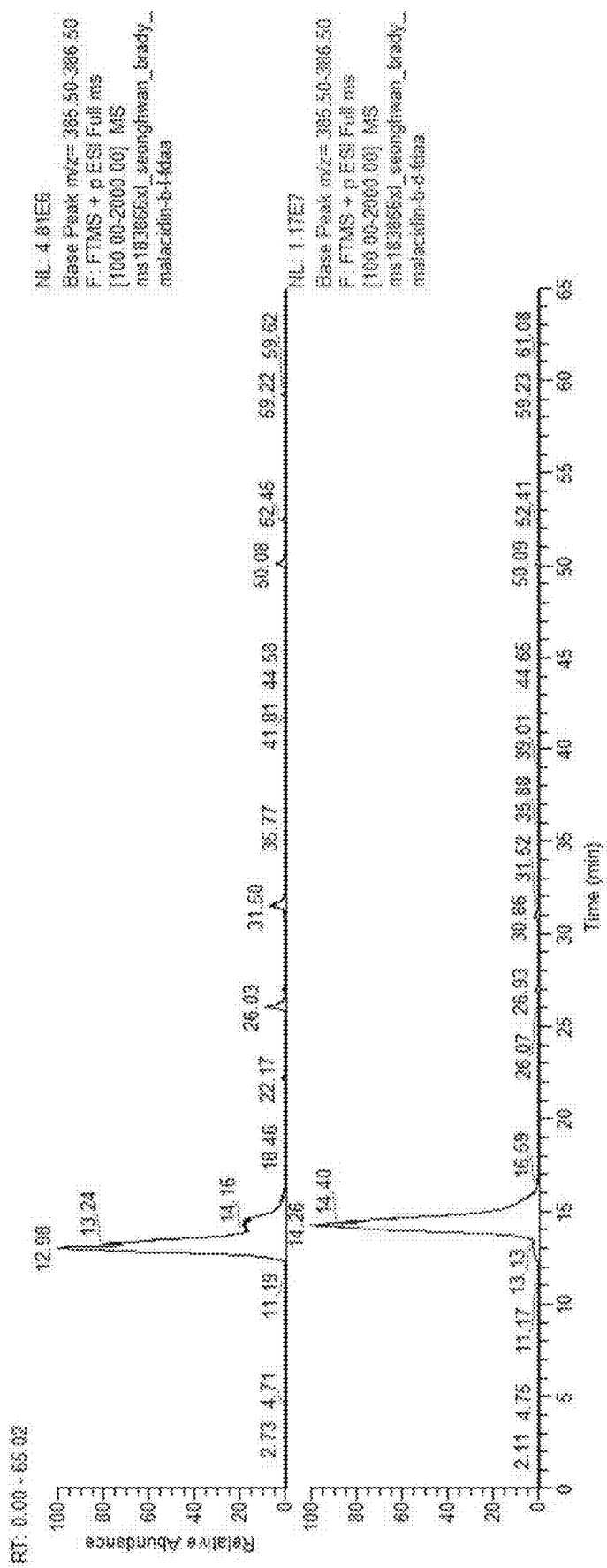
Figure 26:
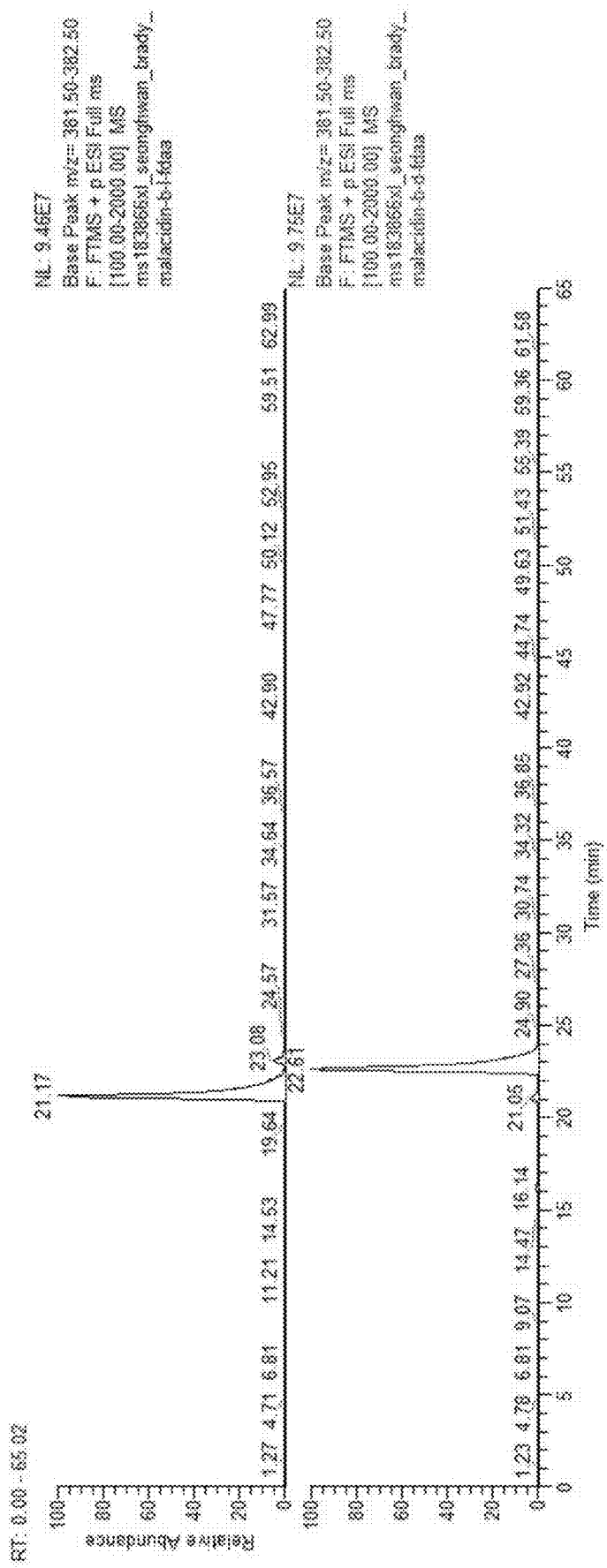

Epimerization domains located at the ends of the MlcK and MlcL NRPSs are predicted to change the stereochemistry of the Val at position 3 and the MeAsp at position 8 from an Lconfiguration to a D-configuration. To empirically support these and the rest of the stereochemical predictions, Marfey's reagent was used to analyze the amino acids in both malacidin A and B. Initially, malacidin A and B were individually hydrolyzed under acidic conditions. The hydrolyzed amino acids were derivatized with Marfey's reagents (L,D-FDAA) and the resulting Marfey's derivatives were analyzed by LC/MS to determine the absolute configuration for each amino acid (Table 4, FIGS. 25-26). Based on the elution order of diasteromer standards tested in-house as well as elution order data from the literature, the absolute configuration of L-Lys, L-HyAsp and L-Asp, were readily determined (Schubert et al., 2014, Chemistry 20:4948-55; Fujii et al., Anal Chem 69:3346052). As predicted bioinformatically, both D-Val and L-Val were observed. These configurations are identical for both malacidin A and B and match the bioinformatic predictions in all cases. The relative configuration of C-2 and C-4 in L-MePro was determined both by Marfey's analysis of the commercial standard, (2S,4R)-4-methylpyrrolidine-2-carboxylic acid, and through a ROESY NMR experiment (FIGS. 23-24). Due a lack of readily available commercial standards for LD-MeDap and LD-MeAsp, not all of the stereochemistry configurations in malacidin could be resolved by Marfey's analysis or NMR. However it was able to be predicted through bioinformatics analysis the likely stereochemistry of the α-carbons for residues 1, 2, and 8 to be L-MeAsp, L-MeDap, and DMeAsp, respectively (FIG. 27-29). These were determined through a detailed comparison of the chemical and biosynthetic similarities between the MeDap and MeAsp residues in malacidin to that of residues found in other evolutionarily related LD-MeDap, LD-Dap, or LD-MeAsp containing molecules (Muller et al., 2007, Antimicrob Agents Ch 51:1028-37; Miao et al., 2005, Microbiol 151:150-1523; Miao et al., 2006, J Ind Microbiol Biotechnol 33:129-40). For example, the malacidin gene cluster encodes for homologs to the DabA, DabB, DabC enzymes that transfer an amine from L-Orn to L-Thr to yield a stereospecific L-threo-MeDap in fruilimicin biosynthesis. 4 Sharing a similar domain structure as fruilimicin at the position, it is likely that malacidin incorporates an identical L-MeDap. In a similar scope, the malacidin gene cluster shares related enzymes to fruilimicin for the biosynthesis of 3-methylaspartic acids. These cobalamin-dependent glutamate mutase enzymes, GlmA and GlmB, produce L-threo-3-MeAsp from L-Glu in friulimicin biosynthesis. While malacidin gene cluster incorporates two 3-methylaspartic acids (position 1 & 8), the second is encoded by a NRPS module in the MlcL synthetase that contains an epimerization domain that is responsible for changing the stereochemistry to DMeAsp.

Determination of Absolute Configuration of Amino Acids of Malacidins

Malacidin A and B (0.5 mg) were dissolved in 6 N HCl (500 µl) separately and heated at 115° C. for 10 h. For each antibiotic, four separate reactions were set up. After hydrolysis, the reaction mixtures were cooled in ice water for 5 min. The reaction solvent was evaporated in vacuo. The dried reaction was resuspended in 500 µl of water and the water was evaporated in vacuo. This process was repeated three times. The hydrolysates, containing free amino acids, were dissolved in 100 µl of 1 N $NaHCO_3$. Either 100 µl of L-FDAA (1-fluro-2,4-dinitrophenyl-5-$_L$-alanine amide) or 100 µl of D-FDAA in acetone (10 mg ml) was added to each of the four vials and they were incubated at 42° C. for 1 h. To neutralize the reaction, 100 µl of 2 N HCl was added to each reaction mixture. Reactions were then diluted with 300 µl of 50% acetonitrile/water. Five microlitres of each reaction mixture was analysed by liquid chromatography-high-resolution mass spectrometry with a gradient solvent system (20%-60% acetonitrile/water with 0.1% formic acid over 40 min; flow rate 0.2 ml $min^{-1}$) on the RP column (Thermo Acclaim 120, Cis 2.1×150 mm).

Microbial Susceptibility Assays

The malacidins were screened against a panel of assay strains and pathogenic bacteria as indicated in Table 4. MIC assays were performed in duplicate in 96-well microtiter plates on the basis of the protocol recommended by the Clinical and Laboratory Standards Institute (Cockerill, 2012, Clinical and Laboratory Standards Institute). All presented data are the average of at least three independent assays. Stock solutions of malacidin or daptomycin (2 mg $ml^{-1}$ in H2O) were added to the first well in a row and serially diluted (twofold per transfer) across the microtiter plate. $CaCl_2$ was supplemented to media at a final concentration of 15 mM and fetal bovine serum (ATCC) was added to media (1:10) to test the effect of serum. Overnight cultures of bacteria were diluted 5,000-fold, and 50 µl was used as an inoculum in each well. MIC values were determined by visual inspection after 18 h incubation (30° C., static growth). For the enhanced calcium titration experiments, standard MIC assays were performed with methicillin-resistant *Staphylococcus aureus* (MRSA) PFGE strain type USA300 in media supplemented with $CaCl_2$ at: 25.0, 18.8, 14.1, 7.03, 3.52, 2.50, 1.76, 0.880, 0.440, 0.250 and 0 mM. To assess the effects of monovalent and divalent cations on malacidin activity, standard MIC assays were performed with MRSA USA300 in media supplemented with 15 mM $CaCl_2$, $MgCl_2$, $MnCl_2$, $ZnCl_2$, $SrCl_2$, NaCl and KCl. To evaluate the effects of pulmonary surfactants on activity against a community-acquired pneumonia-causing pathogen, standard MIC assays were performed with *Streptococcus pneumoniae* TCH8431 in media supplemented with both 15 mM $CaCl_1$ and Survanta (beractant) at a final concentration of 5, 1, 0.5, 0.25 or 0% (volume/volume (v/v) percent).

Mammalian Cytotoxicity Assays

Cytotoxicity against human cell lines was tested using an ATP release assay, CellTiter-Glo (Promega), according to the manufacturer's instructions. HEK293 cells (293FT, Thermo Fisher Scientific, no. R700-07) and MRC5 cells (ATCC CCL-171) were grown in complete DMEM media supplemented with 10% FBS, and were inspected visually for authentication and tested for *mycoplasma* contamination using a MycoAlert detection kit (Lonza). Cells were grown to confluence, trypsinized, counted and plated in 384-well cell culture plates at an appropriate density (2,500 cells per well for HEK293 and 1000 cells per well for MRC5). The test compound was added 24 h later in the presence of calcium, and viability was determined after 4.5 h of incubation. Experiments were performed with biological replicates. Haemolytic activity was evaluated by a red blood cell disc diffusion assay. Twenty-microlitre stocks of malacidin A and Triton X-100 were infused on filter discs, dried completely and then overlaid on 5% sheep blood agar plates (Hardy Diagnostics). The plates were incubated for 24 h at 20° C., and then checked for lysis.

Rat Cutaneous Wound Infection Model

Methicillin-resistant *Staphylococcus aureus* strain MW2 was grown in Mueller Hinton broth at 37° C. with shaking overnight. The culture was centrifuged, supernatant aspirated and the bacteria were gently washed once in sterile saline. The optical density was determined at 600 nm. The bacterial suspension was diluted to provide a challenge inoculum of approximately 500 CFU per wound in a volume of 0.05 ml in sterile 0.9% NaCl. The inoculum count was verified by viable counts on Mannitol Salt Agar plates spread with proper dilutions of the inoculum and incubated at 37° C. for 24-48 h. For the wound infection model, 8-week-old male (~200 g) Sprague Dawley rats were given two wounds each. Two rats were used at each time point (day 1 and day 3) for each treatment group for a total of 4 rats (8 wounds) per drug. This sample size was statistically calculated on the basis of previous in-house wound burden studies comparing vehicle-treated groups with antibiotic controls. Rats were randomly selected into the treatment groups. To generate wounds, the rats were anaesthetized by intraperitoneal injection of 100 mg $kg^{-1}$ ketamine+10 ng $kg^{-1}$ xylazine and the dorsal side of the rats was shaved with electrical clippers and then depilated with Nair. The exposed skin was wiped with betadine. Two symmetrical wounds were made on the dorsum of each rat using a 0.8-cm-diameter disposable biopsy punch. Sterile polyurethane rings serving as wound chambers were placed over the fresh wounds and attached by surgical adhesive. After the wound creation, rats from each group were infected with 0.05 ml of the bacterial suspension for a final infection dose of 500 CFU per wound. Wounds were covered with Tegaderm visible adhesive dressing, and the rats were rehydrated with physiological saline administered via intraperitoneal injection. The analgesic buprenorphine (0.05 ng $kg^{-1}$) was administered to minimize pain during surgical recovery. At 30 min post infection, rats were given single daily topical treatments of vehicle (25 mM $CaCl_2$ in sterile water), or 0.5 mg malacidin A or daptomycin suspended in 25 mM $CaCl_2$, and the wounds were covered in fresh Tegaderm dressing. At 1 day and 3 days post infection, the rats were humanely euthanized and wounds were excised and assessed for bacterial burdens by plating on MSA. Rats were observed twice daily for morbidity and possible signs of acute toxicity. Abnormal clinical signs were recorded if observed.

Selection for Malacidin-Resistant Mutants

To select for resistant mutants, a single MRSA USA300 colony from a freshly struck plate was inoculated into LB media and grown overnight at 37° C. The saturated overnight culture was diluted 100-fold, supplemented with a sub-lethal dose (0.5×MIC) of malacidin A, vancomycin, daptomycin or rifamycin and 15 mM calcium. Two-hundred-microlitre aliquots were then distributed into microtiter plate wells. The next day, 3 μl of culture from each well was used to inoculate 200 μl of calcium-supplemented media (15 mM calcium) with fresh antibiotic at 0.5× and 4×MIC. This process was repeated for 20 days. In the cases where bacterial growth was observed in the 4' MIC overnight cultures, the resistant culture was plated in successively higher concentrations of antibiotic the following day. This was repeated over the course of the experiment to assess fold change in MIC at day 0 to day 20.

Membrane Leakage and Depolarization Assays

The effects of malacidin on membrane integrity was assessed using SYTOX green. In brief, single colonies of MRSA USA300 were grown in LB media with and without 15 mM $CaCl_2$ to an $OD_{600\ nm}$ of 0.35. Nine hundred microlitres of cells were mixed with 100 μL of 17 μM SYTOX green dye (Thermo Fisher). The resulting mixture was incubated for 5 min at 22° C., and then distributed to a microtiter plate at 50 μl per well. An initial reading of fluorescence pre-antibiotic addition was measured at excitation and emission wavelengths of 488 nm and 523 nm, respectively. Fifty microlitres of antibiotics was added to respective wells at a final concentration of 20 μg $ml^{-1}$. Measurements were immediately collected for 10 min. To assess the effects of malacidin on membrane depolarization, similar assays were set up using the membrane potential probe, DiBAC4 (bis-(1,3-dibutylbarbituric acid)trimethine oxonol). Single colonies of MRSA USA300 were grown in LB media with and without 15 mM $CaCl_2$ to an $OD_{600\ nm}$ of 0.35. Nine hundred microlitres of cells were mixed with 100 μl of 20 μg ml DiBAC4dye (Thermo Fisher). The resulting mixture was incubated for 5 min at 22° C., and then distributed to a microtiter plate at 50 μl per well. An initial reading of fluorescence pre-antibiotic addition was measured at excitation and emission wavelengths of 492 nm and 515 nm, respectively. Fifty microlitres of antibiotics was added to respective wells at a final concentration of 20 μg $ml^{-1}$. Measurements were immediately collected for 10 min. Representative examples from three technical replicates are shown.

UDP-MurNAc-Pentapeptide Accumulation Assay

The intracellular accumulation of the cell wall precursor UDP-MurNAc-pentapeptide after treatment of MRSA USA300 with malacidin was assessed as previously described (Schneider et al., 299, Antimicrob Agents Ch 53:1610-18). In brief, single colonies of MRSA USA300 were grown in LB media with and without 15 mM $CaCl_2$ to an $OD_{600\ nm}$ of 0.6. One microlitre of cells and medium were incubated with a final concentration of 130 μg $ml^{-1}$ chloramphenicol for 15 min at 37° C. Antibiotics to be assayed were added at 10 μg $ml^{-1}$ and incubated for 60 min at 37° C. Vancomycin, known to form a complex with lipid II, was used as a positive control. Cells were collected by centrifugation, and resuspended in 30 μl dH$_2$O and incubated in boiling water for 15 min. The cell extract was then centrifuged at 14,000 g. Supernatant was analysed for UDP-linked cell wall precursors by a UPLC-MS system. Experiments were performed with biological replicates.

Complex Formation with Cell Wall Precursors

Binding of malacidin to C55-P and lipid II was evaluated by incubating 1 nmol of each purified precursor with 0.5 nmol of malacidin or daptomycin in 100 mM Tris-HCl, pH 7.5, 0.1% Triton X-100, 13 mM MgCl$_2$, and with or without 25 mM CaCl$_2$, for 60 min at 37° C. Subsequently, the mixture was extracted twice with n-BuOH/6 M pyridinium acetate buffer, pH 4.2 (3:1, v/v). The butanol fraction was evaporated and the residue was dissolved in CHCl$_3$/methanol (1:1, v/v). The resuspension was analysed for the loss of unbound malacidin or daptomycin to a complex by TLC analysis using chloroform/methanol/water/ammonia (88:48:10:1, v/v/v/v) as the solvent and detection by 254/366 nm visualization. Experiments were performed with biological replicates.

The disclosures of each and every patent, patent application, and publication cited herein are hereby incorporated herein by reference in their entirety. While this invention has been disclosed with reference to specific embodiments, it is apparent that other embodiments and variations of this invention may be devised by others skilled in the art without departing from the true spirit and scope of the invention. The appended claims are intended to be construed to include all such embodiments and equivalent variations.

What is claimed is:

1. A compound represented by formula (I)

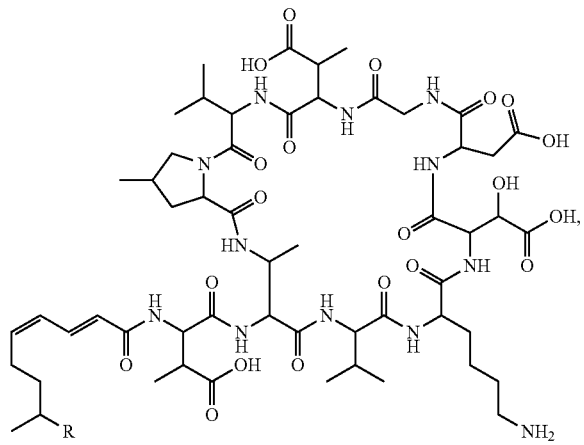

(I)

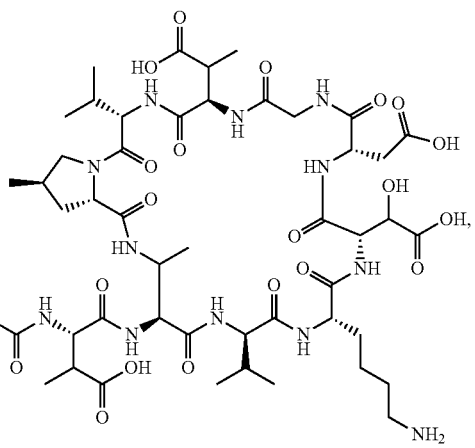

(II)

wherein R is a hydrogen, alkyl, aryl or heteroaryl group.

4. The compound of claim 3, wherein R is a $C_3$-$C_{10}$ alkyl.

5. A pharmaceutical composition comprising a compound of claim 1.

6. A method of treating or preventing a bacterial infection in a subject in need thereof, the method comprising administering a composition comprising a compound of claim 1 to the subject.

7. The method of claim 6, wherein the subject is exposed to or infected with a bacteria.

8. The method of claim 7, wherein the bacteria is a gram positive bacteria.

9. The method of claim 7, wherein the bacteria is a drug resistant bacteria.

10. The method of claim 6, wherein the method further comprises administering a second therapeutic.

11. The method of claim 10, wherein the second therapeutic is an antibiotic.

12. A method of inhibiting the growth of or killing a bacterial cell, the method comprising, contacting the bacterial cell with a composition comprising a compound of claim 1.

13. A method of biosynthesizing the malacidin of claim 1, the method comprising providing a heterologous nucleic acid of the invention to a host, incubating the host in a growth medium, and isolating the malacidin from the host or the growth medium.

14. The method of claim 13, wherein the heterologous nucleic acid comprises a sequence at least 90% homologous to SEQ ID NO:4.

wherein R is a hydrogen, $C_3$-$C_{10}$ alkyl, aryl, or heteroaryl group.

2. The compound of claim 1, wherein R is a $C_3$-$C_{10}$ alkyl.

3. The compound of claim 1, wherein the compound represented by formula (I) is a compound represented by formula (II):

* * * * *